US012662472B2

(12) United States Patent
Li et al.

(10) Patent No.: US 12,662,472 B2
(45) Date of Patent: Jun. 23, 2026

(54) ORGANIC MATERIAL COMPOSITION AND APPLICATIONS THEREOF

(71) Applicant: Ningbo Lumilan Advanced Materials Co., Ltd., Ningbo City (CN)

(72) Inventors: Xiangzhi Li, Ningbo City (CN); Ye Cai, Ningbo City (CN); Ting-Wei Wei, Ningbo City (CN); Zhi-Kuan Chen, Ningbo City (CN)

(73) Assignee: NINGBO LUMILAN ADVANCED MATERIALS CO., LTD., Ningbo City (CN)

( * ) Notice: Subject to any disclaimer, the term of this patent is extended or adjusted under 35 U.S.C. 154(b) by 944 days.

(21) Appl. No.: 17/952,136

(22) Filed: Sep. 23, 2022

(65) Prior Publication Data

US 2023/0140609 A1 May 4, 2023

(30) Foreign Application Priority Data

Sep. 26, 2021 (CN) .......................... 202111129858.4
Aug. 5, 2022 (CN) .......................... 202210936599.4

(51) Int. Cl.

| | |
|---|---|
| *C07D 409/12* | (2006.01) |
| *C07D 241/42* | (2006.01) |
| *C07D 247/02* | (2006.01) |
| *C07D 249/20* | (2006.01) |
| *C07D 251/24* | (2006.01) |
| *C07D 403/10* | (2006.01) |
| *C07D 405/04* | (2006.01) |
| *C07D 405/08* | (2006.01) |
| *C07D 405/10* | (2006.01) |
| *C07D 405/12* | (2006.01) |
| *C07D 405/14* | (2006.01) |
| *C09K 11/06* | (2006.01) |
| *H10K 85/60* | (2023.01) |

(52) U.S. Cl.

CPC ......... *C07D 409/12* (2013.01); *C07D 241/42* (2013.01); *C07D 247/02* (2013.01); *C07D 249/20* (2013.01); *C07D 251/24* (2013.01); *C07D 403/10* (2013.01); *C07D 405/04* (2013.01); *C07D 405/08* (2013.01); *C07D 405/10* (2013.01); *C07D 405/12* (2013.01); *C07D 405/14* (2013.01); *C09K 11/06* (2013.01); *H10K 85/622* (2023.02); *H10K 85/6572* (2023.02); *C09K 2211/18* (2013.01)

(58) Field of Classification Search

None

See application file for complete search history.

(56) References Cited

U.S. PATENT DOCUMENTS

2022/0123230 A1* 4/2022 Kang .................. C07D 403/04

* cited by examiner

*Primary Examiner* — Vu A Nguyen

(74) *Attorney, Agent, or Firm* — MUNCY, GEISSLER, OLDS & LOWE, P.C.

(57) ABSTRACT

The present invention provides an organic material composition and applications thereof. By the combination of the compounds comprised in the organic material composition, the organic material composition makes the element have a lower driving voltage, a higher current efficiency and a longer service life.

12 Claims, 1 Drawing Sheet

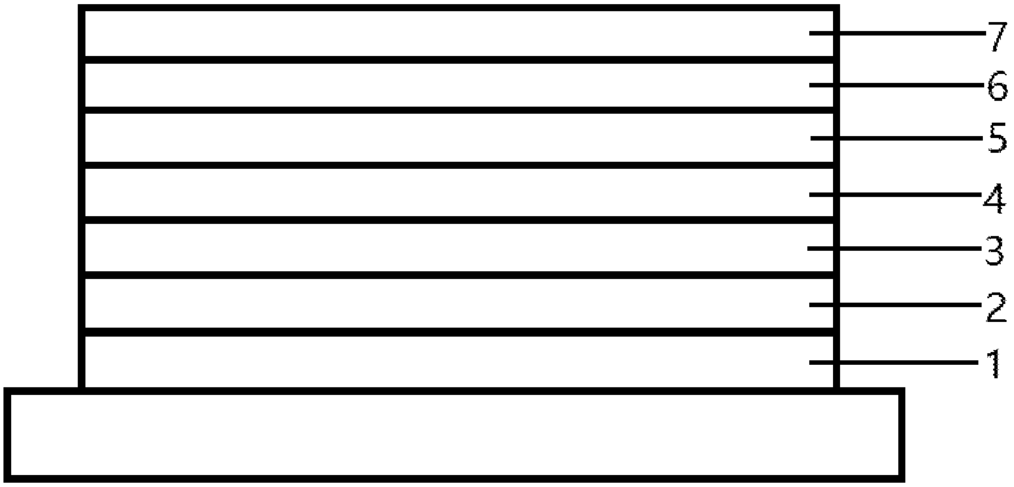
7
6
5
4
3
2
1

ORGANIC MATERIAL COMPOSITION AND APPLICATIONS THEREOF

CROSS-REFERENCE TO RELATED APPLICATION

Pursuant to 35 U.S.C. § 119(a), this application claims the benefit of the priority to Chinese Patent Application No. 202111129858.4, filed on Sep. 26, 2021, and to Chinese Patent Application No. 202210936599.4, filed on Aug. 5, 2022. The contents of the prior applications are incorporated herein by their entirety.

BACKGROUND OF THE INVENTION

1. Field of the Invention

The present invention belongs to the field of organic electroluminescence, which relates to an organic material composition and applications thereof.

2. Description of the Prior Arts

An electroluminescence (EL) device is a self-luminous display device which is advantageous for its wider angle of view, higher contrast ratio, and faster response time.

The most important key factor to decide the light-emitting efficiency of an EL device is the light-emitting material. A light-emitting material needs to have the following characteristics: high quantum efficiency, high mobility of electrons and holes, and the uniformity and stability of the light-emitting layer formed by the light-emitting material.

Recently, it is urgent to develop an organic EL device having higher light-emitting efficiency and longer service life. Specifically, in light of the EL characteristics needed for medium and large organic light-emitting diodes (OLED) panels, an excellent light-emitting material superior to regular materials is urgently needed. Thus, a high glass transition temperature and a high pyrolysis temperature are required for the host material in order to achieve high thermal stability and high electrochemical stability, thereby resulting in a longer service life, good formability of amorphous films, good adhesion with adjacent layers, and good immobility between layers.

To enhance color purity, light-emitting efficiency and stability, the light-emitting material can be used in a combination of a host material and a dopant. Generally, an EL device with good characteristics has an emitting layer structure formed by a material in which a dopant is doped into a host material. When the dopant/host material system is used as the light-emitting material, the host material will greatly influence the efficiency and service life of the EL device. Thus, in the field of the present invention, it is important to the development of a host material.

SUMMARY OF THE INVENTION

To overcome the shortcomings of the existing technology, the objective of the present invention is to provide an organic material composition and applications thereof.

To achieve the above objective, the present invention uses the following technical approaches:

In one aspect, the present invention provides an organic material composition comprising at least one compound having a structure represented by Formula 1 and at least one compound having a structure represented by Formula 2, Formula 1

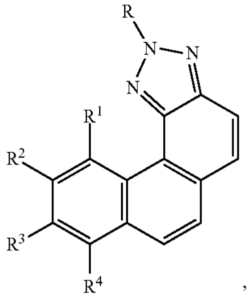

, wherein, R is selected from hydrogen, deuterium, halogen, a cyano group, a substituted or unsubstituted C1-C30 alkyl group, a substituted or unsubstituted C3-C30 cycloalkyl group, a substituted or unsubstituted C6-C30 aryl group, and a substituted or unsubstituted C3-C30 heteroaryl group;

$R^1$ is $-L^1Ar^1$; $R^2$ is $-L^2Ar^2$; $R^3$ is $-L^3Ar^3$; $R^4$ is $-L^4Ar^4$;

$L^1$ to $L^4$ are each independently selected from a bond, a substituted or unsubstituted C6-C30 arylene group, and a substituted or unsubstituted C3-C30 heteroarylene group; and $Ar^1$ to $Ar^4$ are each independently selected from hydrogen, deuterium, halogen, a cyano group, a substituted or unsubstituted C6-C60 arylamino group, a substituted or unsubstituted C3-C60 heteroarylamino group, a substituted or unsubstituted C6-C60 aryl group, and a substituted or unsubstituted C3-C60 heteroaryl group;

Formula 2

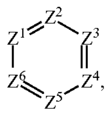

$Z^1$ is selected from N and $CL^{Y1}Ar^{Y1}$; $Z^2$ is selected from N and $CL^{Y2}Ar^{Y2}$; $Z^3$ is selected from N and $CL^{Y3}Ar^{Y3}$; $Z^4$ is selected from N and $CL^{Y4}Ar^{Y4}$; $Z^5$ is selected from N and $CL^{Y5}Ar^{Y5}$; $Z^6$ is selected from N and $CL^{Y6}Ar^{Y6}$.

$L^{Y1}$, $L^{Y2}$, $L^{Y3}$, $L^{Y4}$, $L^{Y5}$ and $L^{Y6}$ are each independently selected from a bond, a substituted or unsubstituted C6-C30 arylene group, and a substituted or unsubstituted C3-C30 heteroarylene group;

$Ar^{Y1}$, $Ar^{Y2}$, $Ar^{Y3}$, $Ar^{Y4}$, $Ar^{Y5}$ and $Ar^{Y6}$ are each independently selected from hydrogen, deuterium, halogen, a cyano group, a substituted or unsubstituted C1-C30 alkyl group, a substituted or unsubstituted C3-C30 cycloalkyl group, a substituted or unsubstituted C6-C60 aryl group, and a substituted or unsubstituted C3-C60 heteroaryl group; and $L^{Y1}$ $Ar^{Y1}$, $L^{Y2}Ar^{Y2}$, $L^{Y3}Ar^{Y3}$, $L^{Y4}Ar^{Y4}$, $L^{Y5}Ar^{Y5}$ and $L^{Y6}Ar^{Y6}$ are present individually without forming a ring, or any adjacent two of $L^{Y1}Ar^{Y1}$, $L^{Y2}Ar^{Y2}$, $L^{Y3}Ar^{Y3}$, $L^{Y4}Ar^{Y4}$, $L^{Y5}Ar^{Y5}$ and $L^{Y6}Ar^{Y6}$ joined to form a substituted or unsubstituted C6-C30 aromatic ring, or a substituted or unsubstituted C3-C30 heteroaromatic ring.

Preferably, in Formula 1, at least one of $Ar^1$ to $Ar^4$ is a group represented by Formula b:

Formula b

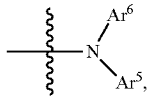

$Ar^5$ and $Ar^6$ are each independently selected from a substituted or unsubstituted C6-C30 aryl group, and a substituted or unsubstituted C3-C30 heteroaryl group.

Preferably, $Ar^5$ and $Ar^6$ are each independently selected from a phenyl group, a biphenylyl group, a terphenylyl group, a naphthyl group, a phenanthryl group, an anthryl group, a triphenylenylene group, a phenylnaphthyl group, a naphthylphenyl group, a pyridyl group, a bipyridyl group, a dibenzofuryl group, a dibenzothiophenyl group, a benzonaphthofuryl group, a benzonaphthothiophenyl group, a dinaphthofuryl group, a dinaphthothiophenyl group, a dibenzofurylphenyl group, a dibenzothiophenylphenyl group, a dimethylfluorenyl group, a benzodimethylfluorenyl group, a diphenylfluorenyl group, a spiro-bifluorenyl group, and a dimethylfluorenylphenyl group, each of which is substituted or unsubstituted.

Preferably, in Formula 1, at least one of $Ar^1$ to $Ar^4$ is

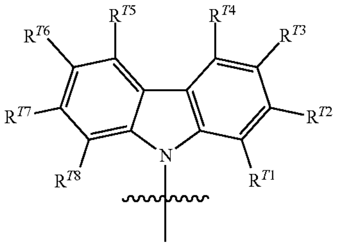

$R^{T1}$ to $R^{T8}$ are each independently selected from hydrogen, deuterium, halogen, a cyano group, a substituted or unsubstituted C1-C30 alkyl group, a C1-C30 alkyl group in which one or more methylene groups are independently substituted by —O— and/or —S— in a manner that O atom and/or S atom are not adjacent to each other, a substituted or unsubstituted C7-C30 arylalkyl group, a substituted or unsubstituted C6-C30 aryl group, a substituted or unsubstituted C3-C30 heteroaryl group, a substituted or unsubstituted C4-C30 heteroarylalkyl group, a substituted or unsubstituted C3-C30 cycloalkyl group, a substituted or unsubstituted C3-C30 heterocycloalkyl group, a substituted or unsubstituted C3-C30 cycloalkenyl group, a substituted or unsubstituted C1-C30 alkoxy group, and a substituted or unsubstituted C6-C30 aryloxy group;

$R^{T1}$ to $R^{T8}$ are present individually without forming a ring, or any adjacent two of $R^{T1}$ to $R^{T8}$ joined to form a ring B, and the ring B is a substituted or unsubstituted C6-C30 aromatic ring.

Preferably, the ring B is a benzene ring or a naphthalene ring.

Preferably, the group represented by Formula b is any one selected from b-1, b-2, b-3, b-4, b-5 and b-6 as below:

b-1

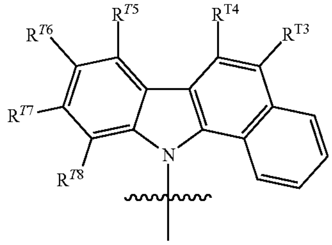

, b-2

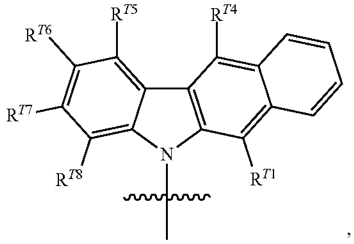

, b-3

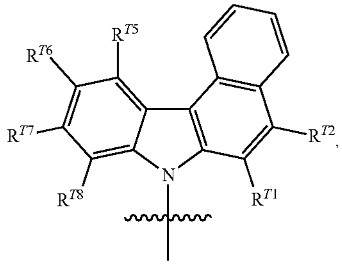

b-4

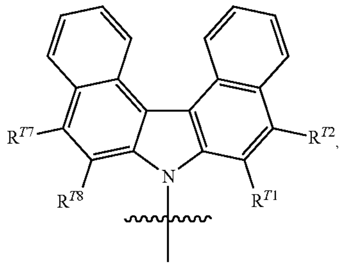

b-5

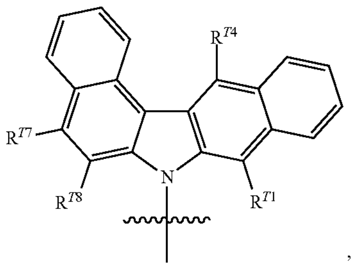

, and b-6

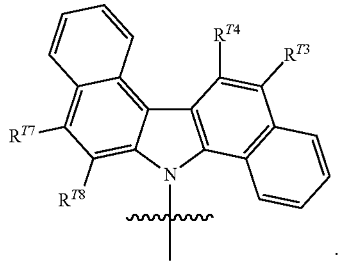

.

Preferably, $R^{T1}$ to $R^{T8}$ are each independently selected from hydrogen, deuterium, and a group selected from a methyl group, an ethyl group, a tert-butyl group, an adamantly, a phenyl group, a biphenylyl group, a terphenylyl group, a naphthyl group, a phenanthryl group, an anthryl group, a triphenylenylene group, a phenylnaphthyl group, a naphthylphenyl group, a pyridyl group, a bipyridyl group, a dibenzofuryl group, a dibenzothiophenyl group, a benzonaphthofuryl group, a benzonaphthothiophenyl group, a dinaphthofuryl group, a dinaphthothiophenyl group, a dibenzofurylphenyl group, a dibenzothiophenylphenyl group, a dimethylfluorenyl group, a benzodimethylfluorenyl group, a diphenylfluorenyl group, a spiro-bifluorenyl group, and a dimethylfluorenylphenyl group, each of which is substituted or unsubstituted.

Preferably, $Ar^1$ to $Ar^4$ are each independently selected from hydrogen, deuterium, and a group selected from a phenyl group, a naphthyl group, a biphenylyl group, a terphenylyl group, a phenanthryl group, a fluoranthenyl group, a triphenylenylene group, a dimethylfluorenyl group, a diphenylfluorenyl group, a spiro-bifluorenyl group, a benzodimethylfluorenyl group, a benzodiphenylfluorenyl group, a benzo-spiro-bifluorenyl group, a dibenzofuryl group, a dibenzothiophenyl group, a carbazolyl group, a benzocarbazolyl group, and a dibenzocarbazolyl group, each of which is substituted or unsubstituted.

Preferably, in Formula 1, at least one of $R^1$, $R^2$, $R^3$ and $R^4$ is hydrogen.

Preferably, at least two of $R^1$, $R^2$, $R^3$ and $R^4$ are hydrogen.

Preferably, at least three of $R^1$, $R^2$, $R^3$ and $R^4$ are hydrogen.

Preferably, $R^2$ is $-L^2Ar^2$; and $R^1$, $R^3$, and $R^4$ are all hydrogen.

Preferably, $R^3$ is $-L^3Ar^3$; and $R^1$, $R^2$, and $R^4$ are all hydrogen.

Preferably, R is selected from a phenyl group and a biphenylyl group, each of which is substituted or unsubstituted.

Preferably, $L^1$ to $L^4$ are each independently selected from a bond, a substituted or unsubstituted phenylene group, a substituted or unsubstituted naphthylene group, a substituted or unsubstituted biphenylene group, and a substituted or unsubstituted terphenylene group.

Preferably, the compound having a structure represented by Formula 1 is selected from the following compounds:

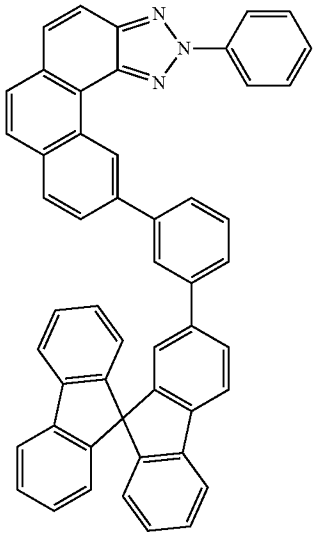

-continued

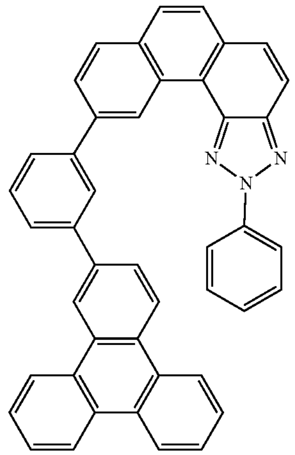

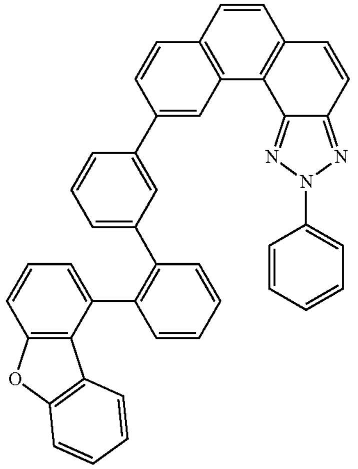

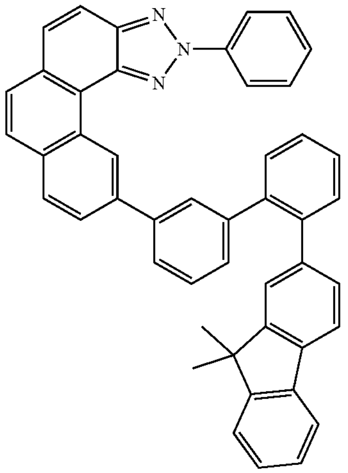

-continued
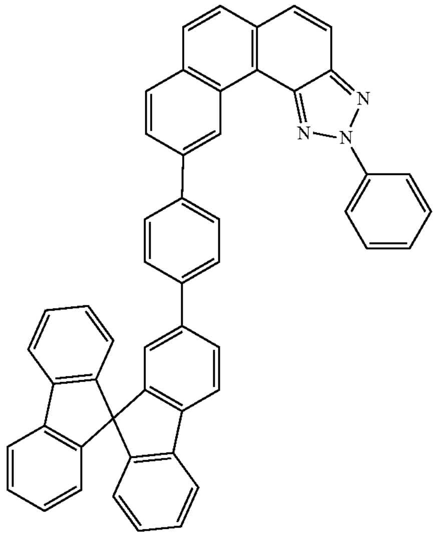
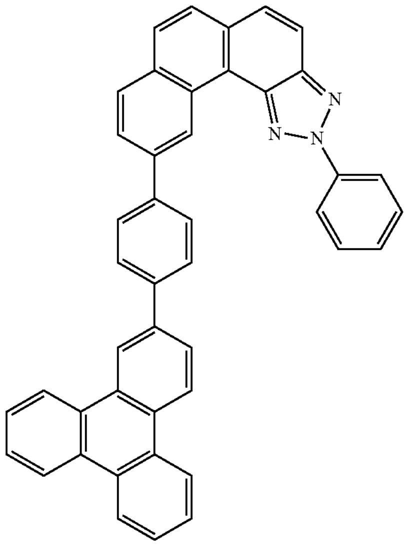
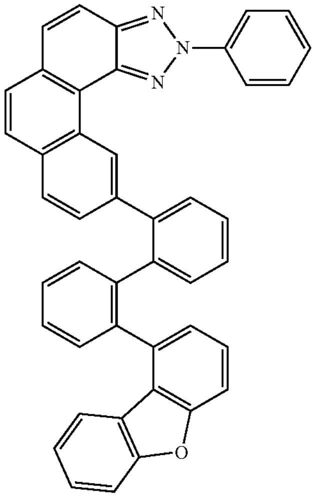
-continued
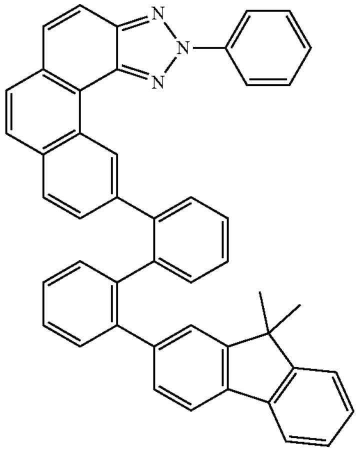
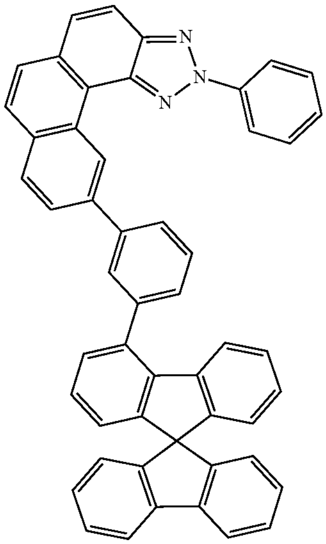
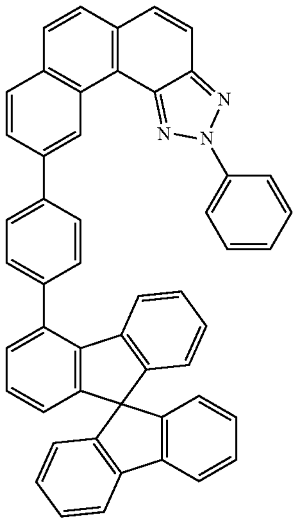

-continued
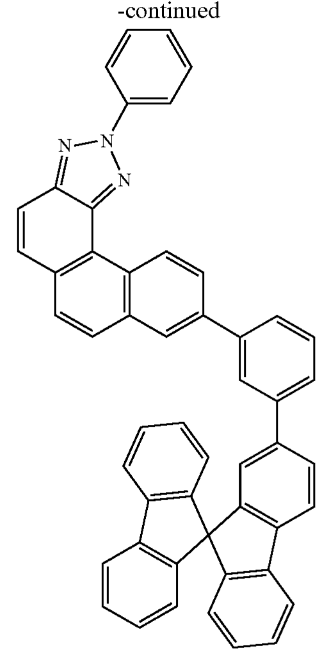
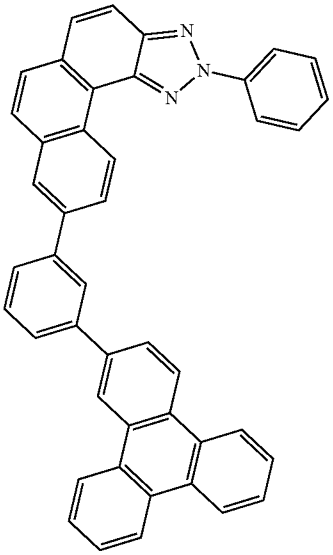
-continued
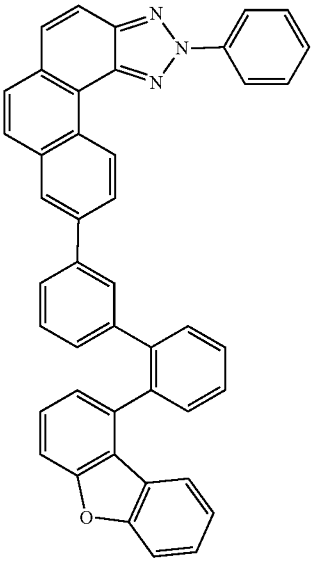
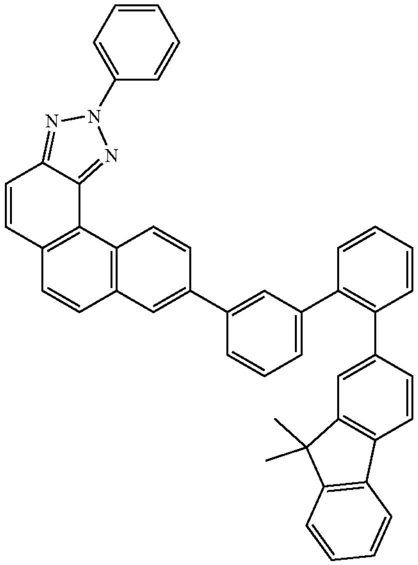
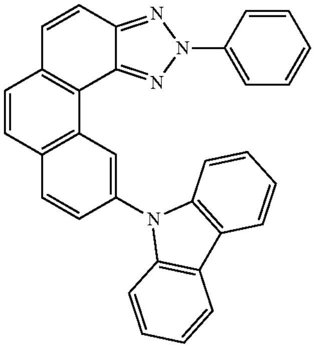

-continued
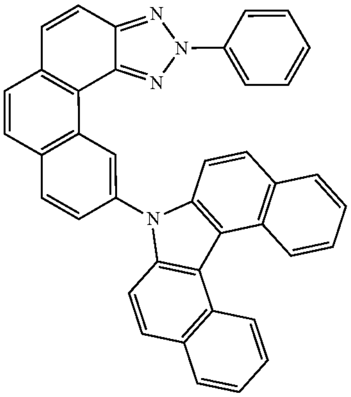
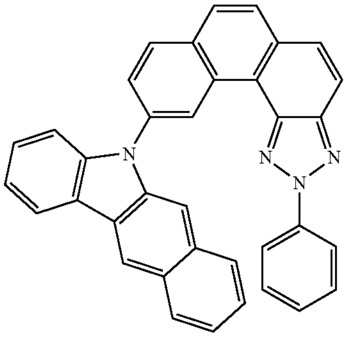
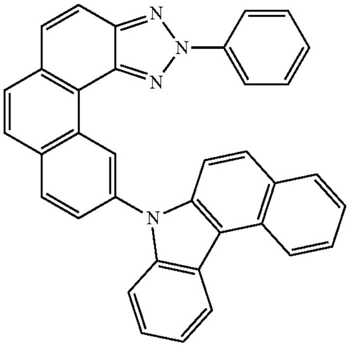
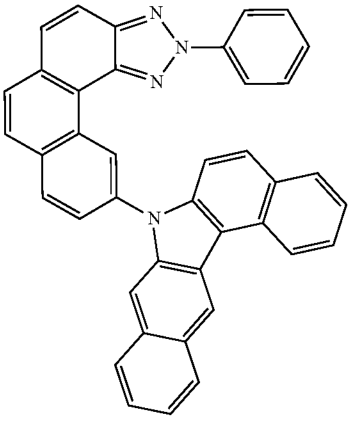
-continued
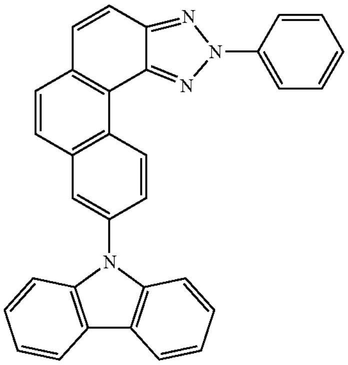
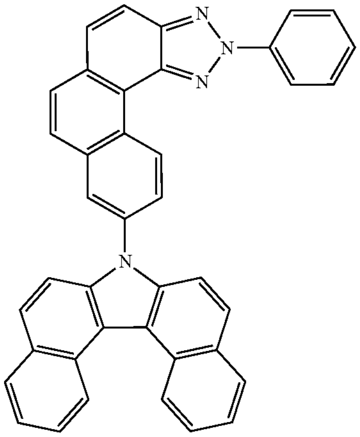
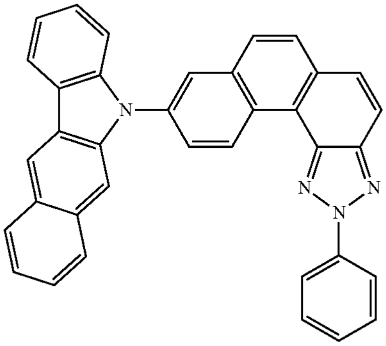
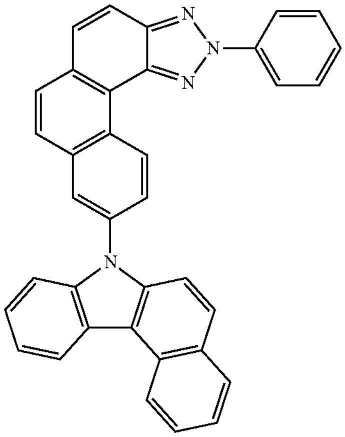

-continued
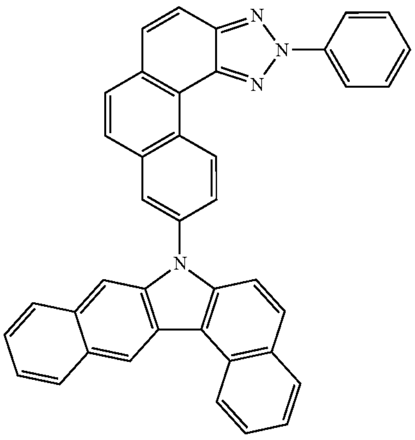
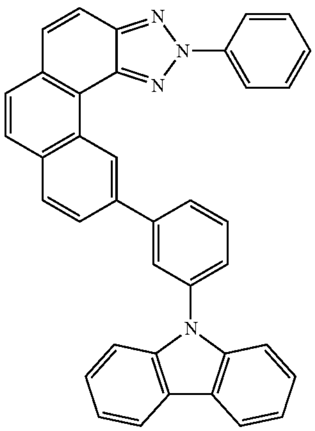
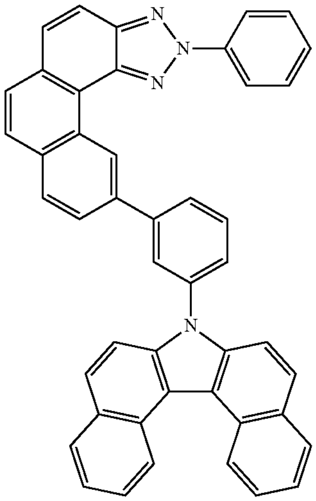
-continued
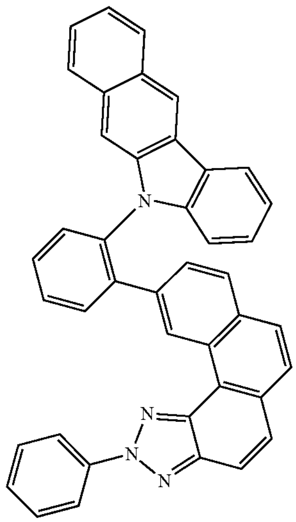
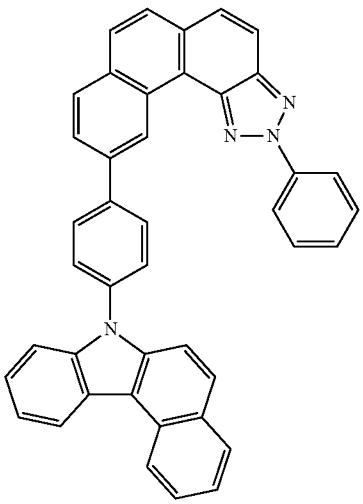
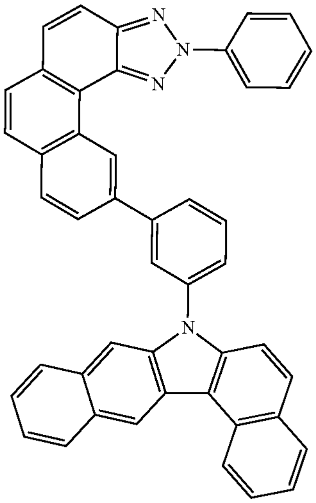

-continued
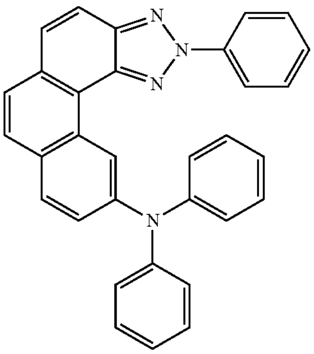
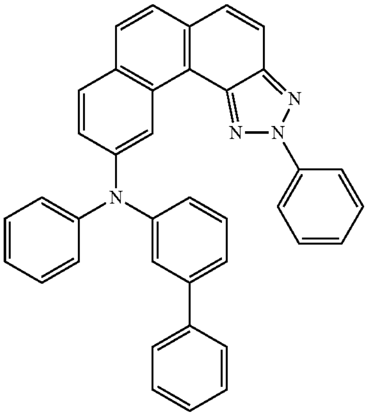
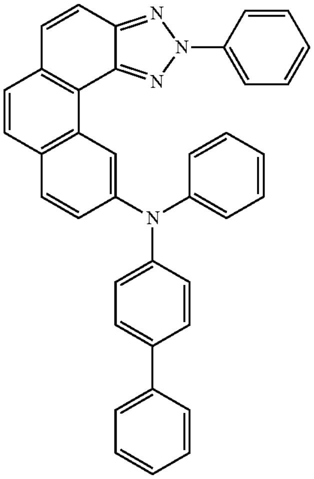
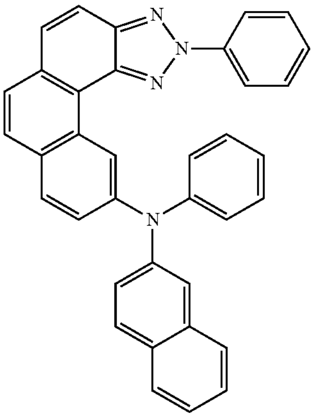
-continued
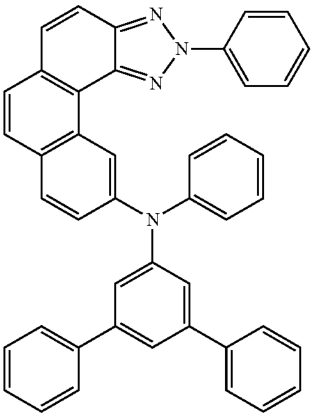
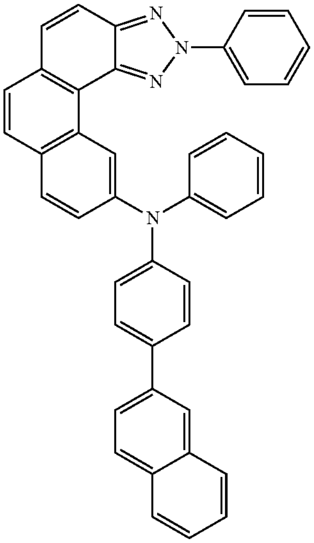
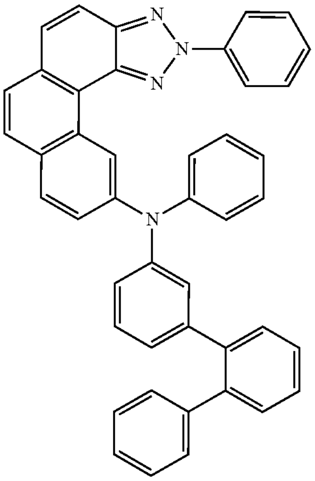

-continued
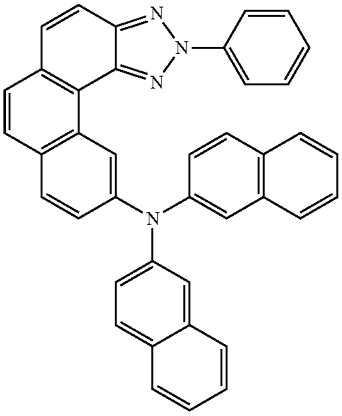
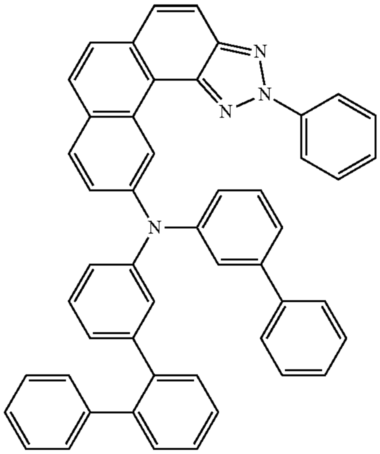
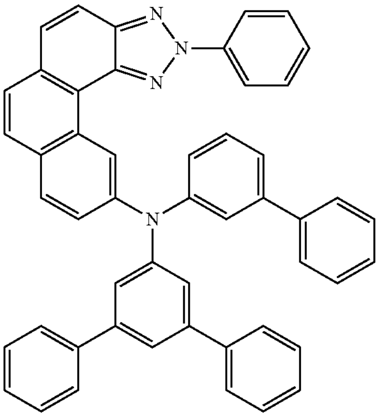
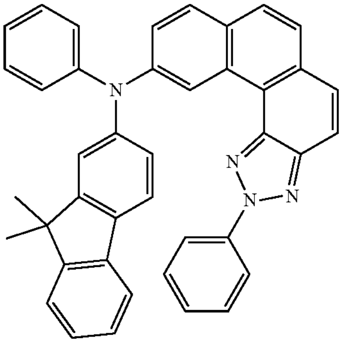
-continued
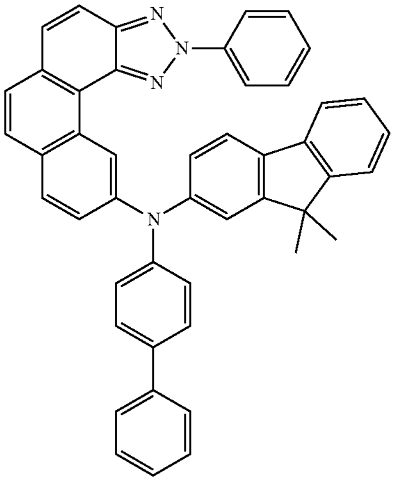
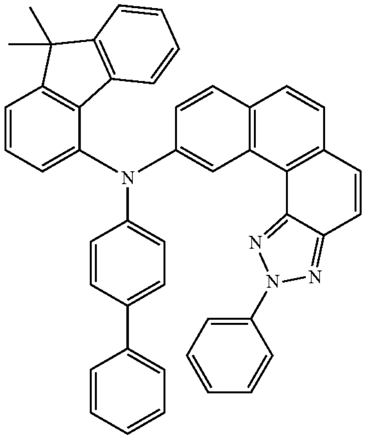
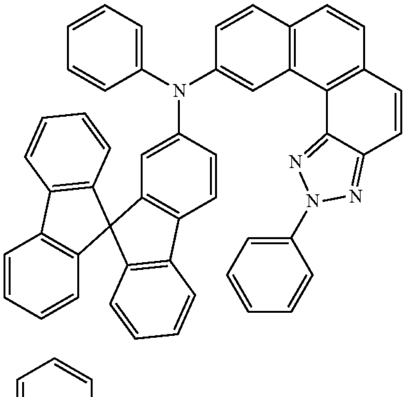
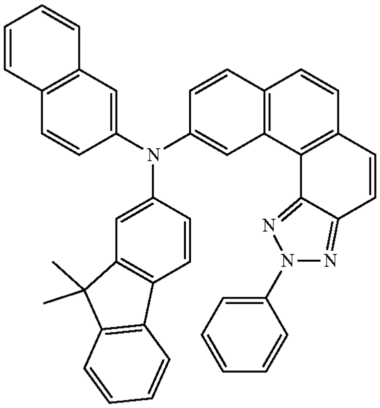

-continued
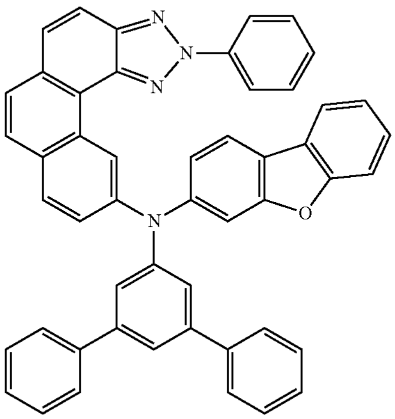
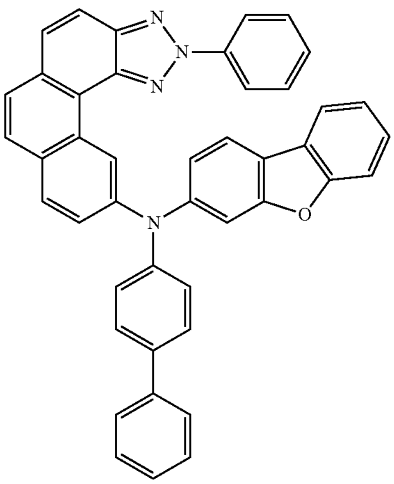
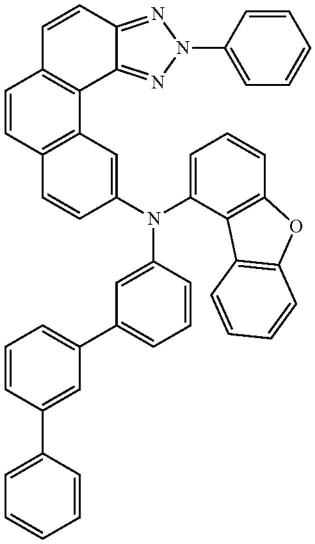
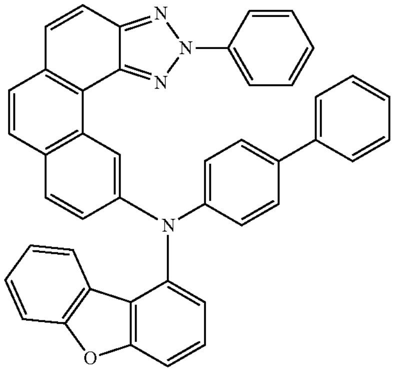
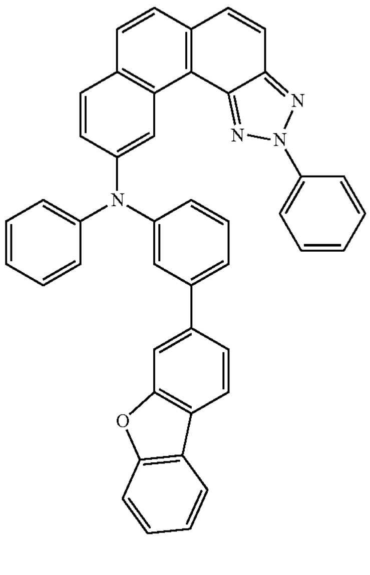
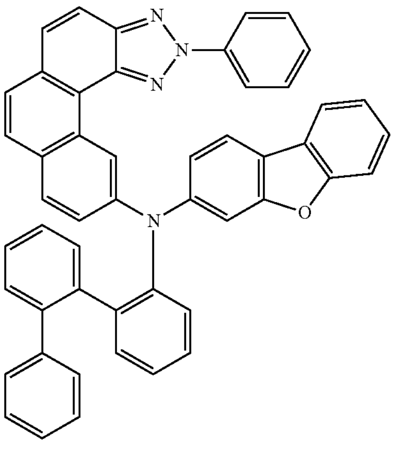

-continued
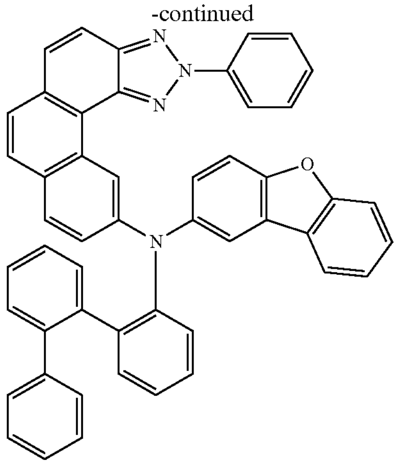
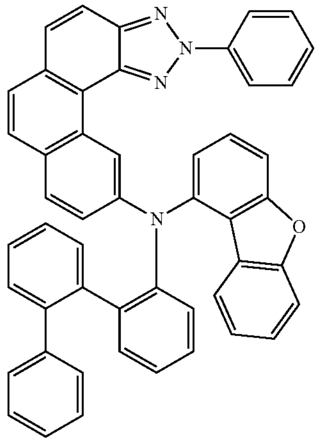
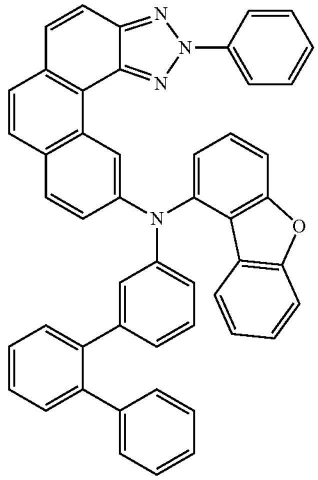
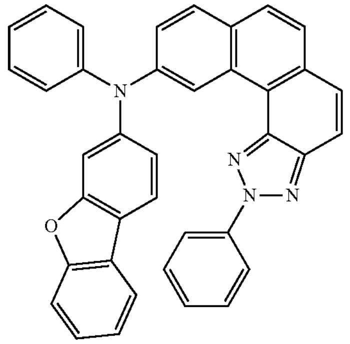
-continued
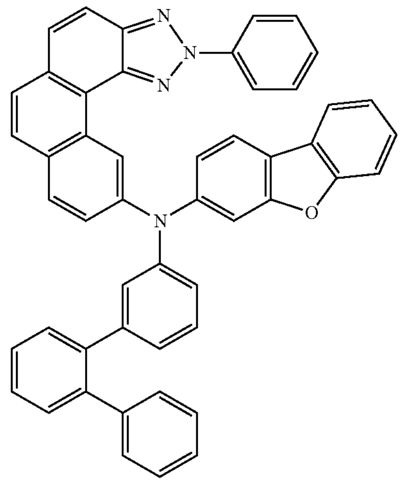
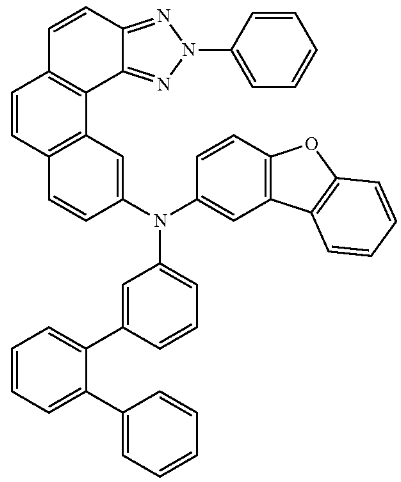
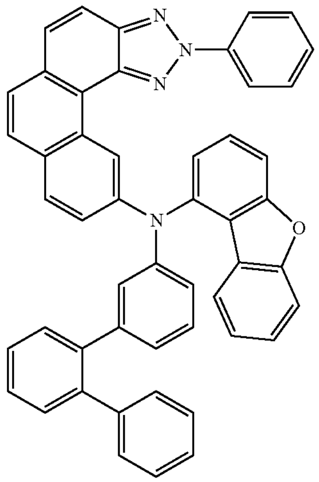

-continued
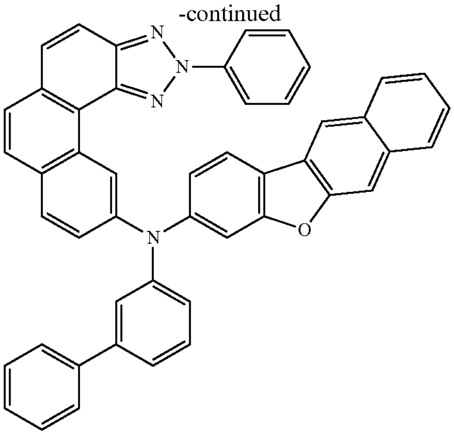
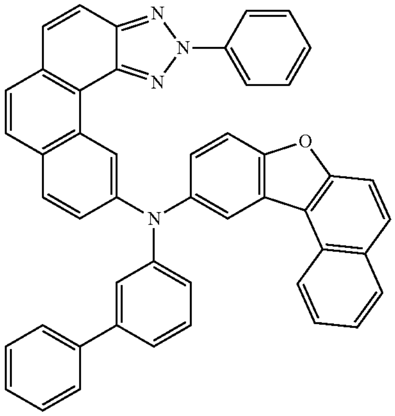
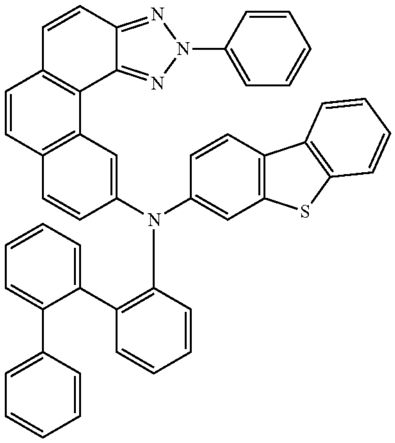
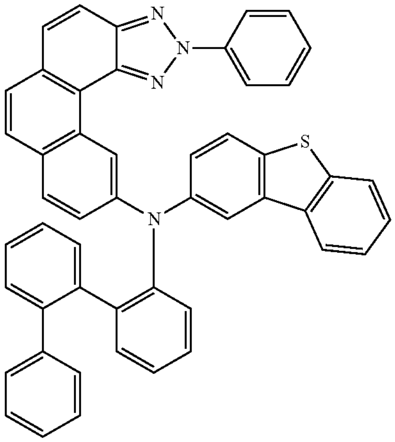
-continued
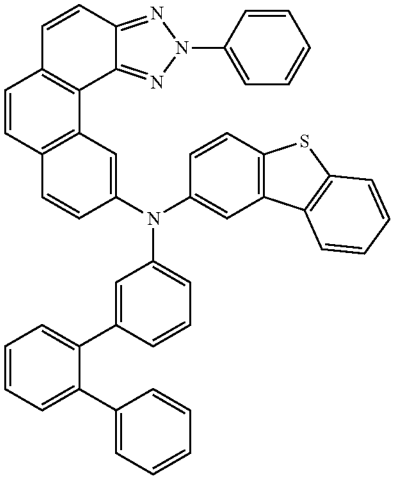
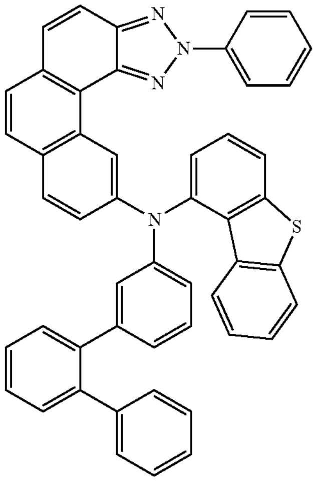
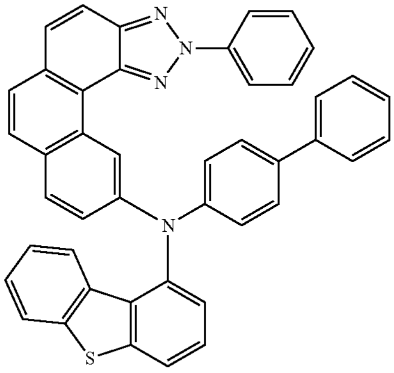

-continued
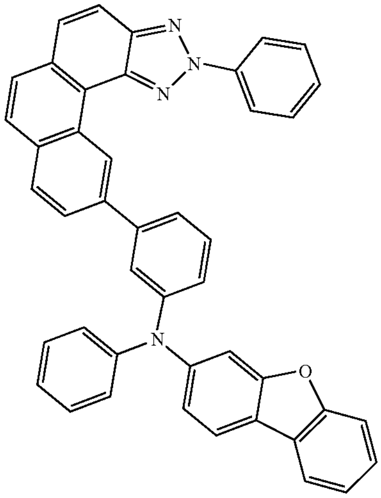
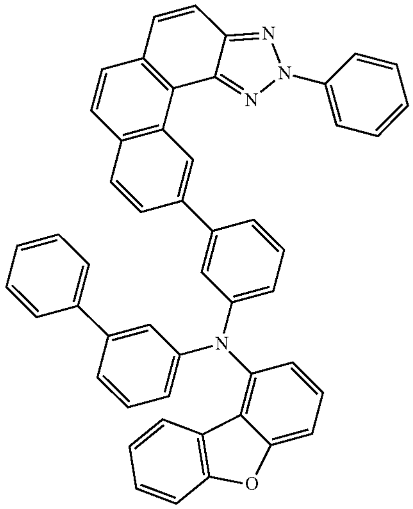
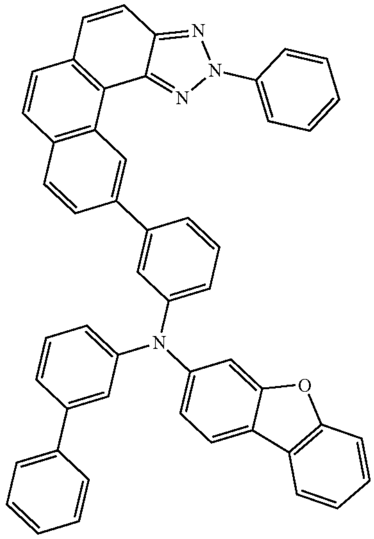
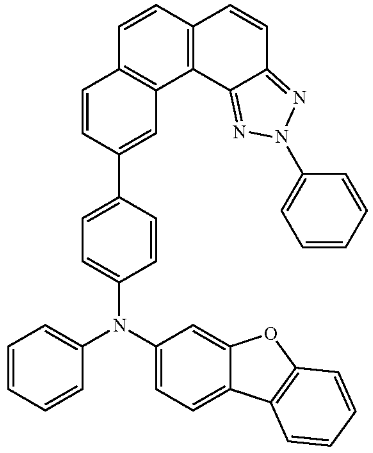
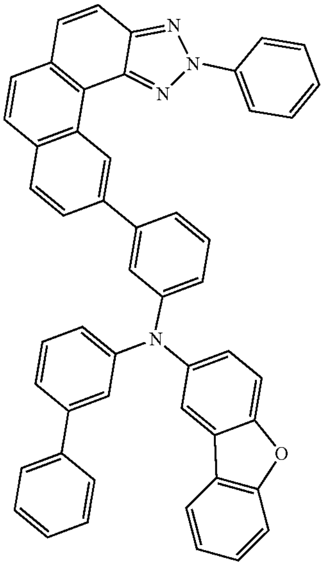
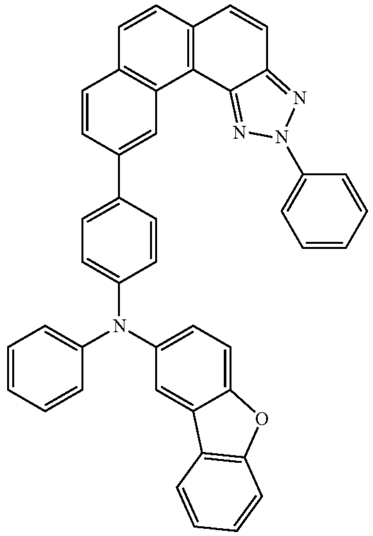
-continued -continued
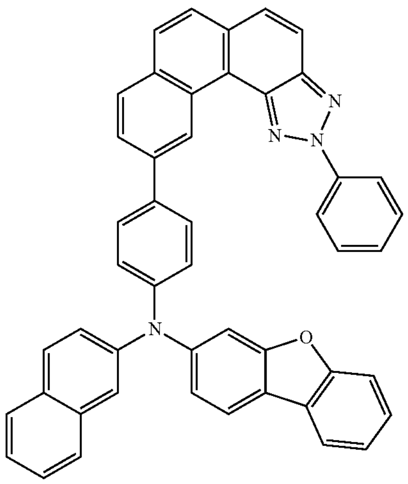
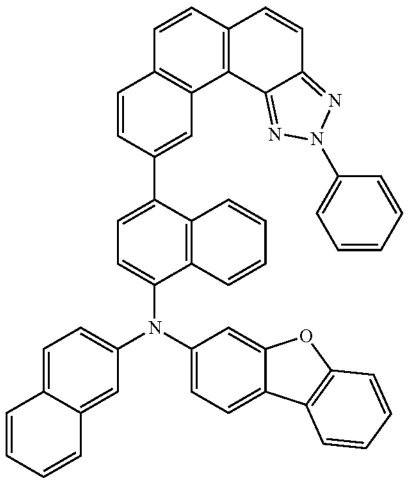
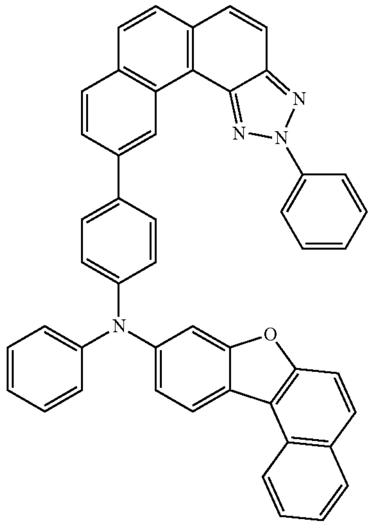
-continued
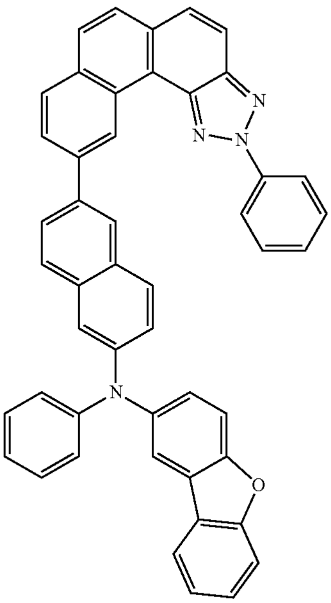
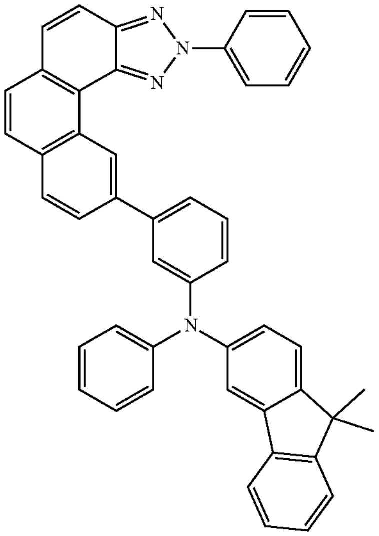
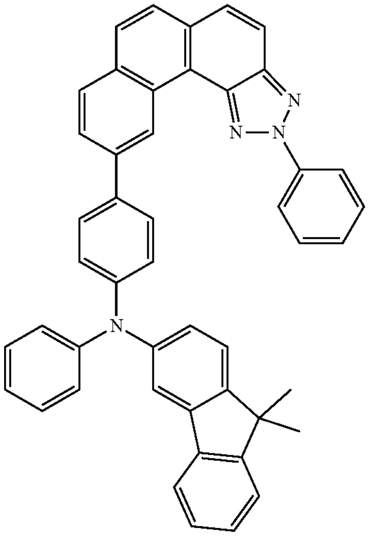

-continued
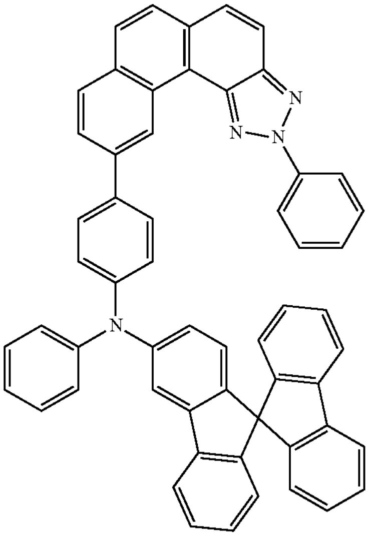
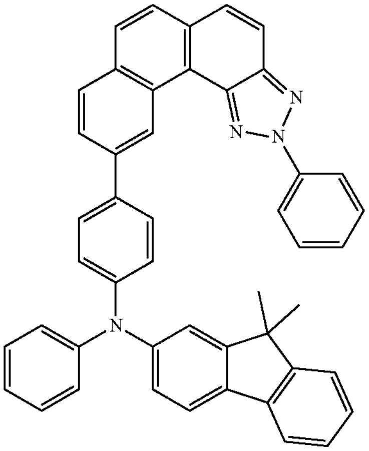
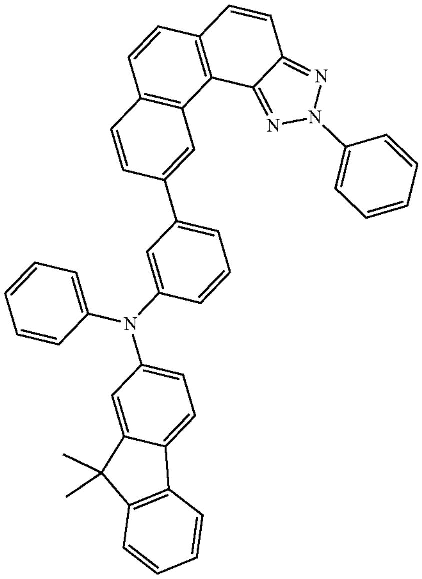
-continued
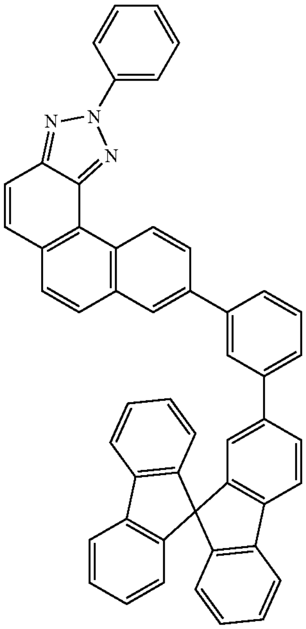
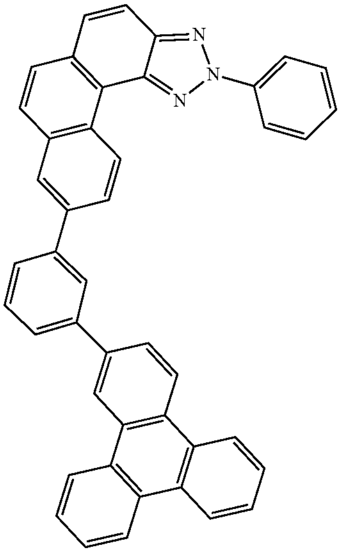

-continued
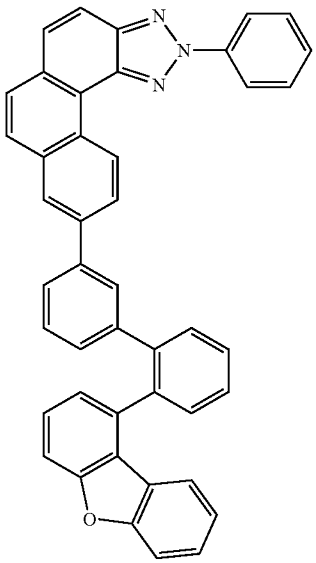
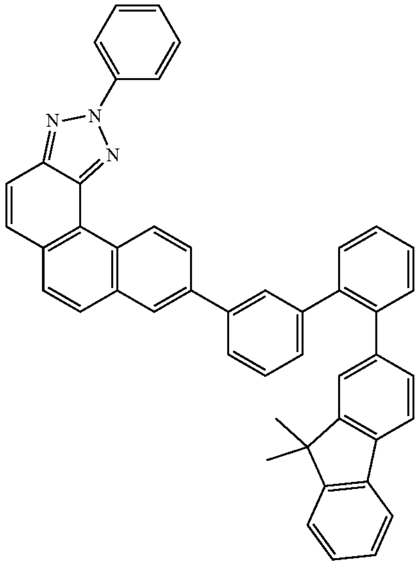
-continued
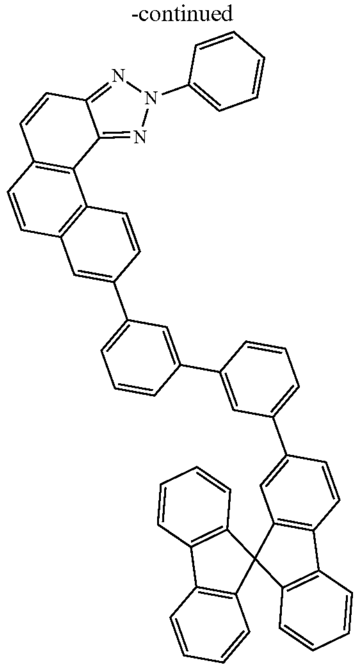
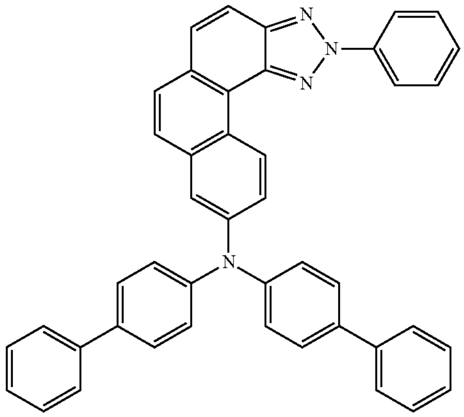
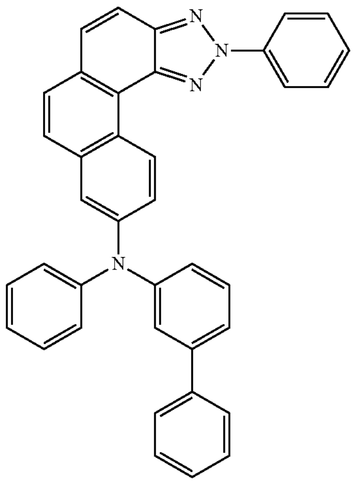

-continued
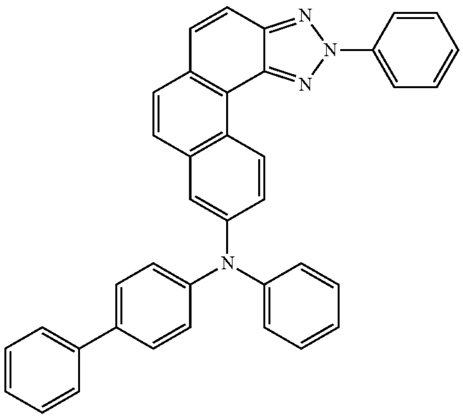
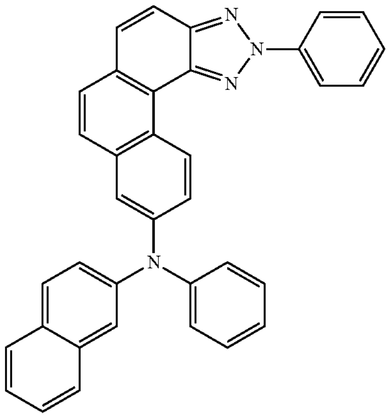
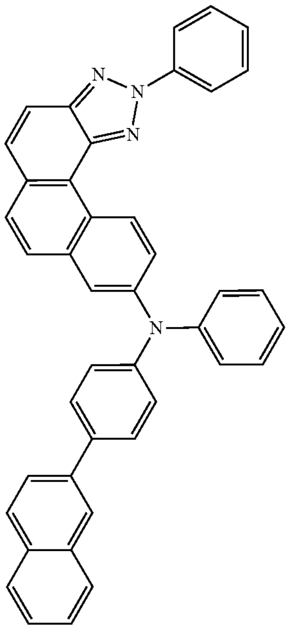
-continued
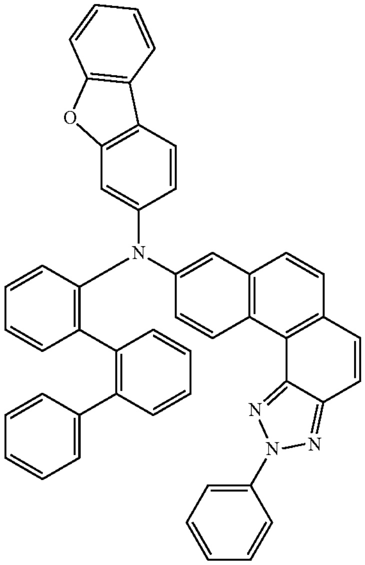
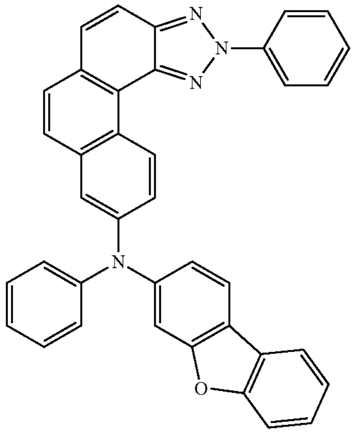
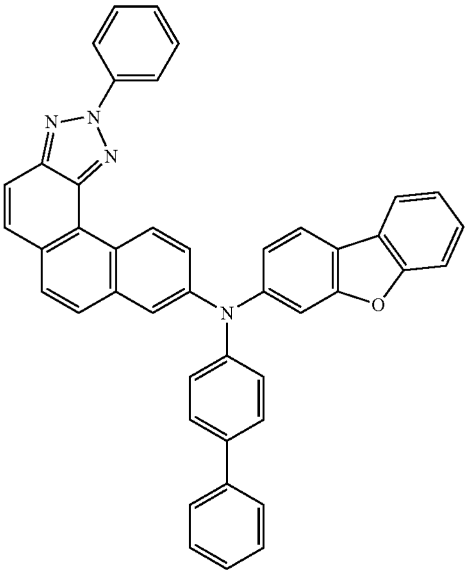

-continued
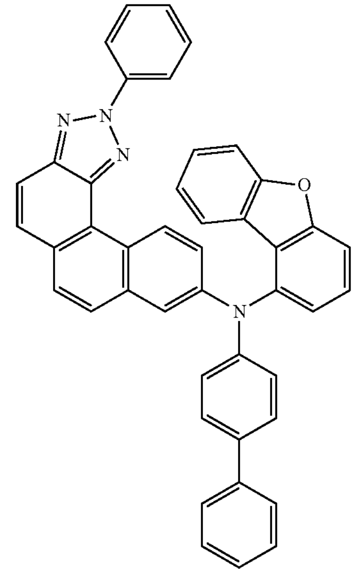
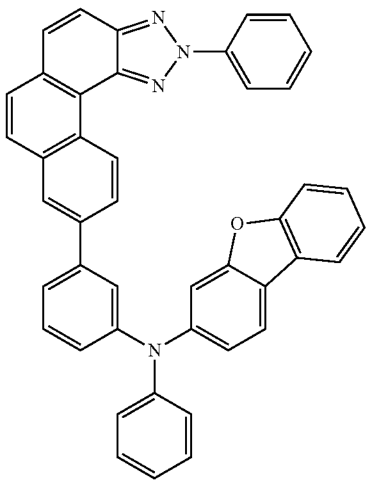
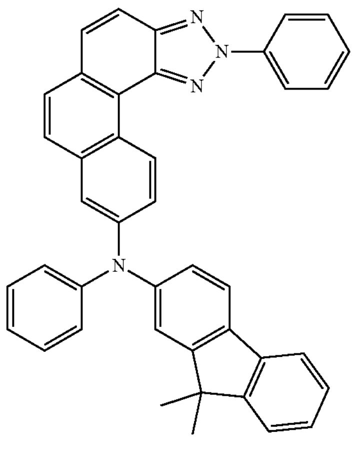
-continued
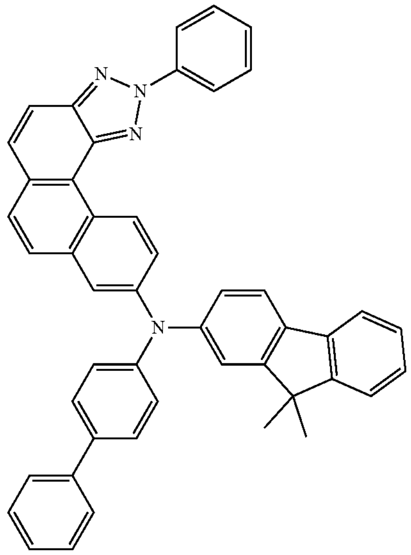
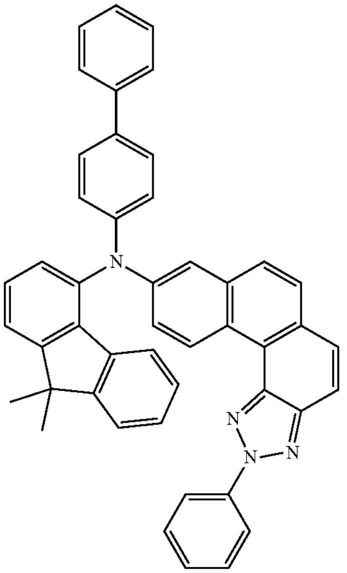
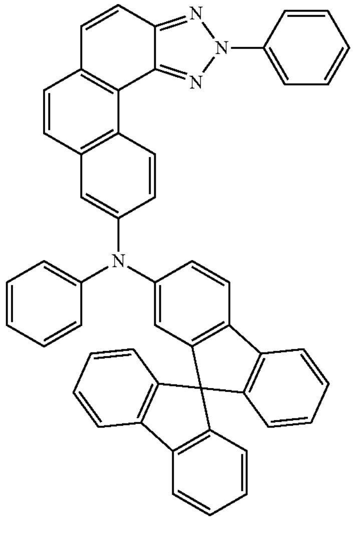

-continued
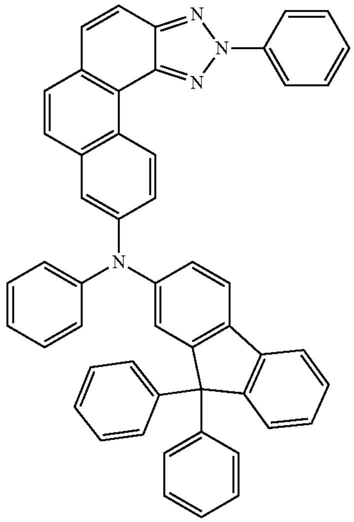
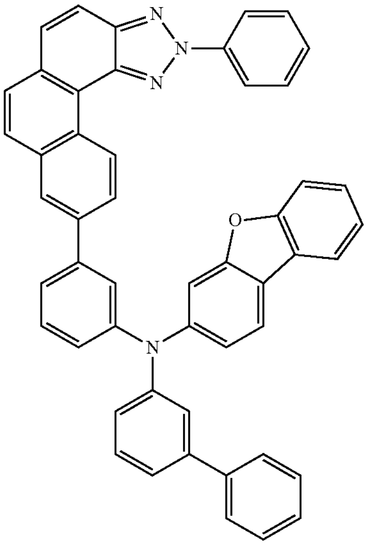
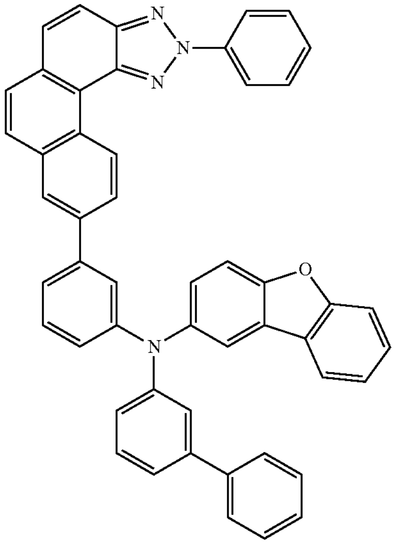
-continued
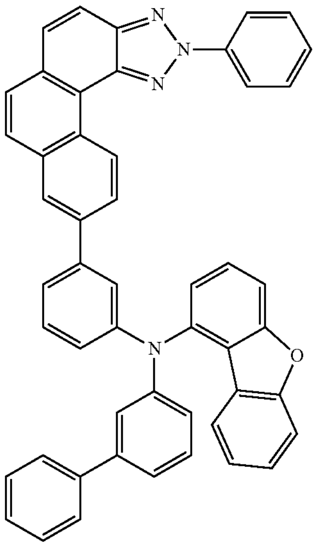
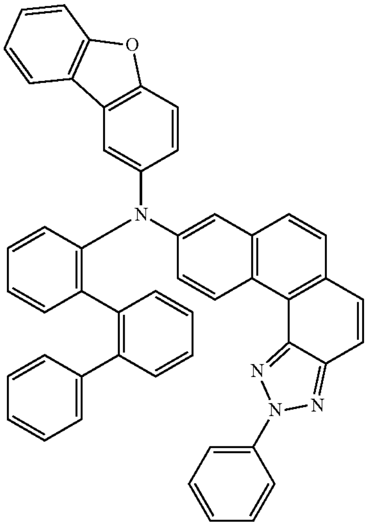
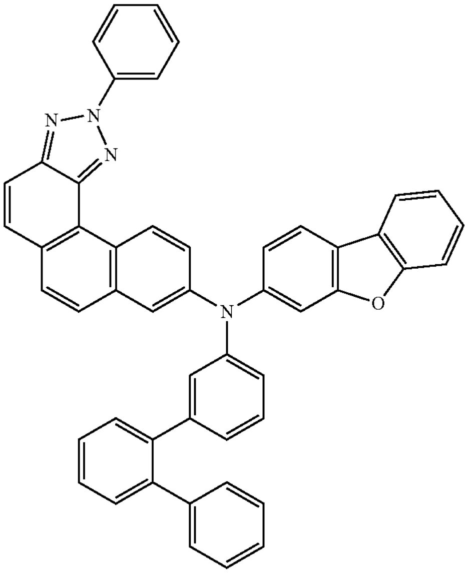

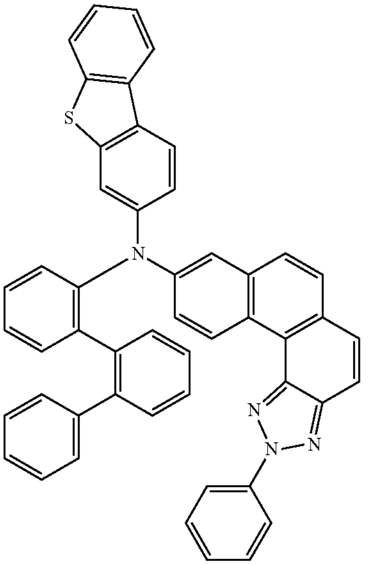
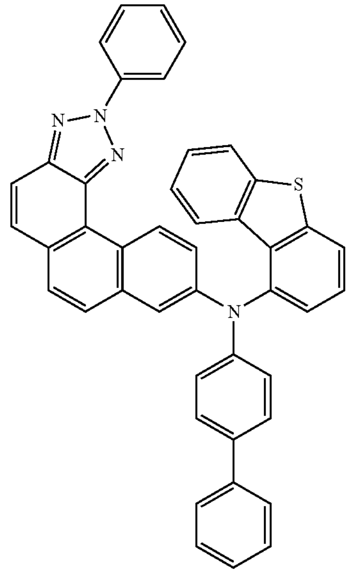
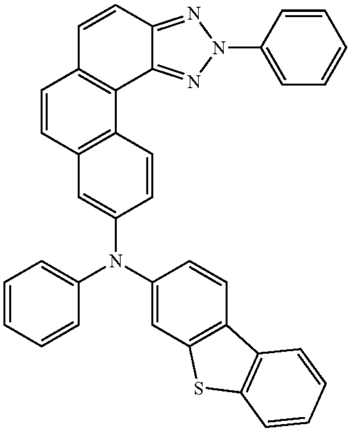
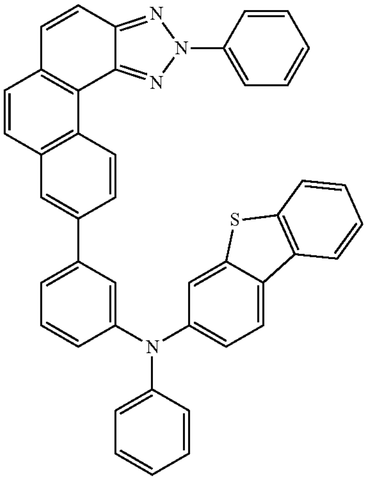
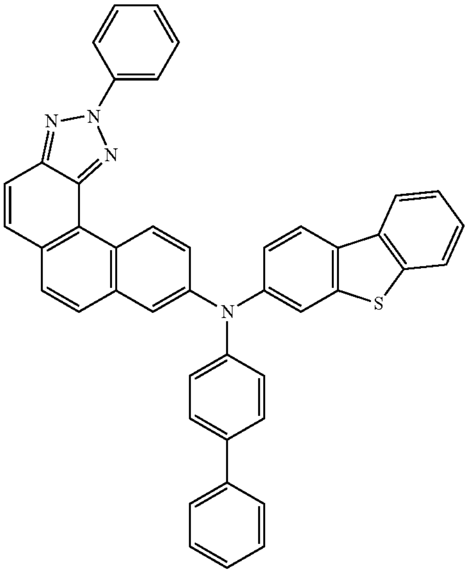
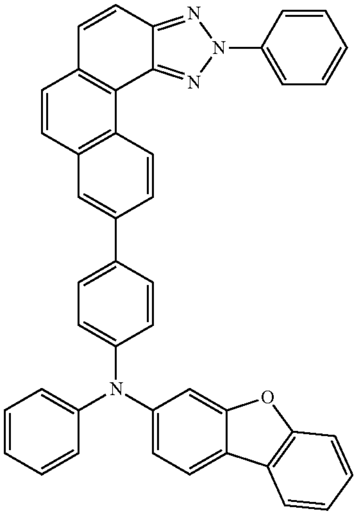

-continued
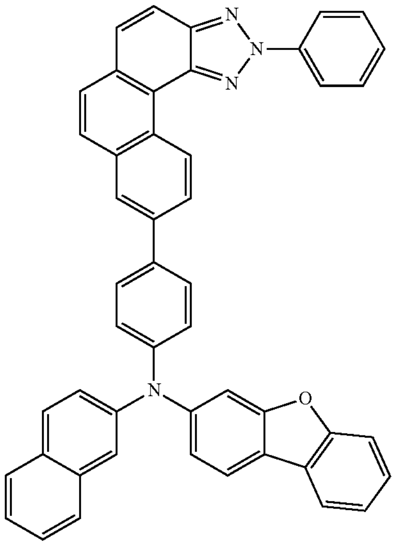
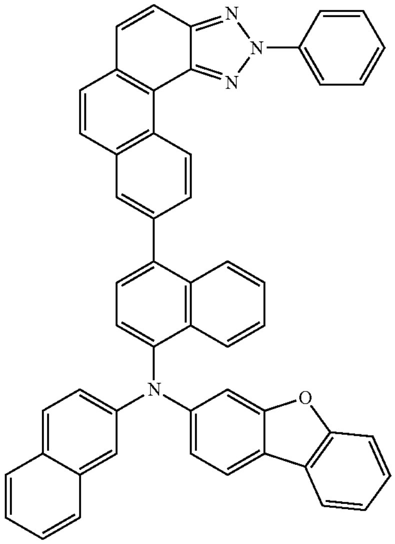
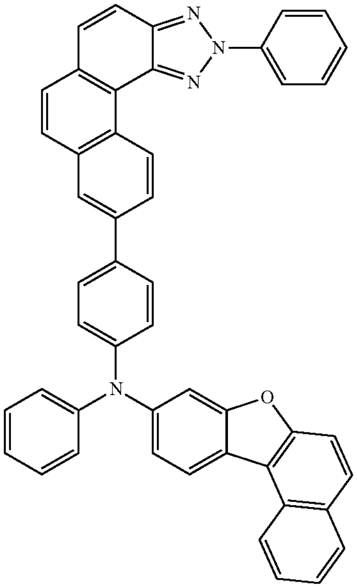
-continued
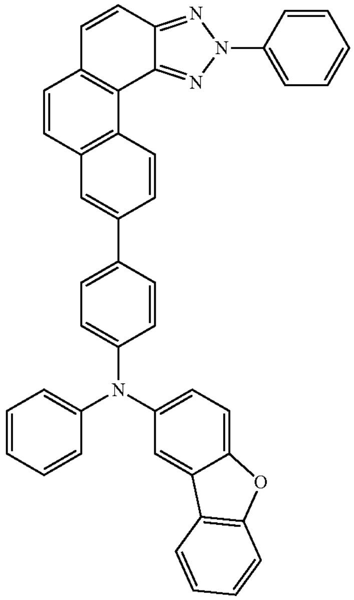
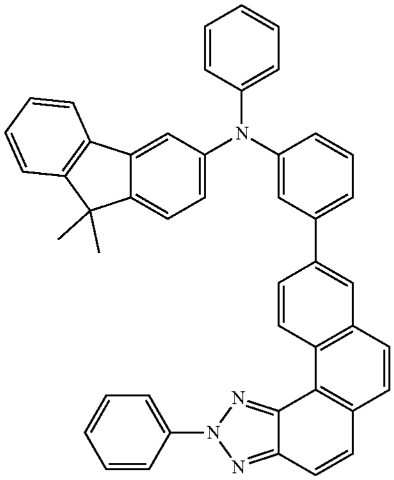
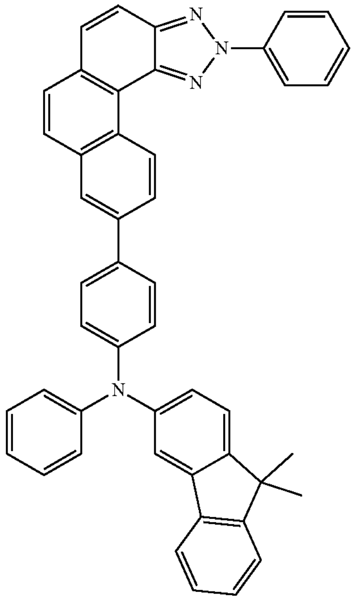

-continued

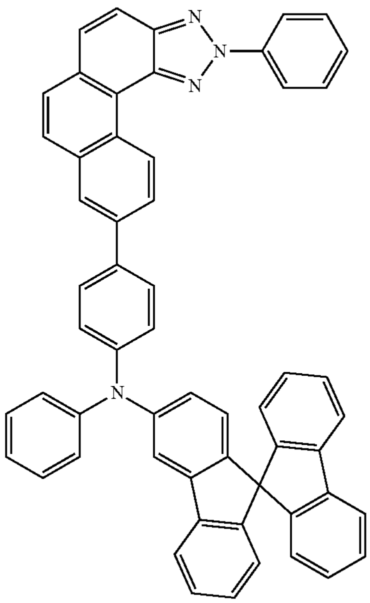

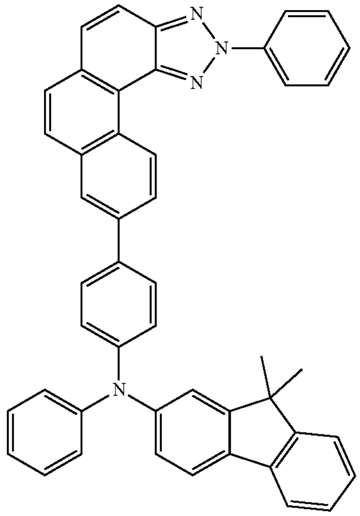

-continued

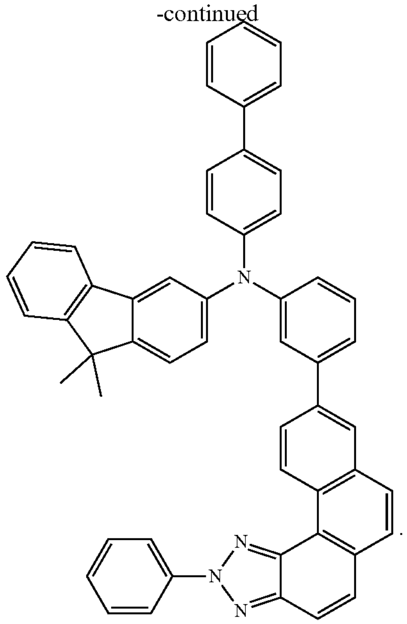

Preferably, in Formula 2, at least two of $Z^1$, $Z^2$, $Z^3$, $Z^4$, $Z^5$ and $Z^6$ are N.

Preferably, the compound having a structure represented by Formula 2 is the compound having a structure represented by Formula 2-1, wherein at least two of $Z^1$, $Z^3$ and $Z^5$ are N;

Formula 2-1

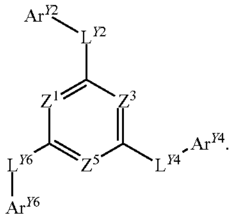

Preferably, $Z^1$ and $Z^3$ are N; $Z^5$ is $CL^{Y5}Ar^{Y5}$.

Preferably, $Z^1$ and $Z^5$ are N; $Z^3$ is $CL^{Y3}Ar^{Y3}$.

Preferably, $Z^3$ and $Z^5$ are N; $Z^1$ is $CL^{Y1}Ar^1$.

Preferably, $Z^1$, $Z^3$, and $Z^5$ are N.

Preferably, in Formula 2, $L^{Y5}Ar^{Y5}$ and $L^{Y6}Ar^{Y6}$ joined to form a substituted or unsubstituted benzene ring.

Preferably, the compound having a structure represented by Formula 2 is the compound having a structure represented by Formula 2-2, Formula 2-2

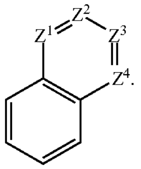

Preferably, $Z^1$ and $Z^4$ are N; $Z^2$ is $CL^{Y2}Ar^{Y2}$; $Z^3$ is $CL^{Y3}Ar^{Y3}$.

Preferably, $Z^1$ and $Z^3$ are N; $Z^2$ is $CL^{Y2}Ar^{Y2}$; $Z^4$ is $CL^{Y4}Ar^{Y4}$.

Preferably, $Ar^{Y1}$, $Ar^{Y2}$, $Ar^{Y3}$, $Ar^{Y4}$, $Ar^{Y5}$ and $Ar^{Y6}$ are each independently selected from hydrogen, deuterium, halogen, a cyano group, and a group selected from a phenyl group, a biphenylyl group, a terphenylyl group, a naphthyl group, a phenylnaphthyl group, a naphthylphenyl group, a triphenylenylene group, an anthryl group, a phenanthryl group, a chrysenyl group, each of which is substituted or unsubstituted; and a group represented by Formula 3:

Formula 3

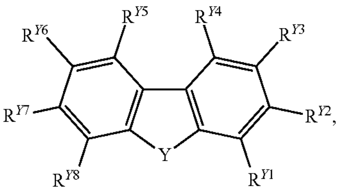

Y is selected from O, S, and $CR^{W1}R^{W2}$;

when at least one of $Ar^{Y1}$, $Ar^{Y2}$, $Ar^{Y3}$, $Ar^{Y4}$, $Ar^{Y5}$ and $Ar^{Y6}$ is Formula 3, any one of $R^{Y1}$ to $R^{Y8}$, $R^{W1}$ and $R^{W2}$ in Formula 3 is connected to $L^{Y2}$, $L^{Y4}$ or $L^{Y6}$ in Formula 2-1 by chemical bonding; or, any one of $R^{Y1}$ to $R^{Y8}$, $R^{W1}$ and $R^{W2}$ in Formula 3 is connected to $L^{Y2}$, $L^{Y3}$ or $L^{Y4}$ in Formula 2-2 by chemical bonding; or, any one of $R^{Y1}$ to $R^{Y8}$, $R^{W1}$ and $R^{W2}$ in Formula 3 is connected to $L^{Y1}$, $L^{Y2}$, $L^{Y3}$, $L^{Y4}$, $L^{Y5}$ or $L^{Y6}$ in Formula 2 by chemical bonding;

$Ar^{Y1}$, $Ar^{Y2}$, $Ar^{Y3}$, $Ar^{Y4}$, $Ar^{Y5}$ and $Ar^{Y6}$ are the same or different;

$R^{Y1}$ to $R^{Y8}$ are each independently selected from hydrogen, deuterium, halogen, a cyano group, a substituted or unsubstituted C1-C30 alkyl group, a C1-C30 alkyl group in which one or more methylene groups are independently substituted by —O— and/or —S— in a manner that O atom and/or S atom are not adjacent to each other, a substituted or unsubstituted C7-C30 arylalkyl group, a substituted or unsubstituted C6-C30 aryl group, a substituted or unsubstituted C3-C30 heteroaryl group, a substituted or unsubstituted C4-C30 heteroarylalkyl group, a substituted or unsubstituted C3-C30 cycloalkyl group, a substituted or unsubstituted C3-C30 heterocycloalkyl group, a substituted or unsubstituted C3-C30 cycloalkenyl group, a substituted or unsubstituted C1-C30 alkoxy group, and a substituted or unsubstituted C6-C30 aryloxy group;

$R^{Y1}$ to $R^{Y8}$ are present individually without forming a ring, or any adjacent two of $R^{Y1}$ to $R^{Y8}$ joined to form a ring A, and the ring A is a substituted or unsubstituted C6-C30 aromatic ring;

$R^{W1}$ and $R^{W2}$ are selected from a substituted or unsubstituted C1-C30 alkyl group, and a substituted or unsubstituted C6-C30 aryl group.

Preferably, the ring A is a substituted or unsubstituted benzene ring.

Preferably, the group represented by Formula 3 is any one selected from the following groups:

3-1

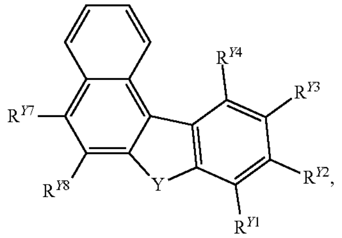

3-2

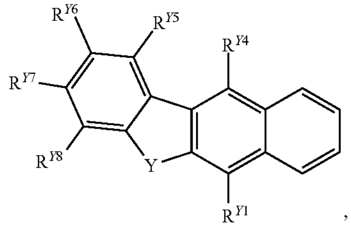

, 3-3

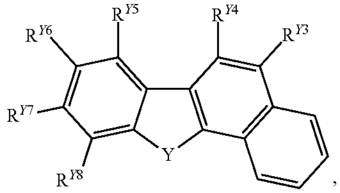

, 3-4

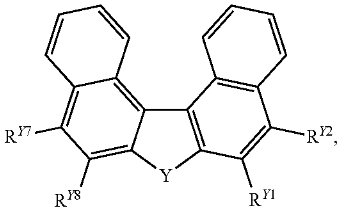

3-5

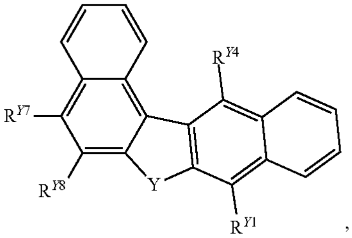

, and 3-6

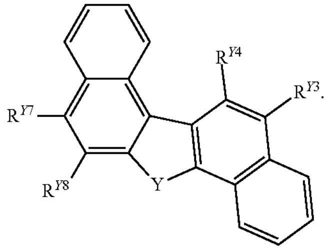

Preferably, $R^{W1}$ and $R^{W2}$ are each independently selected from a methyl group and a phenyl group; or $R^{W1}$ and $R^{W2}$ joined to form a spiro ring; the spiro ring is a fluorene ring.

Preferably, $R^{Y1}$-$R^{Y8}$ are each independently selected from hydrogen, deuterium, a phenyl group, a biphenylyl group, a terphenylyl group, a naphthyl group, a phenylnaphthyl group, a naphthylphenyl group, an anthryl group, a phenanthryl group, a benzophenanthryl group, a pyridyl group, a dibenzofuryl group, a dibenzothiophenyl group, a dibenzofurylphenyl group, a dibenzothiophenylphenyl group, a dimethylfluorenyl group, a diphenylfluorenyl group, a spiro-bifluorenyl group, a benzonaphthofuryl group, and a benzonaphthothiophenyl group, each of which is substituted or unsubstituted; $R^{Y1}$ to $R^{Y8}$ are present individually without forming a ring, or any adjacent two of $R^{Y1}$ to $R^{Y8}$ joined to form a ring A, and the ring A is a substituted or unsubstituted benzene ring.

Preferably, $L^{Y1}$, $L^{Y2}$, $L^{Y3}$, $L^{Y4}$, $L^{Y5}$ and $L^{Y6}$ are each independently selected from a bond, a phenylene group, a biphenylene group, and a naphthylene group.

Preferably, the group represented by Formula 3 is selected from the following groups:

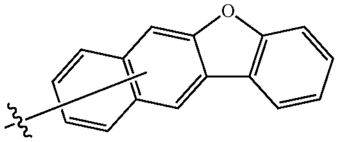

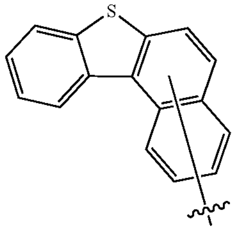

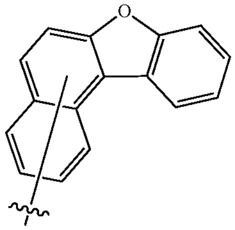

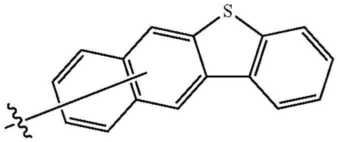

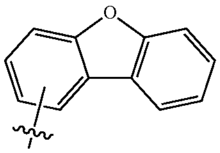

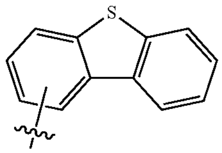

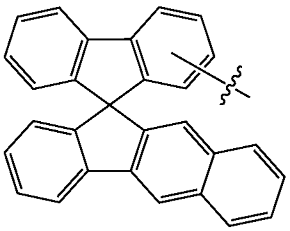

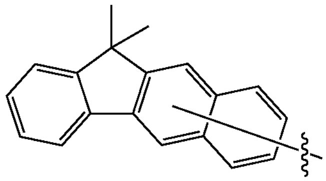

-continued

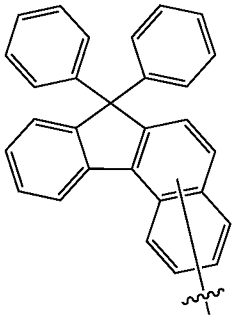

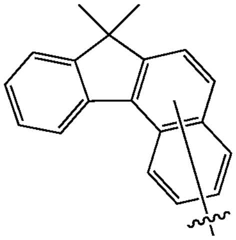

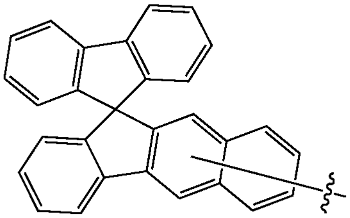

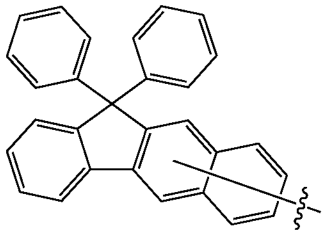

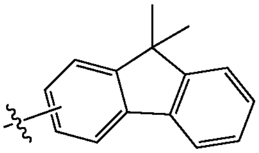

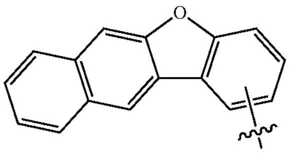

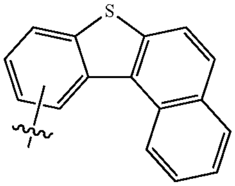

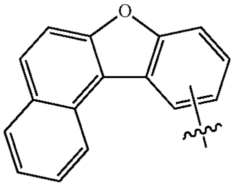

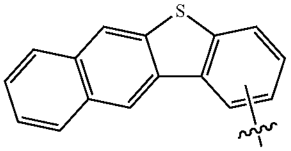

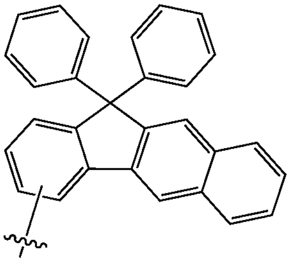

-continued

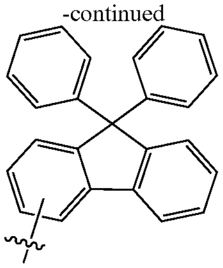

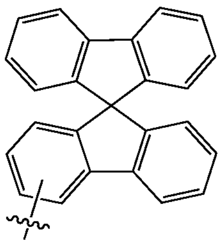

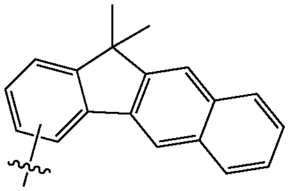

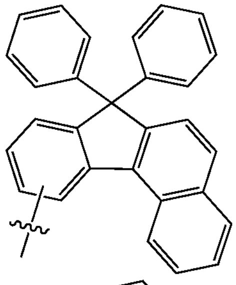

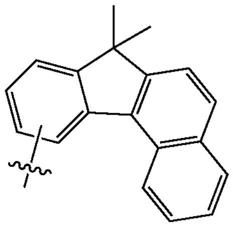

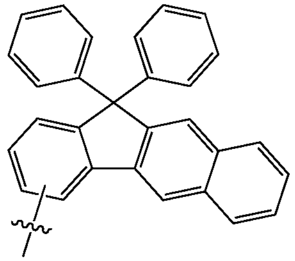

, each of which is substituted or unsubstituted.

In the present invention, preferably, when the above-mentioned group has one or more substituents, the substituents are each independently selected from deuterium, halogen, a cyano group, a nitro group, an unsubstituted or R'-substituted C1-C4 straight or branched alkyl group, an unsubstituted or R'-substituted C6-C20 aryl group, an unsubstituted or R'-substituted C3-C20 heteroaryl group, and an unsubstituted or R'-substituted C6-C20 arylamino group; R' is selected from deuterium, halogen, a cyano group and a nitro group.

Preferably, the aryl group is selected from a phenyl group, a biphenylyl group, a terphenylyl group, a naphthyl group, an anthryl group, a phenanthryl group, a benzophenanthryl group, a naphthylphenyl group, a dimethylfluorenyl group, a diphenylfluorenyl group and a spiro-bifluorenyl group.

Preferably, the heteroaryl group is selected from a pyridyl group, a dibenzofuryl group, a dibenzothiophenyl group, a carbazolyl group, a phenylcarbazolyl group, a pyridylcarbazolyl group, a naphthylcarbazolyl group, a biphenylylcarbazolyl group, a dibenzofurylphenyl group, a dibenzothiophenylphenyl group, a benzonaphthofuryl group, a benzonaphthothiophenyl group, a benzocarbazolyl group and a dibenzocarbazolyl group.

Preferably, the alkyl group is selected from a methyl group, an ethyl group, a propyl group, a tert-butyl group, a cyclohexyl group and adamantyl.

Preferably, the compound having a structure represented by Formula 2 is selected from the compounds shown as below:

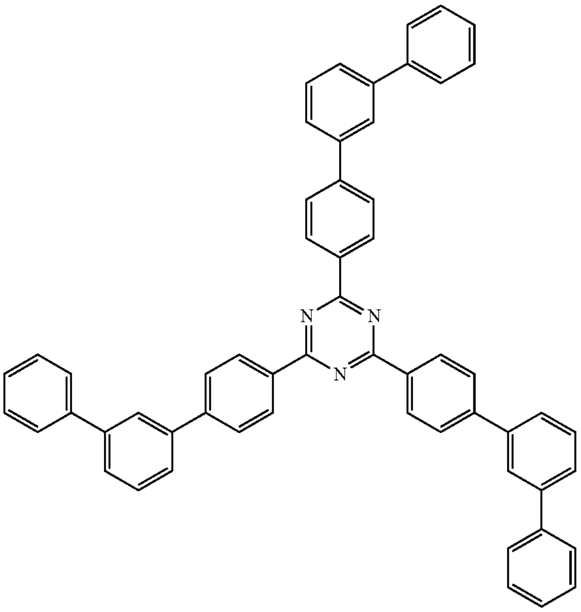

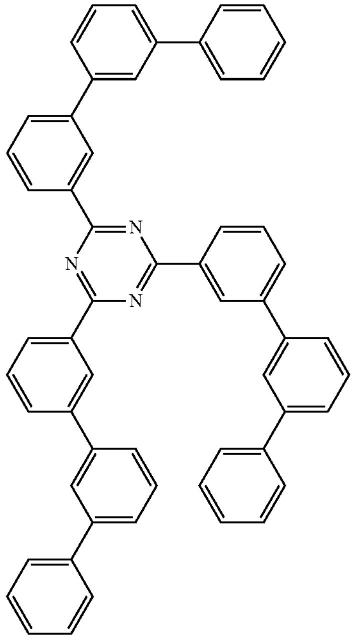

-continued
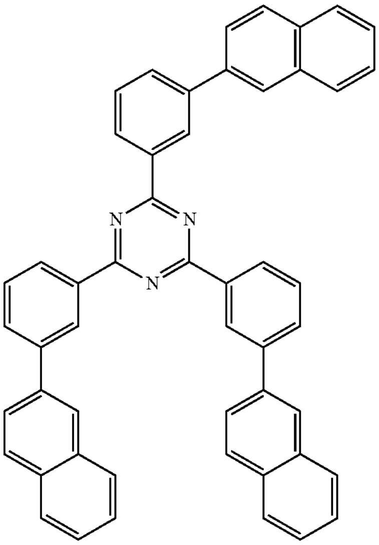
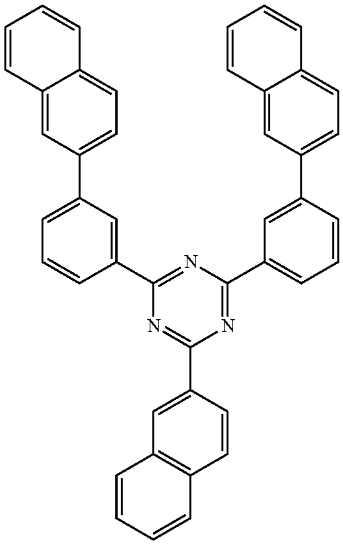
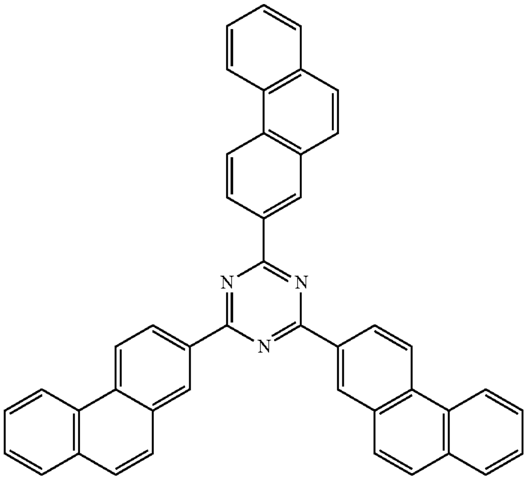
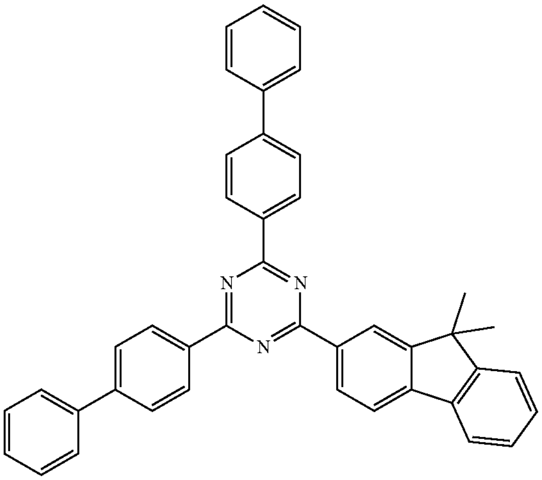
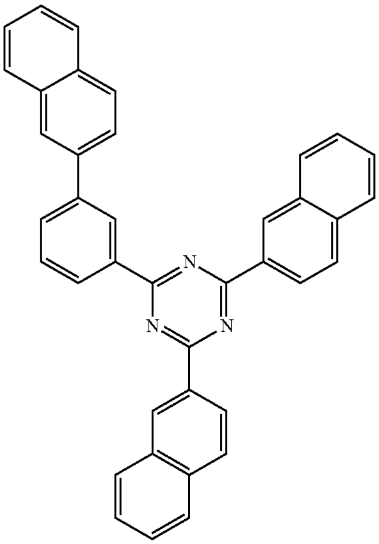
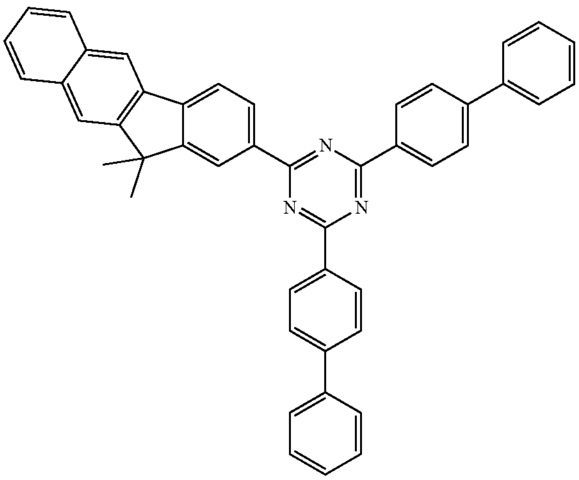
-continued -continued
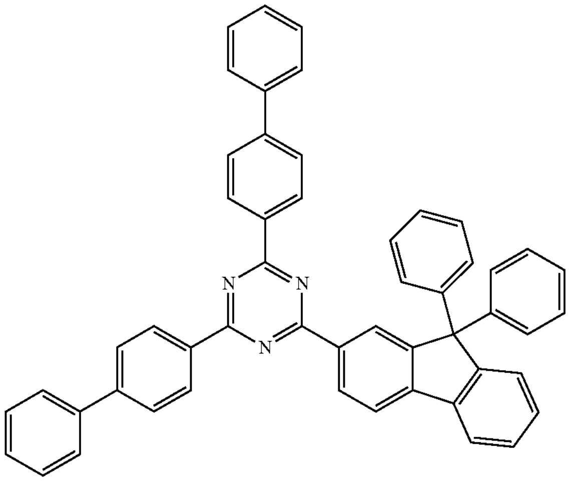
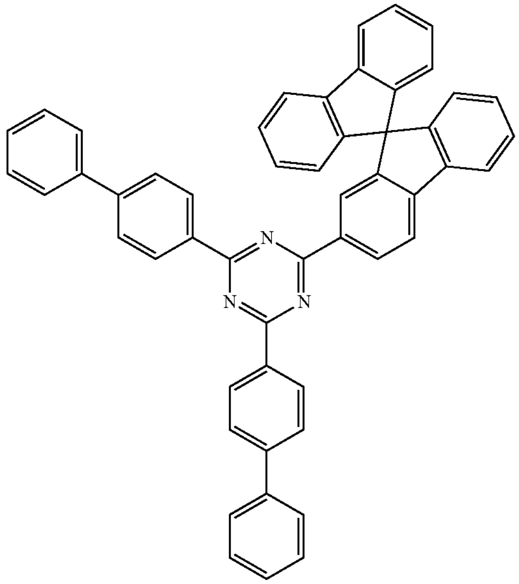
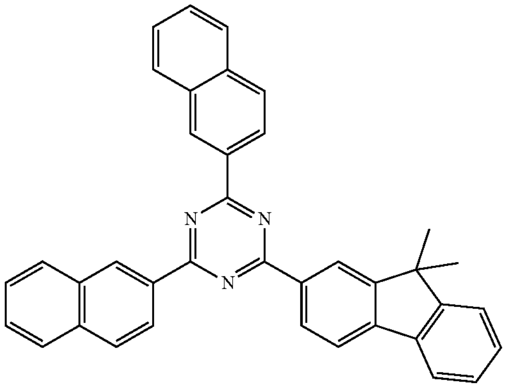
-continued
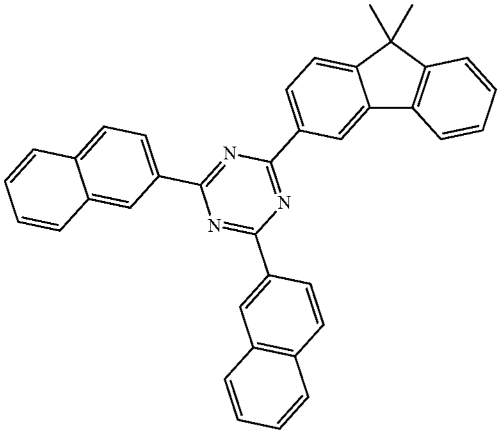
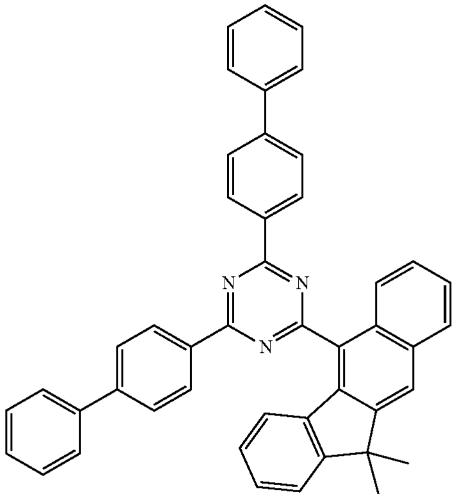
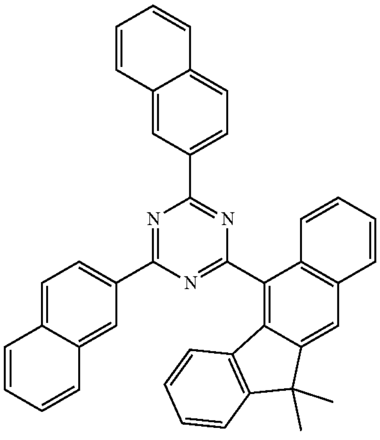

-continued
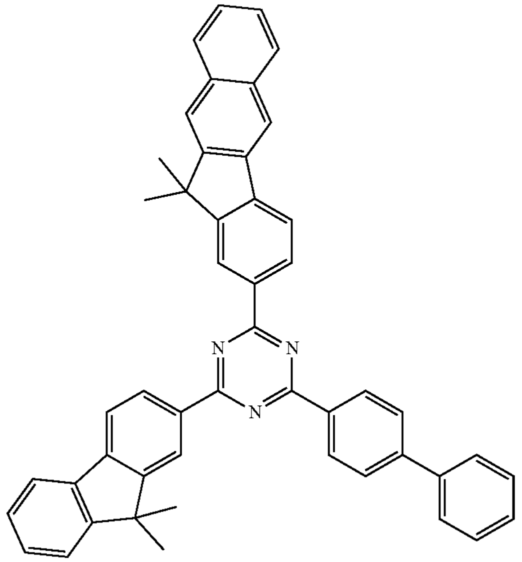
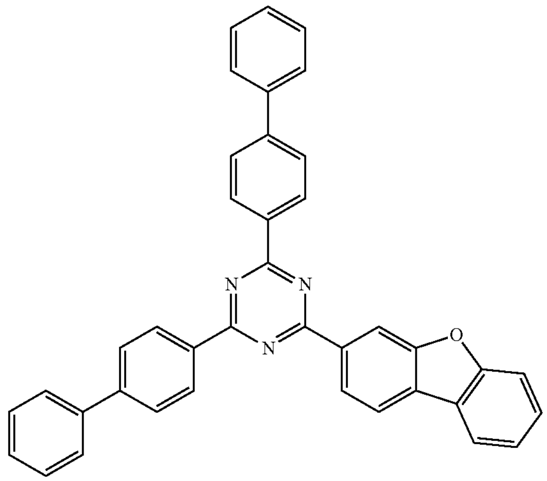
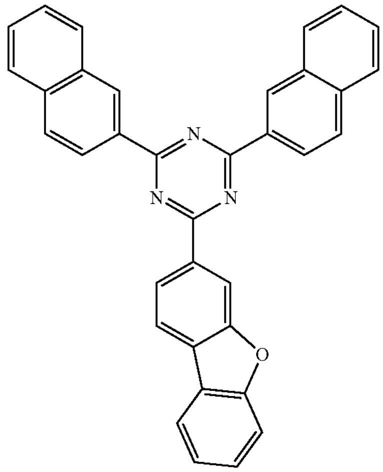
-continued
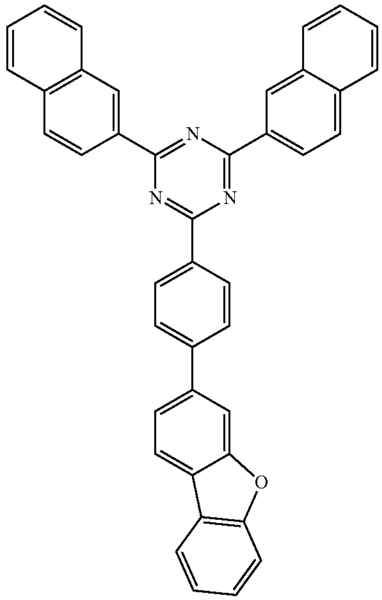
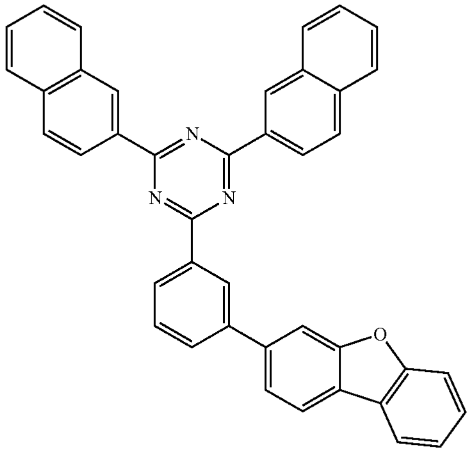
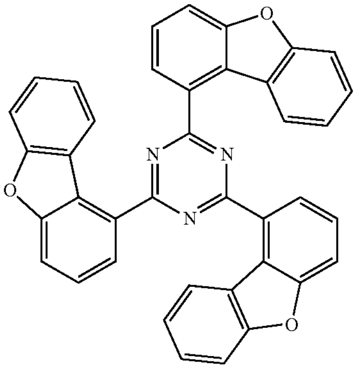

-continued
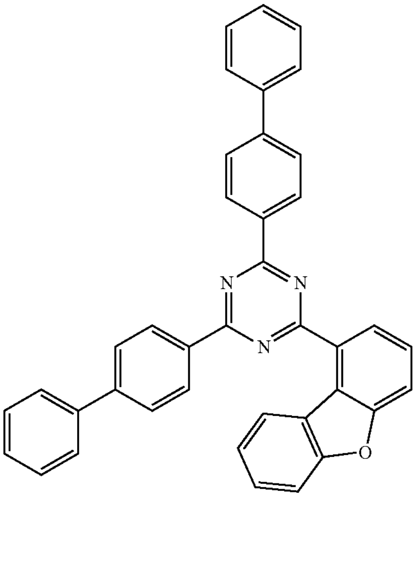
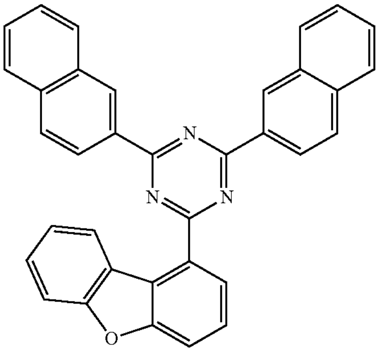
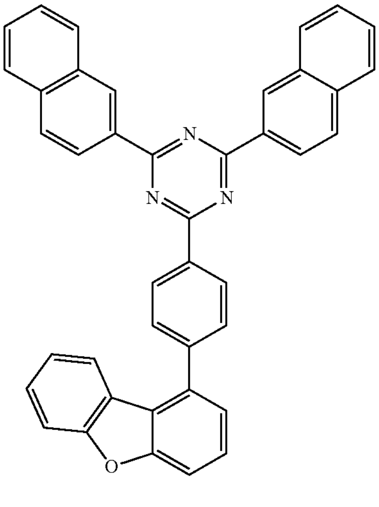
-continued
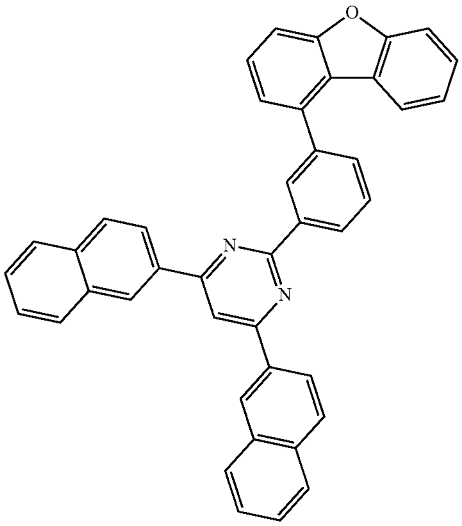
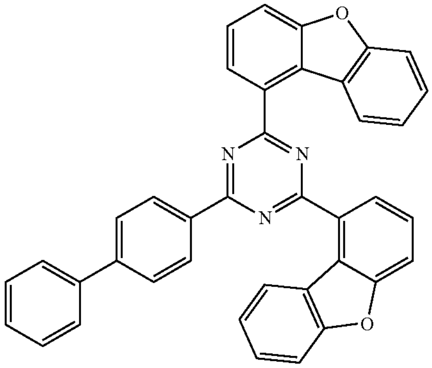
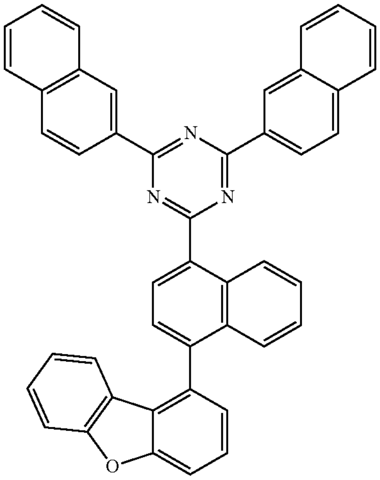

-continued
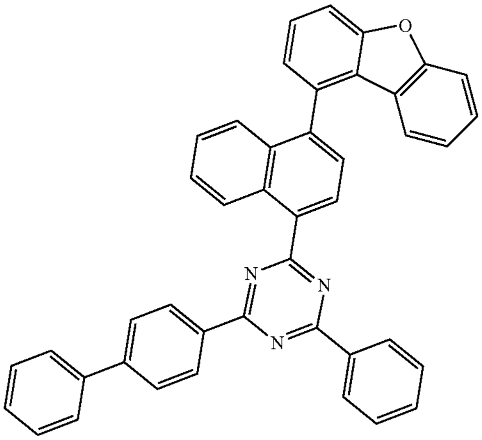
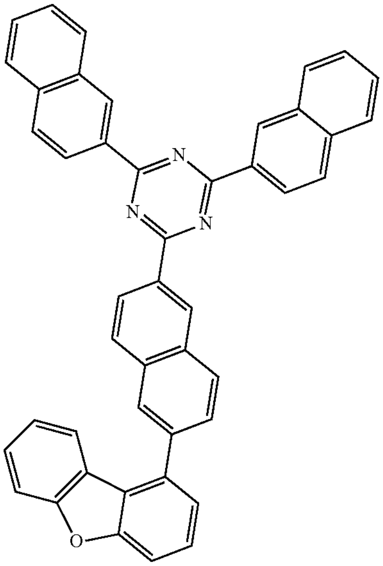
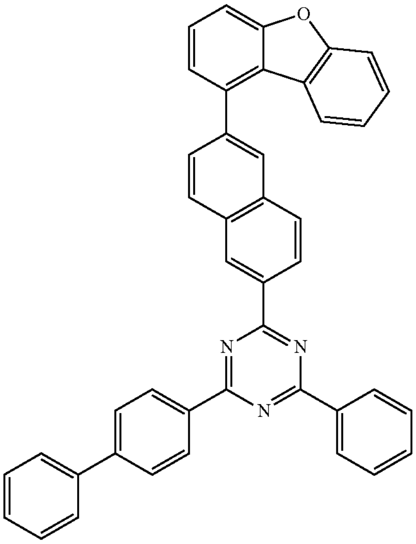
-continued
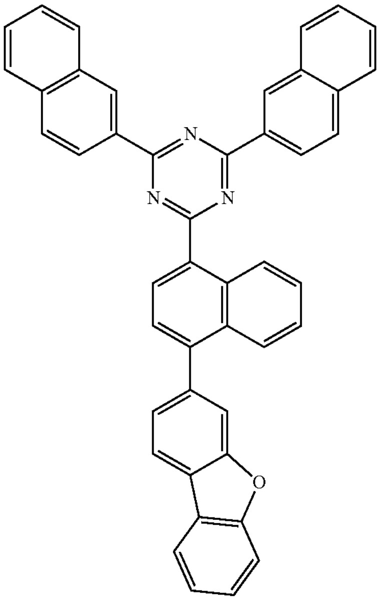
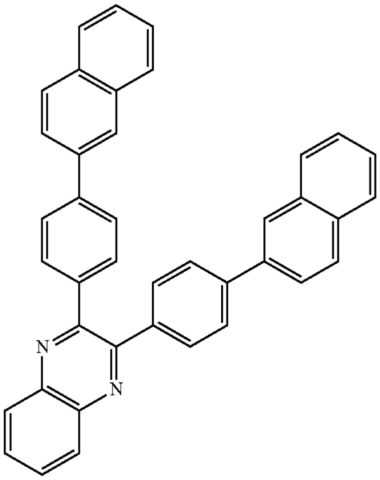
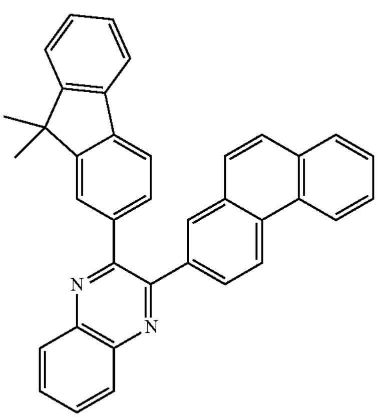

-continued
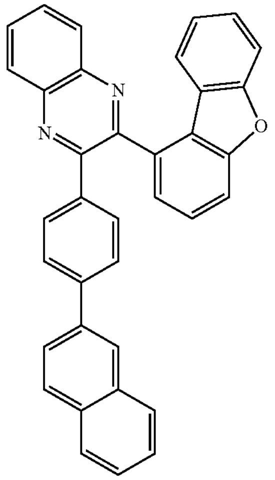
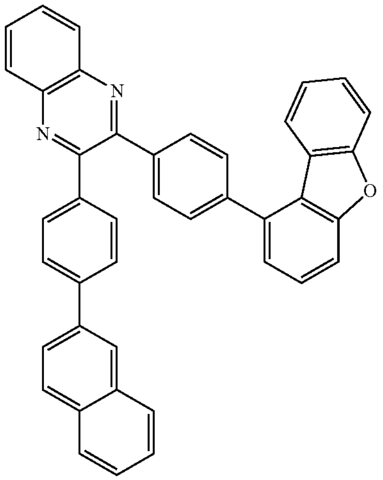
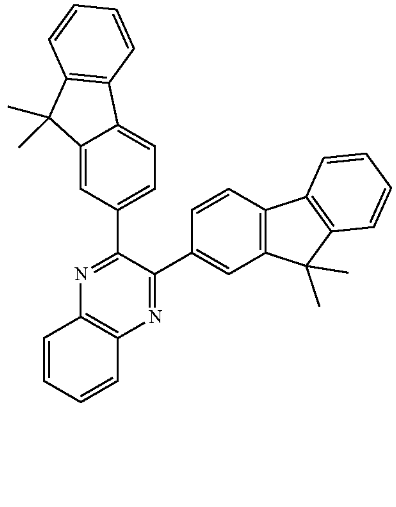
-continued
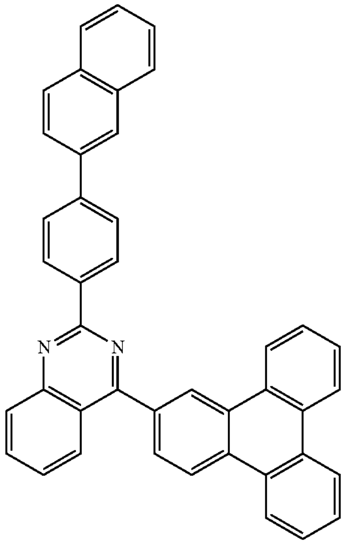
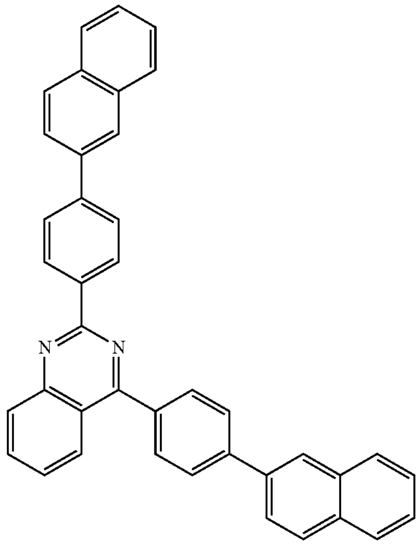
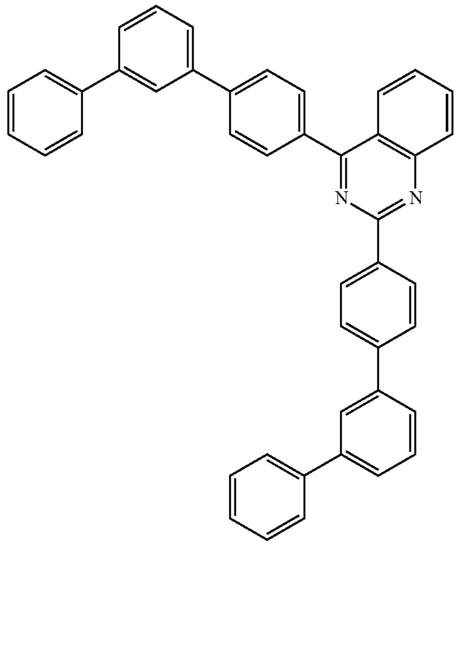

-continued
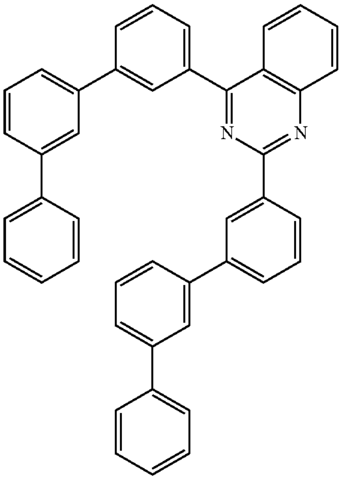
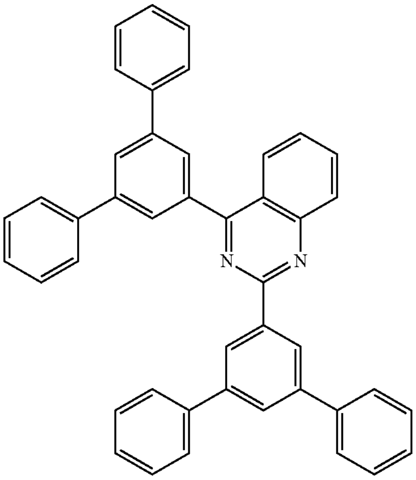
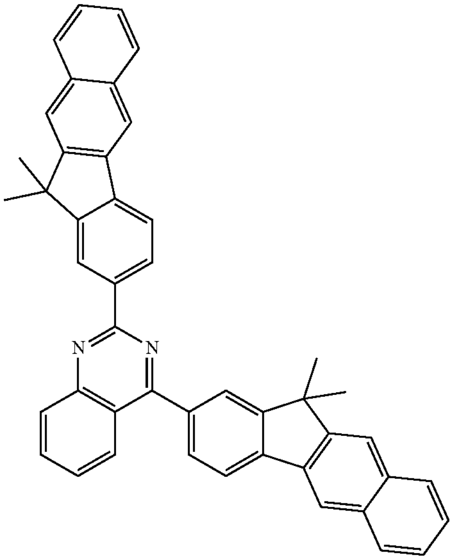
-continued
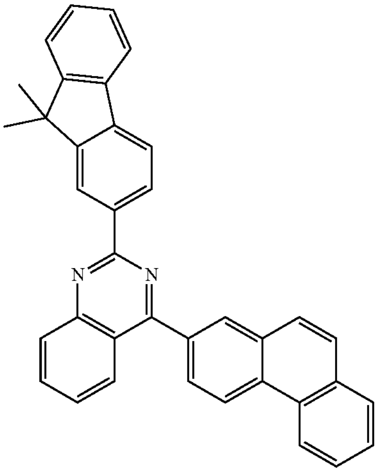
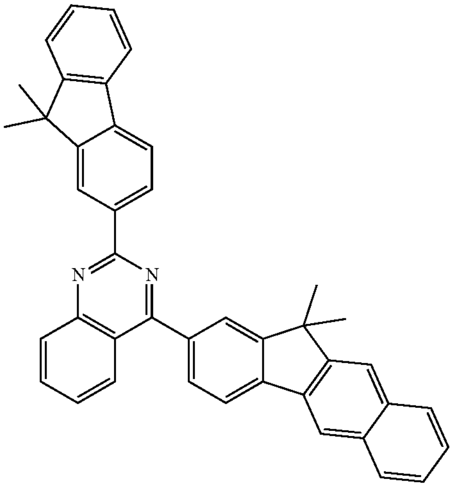
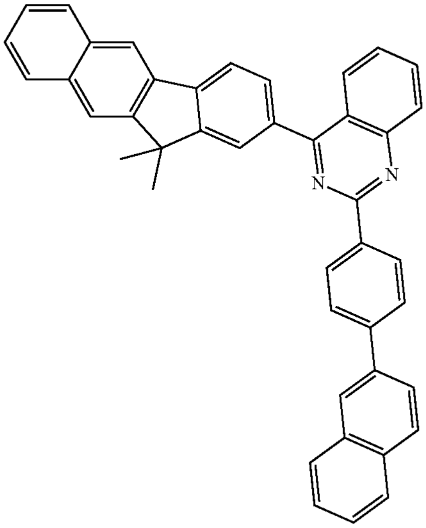

-continued
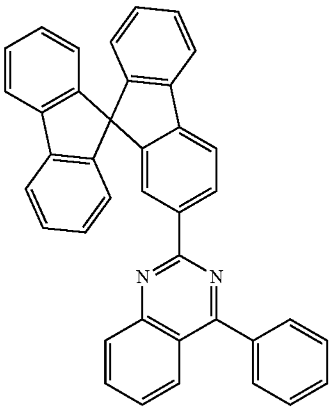
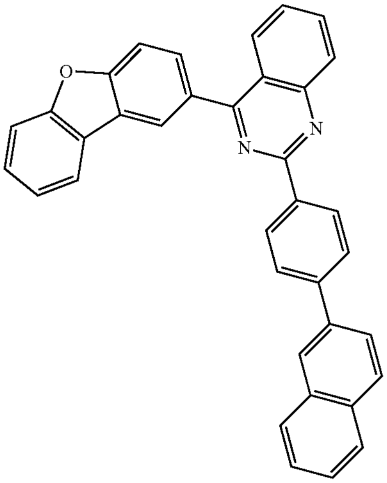
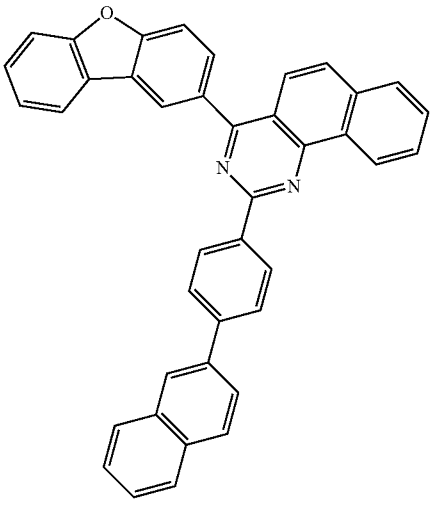
-continued
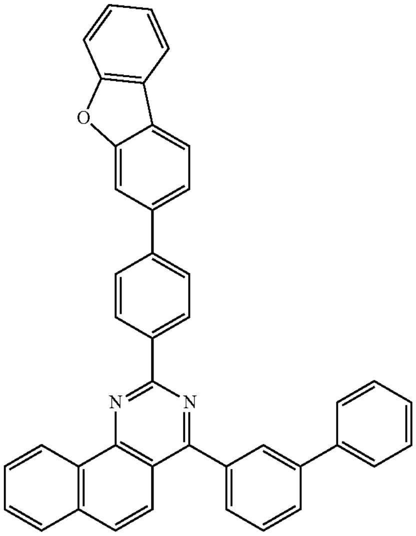
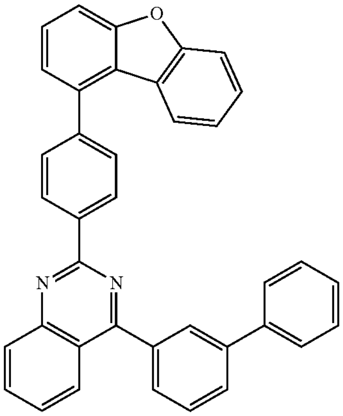
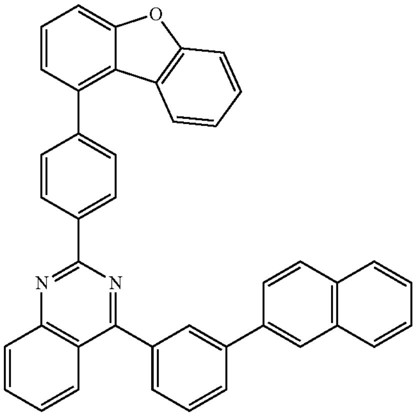

-continued
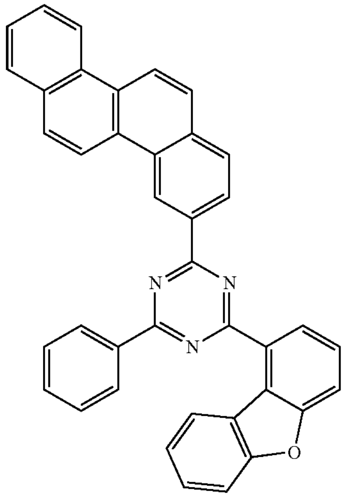
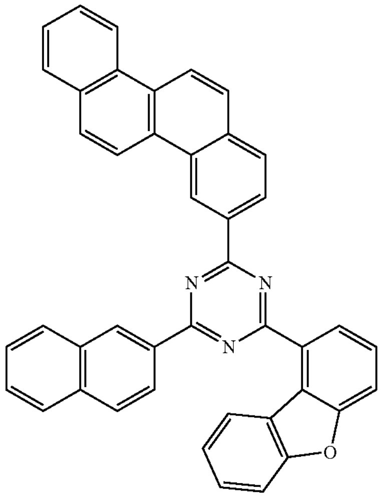
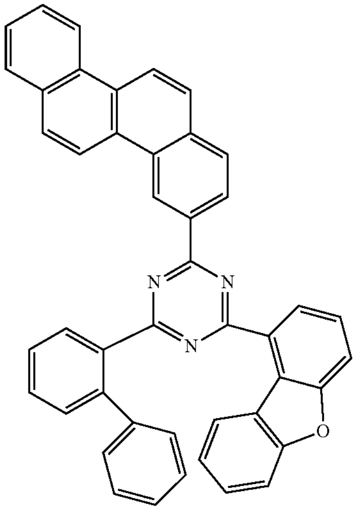
-continued
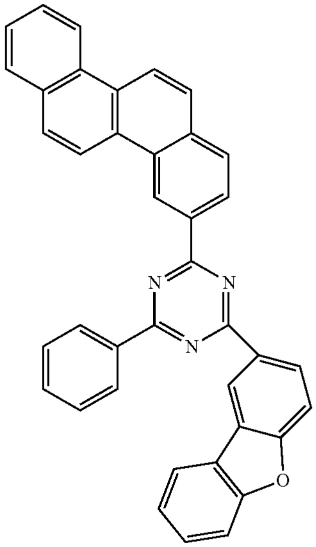
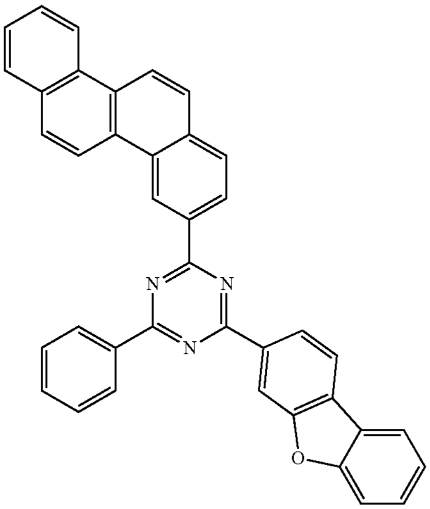
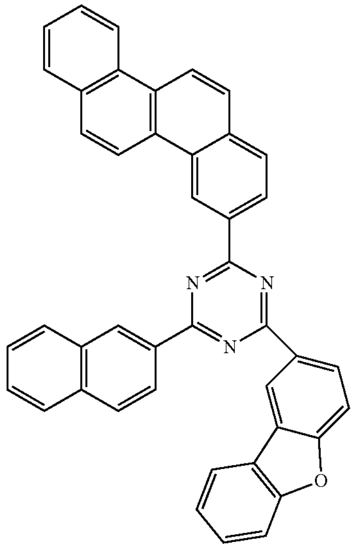

-continued
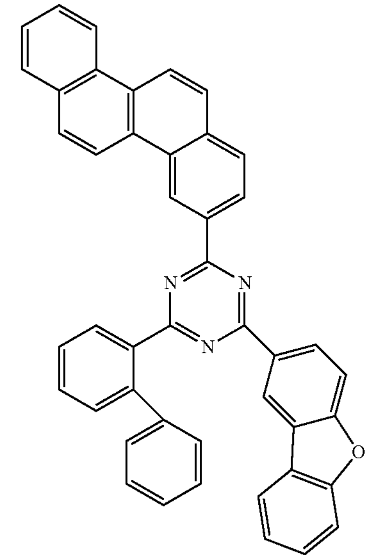
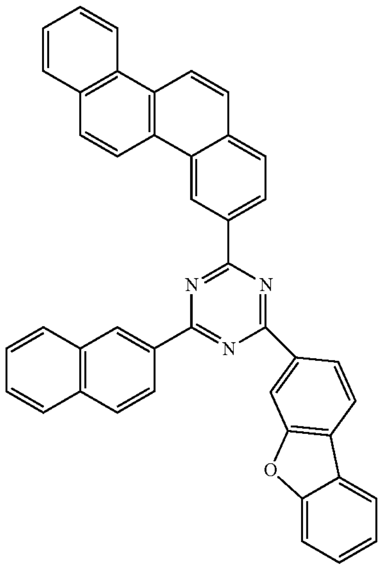
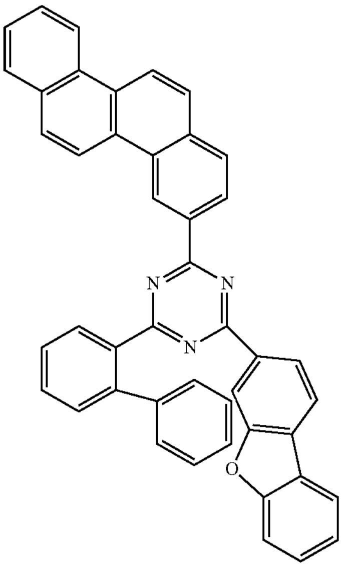
-continued
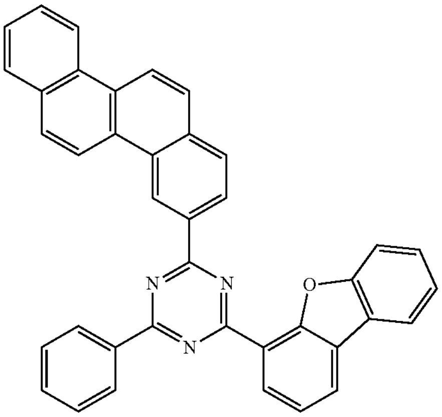
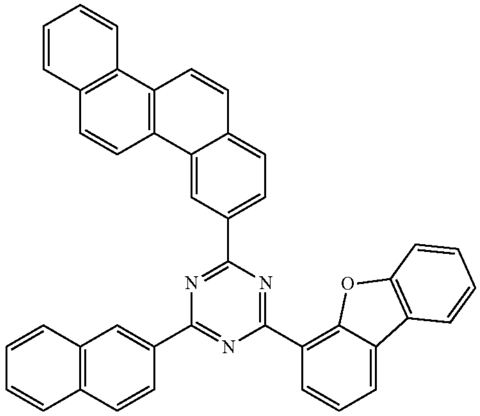
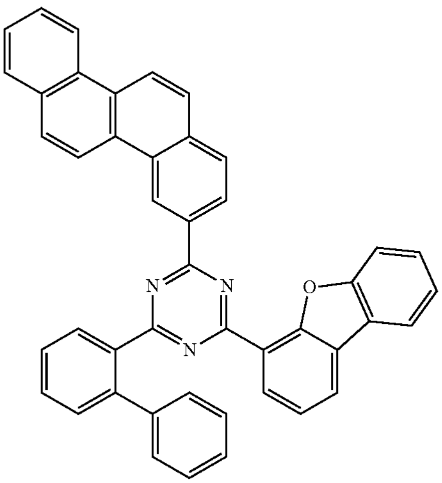

-continued
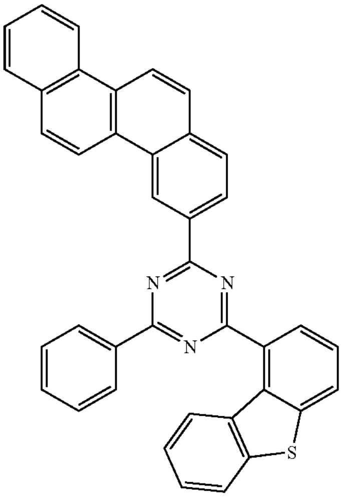
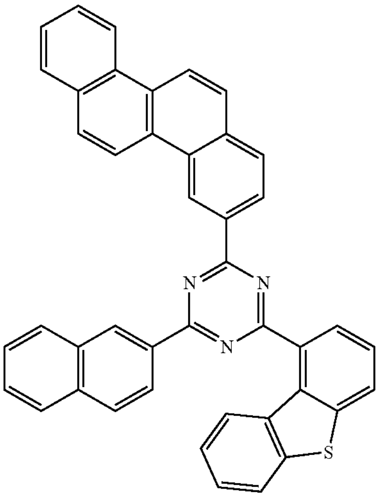
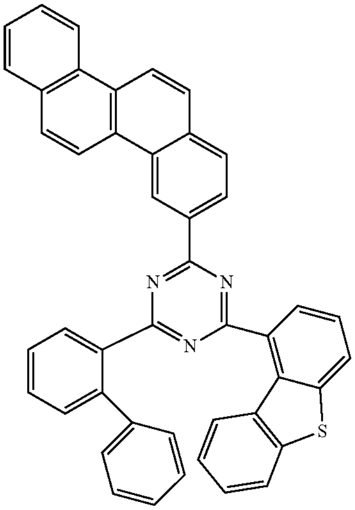
-continued
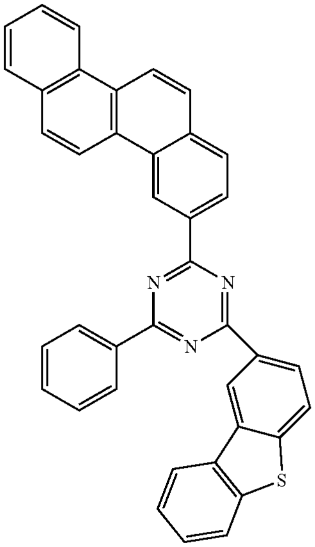
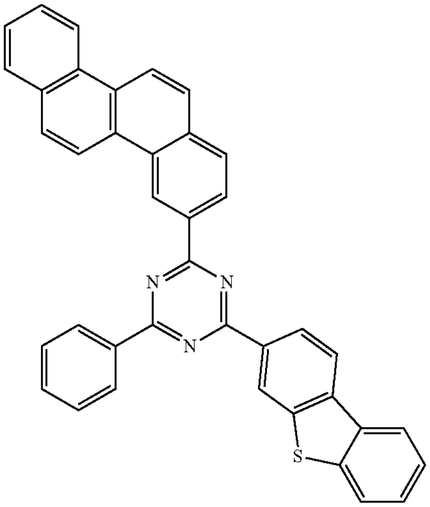
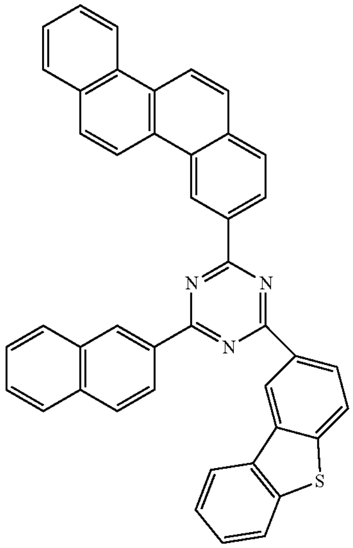

-continued
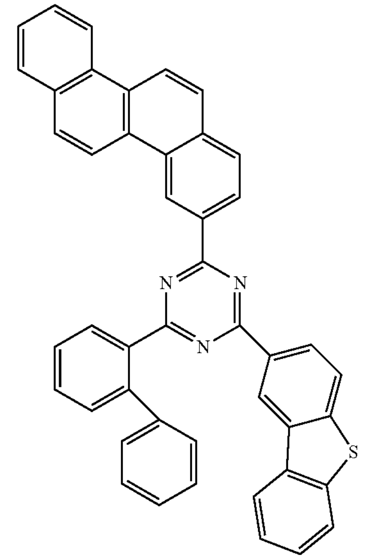
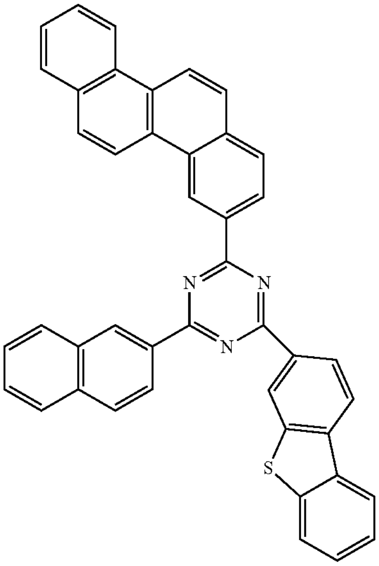
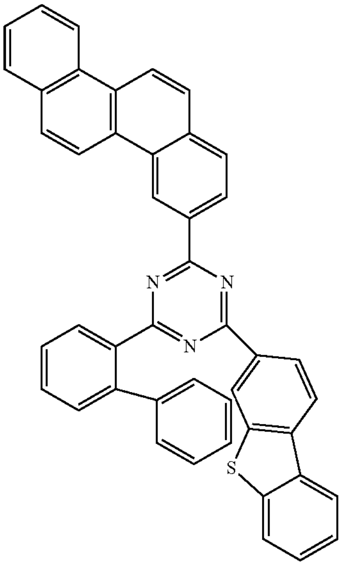
-continued
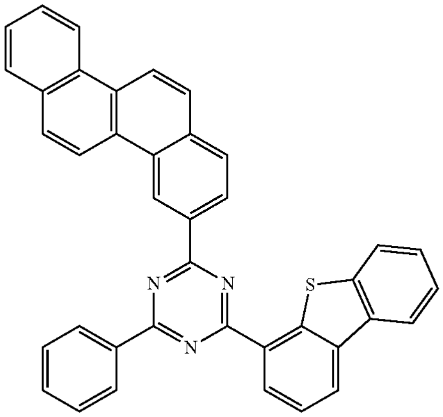
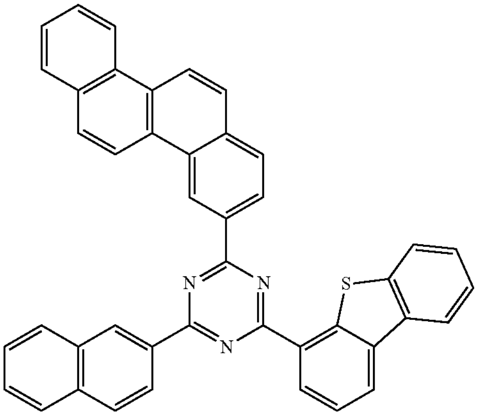
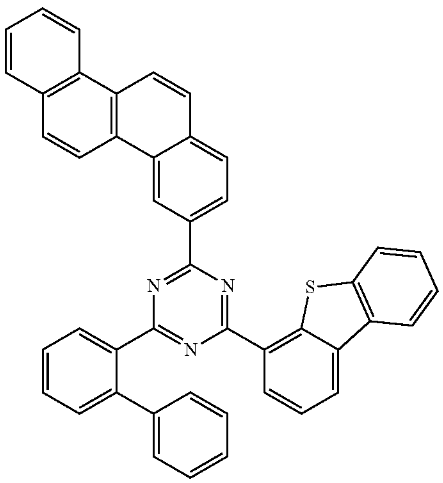

-continued
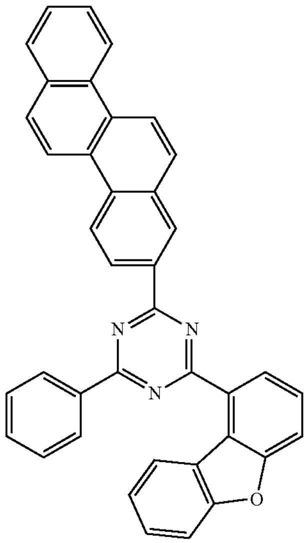
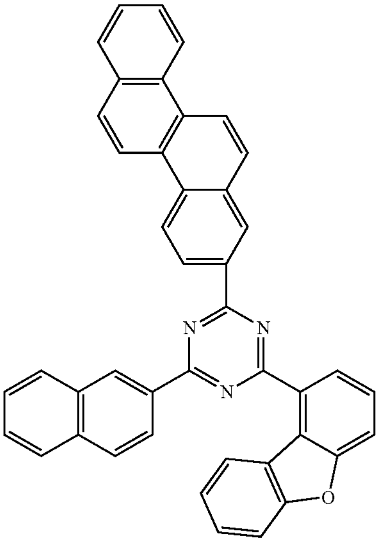
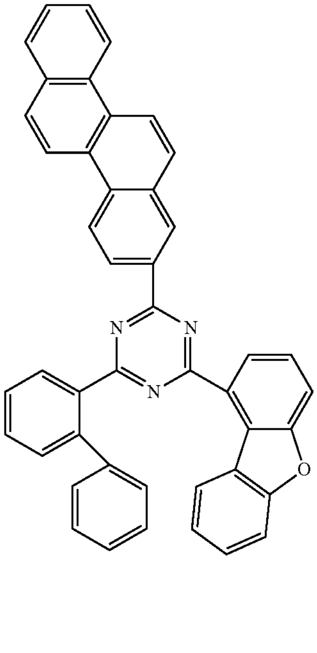
-continued
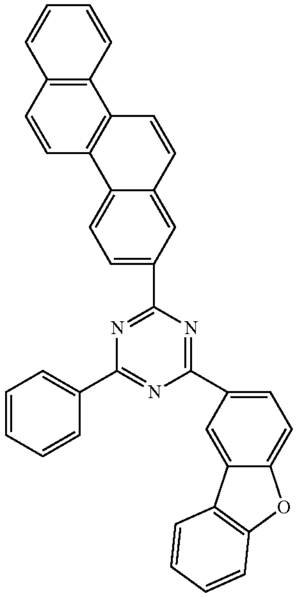
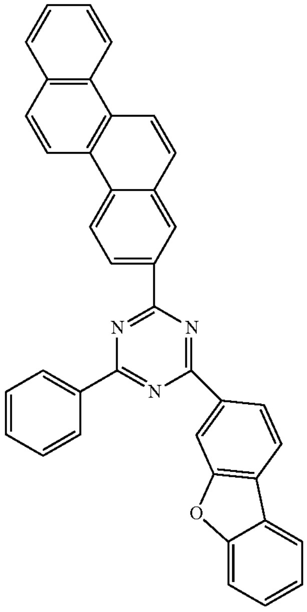

-continued
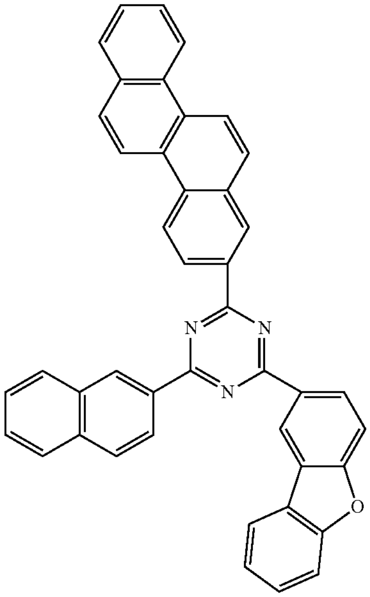
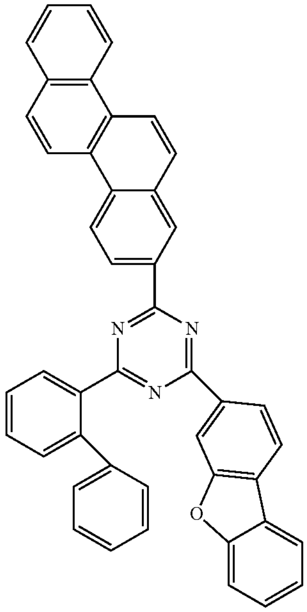
-continued
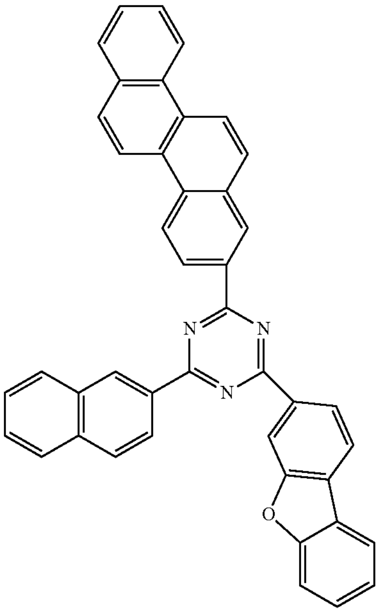
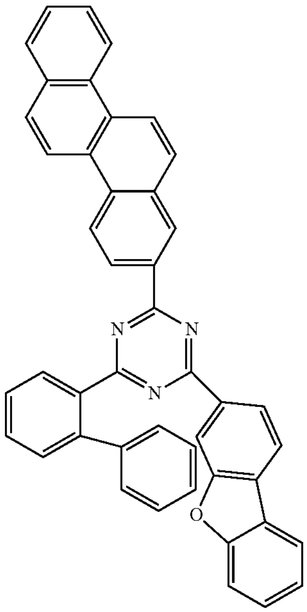
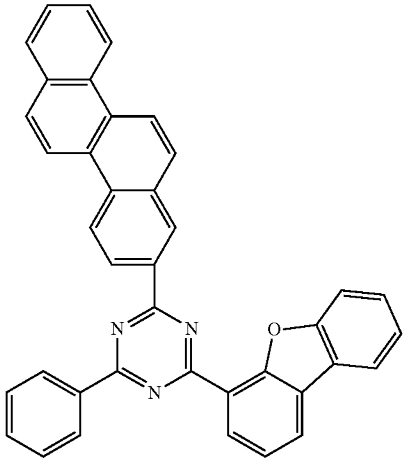

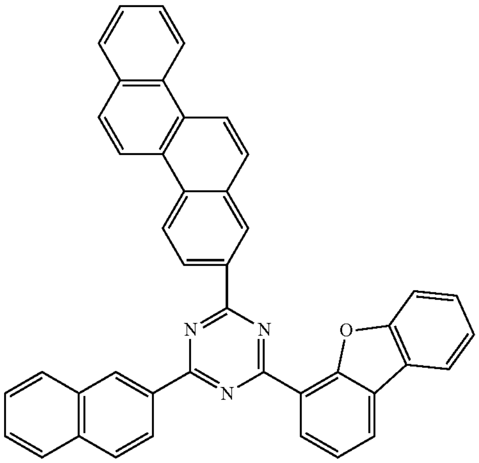
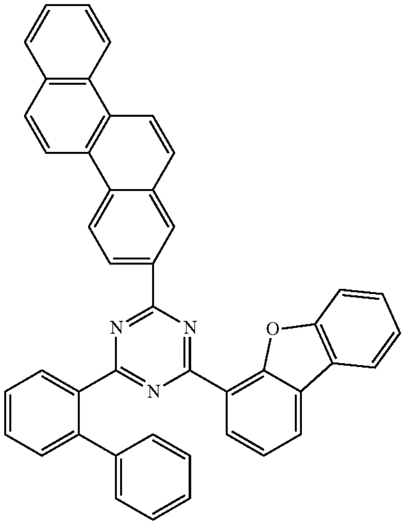
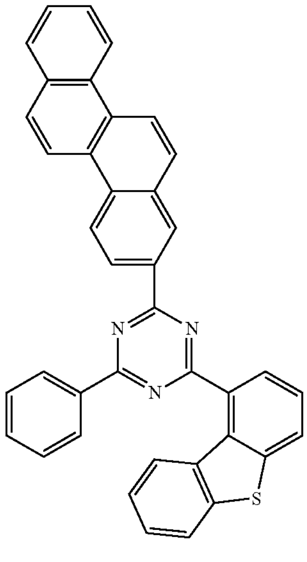
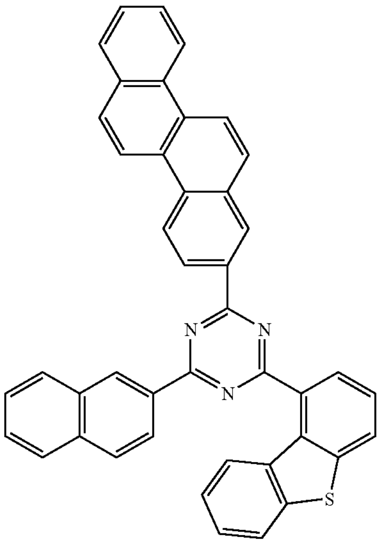
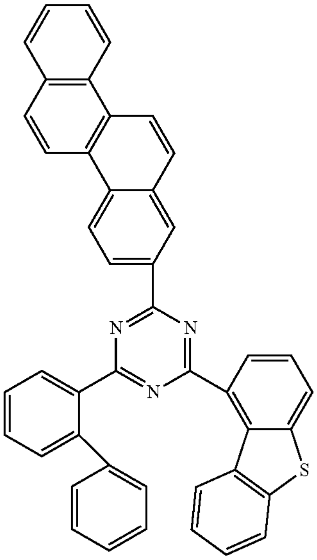
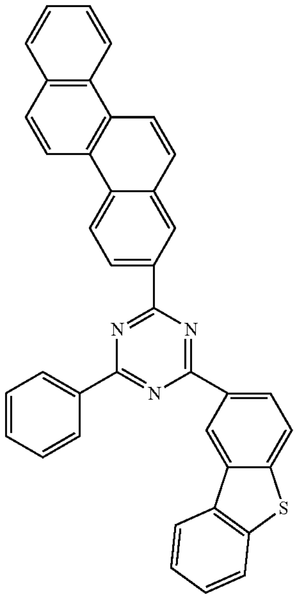

-continued
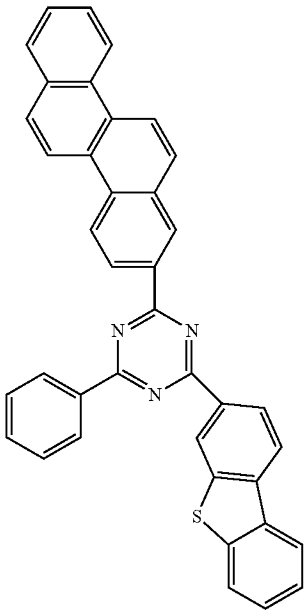
-continued
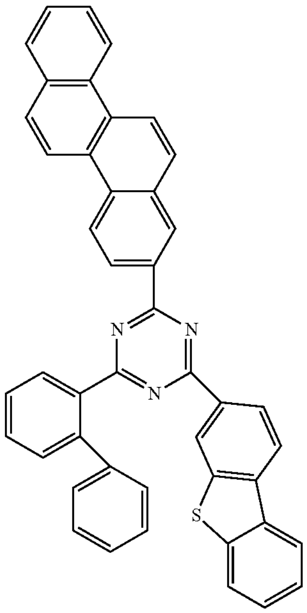
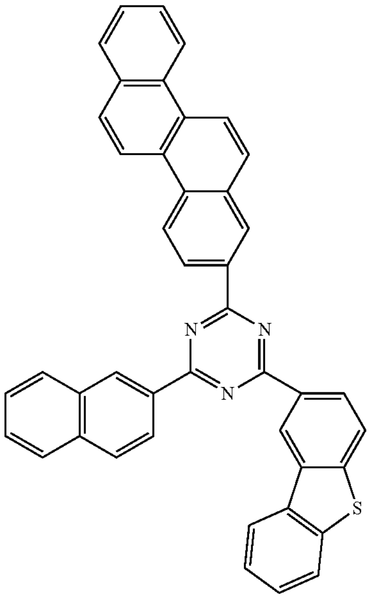
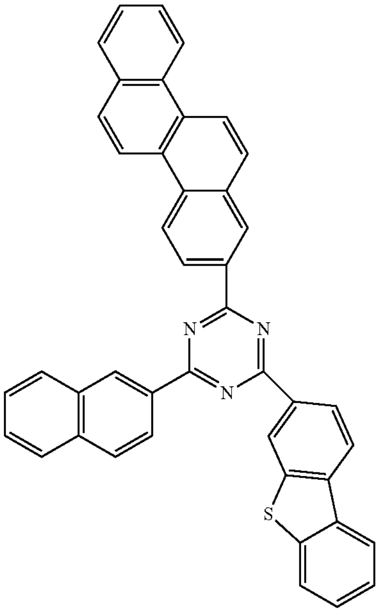

-continued
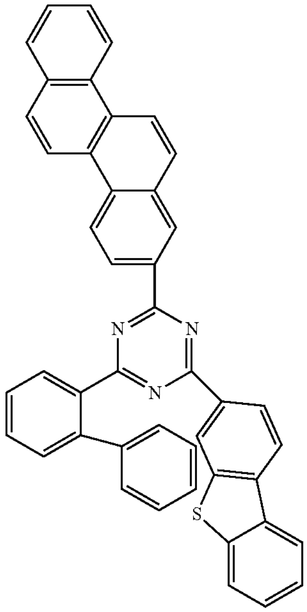
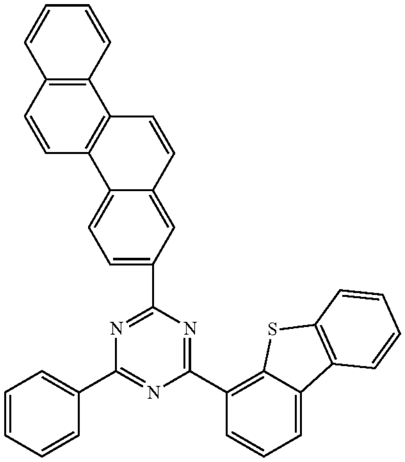
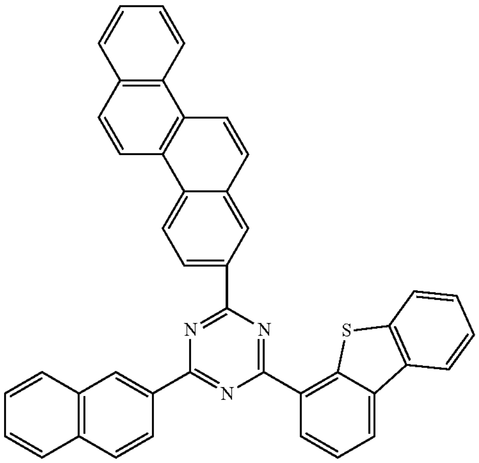
-continued
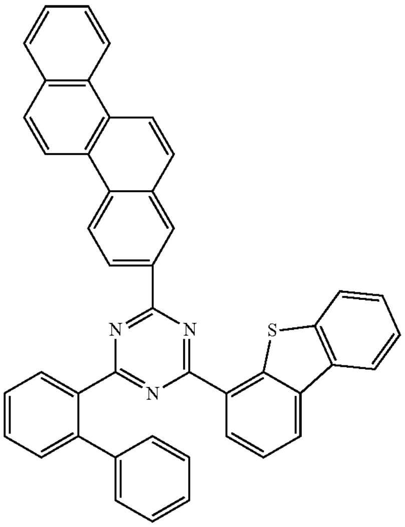
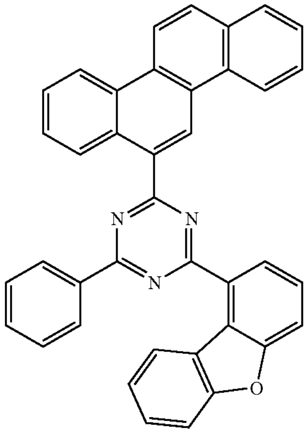
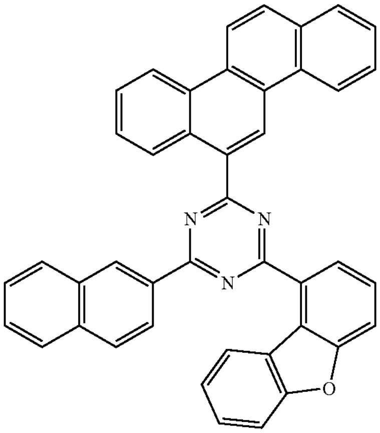

-continued
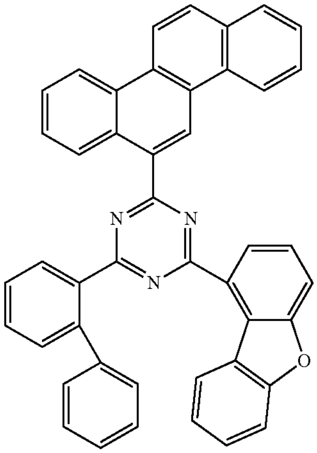
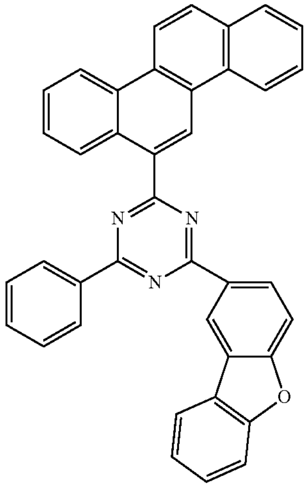
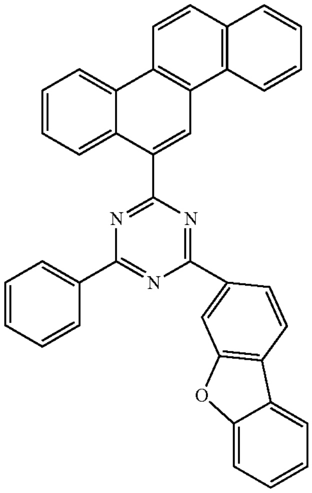
-continued
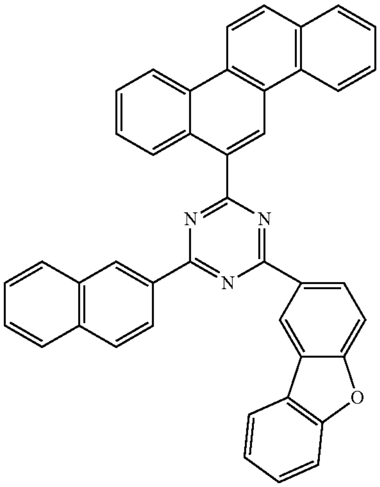
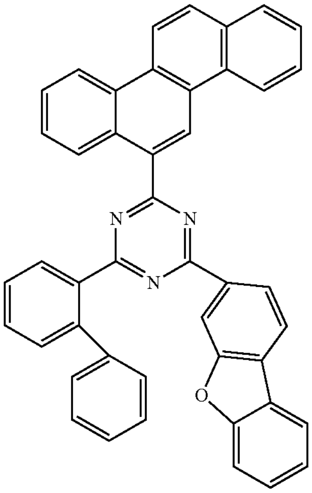
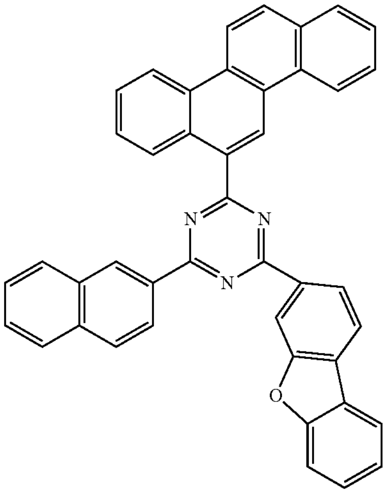

-continued
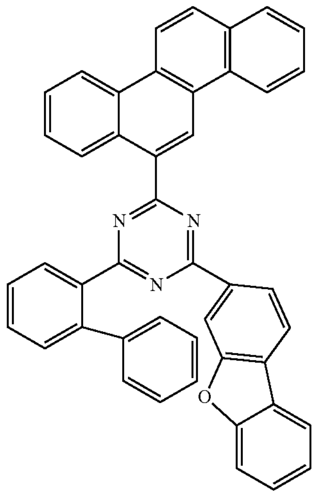
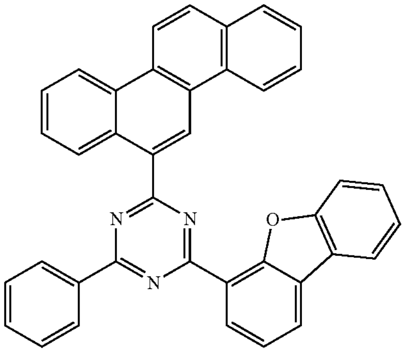
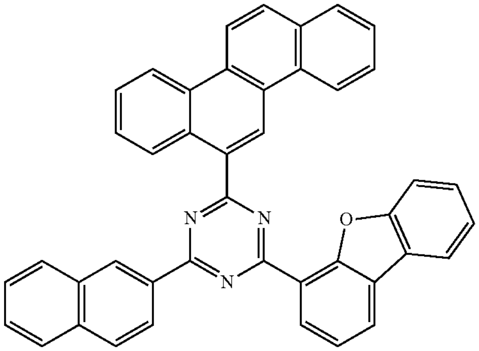
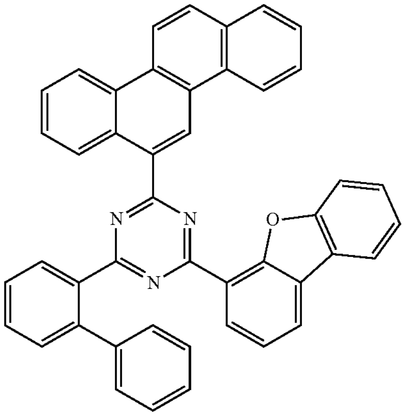
-continued
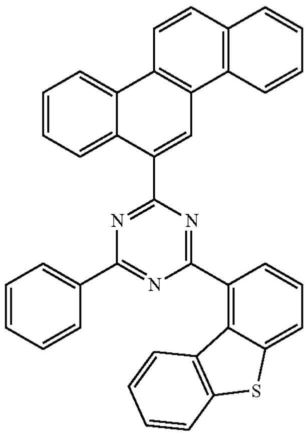
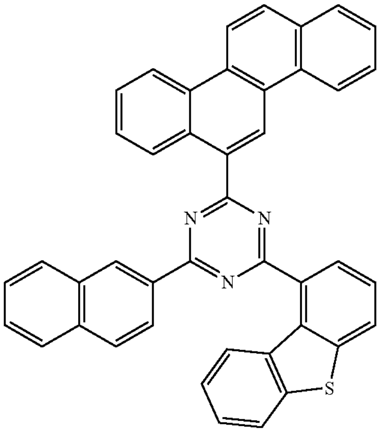
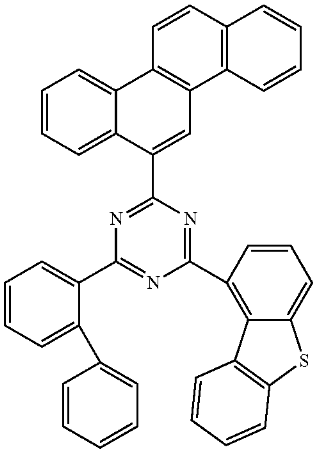

-continued
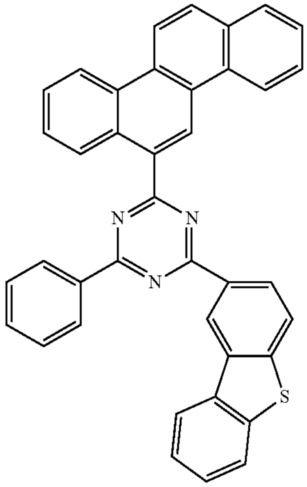
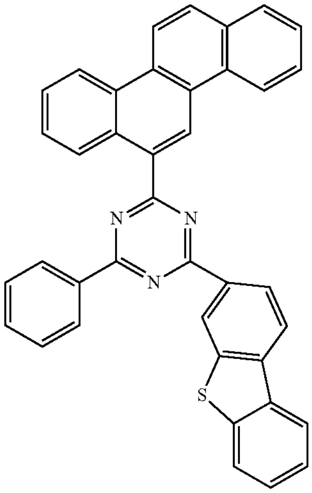
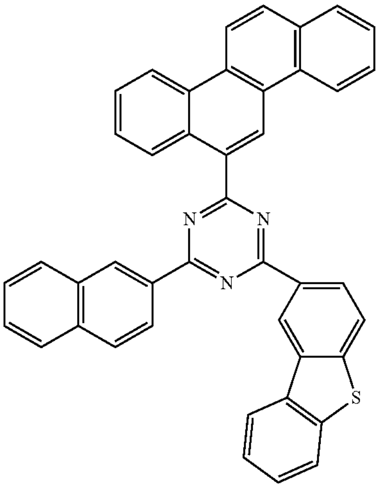
-continued
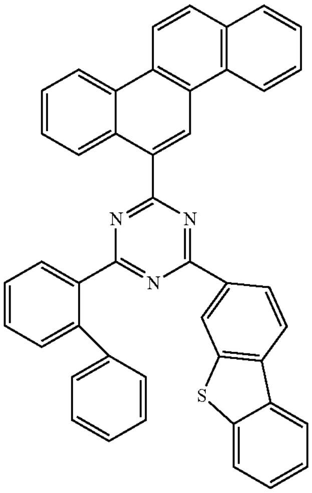
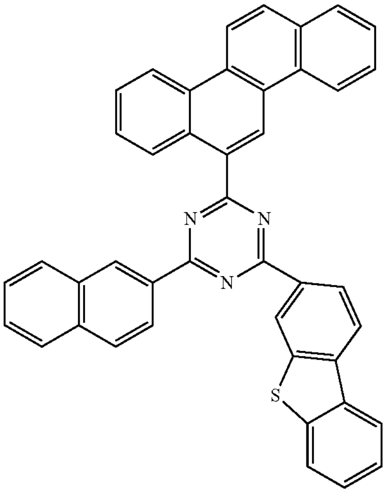
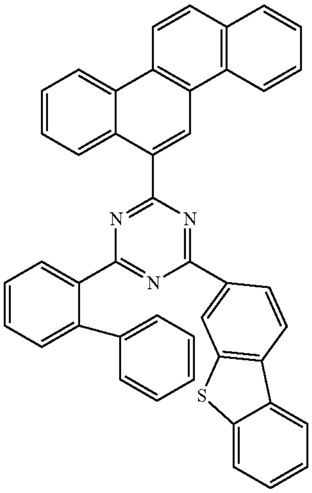

-continued
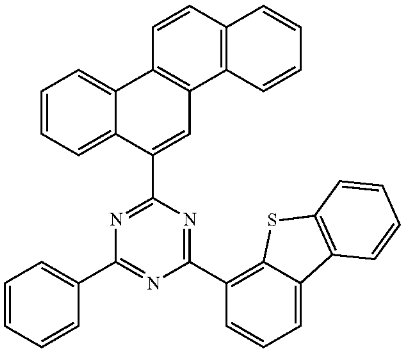
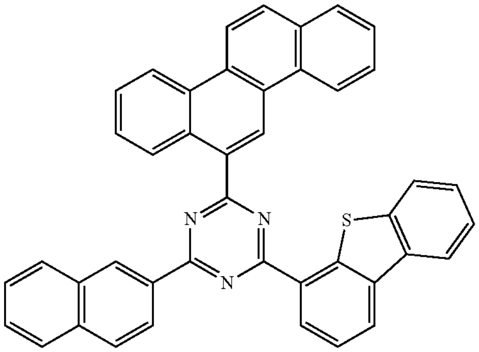
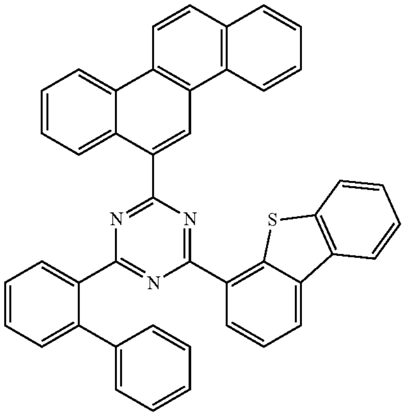
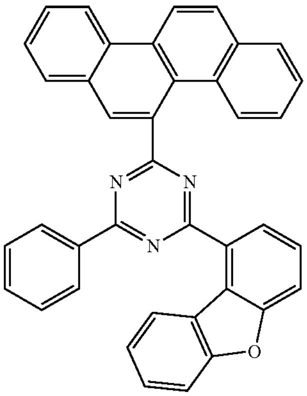
-continued
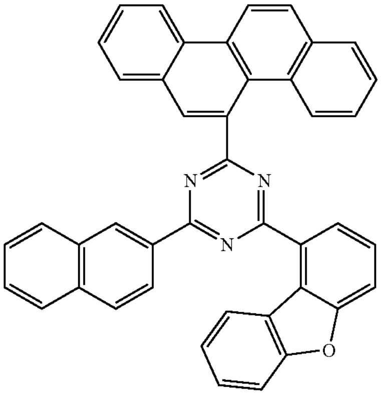
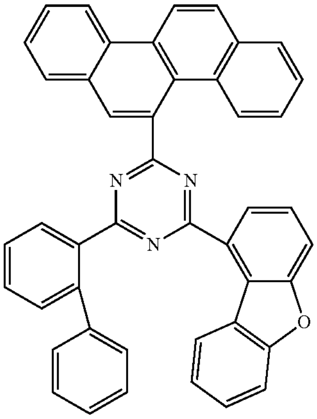
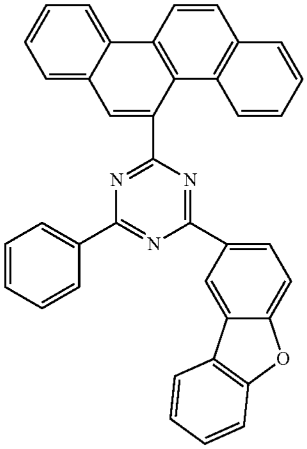
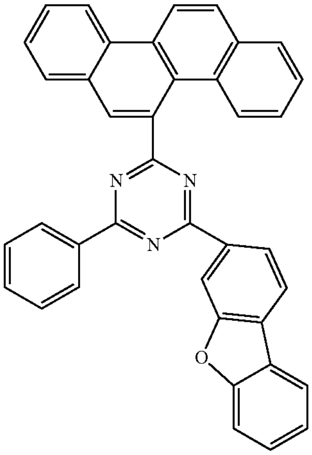

-continued
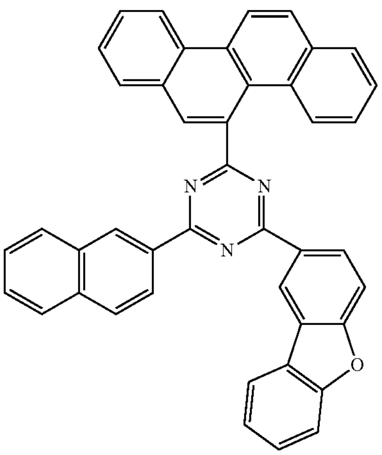
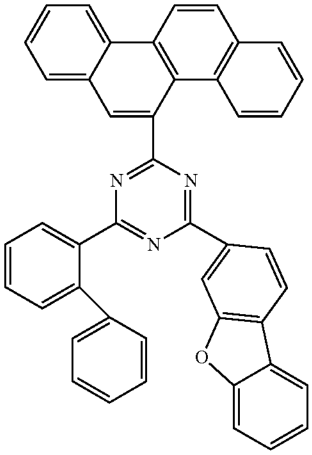
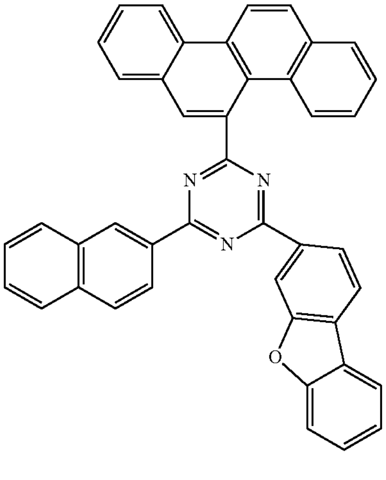
-continued
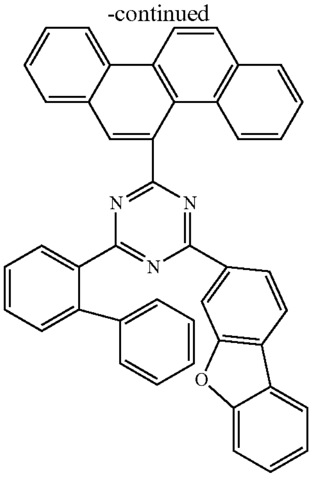
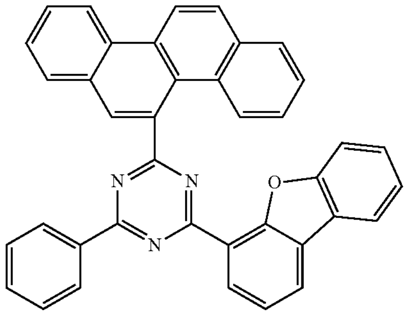
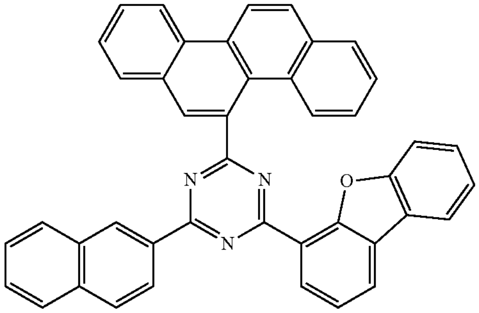
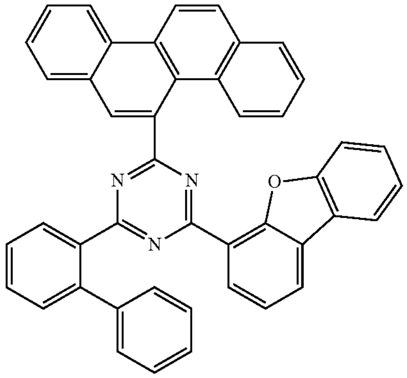

-continued
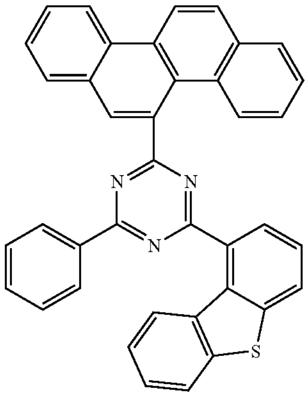
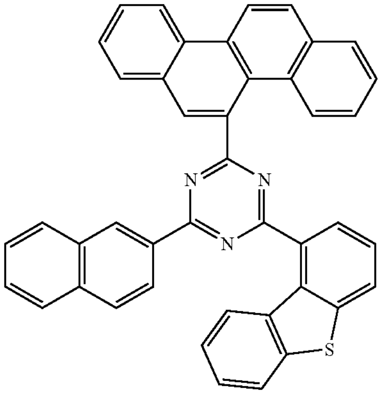
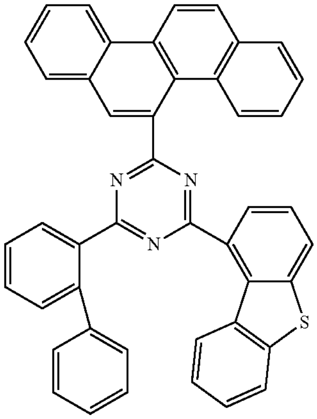
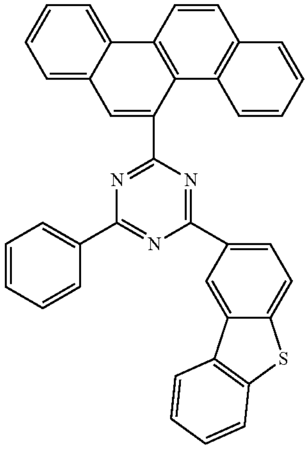
-continued
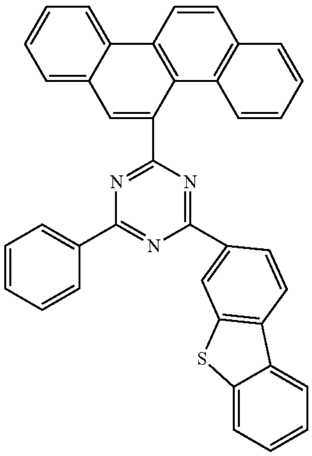
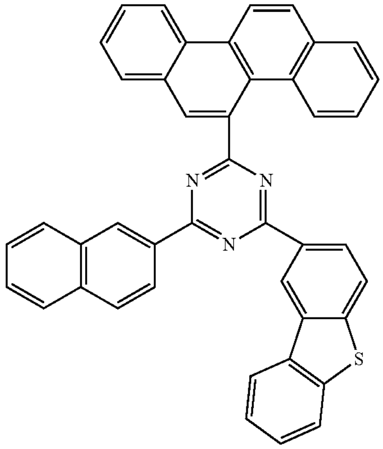
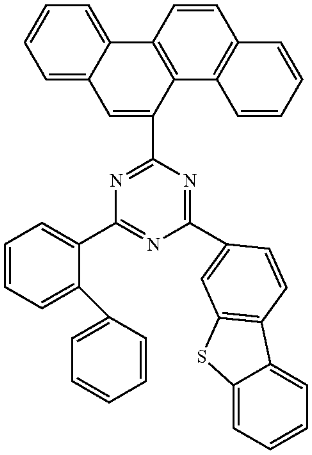

-continued

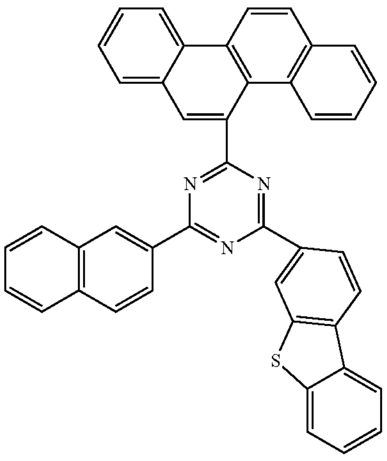

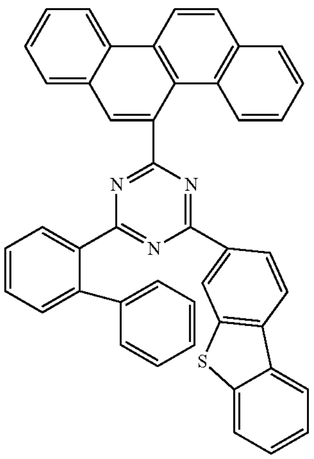

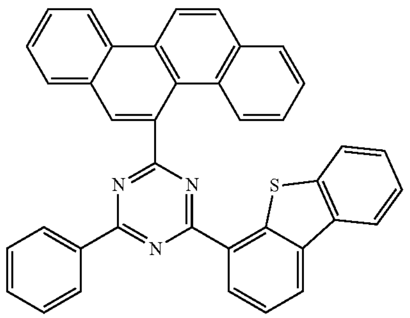

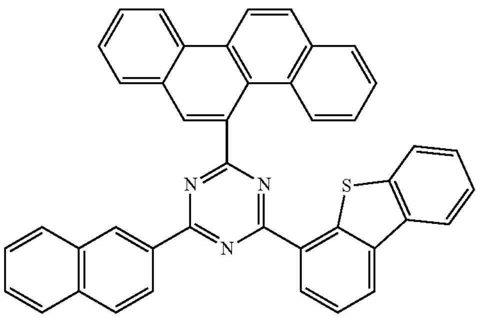

-continued

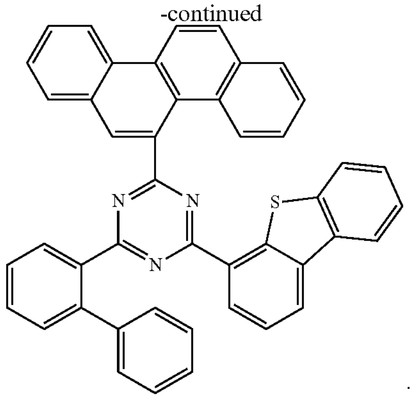

.

Preferably, the compound having a structure represented by Formula 1 and the compound having a structure represented by Formula 2 have a weight ratio of 1:9 to 9:1, such as 1:9, 2:8, 3:7, 4:6, 5:5, 6:4, 7:3, 8:2, 9:1, or the like; preferably 2:8 to 8:2; more preferably 3:7 to 7:3; even more preferably 4:6 to 6:4.

As used in the present invention, the term "organic electroluminescence material" indicates a material that can be used in an organic electroluminescence element, and may comprise at least one compound. The organic electroluminescence material may be comprised in any of the layers which constitute the organic electroluminescence element, if necessary. For example, the organic electroluminescence material may be a hole injection material, a hole transport material, an electron blocking material, an emitting auxiliary material, an emitting layer material (comprising a host material and a dopant material), an electron buffer material, a hole blocking material, an electron transport material, an electron injection material or the like.

As used in the present invention, the term "halogen" may comprise fluorine, chlorine, bromine or iodine.

As used in the present invention, the term "C1-C30 alkyl group" indicates a monovalent substituent derived from a straight or branched saturated hydrocarbon having 1 to 30 carbon atoms, for example, it comprises, but is not limited to, a methyl group, an ethyl group, a propyl group, an isobutyl group, a sec-butyl group, a tert-butyl group, a pentyl group, an isopentyl group, or a hexyl.

As used in the present invention, the term "C3-C30 cycloalkyl group" indicates a group derived from a monocyclic hydrocarbon or a multicyclic hydrocarbon having 1 to 30 carbon atoms on the main chain, and the cycloalkyl group may comprise cyclopropyl, cyclobutyl, adamantyl group, or the like.

In the present invention, the aryl group and arylene group comprise a monocyclic, a multicyclic or a fused cyclic aryl group, in which the rings may be interrupted by a short non-aromatic unit, and they may comprise a spiro-structure. The aryl group and arylene group of the present invention comprise, but are not limited to, a phenyl group, a biphenylyl group, a terphenylyl group, a naphthyl group, a phenanthryl group, an anthryl group, a fluorenyl group, a spiro-bifluorenyl group, or the like.

In the present invention, the heteroaryl group and heteroarylene group comprise a monocyclic, a multicyclic or a fused cyclic heteroaryl group, in which the rings may be interrupted by a short non-aromatic unit, and the hetero atom comprises nitrogen, oxygen or sulfur. The heteroaryl group and heteroarylene group of the present invention comprise, but are not limited to, a furyl group, a thiophenyl group, a pyrrolyl group, an imidazolyl group, a pyrazolyl group, a thiazolyl group, a thiadiazolyl group, an isothiazolyl group, an isoxazolyl group, an oxazolyl group, an oxadizolyl group, a triazinyl group, a tetrazinyl group, a triazolyl group, a tetrazolyl group, a furazanyl group, a pyridyl group, a pyrazinyl group, a pyrimidinyl group, a pyridazinyl group, a benzofuryl group, a benzothiophenyl group, an isobenzofuryl group, a dibenzofuryl group, a dibenzothiophenyl group, a benzimidazolyl group, a benzothiazolyl group, a benzisothiazolyl group, a benzisoxazolyl group, a benzoxazolyl group, an isoindolyl group, an indolyl group, an indazolyl group, a benzothiadiazolyl group, a quinolyl group, an isoquinolyl group, a cinnolinyl group, a quinazolinyl group, a quinoxalinyl group, a carbazolyl group, a phenoxazinyl group, a phenothiazinyl group, a phenanthridinyl group, a 1,3-benzodioxolyl group, a dihydroacridinyl group, or derivatives thereof.

Preferably, the aryl group is selected from a phenyl group, a biphenylyl group, a terphenylyl group, a naphthyl group, an anthryl group, a phenanthryl group, a 9,9'-dimethylfluorenyl group, a 9,9'-diphenylfluorenyl group and spiro-bifluorenyl group.

Preferably, the heteroaryl group is selected from a dibenzofuryl group, a dibenzothiophenyl group, a carbazolyl group, a triazinyl group, a pyridyl group, a pyrimidinyl group, an imidazolyl group, an oxazolyl group, a thiazolyl group, a benzimidazolyl group, a benzoxazolyl group, a benzothiazolyl, a naphthimidazolyl group, a naphthoxazolyl group, a naphthothiazolyl group, a phenanthrimidazolyl group, a phenanthroxazolyl group, a phenanthrothiazolyl group, a quinoxalinyl group, a quinazolinyl group, an indolocarbazolyl group, an indolofluorenyl group, a benzothienopyrazinyl group, a benzothienopyrimidinyl group, a benzofuropyrazinyl group, a benzofuropyrimidinyl group, an indolopyrazinyl group, an indolopyrimidinyl group, an indenopyrazinyl group, an indenopyrimidinyl group, a spiro[fluorene-9,1'-indene]-pyrazinyl group, a spiro[fluorene-9,1'-indene]-pyrimidinyl group, a benzofurocarbazolyl and a benzothienocarbazolyl.

As used in the present invention, the term "C6-C30 aryloxy group" indicates a monovalent substituent represented by ZO—, wherein Z represents an aryl group having 6 to 30 carbon atoms. Examples of such aryloxy group comprise, but are not limited to, a phenoxy group, a naphthyloxy group, a diphenoxy group, or the like.

As used in the present invention, the term "C1-C30 alkoxy group" indicates a monovalent substituent represented by Z'O—, wherein Z' represents an alkyl group having 1 to 30 carbon atoms.

As used in the present invention, the term "substituted" indicates a hydrogen atom comprised in a compound is replaced by another substituent. The position of substitution is not specifically limited, provided that the hydrogen at the position can be replaced by the substituent. When two or more substituents are simultaneously present, the two or more substituents can be the same or different.

As used in the present invention, unless otherwise specified, the hydrogen atom comprises protium, deuterium or tritium.

In the present invention, "adjacent two groups joined to form a ring" indicates that 2 substituents at adjacent positions on the same ring or adjacent rings can be joined to form a ring by chemical bonding. The specific way to form a ring in the present invention is not limited (for example, joined via a single bond, joined via a benzene ring, joined via a naphthalene ring, fused via

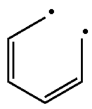

, fused via

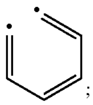

;

wherein the •. represents fusion positions). In the same description present hereinafter, it has the same meaning.

In the present invention, when the range of carbon atom number is limited in the definition of a functional group, the functional group may have a carbon atom number of any integer in the limited range. For example, a C6-C60 aryl group represents an aryl group that may give a carbon number of any one integer comprised in the range of 6 to 60, such as 6, 8, 10, 15, 20, 30, 35, 40, 45, 50, 55 or 60, etc.

In the present invention, the organic compounds substituted at each of the described positions are prepared by a synthesis route shown as below:

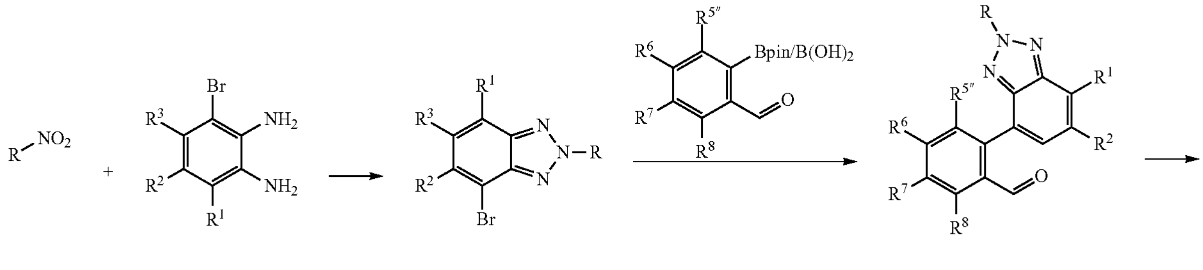

-continued
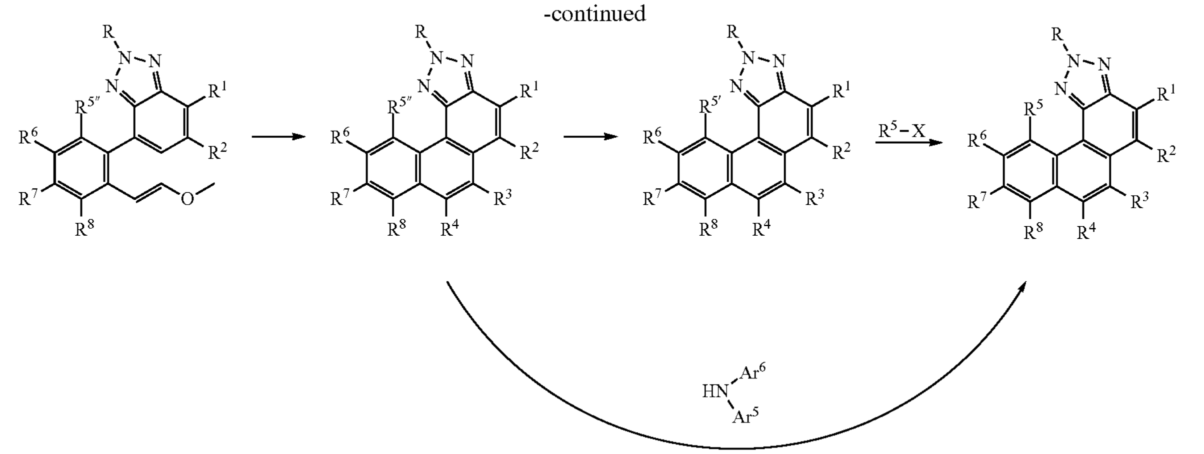
$R^{5''}$ is chlorine; $R^{5'}$ is
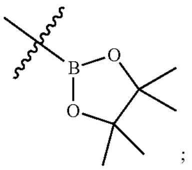 [SMILES: *B1OC(C)(C)C(C)(C)O1]
$R^5$ is
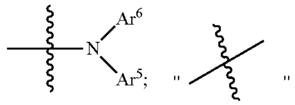
represents the connection position.
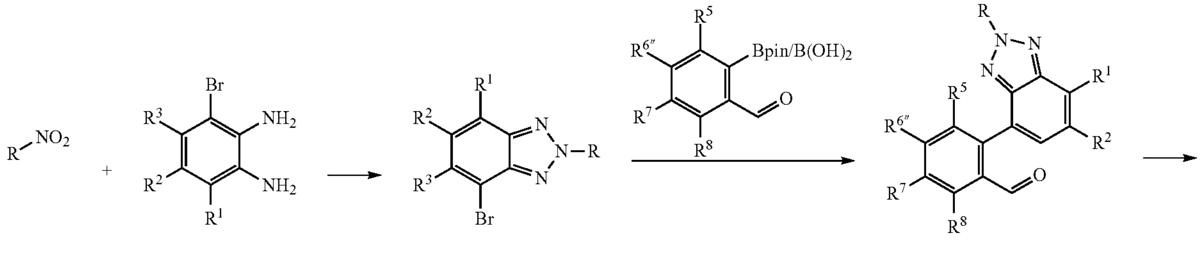
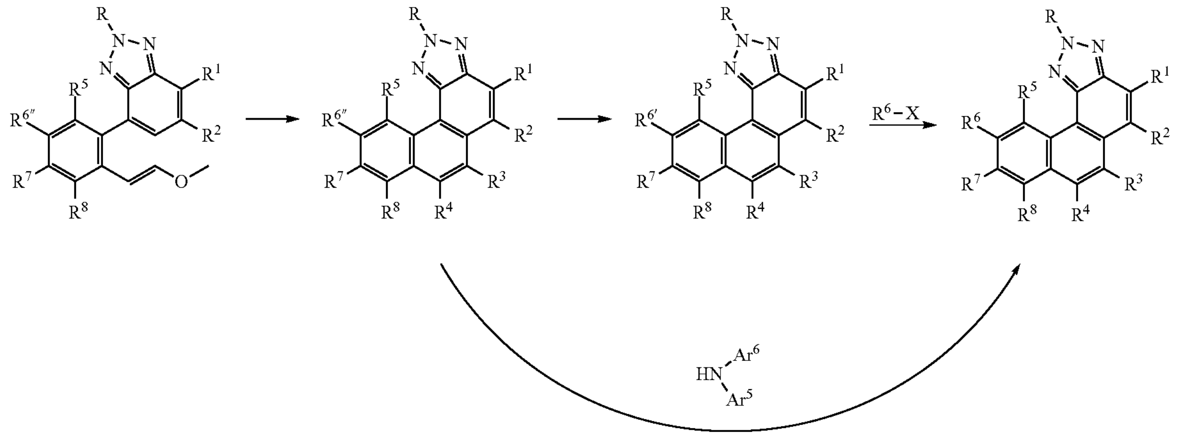

$R^{6''}$ is chlorine; $R^{6'}$ is
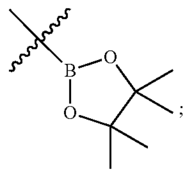 [SMILES: *B1OC(C)(C)C(C)(C)O1]
$R^6$ is
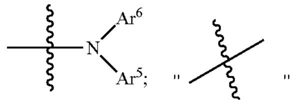
represents the connection position
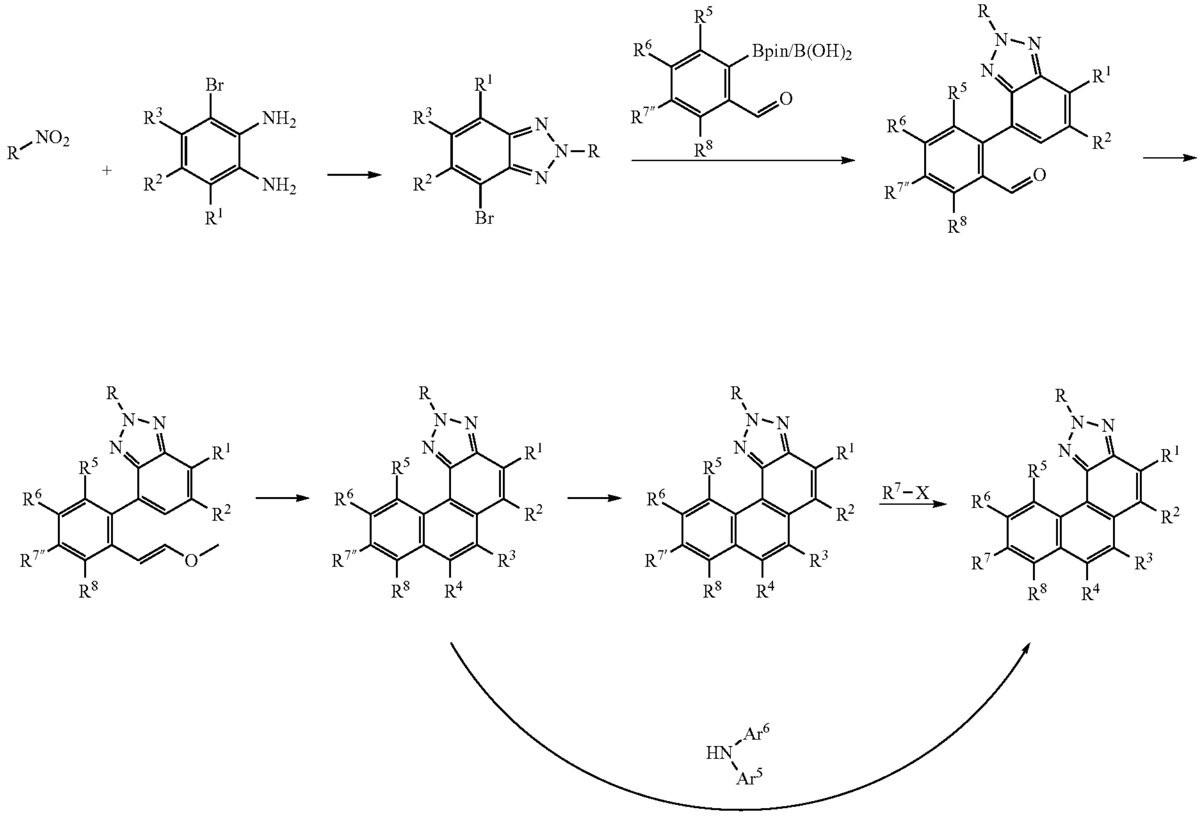
$R^{7''}$ is chlorine; $R^{7'}$ is
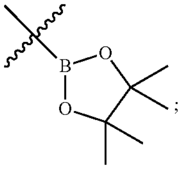 [SMILES: *B1OC(C)(C)C(C)(C)O1]
$R^7$ is
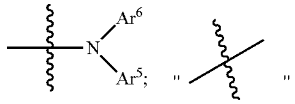
represents the connection position.

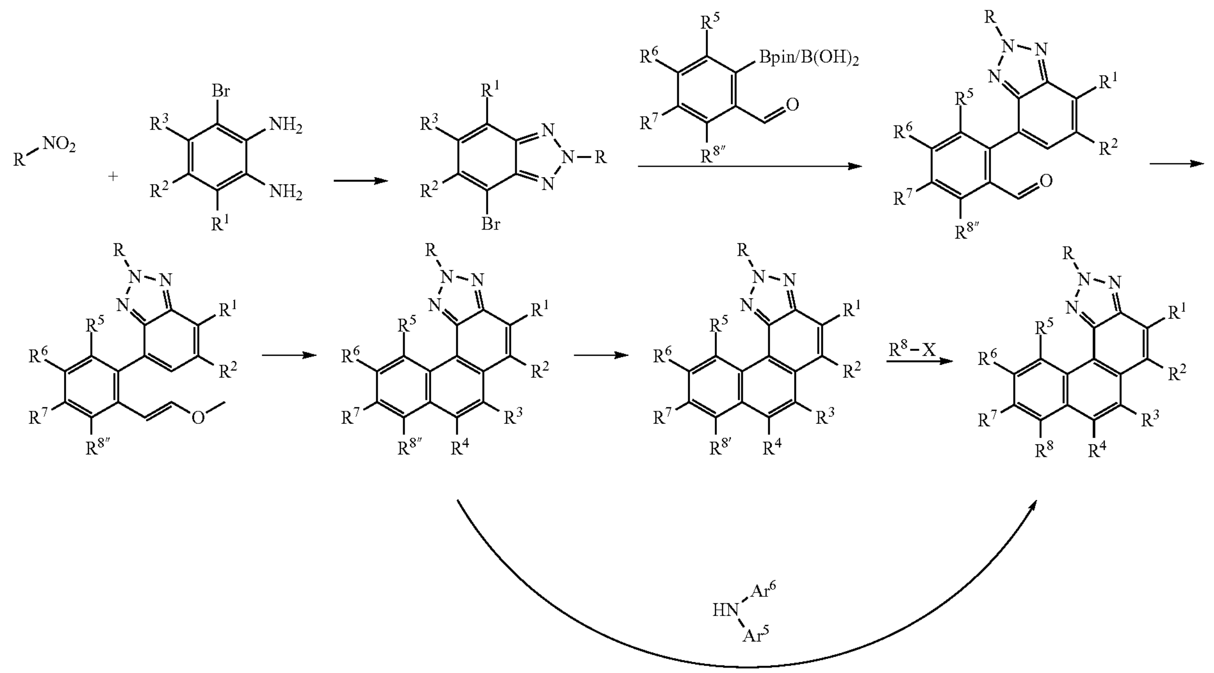

$R^{8''}$ is chlorine; $R^{8'}$ is

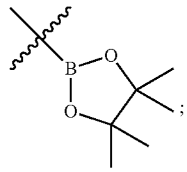 [SMILES: *B1OC(C)(C)C(C)(C)O1]
;

$R^8$ is

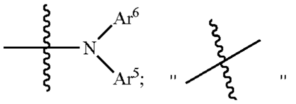

represents the connection position.

Suzuki coupling reaction is mainly used to synthesize the compound of Formula 2.

In another aspect, the present invention provides an organic electroluminescence material, and the organic electroluminescence material comprises the above-mentioned organic material composition.

In another aspect, the present invention provides an application of the above-mentioned organic material composition or the above-mentioned organic electroluminescence material in preparation of an optical element.

Preferably, the optical element comprises any one of an organic electroluminescence element, an organic field-effect transistor, an organic thin film transistor, an organic light-emitting transistor, an organic integrated circuit, an organic solar cell, an organic field quenching element, a light-emitting electrochemical cell, an organic laser diode, and an organic photoreceptor.

In another aspect, the present invention provides an organic electroluminescence element, wherein the organic electroluminescence element comprises an anode, a cathode, and an organic layer disposed between the anode and the cathode, and the organic layer comprises the above-mentioned organic material composition or the above-mentioned organic electroluminescence material.

Preferably, the organic layers comprise a hole injection layer, a hole transport layer, an emitting layer, an electron transport layer and an electron injection layer, which are sequentially layered from a side of the anode to a side of the cathode.

Preferably, the emitting layer is made of a material comprising a host material and a guest material, wherein the host material comprises the above-mentioned organic material composition or the above-mentioned organic electroluminescence material.

Preferably, the guest material comprises a phosphorescence dopant, and the phosphorescence dopant comprises a coordination complex of a transition metal.

In another aspect, the present invention provides an organic electroluminescence device, wherein the organic electroluminescence device comprises the above-mentioned organic electroluminescence element.

Compared to the existing technology, the present invention has the following advantages:

By the combination of at least one compound having a structure represented by Formula 1 and at least one compound having a structure represented by Formula 2, the organic material composition of the present invention has a balanced charge carrier transport ability, thereby the organic electroluminescence element has an enhanced light-emitting efficiency and a prolonged service life.

BRIEF DESCRIPTION OF THE DRAWINGS

The FIGURE is a schematic diagram of the structure of the organic electroluminescence element provided by the application example of the present invention, wherein 1 is an anode, 2 is a hole injection layer, 3 is a hole transport layer,

4 is an emitting layer, 5 is an electron transport layer, 6 is an electron injection layer, and 7 is a cathode.

DETAILED DESCRIPTION OF THE PREFERRED EMBODIMENTS

Specific embodiments are further illustrated by the following examples to demonstrate the technical approaches of the present invention. Those skilled in the art should understand that the illustrative examples are helpful to understand the present invention; however, they should not be construed as being limiting to the scope of the present invention.

Preparation Example of Compound of Formula 1

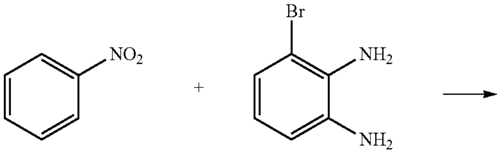

M6-A

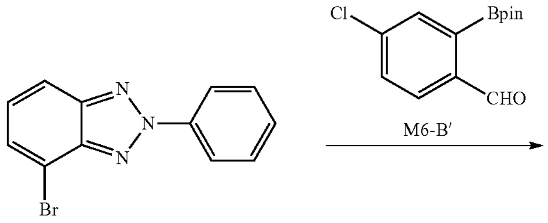

M6-B

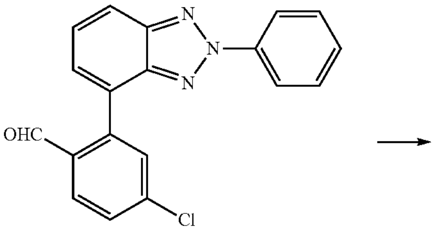

M6-C

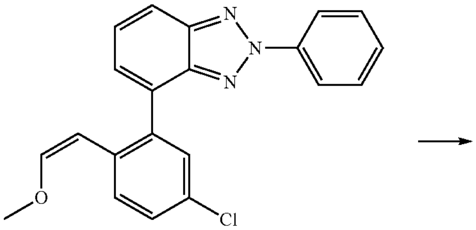

M6-D

-continued

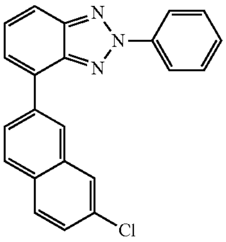

M6-E

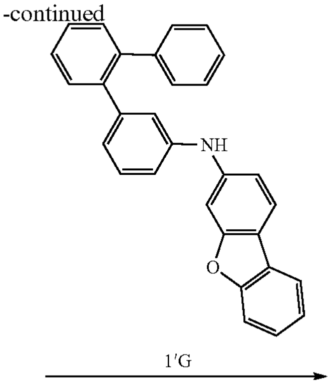

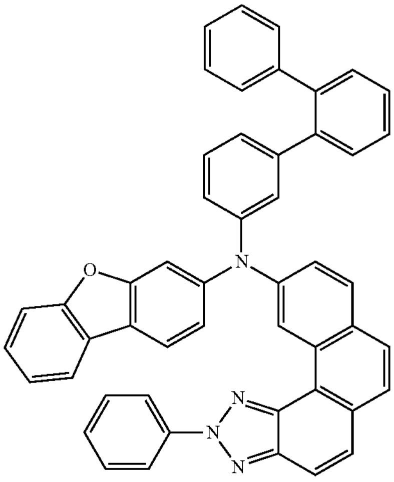

1'

Synthesis of M-6B: In a three-necked bottle of 25 milliliters (mL), M-6A (10 millimoles (mmol)), nitrobenzene (10 mmol), potassium hydroxide (22 mmol), copper(I) thiocyanate (1 mmol) and anhydrous tetrahydrofuran (10 mL) were added, nitrogen gas was purged for three times, and heated to 90° C. under nitrogen gas protection to react for 48 hours (h). After the reaction ended, the reaction mixture was quenched by water, the reaction system was extracted by ethyl acetate, and the organic solvent was removed by rotary evaporation to give a crude product. The crude product was purified by column chromatography (ethyl acetate:n-hexane=1:50 (volume ratio)), to obtain M-6B (1.34 g, 49% yield).

Synthesis of M-6B': In a three-necked bottle of 50 mL, 2-bromo-4-chlorobenzaldehyde (10 mmol), bis(pinacolato) diboron (12 mmol), potassium acetate (100 mmol), [1,1'-bis (diphenylphosphino)ferrocene]palladium(II) dichloride (0.2 mmol) and 1,4-dioxane (25 mL) were added, nitrogen gas was purged, and heated to 100° C. under nitrogen gas protection for reaction. After the reaction ended, the reaction mixture was quenched by water, extracted by methylene dichloride to give a crude product. The crude product was purified by column chromatography (methylene dichloride: n-hexane=1:50 (volume ratio)), to obtain M-6B' (1.7 g, 64% yield).

Synthesis of M-6C: In a three-necked bottle of 50 mL, M-6B (10 mmol), M-6B' (10 mmol), sodium bicarbonate (20 mmol), tetrakis(triphenylphosphine)palladium (0.2 mmol), tetrahydrofuran (20 mL) and water (10 mL) were added, nitrogen gas was purged, and heated to 60° C. under nitrogen gas protection to react overnight. After the reaction ended, the reaction mixture was quenched by water, extracted by methylene dichloride, and the organic solvent was removed by rotary evaporation to give a crude product. The crude product was purified by column chromatography (ethyl acetate:n-hexane=1:50 (volume ratio)), to obtain M-6C (3.06 g, 92% yield).

Synthesis of M-6D: In a three-necked bottle of 50 mL, M-6C (10 mmol), (methoxymethyl)triphenylphosphonium chloride (20 mmol), tetrahydrofuran (10 mL) were added, and the temperature was reduced to 0° C. Potassium tert-butoxide (2 mmol) was resolved in 5 mL tetrahydrofuran. The three-necked bottle was purged with nitrogen gas. Under nitrogen gas protection, the potassium tert-butoxide solution was added dropwise at 0° C. to obtain a mixture. After the addition, the mixture was stirred to react for half an hour. After the reaction ended, the reaction mixture was quenched by water, extracted by methylene dichloride, and the organic solvent was removed by rotary evaporation to give a crude product. The crude product was purified by column chromatography (ethyl acetate:n-hexane=1:50 (volume ratio)), to obtain M-6D (1.8 g, 50% yield).

Synthesis of M-6E: In a three-necked bottle of 25 mL, M-6D (1 mmol) and hexafluoroisopropanol (5 mL) were added, the temperature was reduced to 0° C., and nitrogen gas was purged. Under nitrogen gas protection, trifluoromethanesulfonic acid (1 mL) was added dropwise to obtain a mixture, and the mixture was stirred to react for half an hour to give a crude product. The crude product was purified by column chromatography (ethyl acetate:n-hexane=1:50 (volume ratio)), to obtain M-6E (0.24 g, 73% yield).

Synthesis of compound 1': In a three-necked bottle of 25 mL, nitrogen gas was purged, and then M6-E (1 mmol), compound 1'-G (1 mmol), sodium tert-butoxide (2 mmol), tris(dibenzylideneacetone)dipalladium(0) (0.02 mmol), 50% tri-tert-butylphosphine solution (0.1 mmol) and toluene 8 mL was added, and stirred under reflux for reaction. After the reaction ended, the reaction mixture was cooled to room temperature, the organic layer was extracted by ethyl acetate and $H_2O$, the extracted organic layer was dried by $MgSO_4$, filtered, and the filtrate was concentrated under vacuum to give a crude product. The crude product was purified by column chromatography (ethyl acetate:n-hexane=1:50 (volume ratio)), to obtain compound 1' (0.50 g, 71% yield).

Anal. Calcd. $C_{50}H_{32}N_4O$: C, 85.20; H, 4.58; N, 7.95. Found: C, 85.21; H, 4.60; N, 7.92. HRMS (ESI) m/z $[M+H]^+$: Calcd.: 704.26. Found: 705.31.

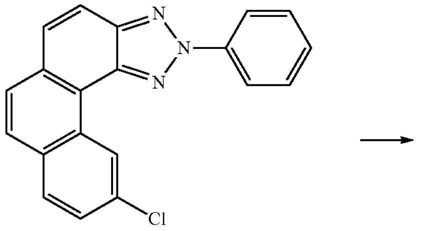

M6-E

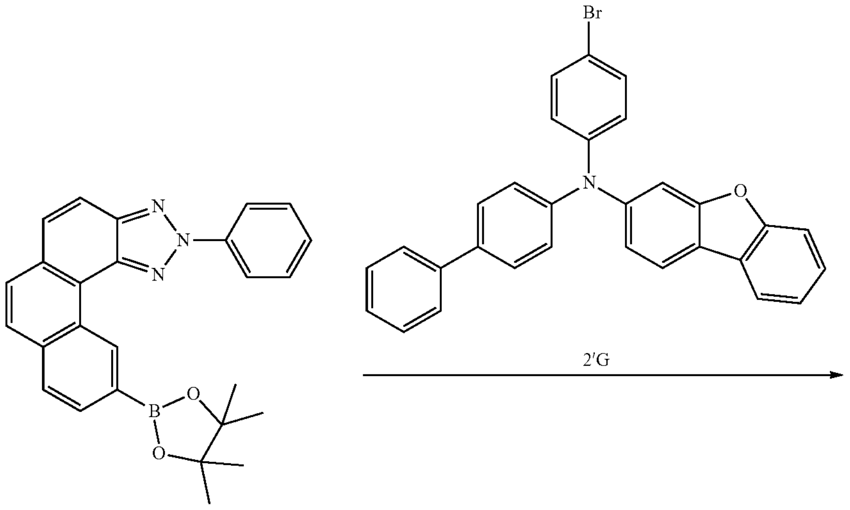

1F

-continued

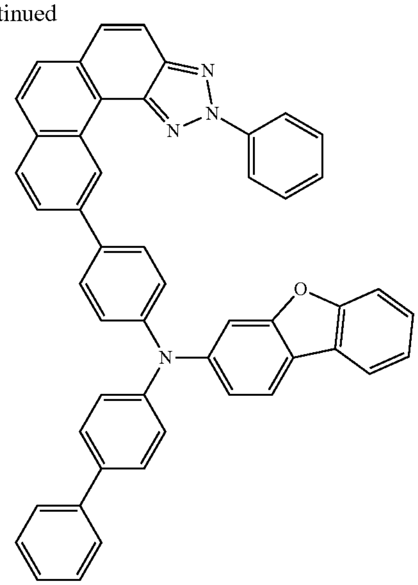

2'

Synthesis of 1F: In a three-necked bottle of 50 mL, M-6E (10 mmol), bis(pinacolato)diboron (12 mmol), sodium acetate (20 mmol), tris(dibenzylideneacetone)dipalladium (0) (0.5 mmol) and 2-dicyclohexylphosphino-2',6'-dimethoxybiphenyl (1.5 mmol) were added, then 1,4-dioxane (20 mL) was added, nitrogen gas was purged for three times, and heated to 100° C. under nitrogen gas protection for reaction. After the reaction ended, the reaction mixture was quenched by water, extracted by methylene dichloride, and the organic solvent was removed by rotary evaporation to give a crude product. The crude product was purified by column chromatography (ethyl acetate:n-hexane=1:50 (volume ratio)), to obtain 1F (3.24 g, 77% yield).

Synthesis of 2': In a two-necked round-bottom flask of 25 mL, a stir bar was put at the bottom and a refluxing tube was connected on the top. The bottle was dried and purged with nitrogen gas, and 1F (0.01 mol), 2'G (0.01 mol), potassium carbonate (0.013 mol), tetrakis(triphenylphosphine)palladium (0.5 mmol), toluene (10 mL), and water (4 mL) were separately added, nitrogen gas was purged for three times, and heated to 85° C. to react for 10 h. After the reaction ended, the reaction mixture was extracted by ethyl acetate, and the resulting extract was dried by magnesium sulfate, filtered, and dried by rotary evaporation to give a crude product. The crude product was purified by column chromatography (ethyl acetate:n-hexane=1:10 (volume ratio)), to obtain compound 2' (4.44 g, 63% yield).

Anal. Calcd. $C_{50}H_{32}N_4O$: C, 85.20; H, 4.58; N, 7.95. Found: C, 85.16; H, 4.60; N, 7.98. HRMS (ESI) m/z ($M^+$): Calcd.: 704.26. Found: 705.28.

The corresponding products shown in Table 1 were prepared by the above-mentioned preparation method using the Material 1 and Material 2 as raw materials. The structure and characteristic data of the products are shown in Table 2.

TABLE 1

| Material 1 | Material 2 | Product | Yield (%) |
|---|---|---|---|
| 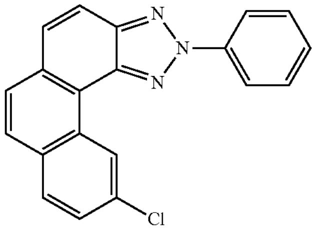 1E | 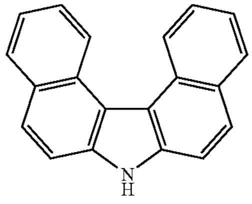 CAS194-59-2 | 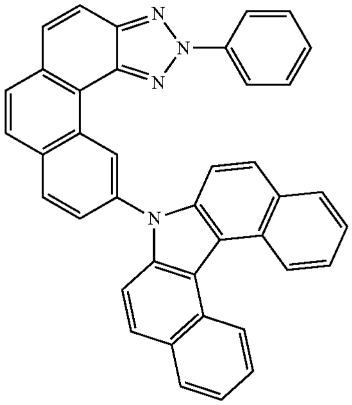 3' | 62 |

TABLE 1-continued
| Material 1 | Material 2 | Product | Yield (%) |
|---|---|---|---|
| 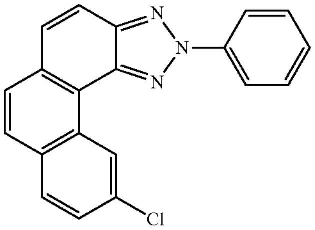 1E | 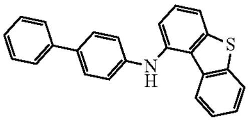 CAS1429933-62-9 | 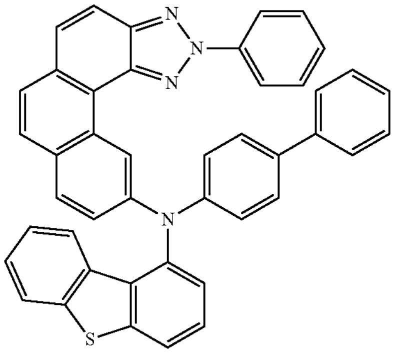 4′ | 60 |
| 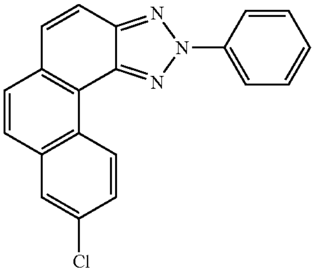 10E | 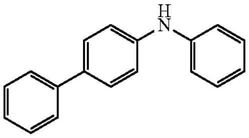 CAS32228-99-2 | 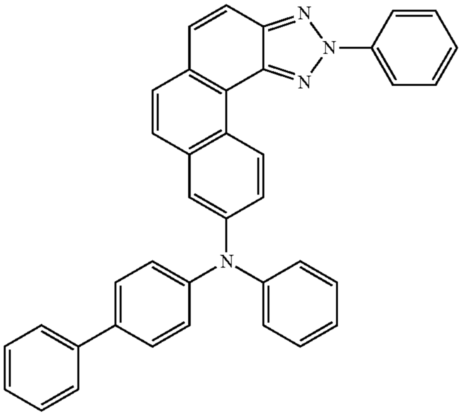 5′ | 61 |
| 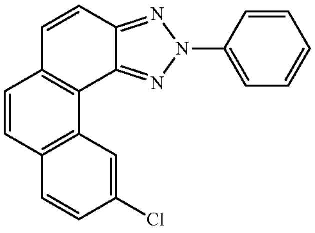 1E | 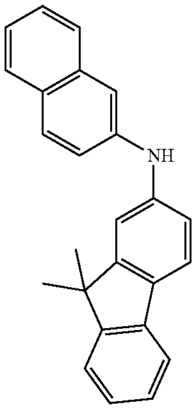 CAS1263001-82-6 | 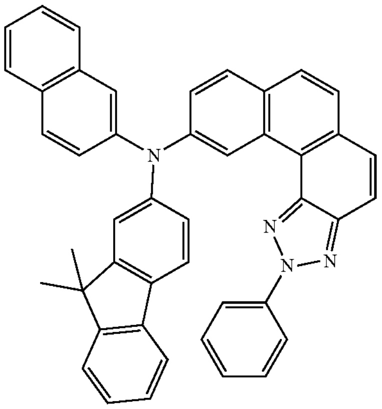 6′ | 64 |

TABLE 1-continued
| Material 1 | Material 2 | Product | Yield (%) |
|---|---|---|---|
| 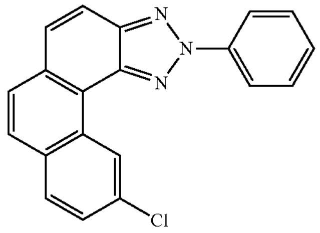 1E | 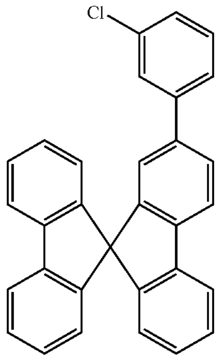 CAS2614439-35-7 | 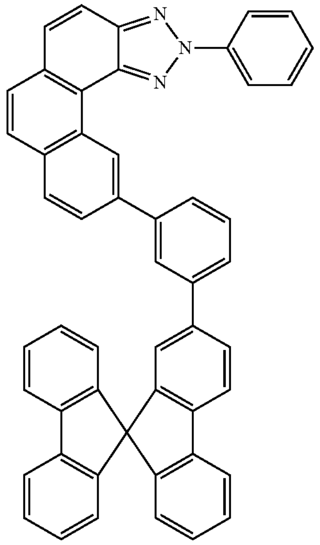 7′ | 68 |
| 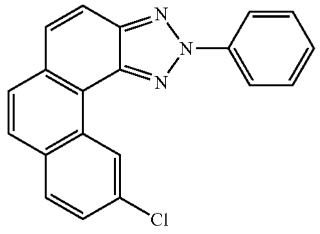 1E | 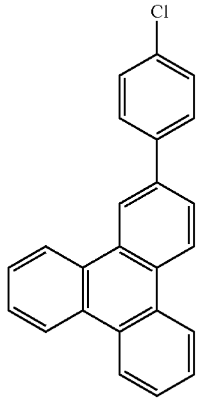 CAS1384206-43-2 | 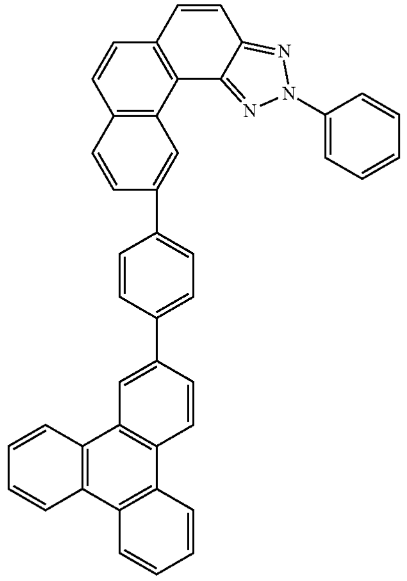 8′ | 62 |

TABLE 1-continued
| Material 1 | Material 2 | Product | Yield (%) |
|---|---|---|---|
| 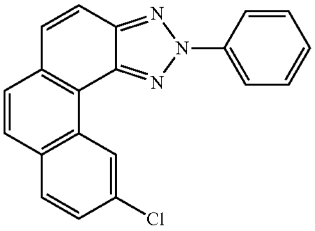 1E | 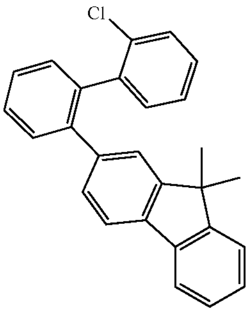 CAS2765448-20-0 | 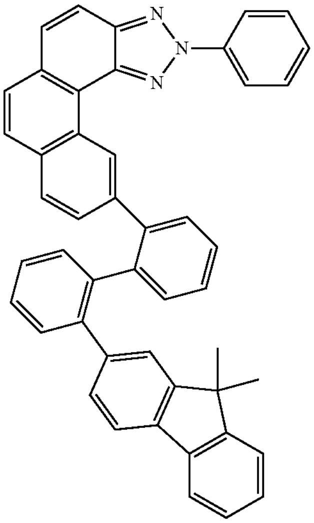 9' | 66 |
TABLE 2
| | Elemental analysis | | HRMS (ESI) m/z $[M + H]^+$ | |
|---|---|---|---|---|
| Compound | Calcd. | Found | Calcd. | Found |
| 3' | C, 85.69; H, 4.31; N, 9.99 | C, 85.75; H, 4.29; N, 9.96 | 560.20 | 561.11 |
| 4' | C, 81.96; H, 4.38; N, 8.69; S, 4.97 | C, 81.91; H, 4.40; N, 8.71; S, 4.98 | 644.20 | 645.30 |
| 5' | C, 84.73; H, 4.87; N, 10.40 | C, 84.70; H, 4.85; N, 10.45 | 538.22 | 539.31 |
| 6' | C, 85.96; H, 5.13; N, 8.91 | C, 86.01; H, 5.10; N, 8.89 | 628.26 | 629.33 |
| 7' | C, 89.32; H, 4.56; N, 6.13 | C, 89.35; H, 4.58; N, 6.08 | 685.83 | 686.76 |
| 8' | C, 88.42; H, 4.55; N, 7.03 | C, 88.43; H, 4.58; N, 6.99 | 597.72 | 598.55 |
| 9' | C, 88.23; H, 5.20; N, 6.57 | C, 88.27; H, 5.21; N, 6.52 | 639.80 | 640.69 |
Preparation Example of Compound of Formula 2
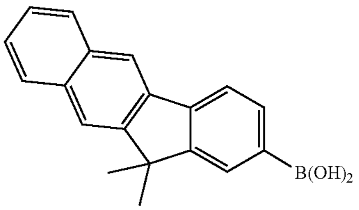
H1-A
+

-continued

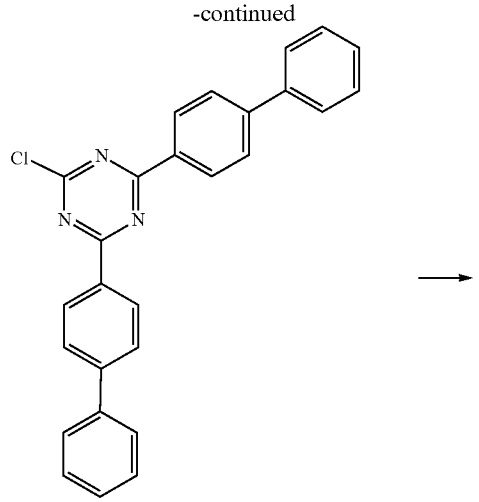

H1-B

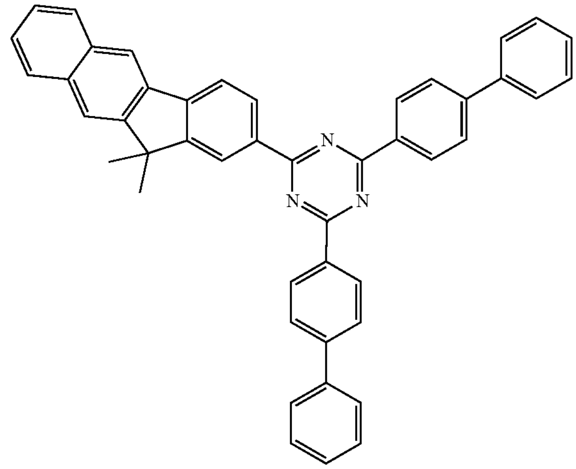

H1

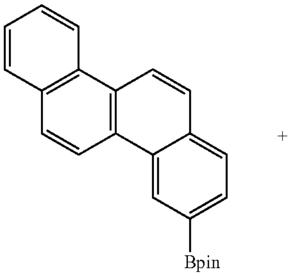

H4-A

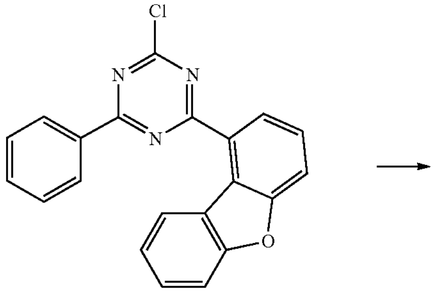

H4-B

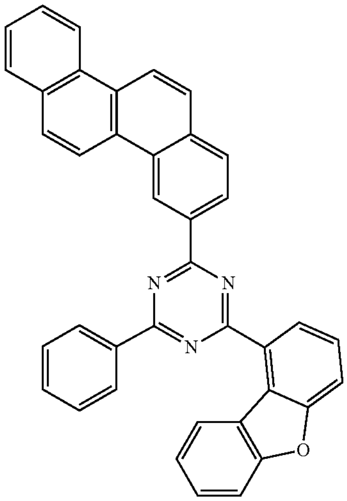

H4

Synthesis of compound H1: In a two-necked round-bottom flask of 25 mL, a stir bar was put at the bottom and a refluxing tube was connected on the top. The bottle was dried and purged with nitrogen gas, and H1-A (1 mmol, CAS1198396-40-5), H1-B (1 mmol), potassium carbonate ($K_2CO_3$, 1.5 mmol), ethanol (3 mL), water (3 mL), toluene (10 mL) and tetrakis(triphenylphosphine)palladium (Pd $(PPh_3)_4$, 0.05 mmol) were separately added, and heated to 60° C. to react for 12 h. After the reaction ended, the reaction mixture was cooled to room temperature, quenched by water, extracted by methylene dichloride (3x20 mL), and the resulting extract was dried by magnesium sulfate, filtered, and dried by rotary evaporation to give a crude product. The crude product was purified by column chromatography (ethyl acetate:n-hexane=1:10 (volume ratio)), to obtain compound H1 (0.46 g, 73% yield).

Anal. Calcd. C46$H_{33}N_3$: C, 88.01; H, 5.30; N, 6.69. Found: C, 88.06; H, 5.32; N, 6.62. HRMS (ESI) m/z $[M+H]^+$: Calcd.: 627.27. Found: 628.21.

Synthesis of compound H4: In a two-necked round-bottom flask of 50 mL, a stir bar was put at the bottom and a refluxing tube was connected on the top. The bottle was dried and purged with nitrogen gas, and H4-A (14.1 mmol, CAS2095370-50-4), H4-B (18.3 mmol), tetrakis(triphenylphosphine)palladium (0.7 mmol), potassium carbonate (28.2 mmol), toluene of 42 mL, ethanol of 10 mL and distilled water of 14 mL and were separately added, and the mixture was stirred at 140° C. for 8 h. After the reaction ended, the reaction mixture was added dropwise into methanol to give a solid. The solid was filtered and purified by column chromatography (ethyl acetate:n-hexane=1:10 (volume ratio)), to obtain compound H4 (5.8 g, 75% yield).

Compounds H2 and H3 were prepared by the above-mentioned preparation method of compound H1, and compounds H5 to H7 were prepared by the above-mentioned preparation method of compound H4 using the Material 1 and Material 2 as raw materials, as shown in Table 3. The structure and characteristic data of the products are shown in Table 4.

TABLE 3
| Material 1 | Material 2 | Product | Yield % |
| --- | --- | --- | --- |
| 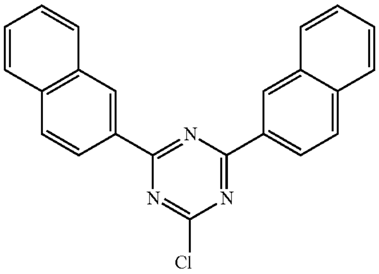 [SMILES: Clc1nc(-c2ccc3ccccc3c2)nc(-c2ccc3ccccc3c2)n1] H2-B CAS1247124-77-1 | 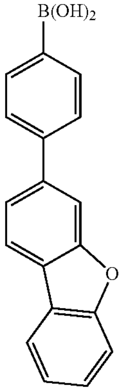 [SMILES: OB(O)c1ccc(-c2ccc3c(c2)oc2ccccc23)cc1] H2-A CAS2095370-50-4 | 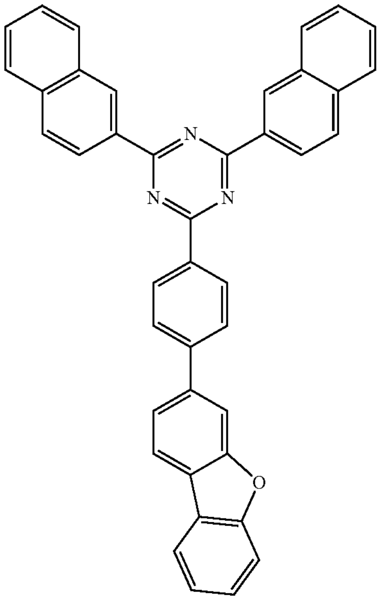 H2 | 70 |
| 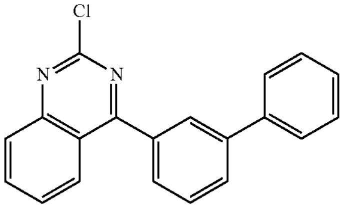 [SMILES: Clc1nc(-c2cccc(-c3ccccc3)c2)c2ccccc2n1] H3-B CAS2259353-95-0 | 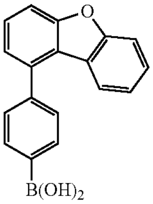 [SMILES: OB(O)c1ccc(-c2cccc3oc4ccccc4c23)cc1] H3-A CAS1413365-66-8 | 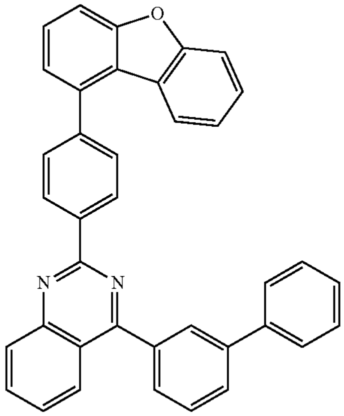 H3 | 68 |
| 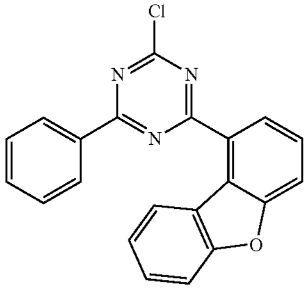 [SMILES: Clc1nc(-c2ccccc2)nc(-c2cccc3oc4ccccc4c23)n1] H4-B CAS1883265-32-4 | 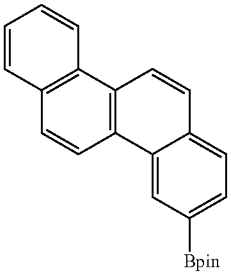 H4-A CAS1593236-00-0 | 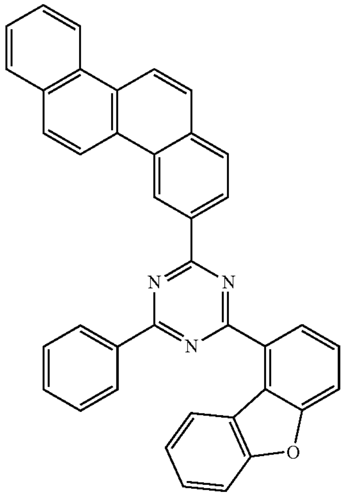 | 75 |

TABLE 3-continued
| Material 1 | Material 2 | Product | Yield % |
|---|---|---|---|
| 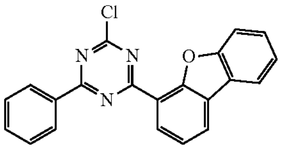 [SMILES: Clc1nc(-c2ccccc2)nc(-c2cccc3c2oc2ccccc23)n1]<br>H5-B<br>CAS1472729-25-1 | 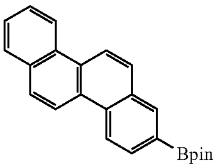<br>H5-A<br>CAS2764616-65-9 | H4<br>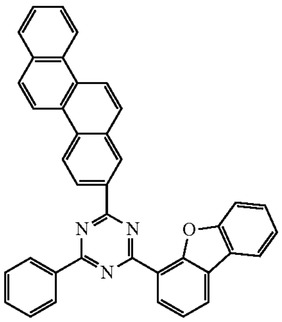 [SMILES: c1ccc(-c2nc(-c3ccc4c(ccc5c6ccccc6ccc45)c3)nc(-c3cccc4c3oc3ccccc34)n2)cc1]<br>H5 | 78 |
| 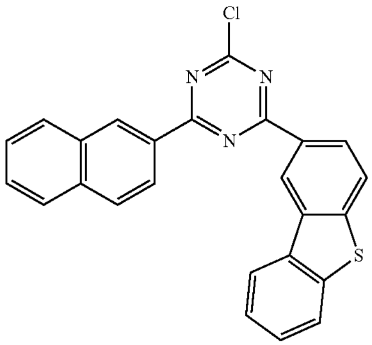 [SMILES: Clc1nc(-c2ccc3ccccc3c2)nc(-c2ccc3sc4ccccc4c3c2)n1]<br>H6-B<br>CAS2379260-71-4 | 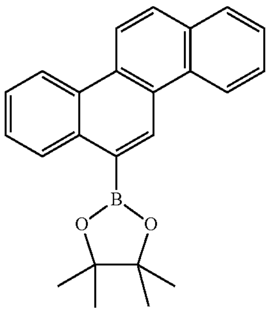 [SMILES: CC1(C)OB(c2cc3c4ccccc4ccc3c3ccccc23)OC1(C)C]<br>H6-A<br>CAS875916-80-6 | 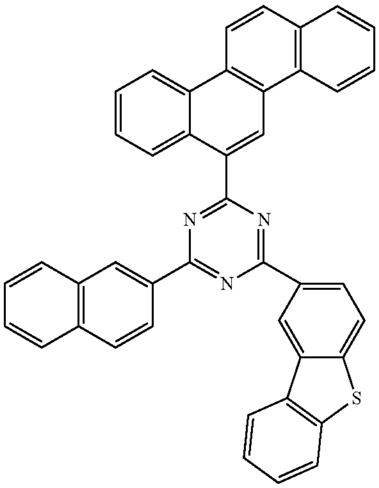 [SMILES: c1ccc2cc(-c3nc(-c4ccc5sc6ccccc6c5c4)nc(-c4cc5c6ccccc6ccc5c5ccccc45)n3)ccc2c1]<br>H6 | 75 |
| 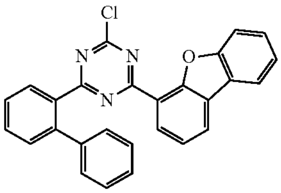 [SMILES: Clc1nc(-c2ccccc2-c2ccccc2)nc(-c2cccc3c2oc2ccccc23)n1]<br>H7-B<br>CAS2650504-90-6 | 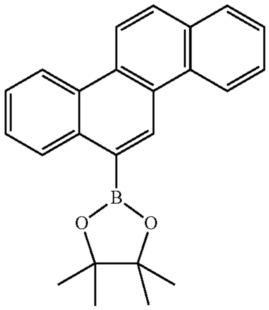 [SMILES: CC1(C)OB(c2cc3c4ccccc4ccc3c3ccccc23)OC1(C)C]<br>H7-A<br>CAS2640287-55-2 | 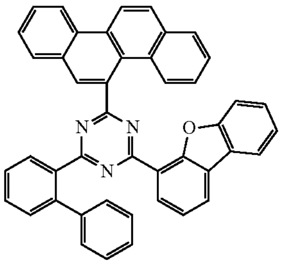 [SMILES: c1ccc(-c2ccccc2-c2nc(-c3cccc4c3oc3ccccc34)nc(-c3cc4ccccc4c4ccc5ccccc5c34)n2)cc1]<br>H7 | 76 |
TABLE 4
| | Elemental analysis | | HRMS (ESI) m/z $[M + H]^+$ | |
|---|---|---|---|---|
| Compound | Calcd. | Found | Calcd. | Found |
| H2 | C, 85.54; H, 4.38; N, 7.30; | C, 85.56; H, 4.40; N, 7.27; | 575.20 | 576.11 |
TABLE 4-continued
| | Elemental analysis | | HRMS (ESI) m/z $[M + H]^+$ | |
|---|---|---|---|---|
| Compound | Calcd. | Found | Calcd. | Found |
| H3 | C, 87.00; H, 4.61; N, 5.34; | C, 86.97; H, 4.60; N, 5.37; | 524.19 | 525.28 |

TABLE 4-continued

| | Elemental analysis | | HRMS (ESI) m/z [M + H]+ | |
|---|---|---|---|---|
| Compound | Calcd. | Found | Calcd. | Found |
| H4 | C, 85.23; H, 4.22; N, 7.65; | C, 85.40; H, 4.24; N, 7.46; | 549.63 | 550.68 |
| H5 | C, 85.23; H, 4.22; N, 7.65; | C, 85.41; H, 4.25; N, 7.44; | 549.63 | 550.71 |
| H6 | C, 83.88; H, 4.09; N, 6.82; S, 5.21; | C, 83.92; H, 4.11; N, 6.75; S, 5.22 | 615.75 | 616.48 |
| H7 | C, 86.38; H, 4.35; N, 6.72; | C, 86.40; H, 4.37; N, 6.68; | 625.73 | 626.71 |

Element Examples

An organic electroluminescence element (such as OLED) having a structure shown in the FIGURE with the following layer structure was provided: base (indium tin oxide (ITO, as an anode 1) coated glass substrate)/hole injection layer 2 (HIL)/hole transport layer 3 (HTL)/emitting layer 4 (EML)/electron transport layer 5 (ETL)/electron injection layer 6 (EIL), and the cathode 7 at last.

The materials needed to prepare OLED are listed below:

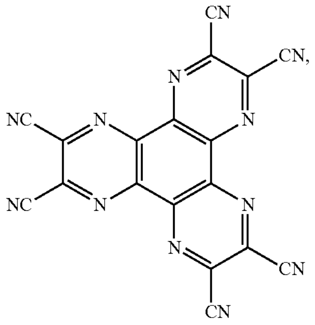

HAT(CN)6

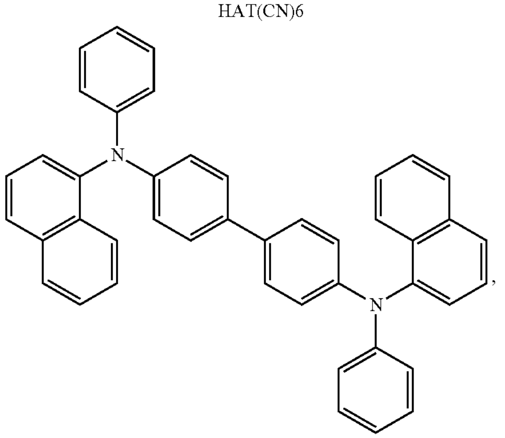

HT

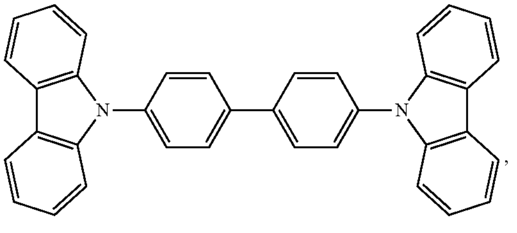

CBP

-continued

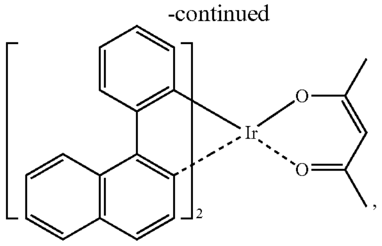

(piq)$_2$Ir(acac)

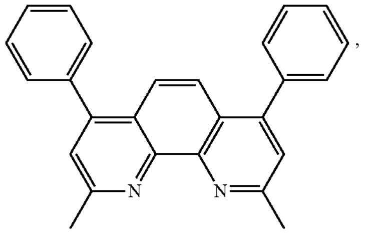

BPhen

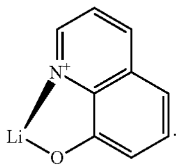

LiQ

The above-mentioned organic electroluminescence elements were prepared by the following steps:

(1) Cleaning the substrate: a glass substrate coated with transparent ITO layer (the anode 1) was ultrasonicated in an aqueous detergent (the content and concentration of the aqueous detergent: an ethylene glycol solvent of ≤10 percent by weight (wt %), triethanolamine of ≤1 wt %), washed in deionized water, degreased in an acetone/ethanol mixed solvent (volume ratio=1:1) by ultrasonication, baked in a clear environment until water was completely removed, and washed by ozone under ultraviolet light.

(2) Depositing organic emitting functional layers:

The glass substrate with the anode 1 was placed in a chamber, and the chamber was vacuumized until $1\times10^{-6}$ Pascal (Pa) to $2\times10^{-4}$ Pa, and a mixture of $HAT(CN)_6$ and HT (mass ratio of $HAT(CN)_6$ and HT is 3:97) was deposited on the anode 1 in vacuum to form a hole injection layer 2, in which the deposited thickness was 10 nanometers (nm).

A hole transport layer 3 was deposited on the hole injection layer 2, in which the deposited thickness was 80 nm.

An emitting layer 4 was deposited on the hole transport layer 3. Specifically, the preparation method was: the light-emitting host material and a guest material were co-deposited in vacuum, in which the total deposited thickness was 30 nm.

An electron transport layer 5 was deposited on the emitting layer 4. Specifically, the preparation method was: BPhen and LiQ were co-deposited in vacuum, in which the total deposited thickness was 30 nm.

An electron injection layer 6 was deposited on the electron transport layer 5, in which the total deposited thickness was 1 nm.

Al (as cathode 7) was deposited on the electron injection layer 6, in which the deposited thickness was 80 nm.

The materials (mat.) of each layer in the element and parameters such as thickness (thk.) of Element Examples 1 to 13 (E1 to E13) and Comparative Element Examples 1 to 13 (CE1 to CE13) are shown in Table 5.

TABLE 5

| No. | HIL mat./thk. | HTL mat./thk. | EML mat./thk. | ETL mat./thk. | EIL mat./thk. | Cath-ode mat./thk. |
|---|---|---|---|---|---|---|
| E1 | $HAT(CN)_6$: HT(mass ratio 3:97)/ 10 nm | HT/ 80 nm | compound 1': compound H1: $(piq)_2Ir(acac)$ (mass ratio 47.5:47.5:5)/ 30 nm | BPhen: LiQ (mass ratio 1:1)/ 30 nm | LiQ/ 1 nm | Al/ 80 nm |
| E2 | $HAT(CN)_6$: HT(mass ratio 3:97)/ 10 nm | HT/ 80 nm | compound 2': compound H1: $(piq)_2Ir(acac)$ (mass ratio 47.5:47.5:5)/ 30 nm | BPhen: LiQ (mass ratio 1:1)/ 30 nm | LiQ/ 1 nm | Al 80 nm |
| E3 | $HAT(CN)_6$: HT (mass ratio 3:97)/ 10 nm | HT/ 80 nm | compound 3': compound H1: $(piq)_2Ir(acac)$ (mass ratio 47.5:47.5:5)/ 30 nm | BPhen: LiQ (mass ratio 1:1)/ 30 nm | LiQ/ 1 nm | Al/ 80 nm |
| E4 | $HAT(CN)_6$: HT (mass ratio 3:97)/ 10 nm | HT/ 80 nm | compound 4': compound H1: $(piq)_2Ir(acac)$ (mass ratio 47.5:47.5:5)/ 30 nm | BPhen: LiQ (mass ratio 1:1)/ 30 nm | LiQ/ 1 nm | Al/ 80 nm |
| E5 | $HAT(CN)_6$: HT (mass ratio 3:97)/ 10 nm | HT/ 80 nm | compound 5': compound H2: $(piq)_2Ir(acac)$ (mass ratio 47.5:47.5:5)/ 30 nm | BPhen: LiQ (mass ratio 1:1)/ 30 nm | LiQ/ 1 nm | Al 80 nm |
| E6 | $HAT(CN)_6$: HT (mass ratio 3:97)/ 10 nm | HT/ 80 nm | compound 6': compound H2: $(piq)_2Ir(acac)$ (mass ratio 47.5:47.5:5)/ 30 nm | BPhen: LiQ (mass ratio 1:1)/ 30 nm | LiQ/ 1 nm | Al 80 nm |
| E7 | $HAT(CN)_6$: HT (mass ratio 3:97)/ 10 nm | HT/ 80 nm | compound 6': compound H3: $(piq)_2Ir(acac)$ (mass ratio 47.5:47.5:5)/ 30 nm | BPhen: LiQ (mass ratio 1:1)/ 30 nm | LiQ/ 1 nm | Al/ 80 nm |
| E8 | $HAT(CN)_6$: HT (mass ratio 3:97)/ 10 nm | HT/ 80 nm | compound 1': compound H4: $(piq)_2Ir(acac)$ (mass ratio 47.5:47.5:5)/ 30 nm | BPhen: LiQ (mass ratio 1:1)/ 30 nm | LiQ/ 1 nm | Al/ 80 nm |
| E9 | $HAT(CN)_6$: HT (mass ratio 3:97)/ 10 nm | HT/ 80 nm | compound 1': compound H5: $(piq)_2Ir(acac)$ (mass ratio 47.5:47.5:5)/ 30 nm | BPhen: LiQ (mass ratio 1:1)/ 30 nm | LiQ/ 1 nm | Al/ 80 nm |
| E10 | $HAT(CN)_6$: HT (mass ratio 3:97)/ 10 nm | HT/ 80 nm | compound 1': compound H6: $(piq)_2Ir(acac)$ (mass ratio 47.5:47.5:5)/ 30 nm | BPhen: LiQ (mass ratio 1:1)/ 30 nm | LiQ/ 1 nm | Al/ 80 nm |
| E11 | $HAT(CN)_6$: HT (mass ratio 3:97)/ 10 nm | HT/ 80 nm | compound 1': compound H7: $(piq)_2Ir(acac)$ (mass ratio 47.5:47.5:5)/ 30 nm | BPhen: LiQ (mass ratio 1:1)/ 30 nm | LiQ/ 1 nm | Al/ 80 nm |
| E12 | $HAT(CN)_6$: HT (mass ratio 3:97)/ 10 nm | HT/ 80 nm | compound 1': compound H1: $(piq)_2Ir(acac)$ (mass ratio 17:2:1)/30 nm | BPhen: LiQ (mass ratio 1:1)/ 30 nm | LiQ/ 1 nm | Al/ 80 nm |

TABLE 5-continued

| No. | HIL mat./thk. | HTL mat./thk. | EML mat./thk. | ETL mat./thk. | EIL mat./thk. | Cath-ode mat./thk. |
|---|---|---|---|---|---|---|
| E13 | $HAT(CN)_6$: HT (mass ratio 3:97)/ 10 nm | HT/ 80 nm | compound 1': compound H1: $(piq)_2Ir(acac)$ (mass ratio 38:57:5)/30 nm | BPhen: LiQ (mass ratio 1:1)/ 30 nm | LiQ/ 1 nm | Al/ 80 nm |
| CE1 | $HAT(CN)_6$: HT (mass ratio 3:97)/ 10 nm | HT/ 80 nm | compound H2: $(piq)_2Ir(acac)$ (mass ratio 95:5)/ 30 nm | BPhen: LiQ (mass ratio 1:1)/ 30 nm | LiQ/ 1 nm | Al/ 80 nm |
| CE2 | $HAT(CN)_6$: HT (mass ratio 3:97)/ 10 nm | HT/ 80 nm | compound 5': $(piq)_2Ir(acac)$ (mass ratio 95:5)/ 30 nm | BPhen: LiQ (mass ratio 1:1)/ 30 nm | LiQ/ 1 nm | Al/ 80 nm |
| CE3 | $HAT(CN)_6$: HT (mass ratio 3:97)/ 10 nm | HT/ 80 nm | compound H1: $(piq)_2Ir(acac)$ (mass ratio 95:5)/ 30 nm | BPhen: LiQ (mass ratio 1:1)/ 30 nm | LiQ/ 1 nm | Al/ 80 nm |
| CE4 | $HAT(CN)_6$: HT (mass ratio 3:97)/ 10 nm | HT/ 80 nm | compound 1': $(piq)_2Ir(acac)$ (mass ratio 95:5)/ 30 nm | BPhen: LiQ (mass ratio 1:1)/ 30 nm | LiQ/ 1 nm | Al/ 80 nm |
| CE5 | $HAT(CN)_6$: HT (mass ratio 3:97)/ 10 nm | HT/ 80 nm | compound 2': $(piq)_2Ir(acac)$ (mass ratio 95:5)/ 30 nm | BPhen: LiQ (mass ratio 1:1)/ 30 nm | LiQ/ 1 nm | Al/ 80 nm |
| CE6 | $HAT(CN)_6$: HT (mass ratio 3:97)/ 10 nm | HT/ 80 nm | compound 3': $(piq)_2Ir(acac)$ (mass ratio 95:5)/ 30 nm | BPhen: LiQ (mass ratio 1:1)/ 30 nm | LiQ/ 1 nm | Al/ 80 nm |
| CE7 | $HAT(CN)_6$: HT (mass ratio 3:97)/ 10 nm | HT/ 80 nm | compound 4': $(piq)_2Ir(acac)$ (mass ratio 95:5)/ 30 nm | BPhen: LiQ (mass ratio 1:1)/ 30 nm | LiQ/ 1 nm | Al/ 80 nm |
| CE8 | $HAT(CN)_6$: HT (mass ratio 3:97)/ 10 nm | HT/ 80 nm | compound 6': $(piq)_2Ir(acac)$ (mass ratio 95:5)/ 30 nm | BPhen: LiQ (mass ratio 1:1)/ 30 nm | LiQ/ 1 nm | Al/ 80 nm |
| CE9 | $HAT(CN)_6$: HT (mass ratio 3:97)/ 10 nm | HT/ 80 nm | compound H3: $(piq)_2Ir(acac)$ (mass ratio 95:5)/ 30 nm | BPhen: LiQ (mass ratio 1:1)/ 30 nm | LiQ/ 1 nm | Al/ 80 nm |
| CE10 | $HAT(CN)_6$: HT (mass ratio 3:97)/ 10 nm | HT/ 80 nm | compound H4: $(piq)_2Ir(acac)$ (mass ratio 95:5)/ 30 nm | BPhen: LiQ (mass ratio 1:1)/ 30 nm | LiQ/ 1 nm | Al/ 80 nm |
| CE11 | $HAT(CN)_6$: HT (mass ratio 3:97)/ 10 nm | HT/ 80 nm | compound H5: $(piq)_2Ir(acac)$ (mass ratio 95:5)/ 30 nm | BPhen: LiQ (mass ratio 1:1)/ 30 nm | LiQ/ 1 nm | Al/ 80 nm |
| CE12 | $HAT(CN)_6$: HT (mass ratio 3:97)/ 10 nm | HT/ 80 nm | compound H6: $(piq)_2Ir(acac)$ (mass ratio 95:5)/ 30 nm | BPhen: LiQ (mass ratio 1:1)/ 30 nm | LiQ/ 1 nm | Al/ 80 nm |
| CE13 | $HAT(CN)_6$: HT (mass ratio 3:97)/ 10 nm | HT/ 80 nm | compound H7: $(piq)_2Ir(acac)$ (mass ratio 95:5)/ 30 nm | BPhen: LiQ (mass ratio 1:1)/ 30 nm | LiQ/ 1 nm | Al/ 80 nm |

Characteristic Tests of Elements:

Instruments: the characteristics such as current, voltage, luminance, emission spectrum and the like of the elements of the above Element Examples 1 to 13 and Comparative Element Examples 1 to 13 were synchronously tested by PR 650 SpectraScan Colorimeter and Keithley K 2400 SourceMeter;

Conditions for testing electrooptical characteristics: a current density of 10 milliamperes/square centimeter ($mA/cm^2$) under room temperature;

Service life test: tested with a current density of 20 $mA/cm^2$ under room temperature, and the time period recorded when the luminance of the tested element was reduced to 980 of the original luminance (in hour).

The test results of the elements are shown in Table 6.

TABLE 6

| No. | Driving voltage (V) | Current efficiency (Cd/A) | Service life (h) |
|---|---|---|---|
| E1 | 3.98 | 17 | 210 |
| E2 | 3.88 | 19 | 232 |
| E3 | 3.97 | 16 | 195 |
| E4 | 4.04 | 17 | 205 |
| E5 | 4.07 | 17 | 190 |
| E6 | 4.01 | 16 | 198 |
| E7 | 4.05 | 17 | 183 |
| E8 | 3.00 | 30 | 268 |
| E9 | 3.35 | 28 | 250 |
| E10 | 3.46 | 29 | 244 |
| E11 | 3.92 | 19 | 226 |
| E12 | 4.01 | 16 | 196 |
| E13 | 3.98 | 17 | 203 |
| CE1 | 4.45 | 12 | 85 |
| CE2 | 4.41 | 10 | 89 |
| CE3 | 4.40 | 14 | 74 |
| CE4 | 4.43 | 9 | 80 |
| CE5 | 3.90 | 13 | 75 |
| CE6 | 4.01 | 15 | 90 |
| CE7 | 3.80 | 11 | 40 |
| CE8 | 4.44 | 13 | 88 |
| CE9 | 4.46 | 10 | 76 |
| CE10 | 4.40 | 11 | 78 |
| CE11 | 4.43 | 13 | 76 |
| CE12 | 4.50 | 16 | 69 |
| CE13 | 4.34 | 10 | 89 |

From Table 6, it is clear that the organic material composition of the present invention obviously prolongs the service life of the element. When the organic material composition is used as the material of an organic functional layer, the element has a lower driving voltage (4.07 voltages (V) or lower), a higher current efficiency (16 Candelas/Ampere (Cd/A) or more) and a longer service life (190 h or more).

By comparison with Element Examples 1-13 and Element Comparative Examples 1-13, it can be found that the components comprised in the organic material composition of the present invention have synergistic effect in lowering driving voltage, enhancing current efficiency and prolonging service life.

The applicant claims herein that even though the organic material composition of the present invention and the applications thereof are demonstrated by the above examples, the scope of the present invention is not limited by these examples. That is to say, it does not mean that the present invention has to be carried out based on the above examples. Those skilled in the art should understand that any improvement of the present invention, equivalent replacement of materials, addition of auxiliary components, selection of specific means and the like are all within the scope of protection and disclosure of the present invention.

What is claimed is:

1. An organic material composition, wherein the organic material composition comprises at least one compound having a structure represented by Formula 1 and at least one compound having a structure represented by Formula 2-1:

Formula 1

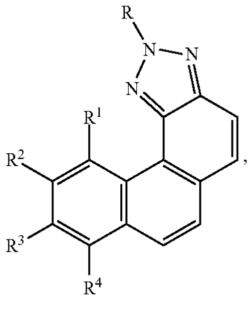

wherein, R is selected from hydrogen, deuterium, halogen, a cyano group, a substituted or unsubstituted C1-C30 alkyl group, a substituted or unsubstituted C3-C30 cycloalkyl group, a substituted or unsubstituted C6-C30 aryl group, and a substituted or unsubstituted C3-C30 heteroaryl group;

$R^1$ is $-L^1Ar^1$; $R^2$ is $-L^2Ar^2$; $R^3$ is $-L^3Ar^3$; $R^4$ is $-L^4Ar^4$;

$L^1$ to $L^4$ are each independently selected from a bond, a substituted or unsubstituted C6-C30 arylene group, and a substituted or unsubstituted C3-C30 heteroarylene group; and $Ar^1$ to $Ar^4$ are each independently selected from hydrogen, deuterium, halogen, a cyano group, a substituted or unsubstituted C6-C60 arylamino group, a substituted or unsubstituted C3-C60 heteroarylamino group, a substituted or unsubstituted C6-C60 aryl group, and a substituted or unsubstituted C3-C60 heteroaryl group;

Formula 2-1

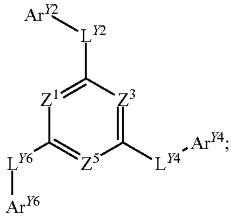

wherein at least two of $Z^1$, $Z^3$ and $Z^5$ are N;

wherein, in $Z^1$, $Z^3$ and $Z^5$, $Z^1$ and $Z^3$ are N, and $Z^5$ is $CL^{Y5}Ar^{Y5}$, in which $L^{Y5}Ar^{Y5}$ and $L^{Y6}Ar^{Y6}$ are present individually without forming a ring, or joined to form a substituted or unsubstituted benzene ring; or $Z^1$, $Z^3$, and $Z^5$ are N; and wherein, $Ar^{Y2}$, $Ar^{Y4}$, $Ar^{Y5}$ and $Ar^{Y6}$ are each independently selected from hydrogen, deuterium, halogen, a cyano group, and a group selected from a phenyl group, a biphenylyl group, a terphenylyl group, a naphthyl group, a phenylnaphthyl group, a naphthylphenyl group, a triphenylenylene group, an anthryl group, a phenanthryl group, a chrysenyl group, each of which is substituted or unsubstituted; and a group represented by Formula 3:

Formula 3

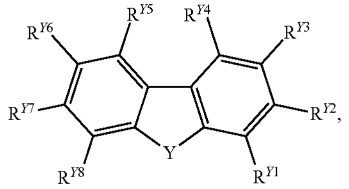

Y is selected from O, S, and $CR^{W1}R^{W2}$;

when at least one of $Ar^{Y2}$, $Ar^{Y4}$, $Ar^{Y5}$ and $Ar^{Y6}$ is selected from Formula 3, any one of $R^{Y1}$ to $R^{Y8}$, $R^{W1}$ and $R^{W2}$ in Formula 3 is connected to $L^{Y2}$, $L^{Y4}$ or $L^{Y6}$ in Formula 2-1 by chemical bonding;

$Ar^{Y2}$, $Ar^{Y4}$, $Ar^{Y5}$ and $Ar^{Y6}$ are the same or different;

$R^{Y1}$ to $R^{Y8}$ are each independently selected from hydrogen, deuterium, halogen, a cyano group, a substituted or unsubstituted C1-C30 alkyl group, a C1-C30 alkyl group in which one or more methylene groups are independently substituted by —O— and/or —S— in a manner that O atom and/or S atom are not adjacent to each other, a substituted or unsubstituted C7-C30 arylalkyl group, a substituted or unsubstituted C6-C30 aryl group, a substituted or unsubstituted C3-C30 heteroaryl group, a substituted or unsubstituted C4-C30 heteroarylalkyl group, a substituted or unsubstituted C3-C30 cycloalkyl group, a substituted or unsubstituted C3-C30 heterocycloalkyl group, a substituted or unsubstituted C3-C30 cycloalkenyl group, a substituted or unsubstituted C1-C30 alkoxy group, and a substituted or unsubstituted C6-C30 aryloxy group;

$R^{Y1}$ to $R^{Y8}$ are present individually without forming a ring, or any adjacent two of $R^{Y1}$ to $R^{Y8}$ joined to form a ring A, and the ring A is a substituted or unsubstituted C6-C30 aromatic ring;

$R^{W1}$ and $R^{W2}$ are selected from a substituted or unsubstituted C1-C30 alkyl group, and a substituted or unsubstituted C6-C30 aryl group;

$L^{Y2}$, $L^{Y4}$, $L^{Y5}$ and $L^{Y6}$ are each independently selected from a bond, a substituted or unsubstituted C6-C30 arylene group, and a substituted or unsubstituted C3-C30 heteroarylene group.

2. The organic material composition according to claim 1, wherein in Formula 1, at least one of $Ar^1$ to $Ar^4$ is a group represented by Formula b:

Formula b

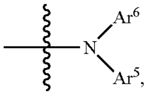

$Ar^5$ and $Ar^6$ are each independently selected from a substituted or unsubstituted C6-C30 aryl group, and a substituted or unsubstituted C3-C30 heteroaryl group.

3. The organic material composition according to claim 1, wherein in Formula 1, at least one of $Ar^1$ to $Ar^4$ is

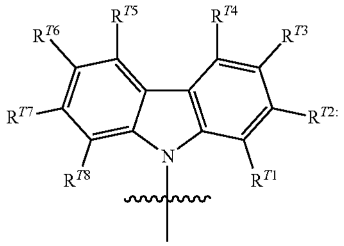

the remaining ones of $Ar^1$ to $Ar^4$ are each independently selected from hydrogen, deuterium, and a group selected from a phenyl group, a naphthyl group, a biphenylyl group, a terphenylyl group, a phenanthryl group, a fluoranthenyl group, a triphenylenylene group, a dimethylfluorenyl group, a diphenylfluorenyl group, a spiro-bifluorenyl group, a benzodimethylfluorenyl group, a benzodiphenylfluorenyl group, a benzo-spiro-bifluorenyl group, a dibenzofuryl group, a dibenzothiophenyl group, a carbazolyl group, a benzocarbazolyl group, and a dibenzocarbazolyl group, each of which is substituted or unsubstituted;

$R^{T1}$ to $R^{T8}$ are each independently selected from hydrogen, deuterium, halogen, a cyano group, a substituted or unsubstituted C1-C30 alkyl group, a C1-C30 alkyl group in which one or more methylene groups are independently substituted by —O— and/or —S— in a manner that O atom and/or S atom are not adjacent to each other, a substituted or unsubstituted C7-C30 arylalkyl group, a substituted or unsubstituted C6-C30 aryl group, a substituted or unsubstituted C3-C30 heteroaryl group, a substituted or unsubstituted C4-C30 heteroarylalkyl group, a substituted or unsubstituted C3-C30 cycloalkyl group, a substituted or unsubstituted C3-C30 heterocycloalkyl group, a substituted or unsubstituted C3-C30 cycloalkenyl group, a substituted or unsubstituted C1-C30 alkoxy group, and a substituted or unsubstituted C6-C30 aryloxy group;

$R^{T1}$ to $R^{T8}$ are present individually without forming a ring, or any adjacent two of $R^{T1}$ to $R^{T8}$ joined to form a ring B, and the ring B is a substituted or unsubstituted C6-C30 aromatic ring.

4. The organic material composition according to claim 1, wherein in Formula 1, R is selected from a phenyl group and a biphenylyl group, each of which is substituted or unsubstituted;

at least one of $R^1$, $R^2$, $R^3$ and $R^4$ is hydrogen;

when $R^1$, $R^2$, $R^3$ or $R^4$ is not hydrogen, $L^1$ to $L^4$ are each independently selected from a bond, a substituted or unsubstituted phenylene group, a substituted or unsubstituted naphthylene group, a substituted or unsubstituted biphenylene group, and a substituted or unsubstituted terphenylene group; and at least one of $Ar^1$ to $Ar^4$ is a group represented by Formula b, and Formula b is any one selected from b-1, b-2, b-3, b-4, b-5 and b-6 as below:

b-1

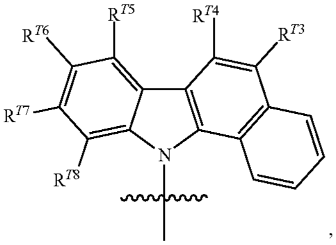

, b-2

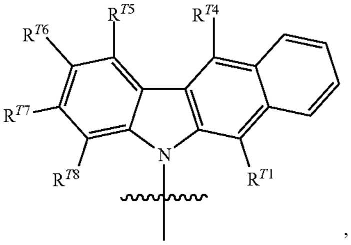

, b-3

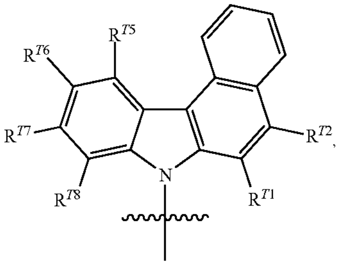

b-4

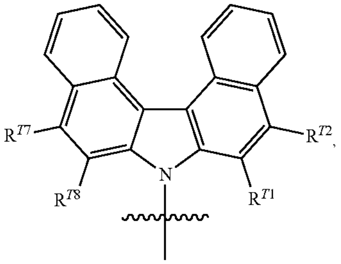

b-5

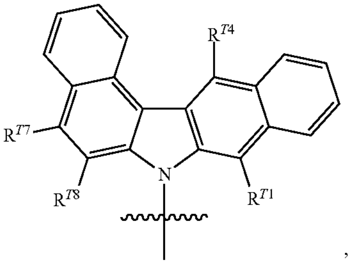

, and

-continued b-6

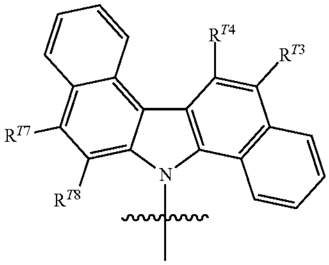

.

$R^{T1}$ to $R^{T8}$ are each independently selected from hydrogen, deuterium, and a group selected from a methyl group, an ethyl group, a tert-butyl group, an adamantly, a phenyl group, a biphenylyl group, a terphenylyl group, a naphthyl group, a phenanthryl group, an anthryl group, a triphenylenylene group, a phenylnaphthyl group, a naphthylphenyl group, a pyridyl group, a bipyridyl group, a dibenzofuryl group, a dibenzothiophenyl group, a benzonaphthofuryl group, a benzonaphthothiophenyl group, a dinaphthofuryl group, a dinaphthothiophenyl group, a dibenzofurylphenyl group, a dibenzothiophenylphenyl group, a dimethylfluorenyl group, a benzodimethylfluorenyl group, a diphenylfluorenyl group, a spiro-bifluorenyl group, and a dimethylfluorenylphenyl group, each of which is substituted or unsubstituted;

$Ar^1$ to $Ar^4$ are each independently selected from hydrogen, deuterium, and a group selected from a phenyl group, a naphthyl group, a biphenylyl group, a terphenylyl group, a phenanthryl group, a fluoranthenyl group, a triphenylenylene group, a dimethylfluorenyl group, a diphenylfluorenyl group, a spiro-bifluorenyl group, a benzodimethylfluorenyl group, a benzodiphenylfluorenyl group, a benzo-spiro-bifluorenyl group, a dibenzofuryl group, a dibenzothiophenyl group, a carbazolyl group, a benzocarbazolyl group, and a dibenzocarbazolyl group, each of which is substituted or unsubstituted.

5. The organic material composition according to claim 1, wherein the compound having a structure represented by Formula 1 is selected from the following compounds:

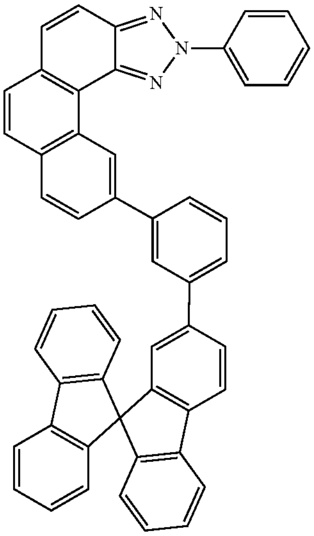

-continued
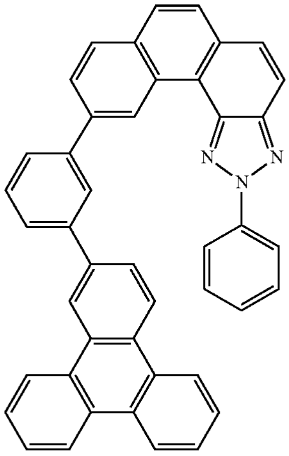
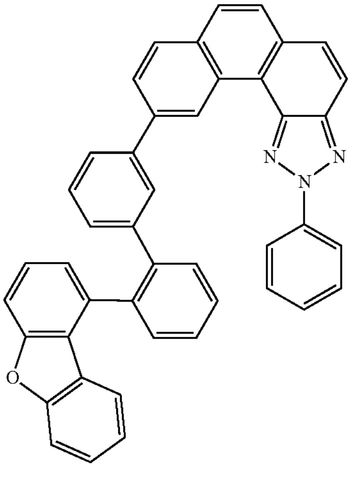
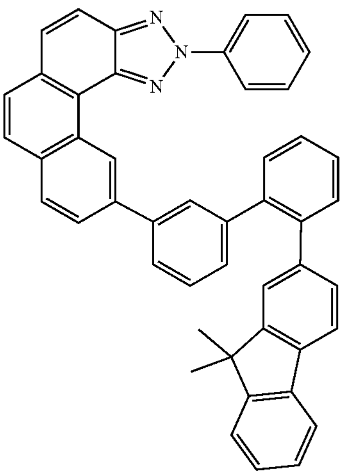
-continued
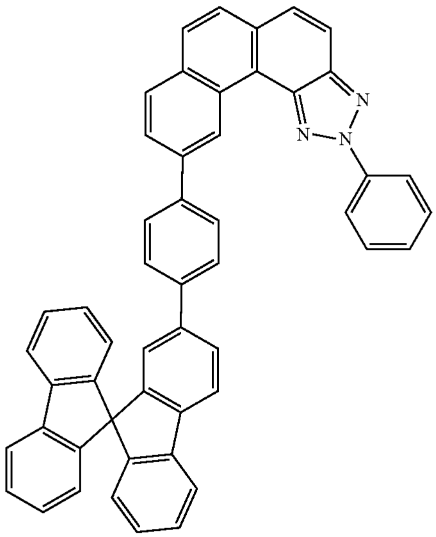
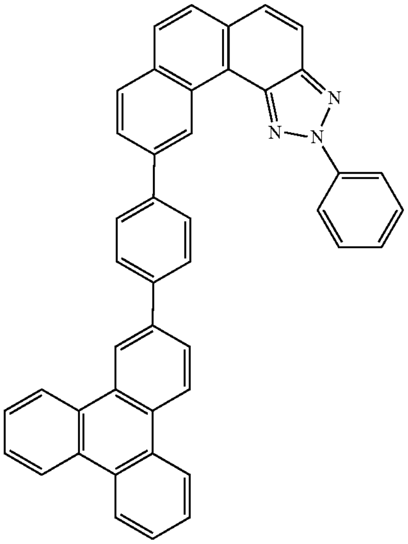
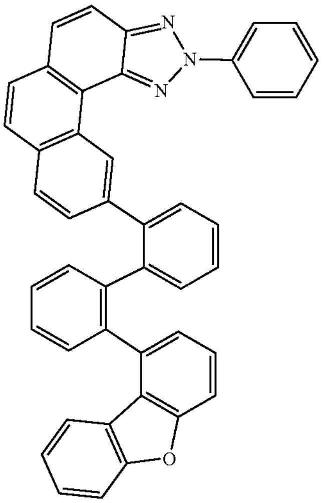

-continued
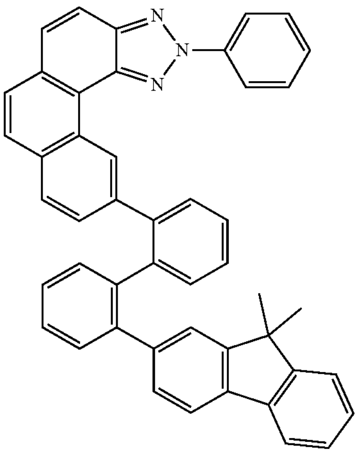
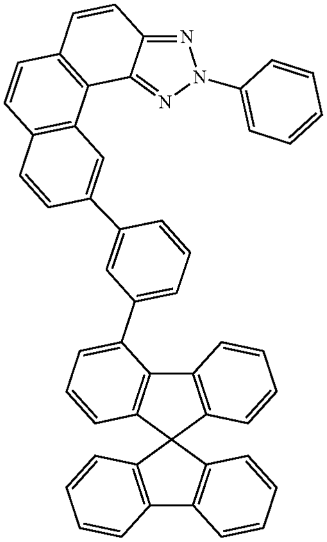
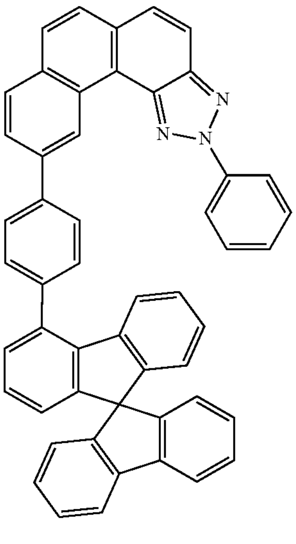
-continued
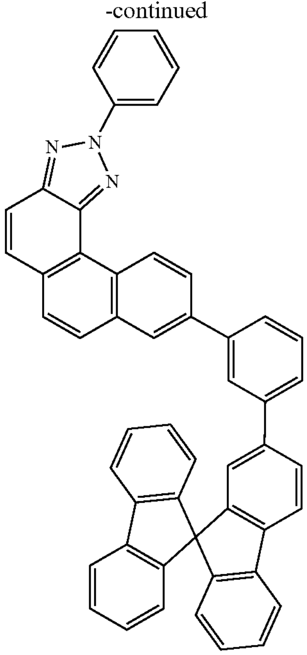
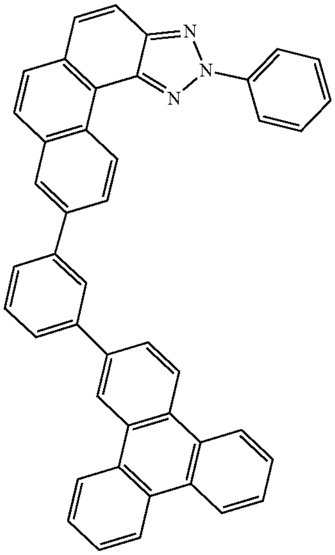

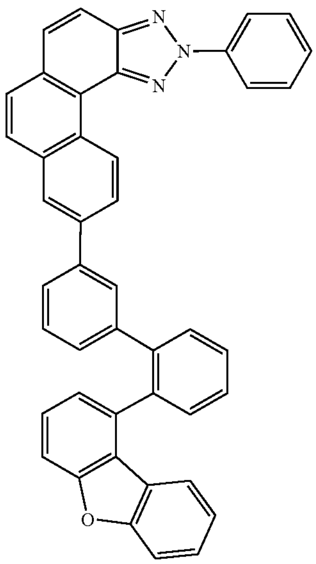
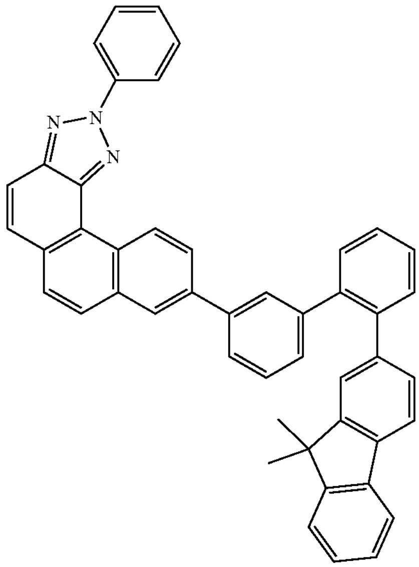
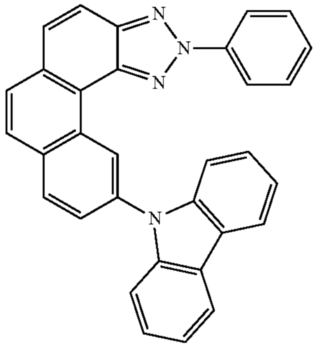
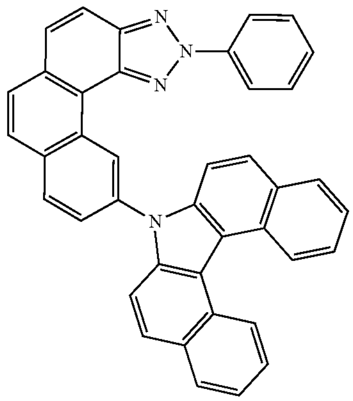
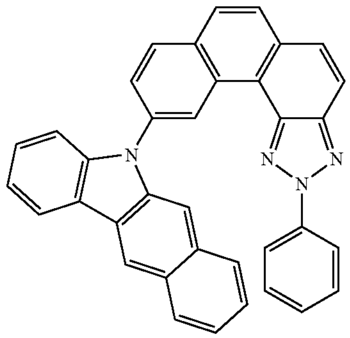
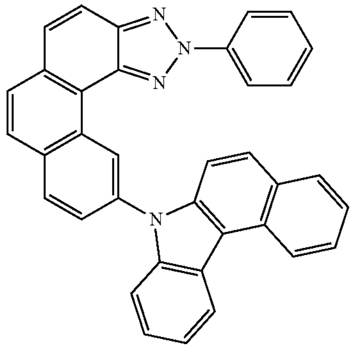
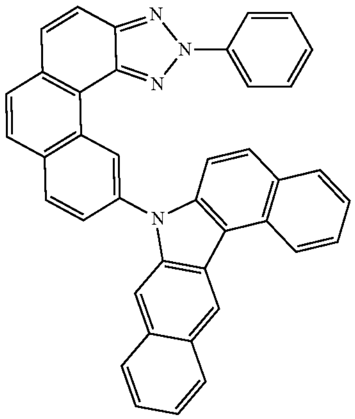

-continued
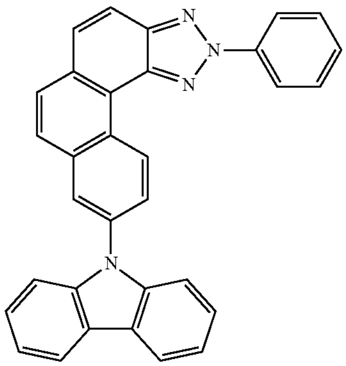
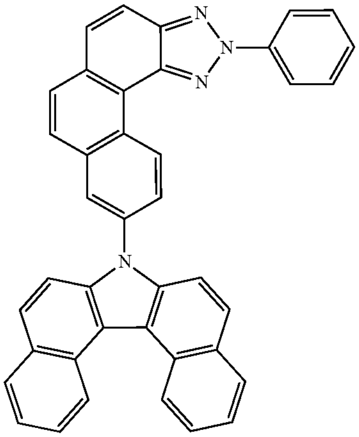
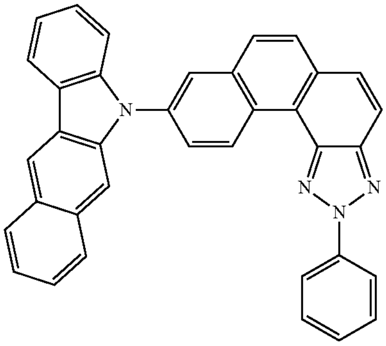
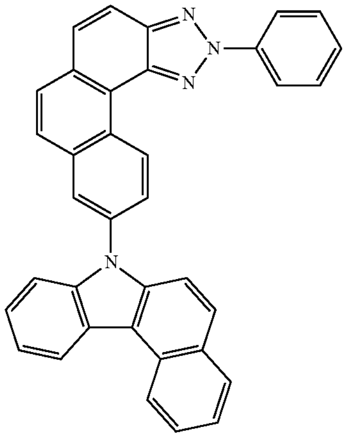
-continued
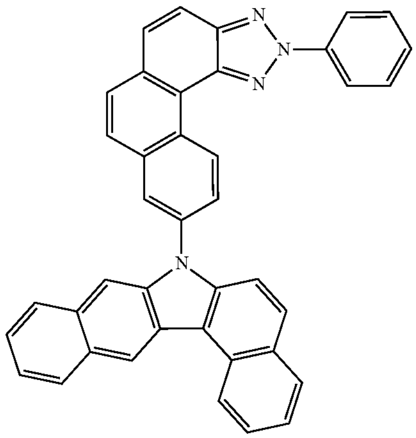
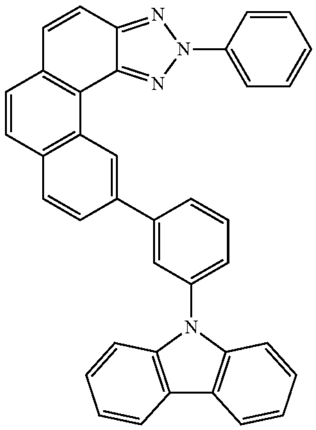
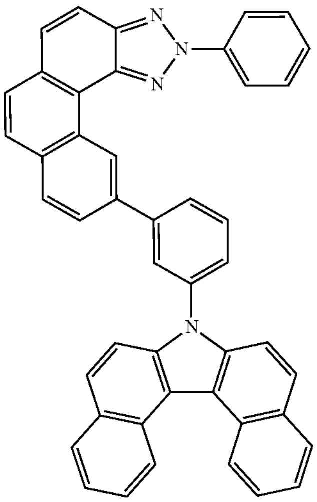

-continued
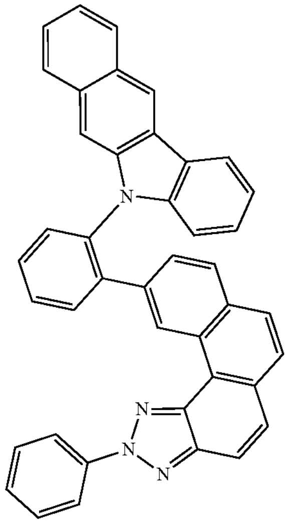
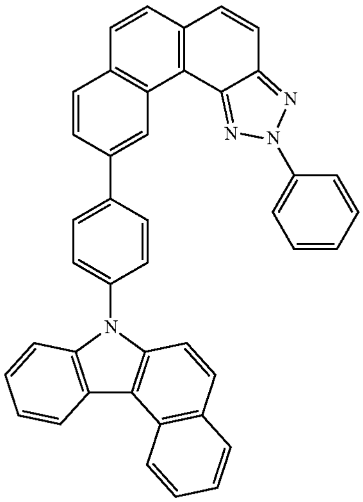
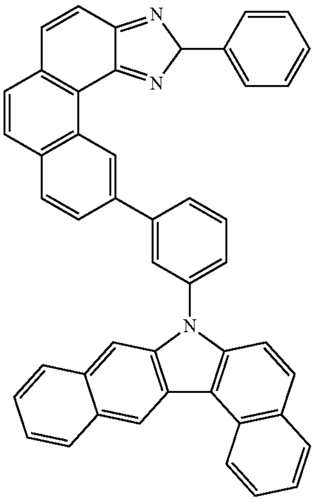
-continued
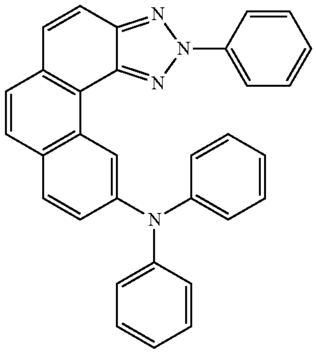
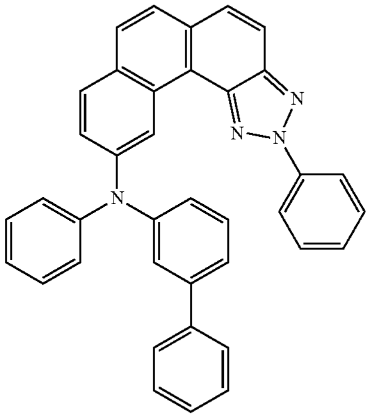
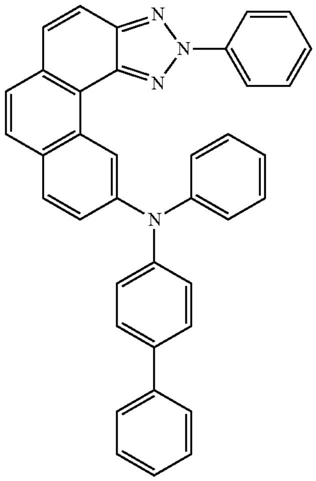
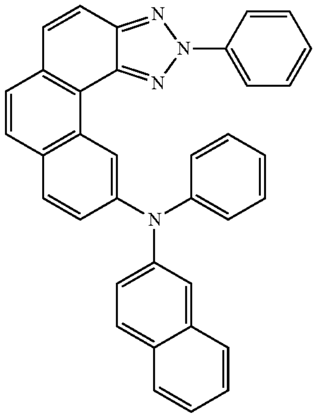

-continued
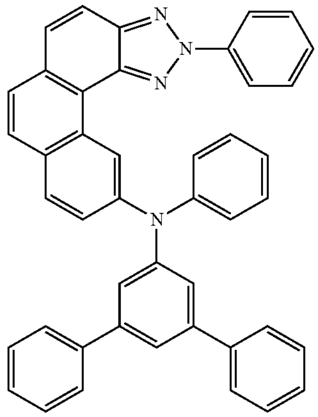
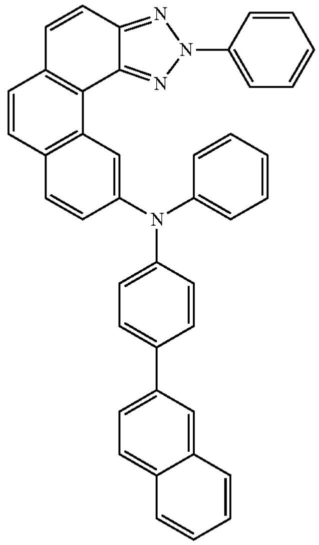
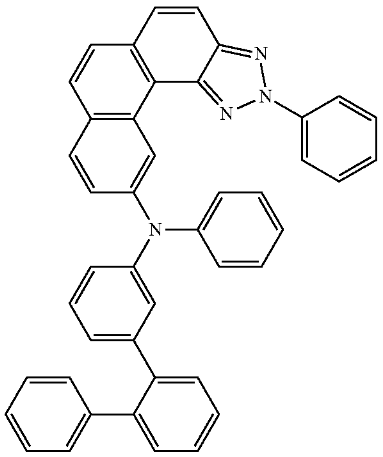
-continued
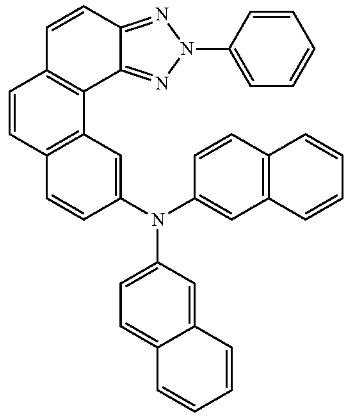
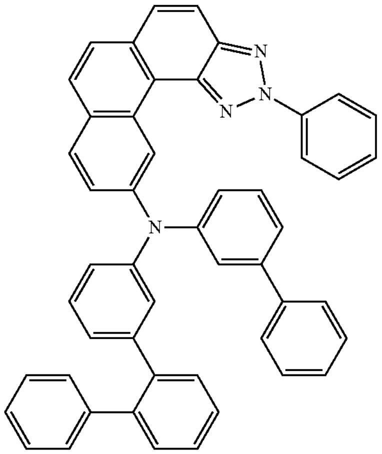
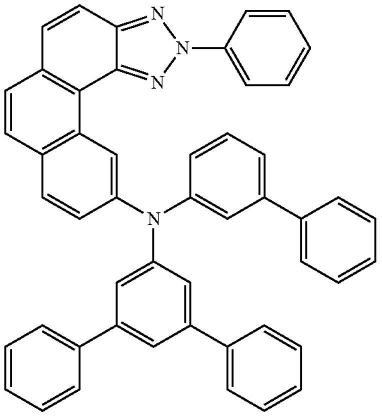
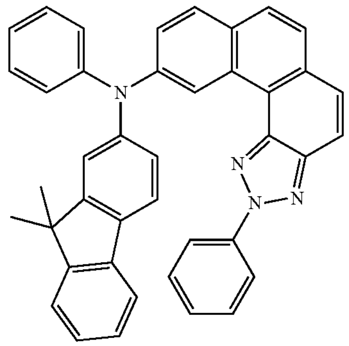

-continued
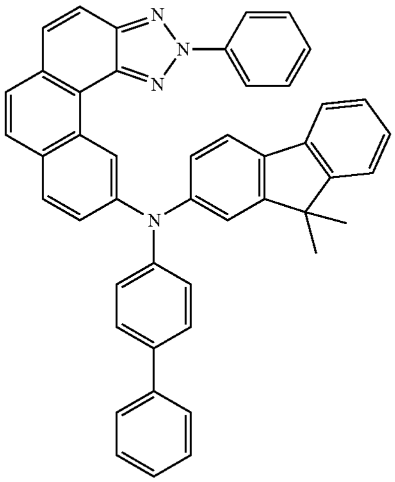
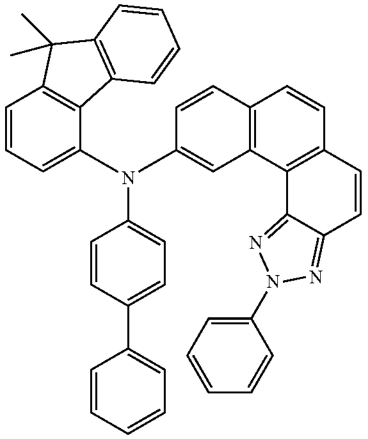
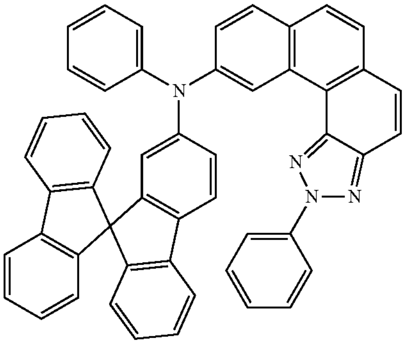
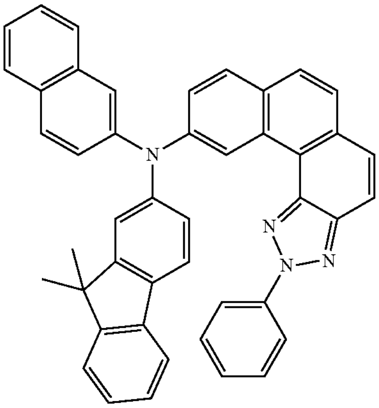
-continued
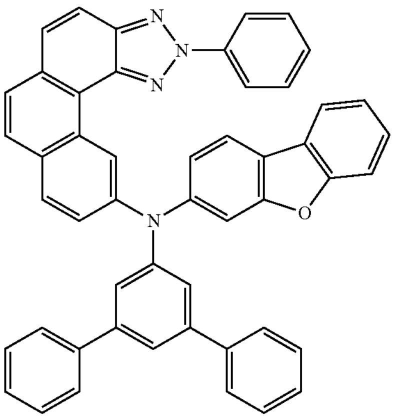
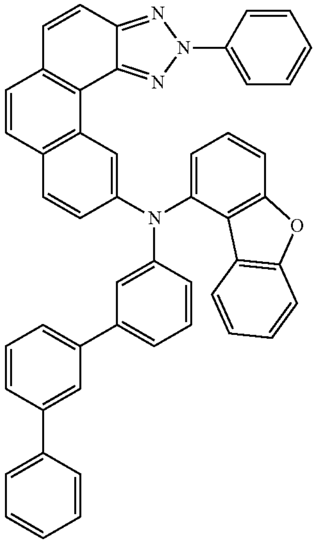
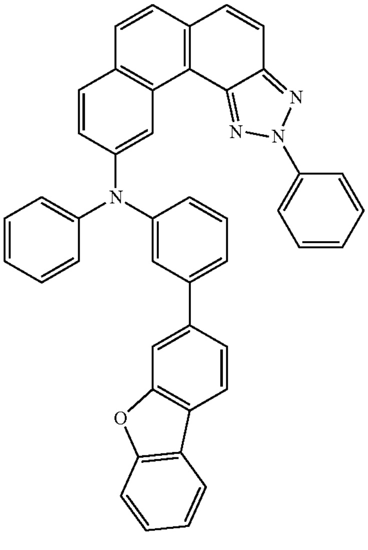

-continued
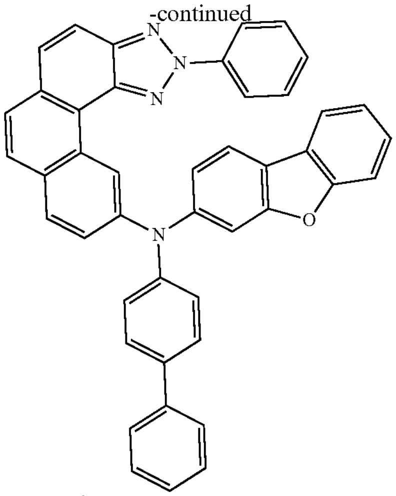
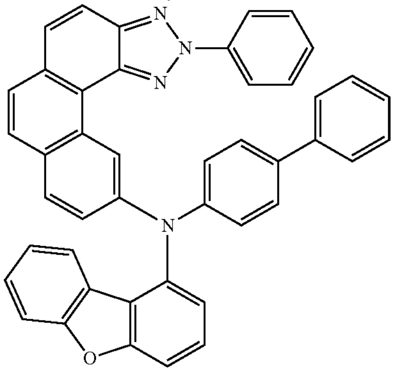
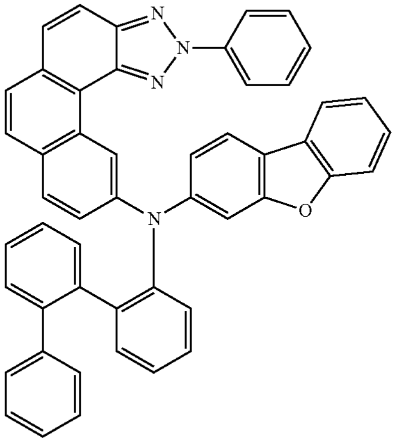
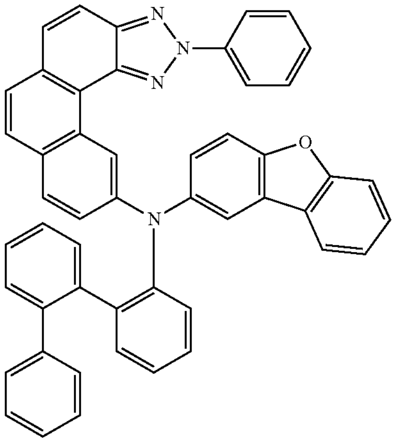
-continued
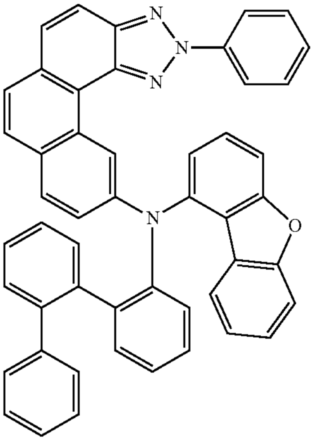
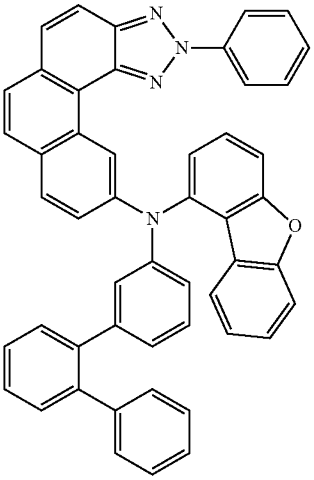
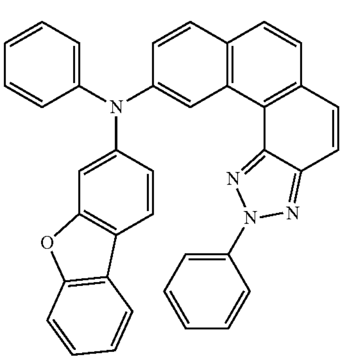

-continued
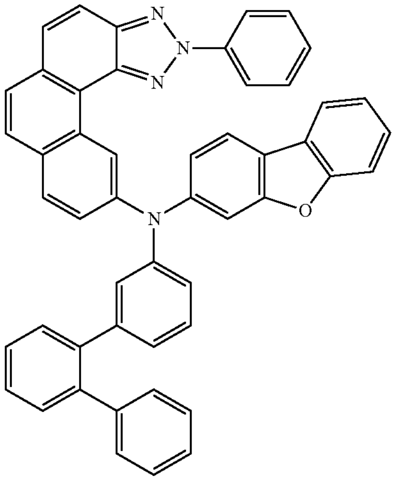
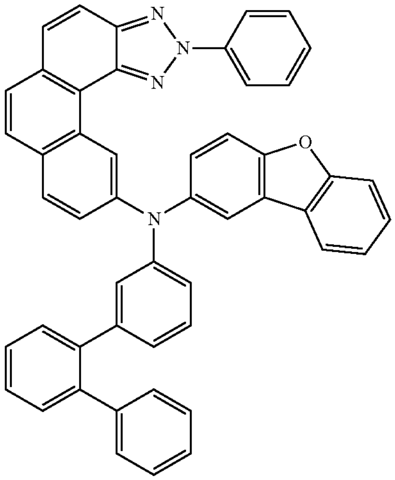
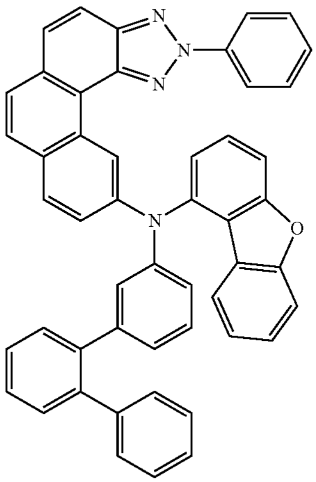
-continued
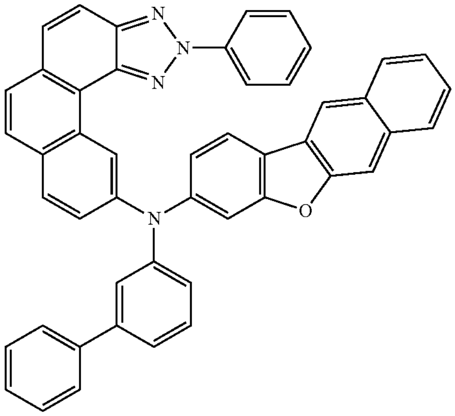
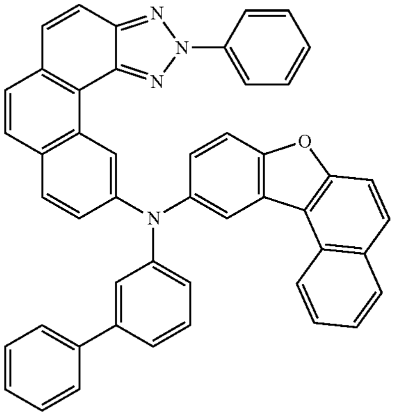
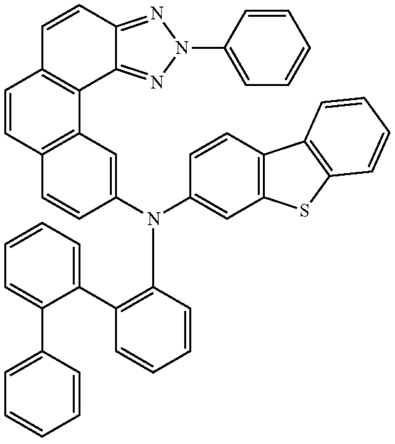
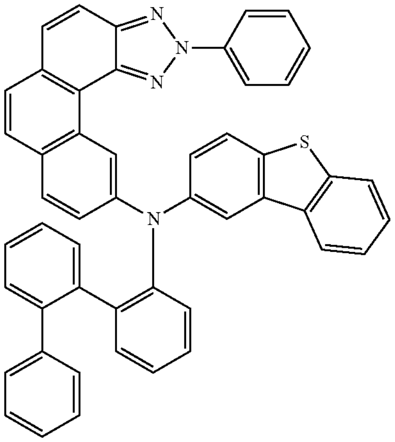

-continued
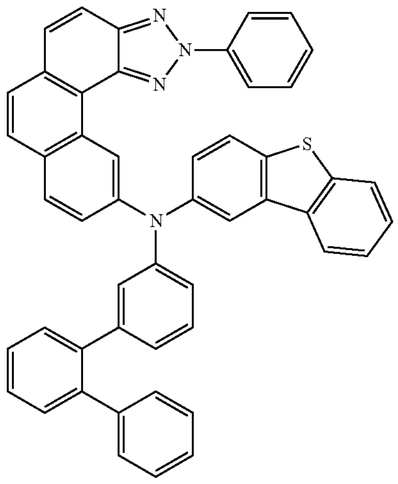
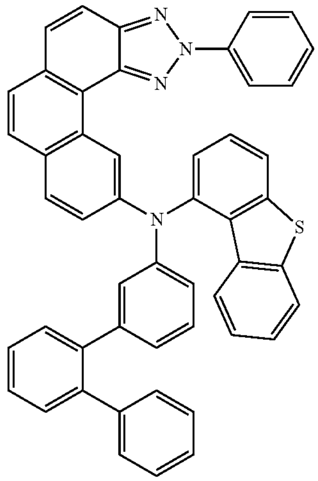
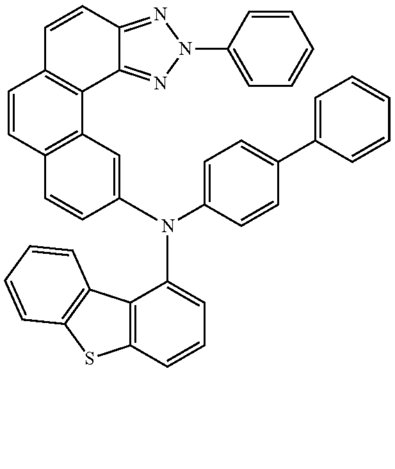
-continued
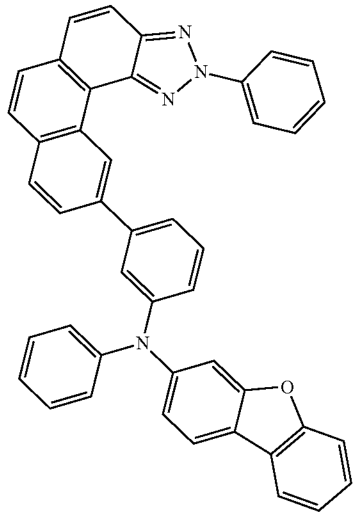
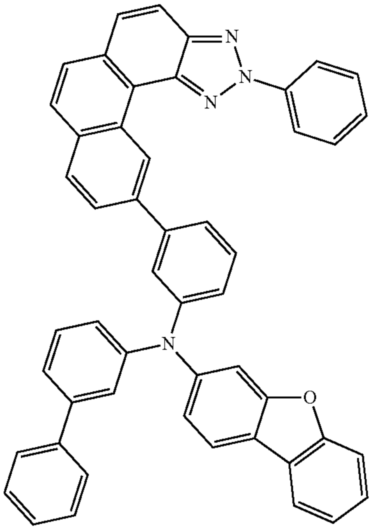
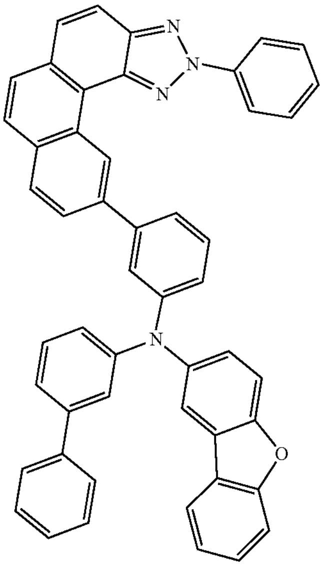

-continued
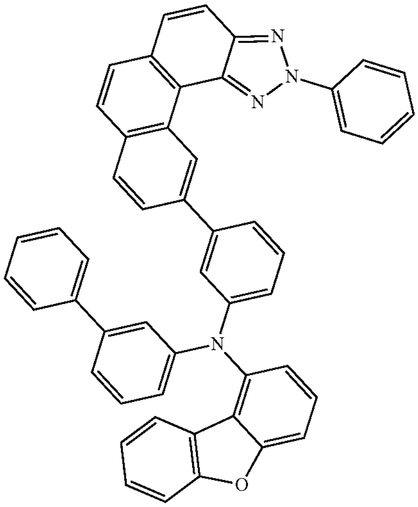
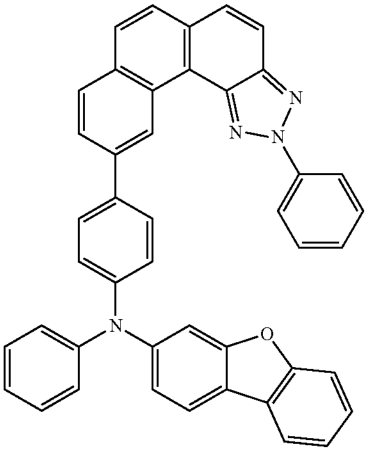
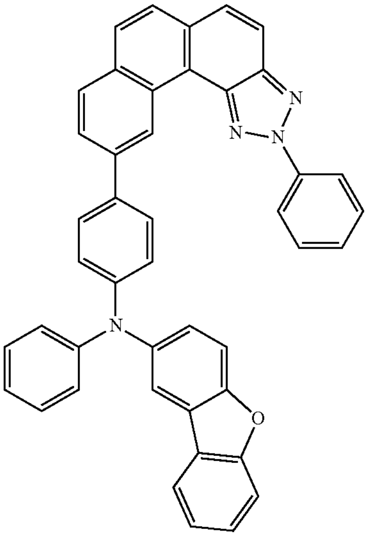
-continued
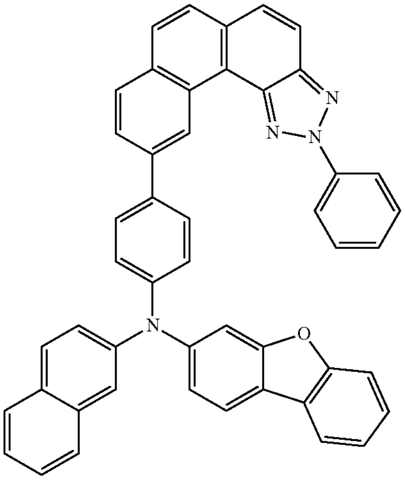
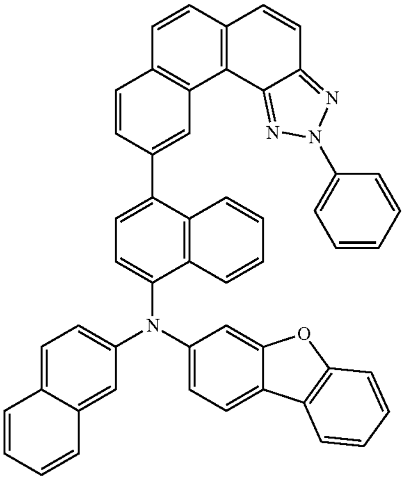
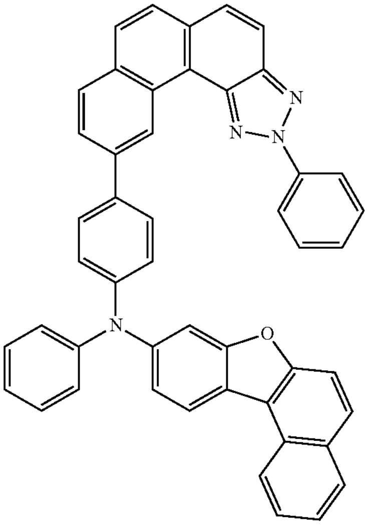

-continued
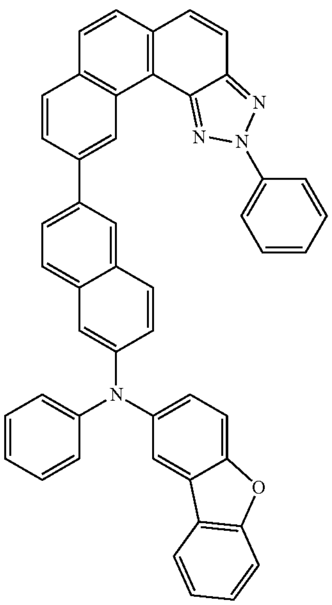
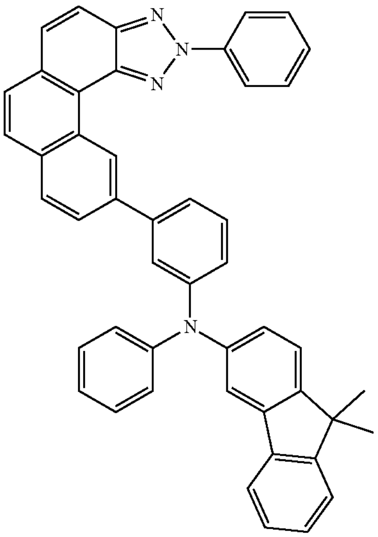
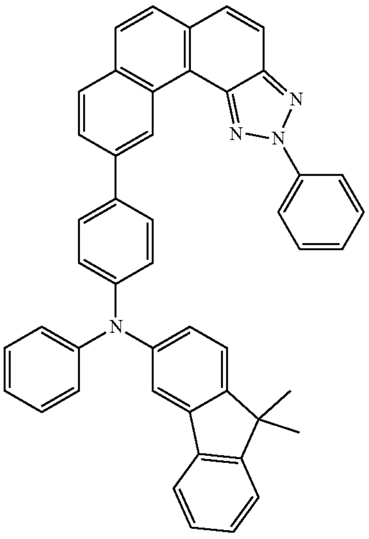
-continued
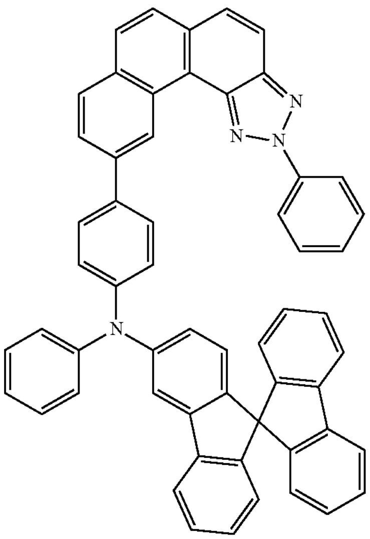
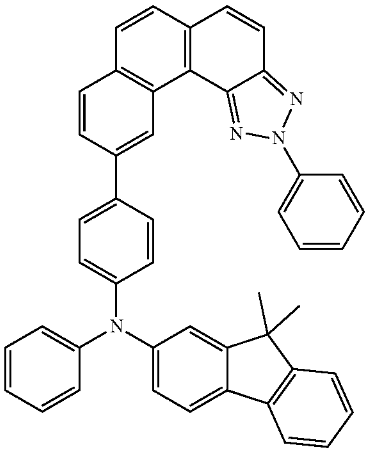
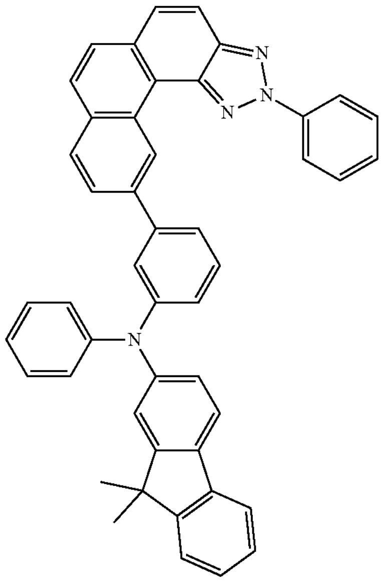

-continued
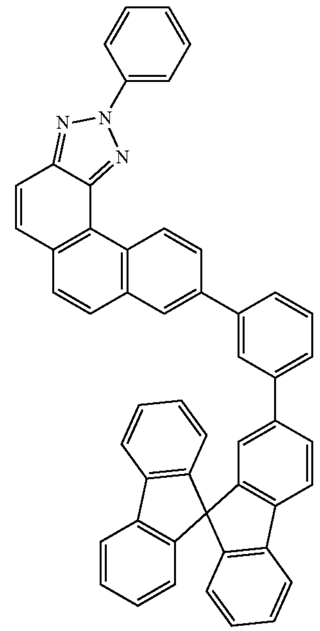
-continued
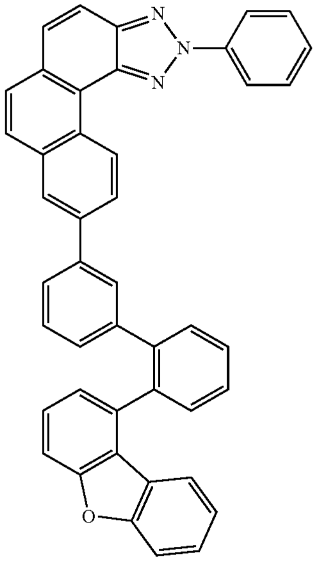
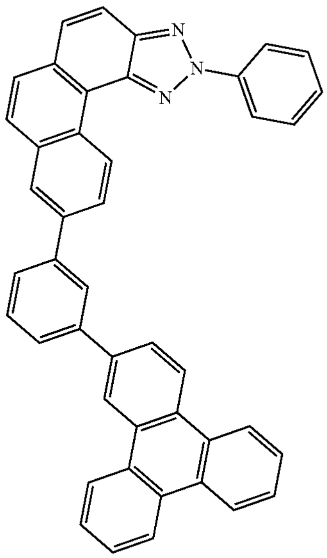
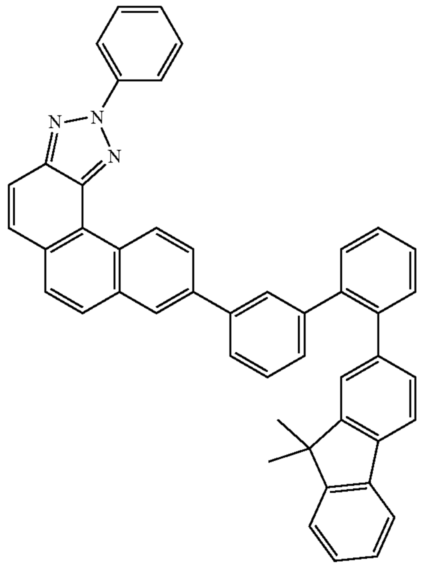

-continued
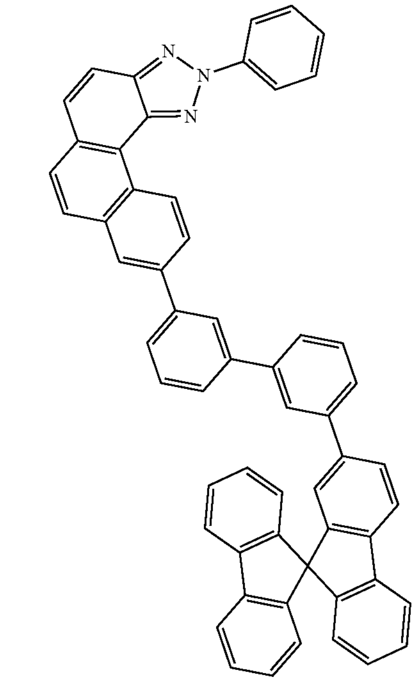
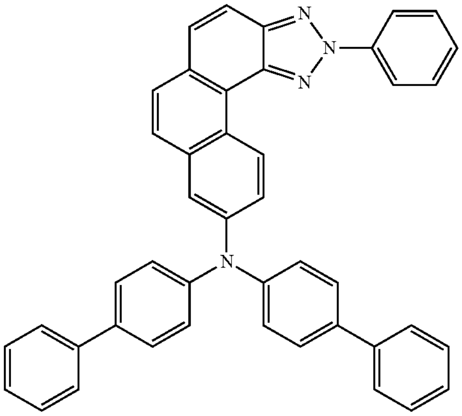
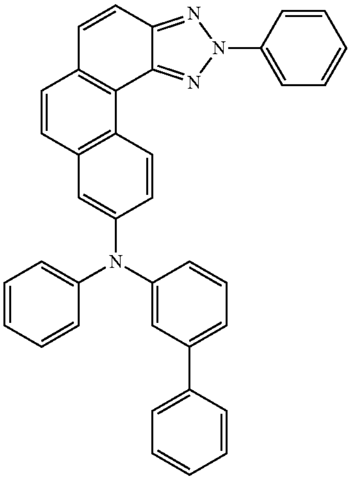
-continued
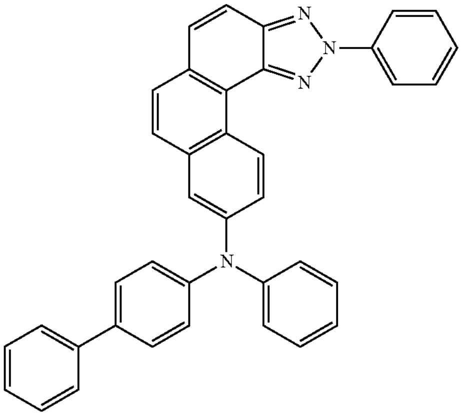
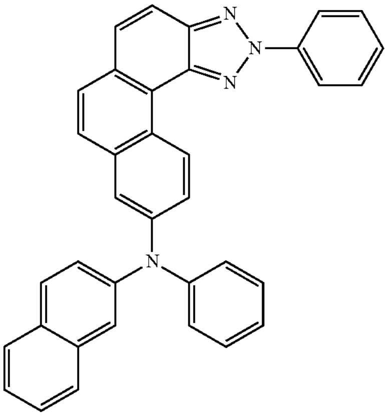
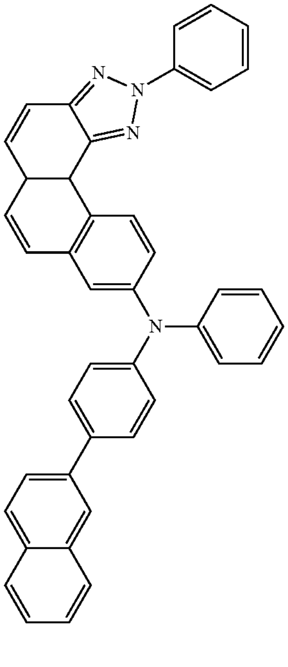

-continued
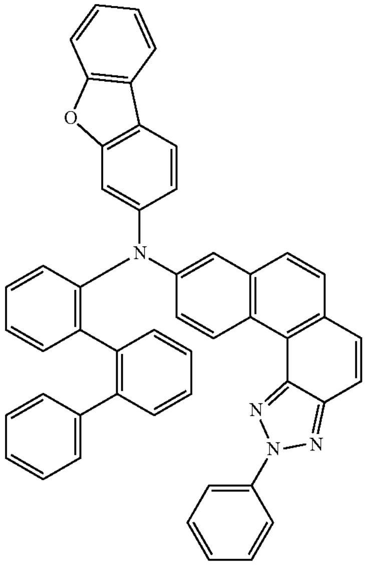
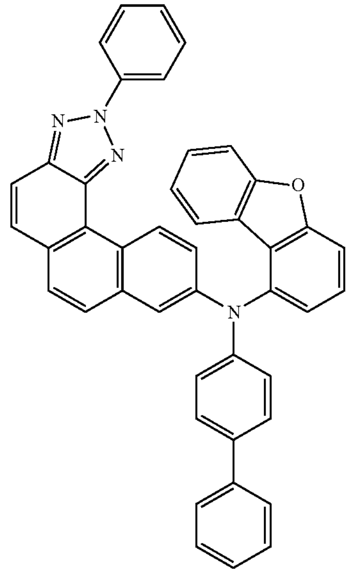
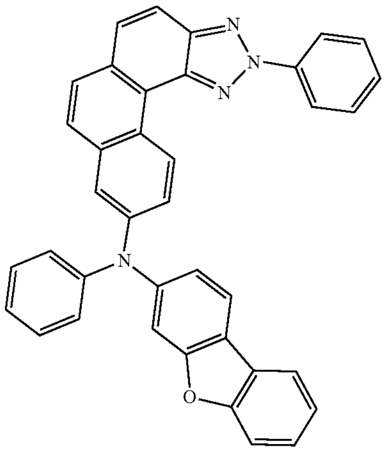
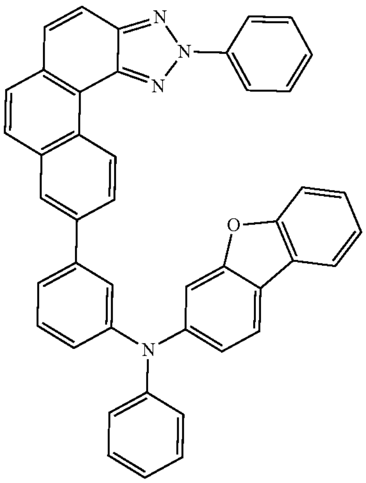
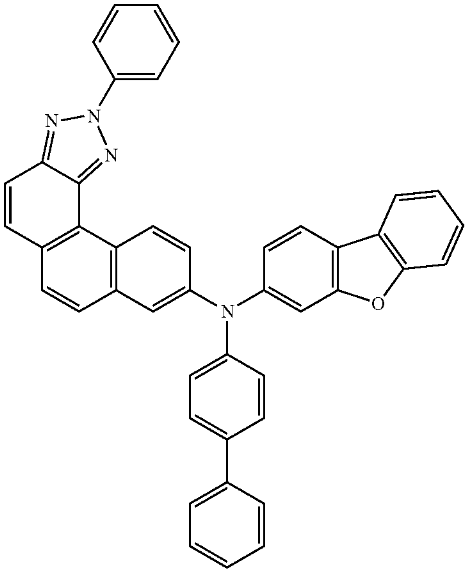
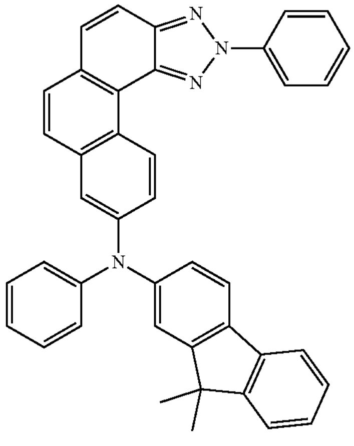
-continued -continued
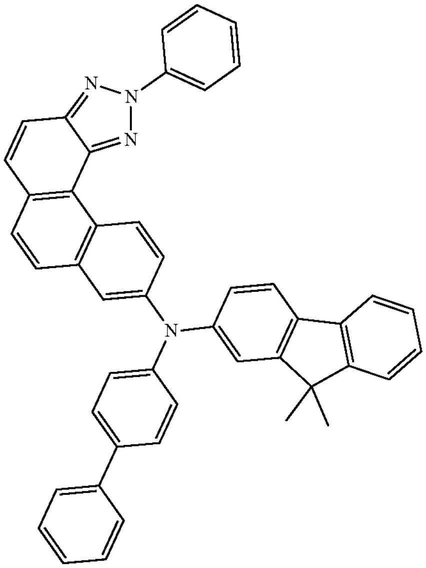
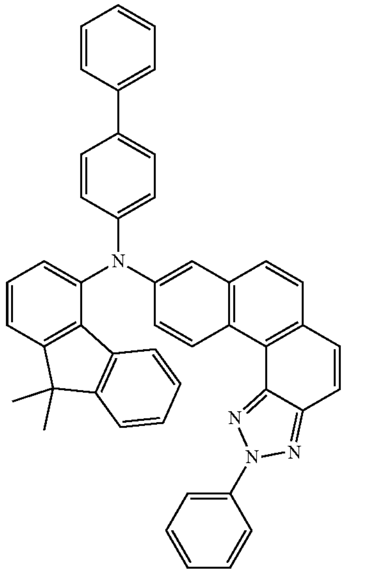
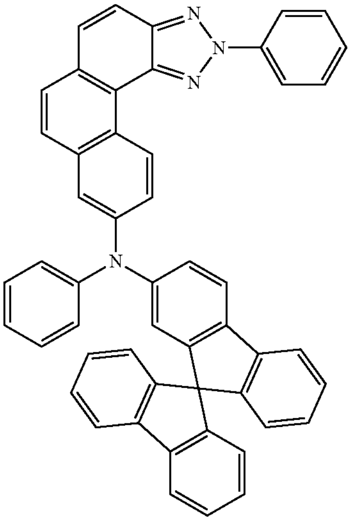
-continued
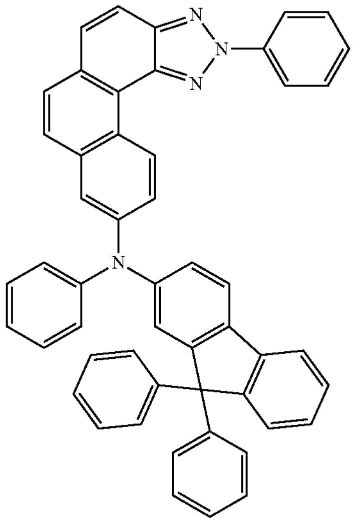
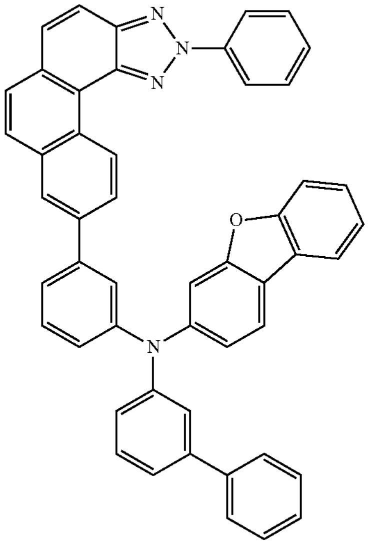
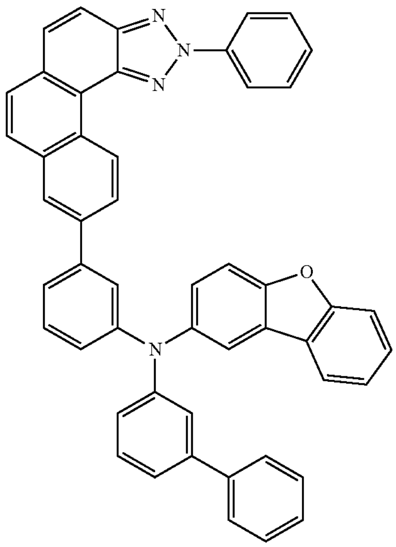

-continued
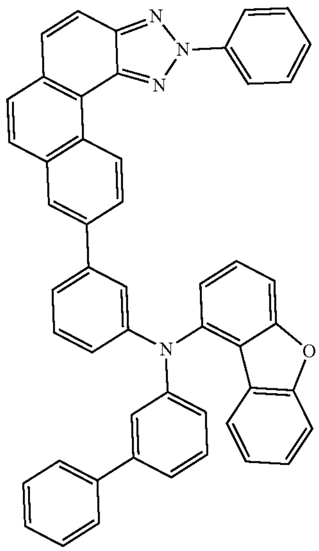
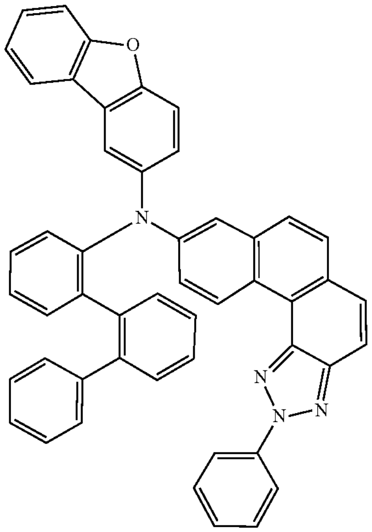
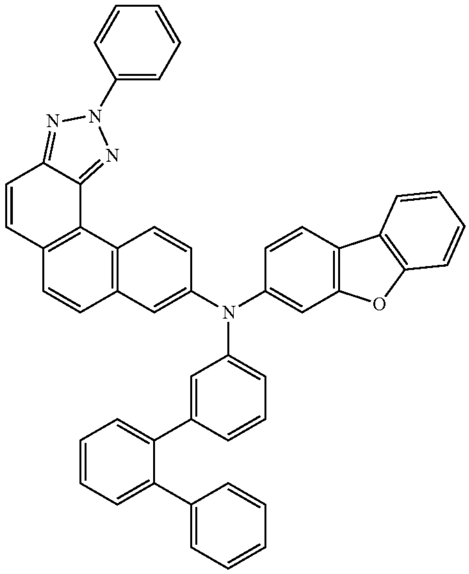
-continued
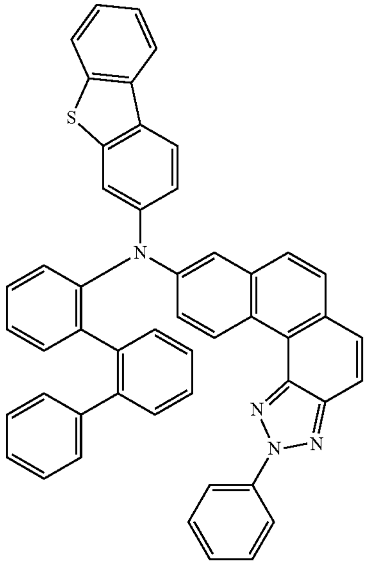
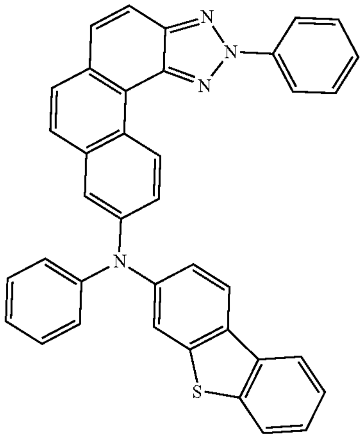
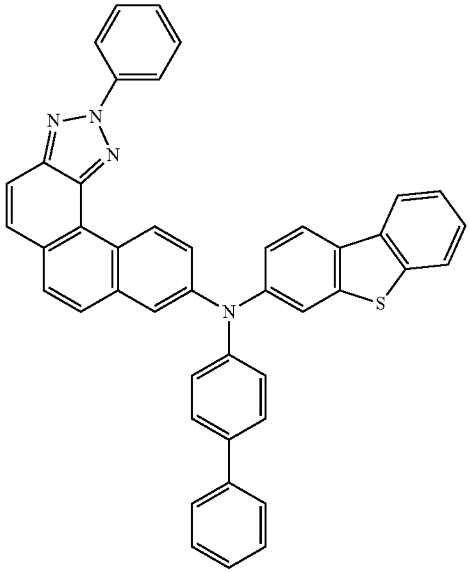

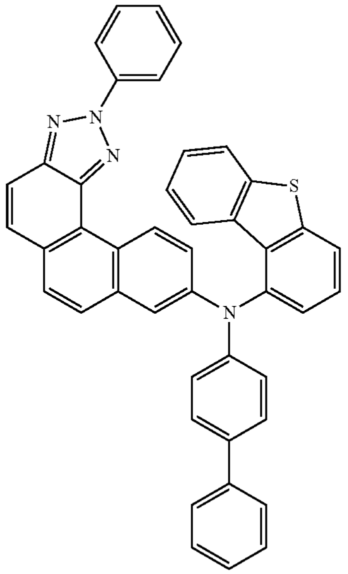
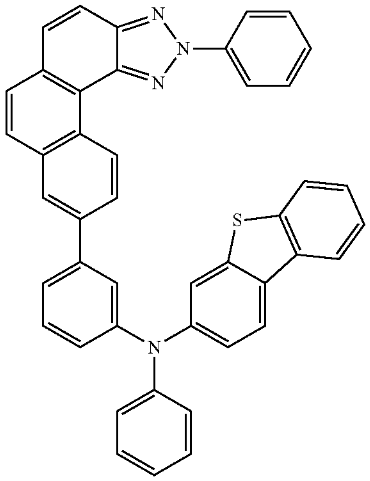
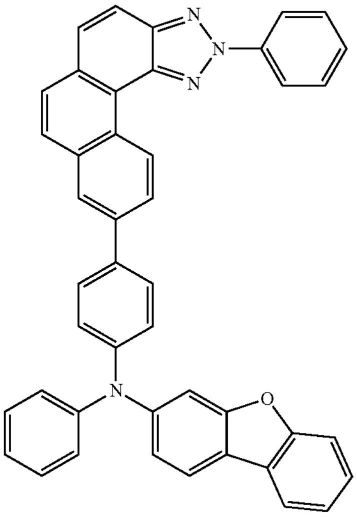
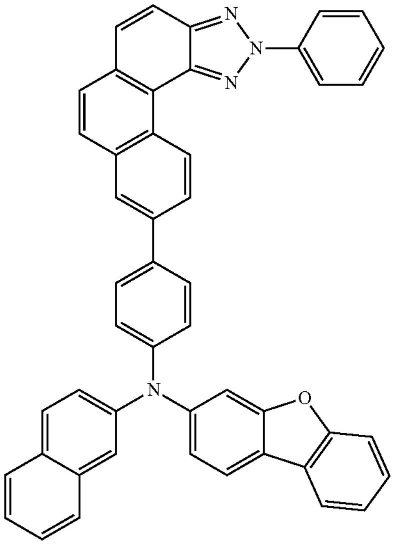
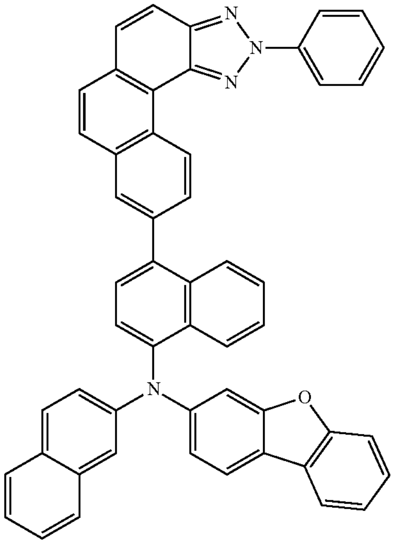
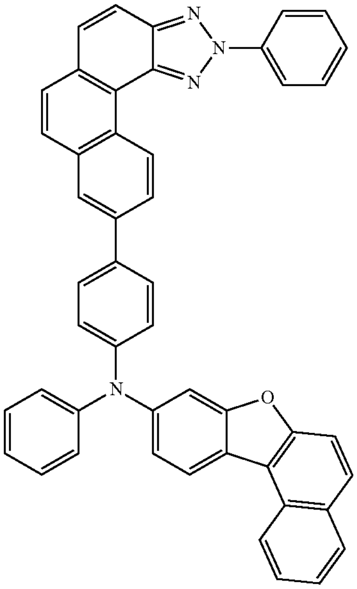

-continued
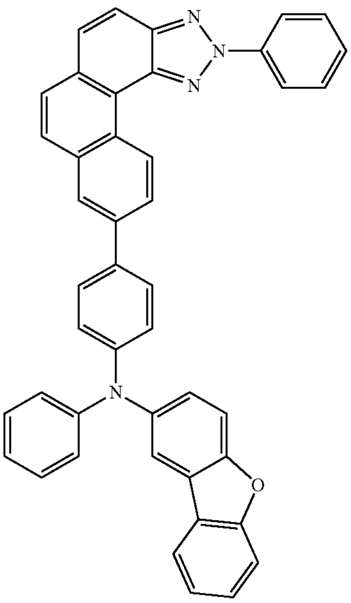
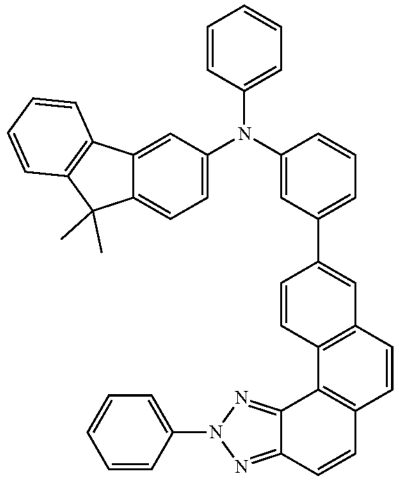
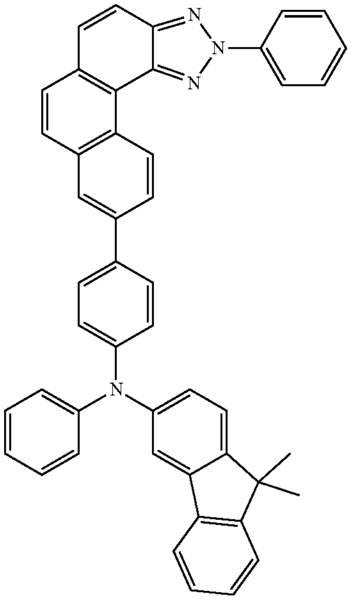
-continued
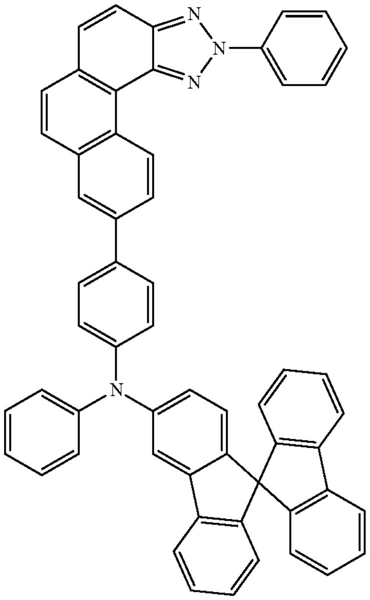
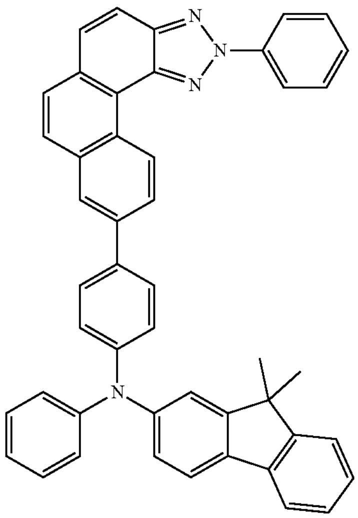

-continued

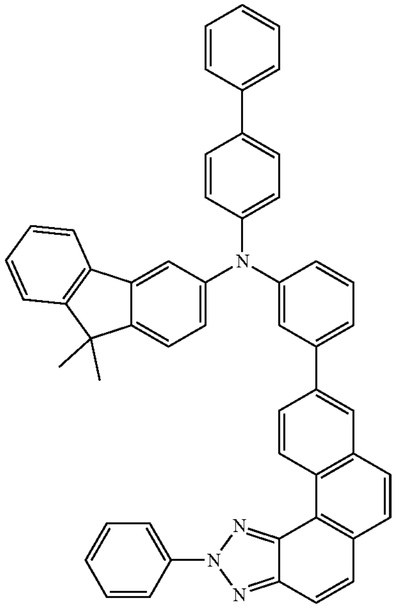

6. The organic material composition according to claim 1, wherein the group represented by Formula 3 is any one selected from the following groups:

3-1

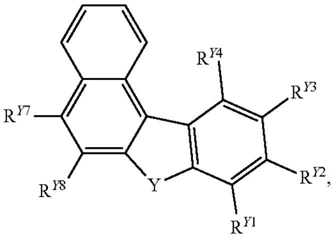

3-2

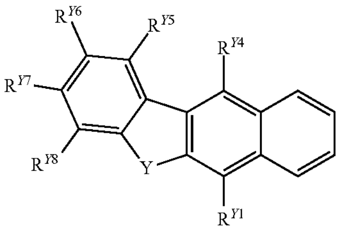

3-3

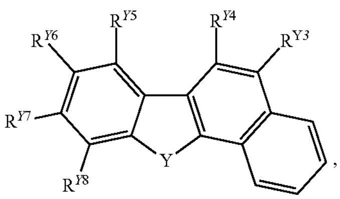

-continued 3-4

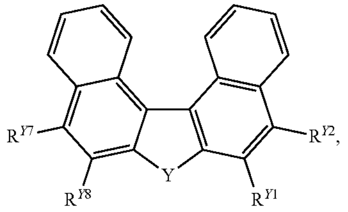

3-5

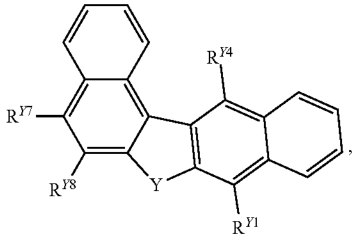

and 3-6

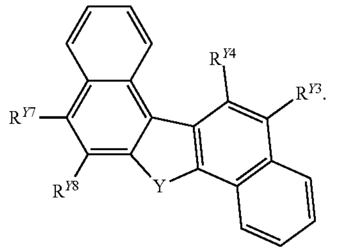

$R^{W1}$ and $R^{W2}$ are each independently selected from a methyl group and a phenyl group; or $R^{W1}$ and $R^{W2}$ joined to form a spiro ring;

$R^{Y1}$-$R^{Y8}$ are each independently selected from hydrogen, deuterium, and a group selected from a phenyl group, a biphenylyl group, a terphenylyl group, a naphthyl group, a phenylnaphthyl group, a naphthylphenyl group, an anthryl group, a phenanthryl group, a benzophenanthryl group, a pyridyl group, a dibenzofuryl group, a dibenzothiophenyl group, a dibenzofurylphenyl group, a dibenzothiophenylphenyl group, a dimethylfluorenyl group, a diphenylfluorenyl group, a spirobifluorenyl group, a benzonaphthofuryl group, and a benzonaphthothiophenyl group, each of which is substituted or unsubstituted; $R^{Y1}$ to $R^{Y8}$ are present individually without forming a ring, or any adjacent two of $R^{Y1}$ to $R^{Y8}$ joined to form a ring A, and the ring A is a substituted or unsubstituted benzene ring;

$L^{Y1}$, $L^{Y2}$, $L^{Y3}$, $L^{Y4}$, $L^{Y5}$ and $L^{Y6}$ are each independently selected from a bond, a phenylene group, a biphenylene group, and a naphthylene group.

7. The organic material composition according to claim 1, wherein the compound having a structure represented by Formula 2-1 is selected from the compounds shown as below:

-continued
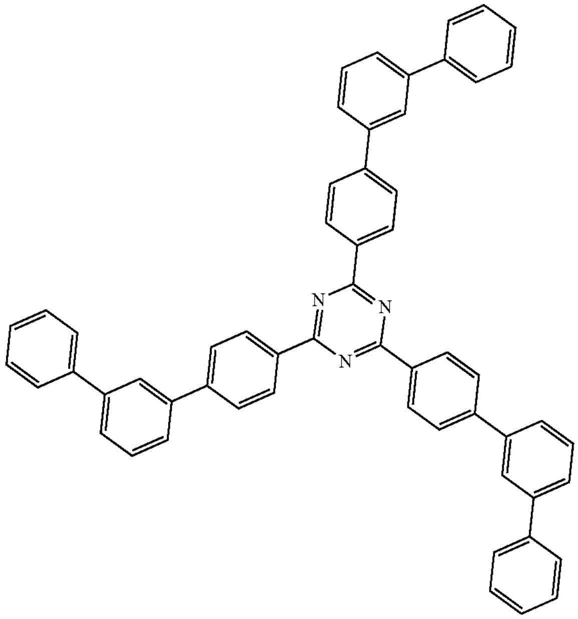
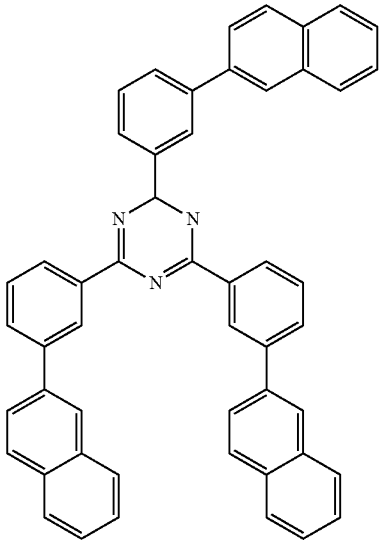
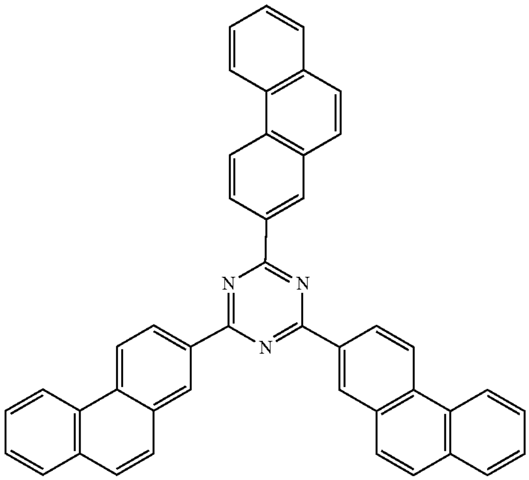
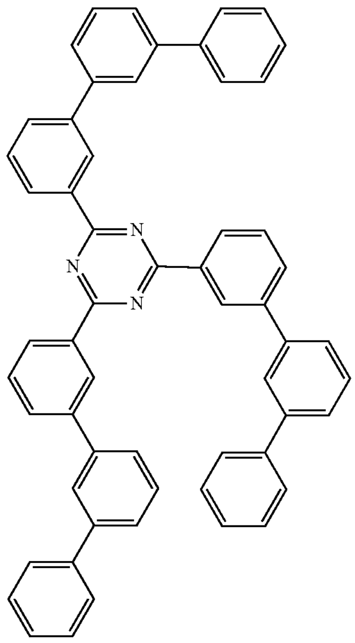
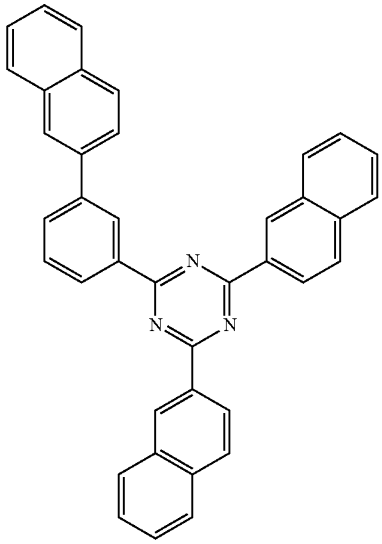

-continued
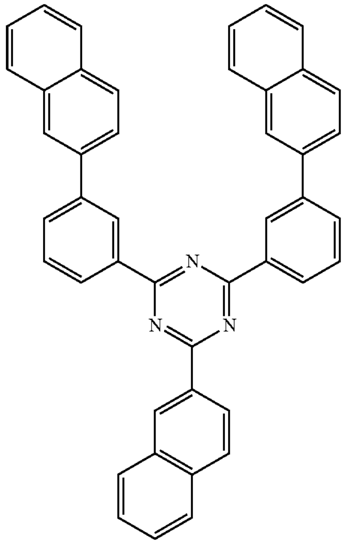
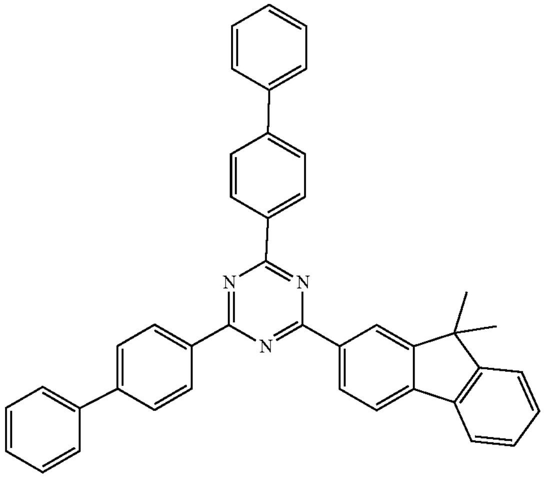
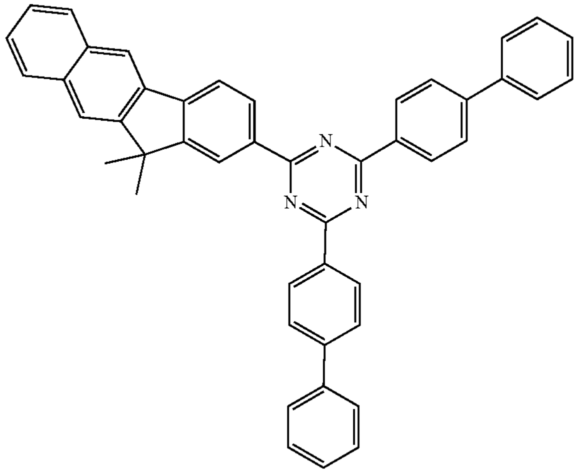
-continued
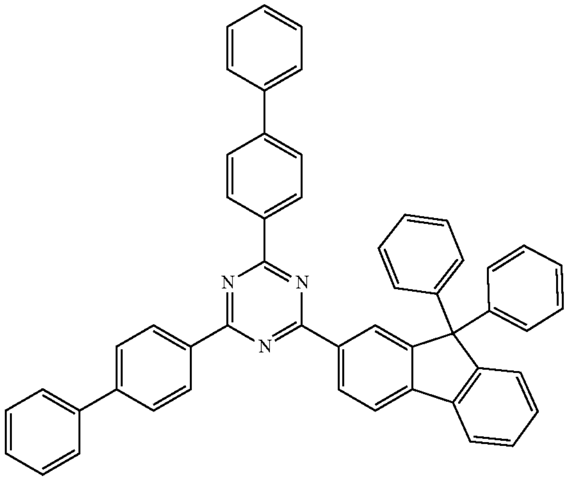
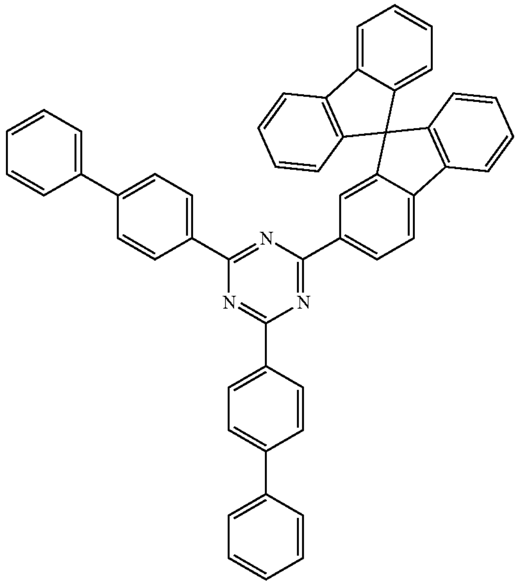
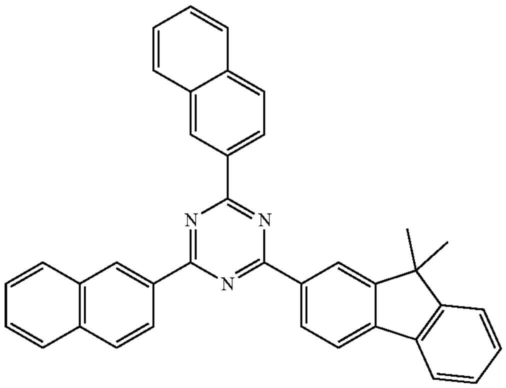

-continued
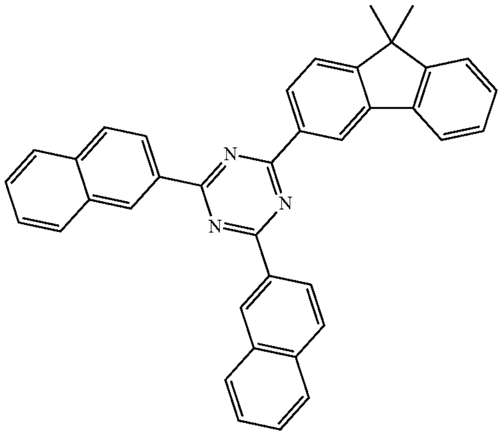
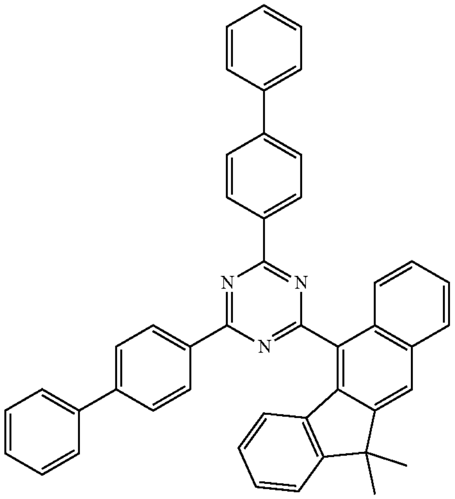
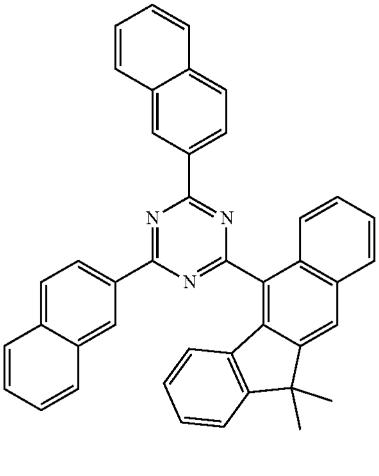
-continued
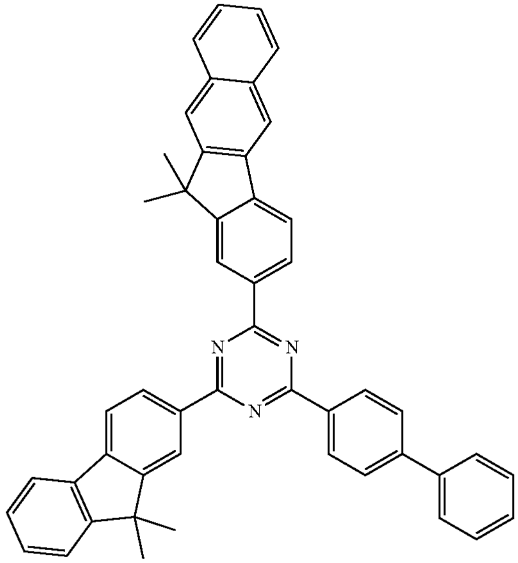
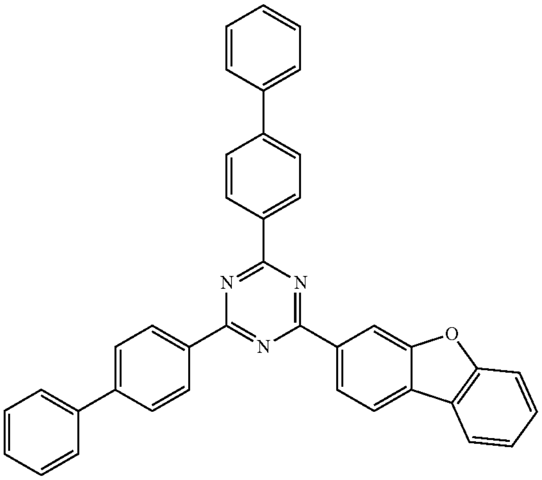
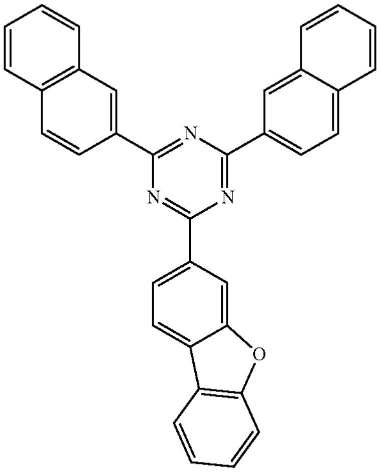

-continued
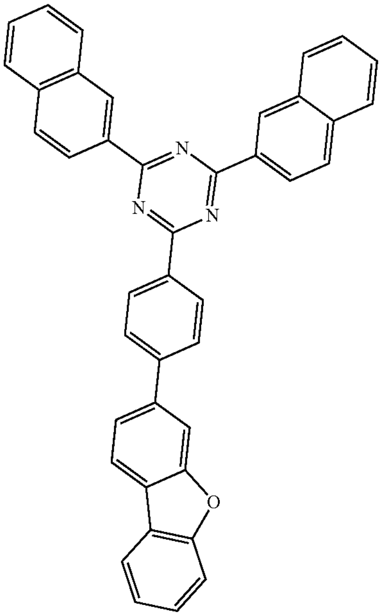
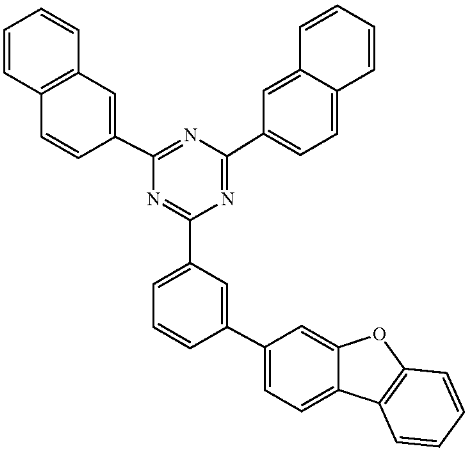
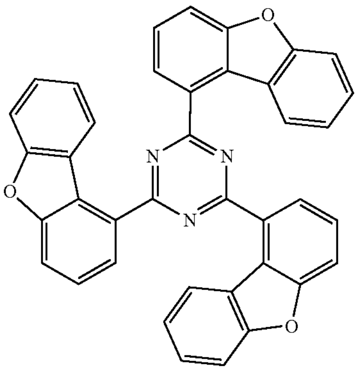
-continued
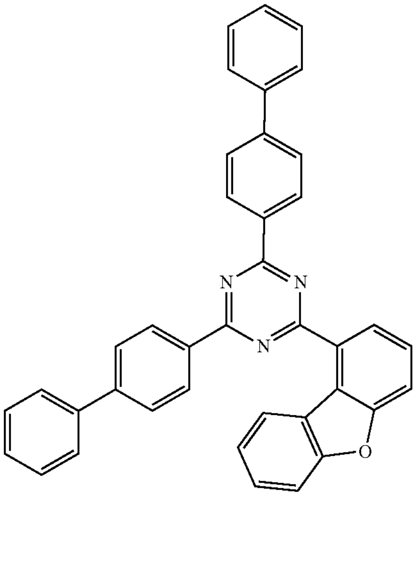
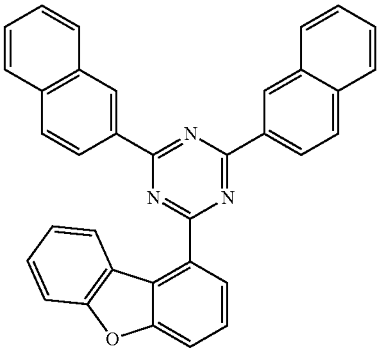
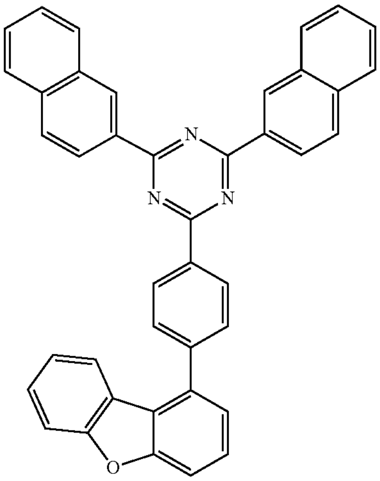

-continued
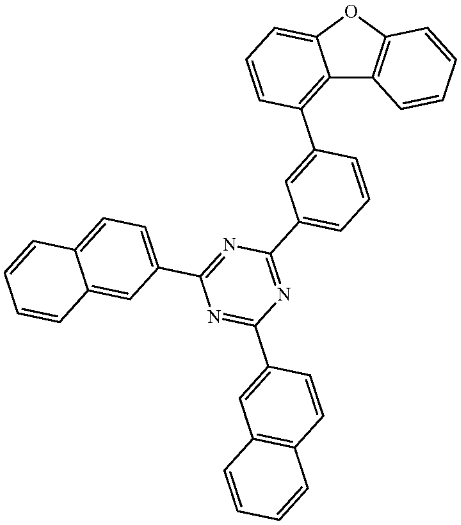
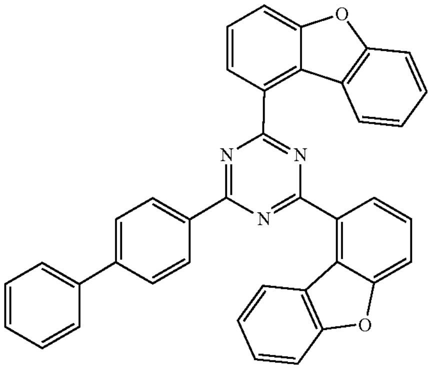
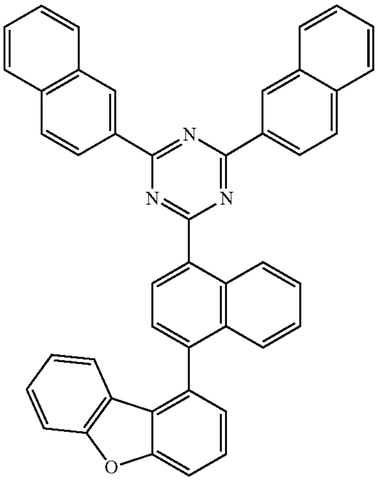
-continued
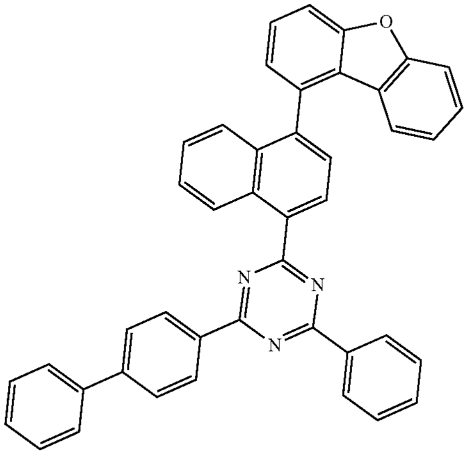
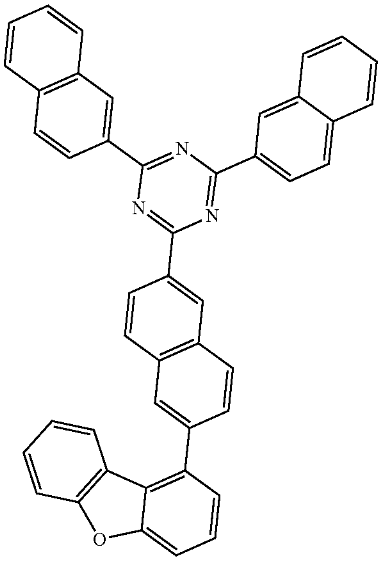
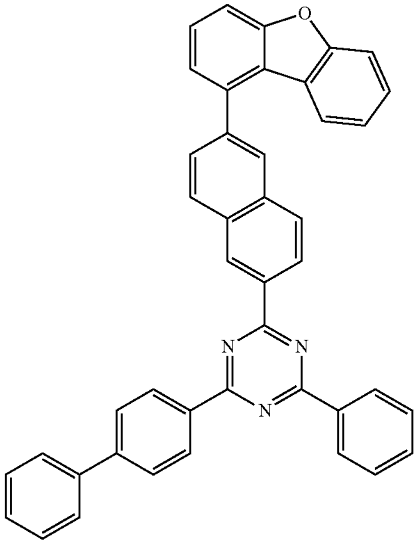

-continued
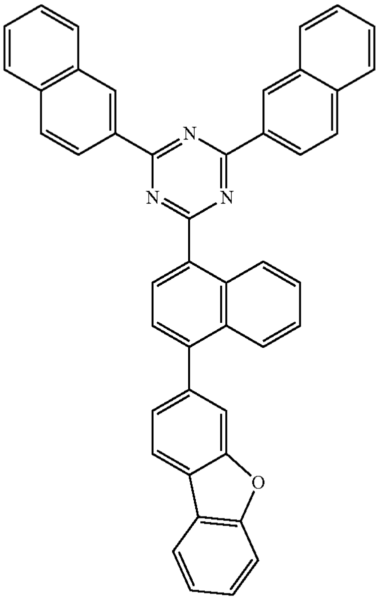
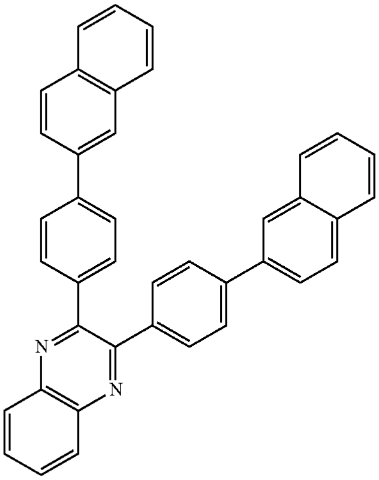
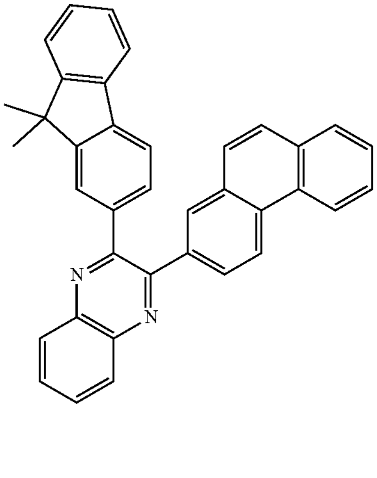
-continued
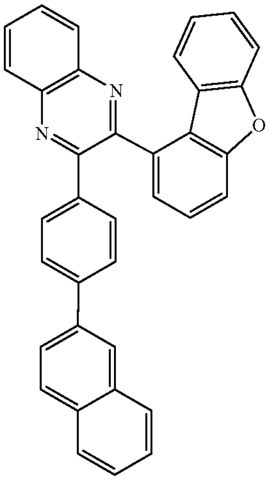
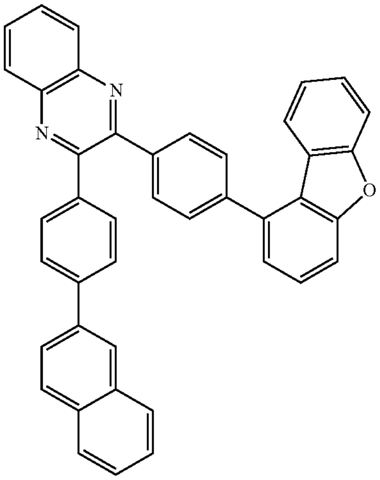
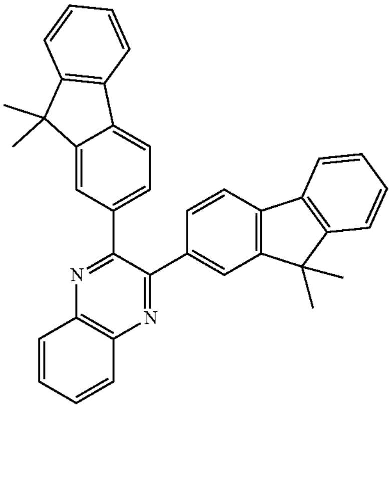

-continued
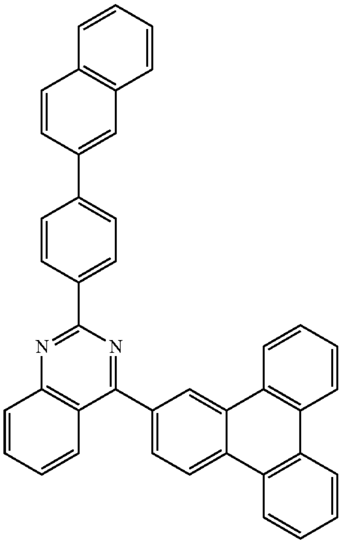
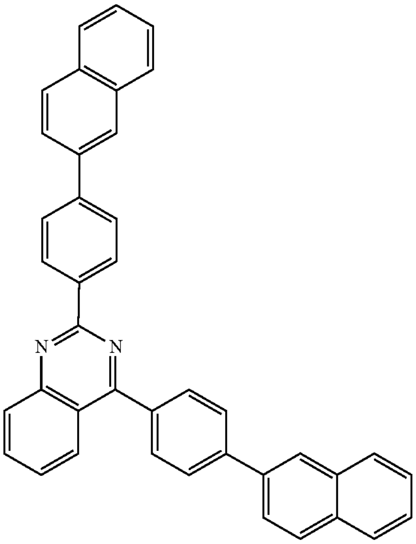
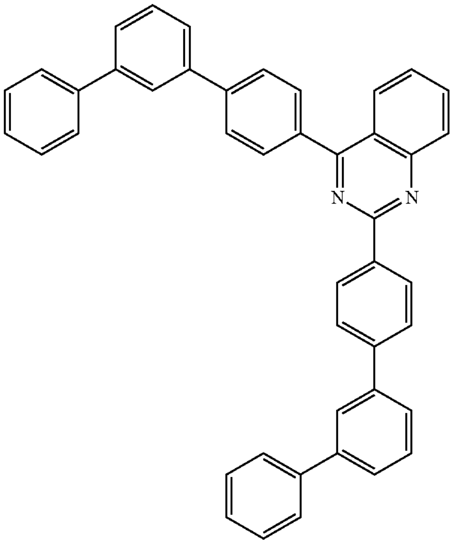
-continued
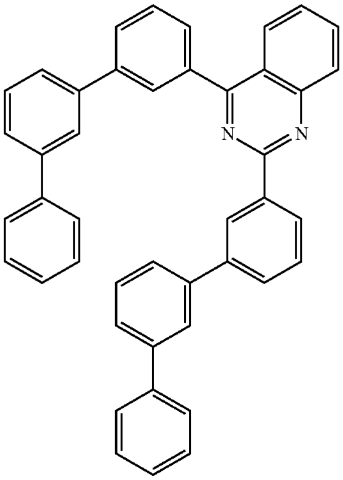
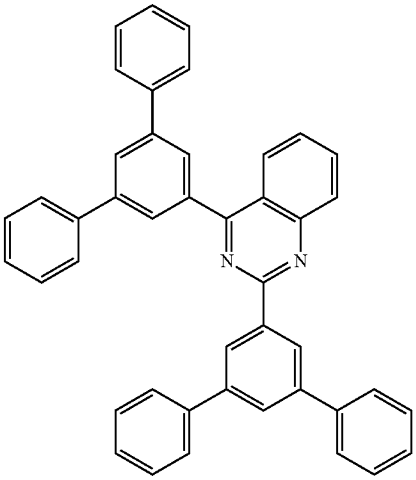
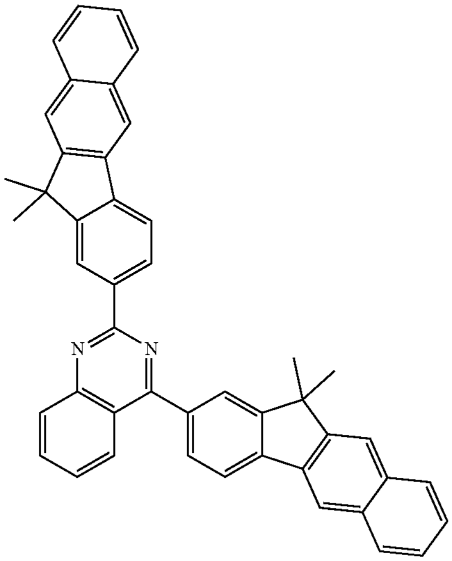

-continued
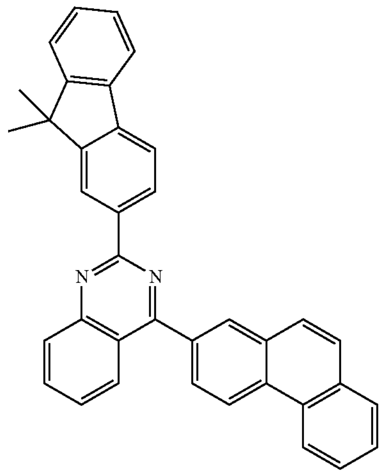
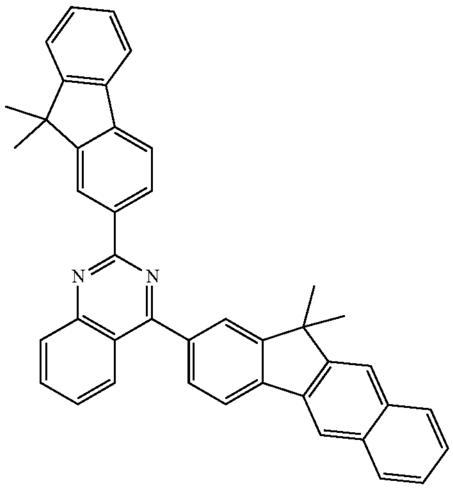
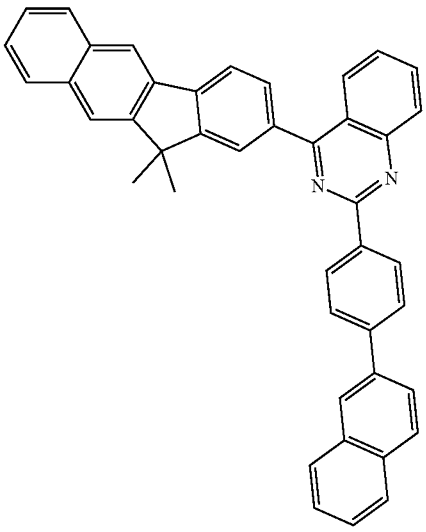
-continued
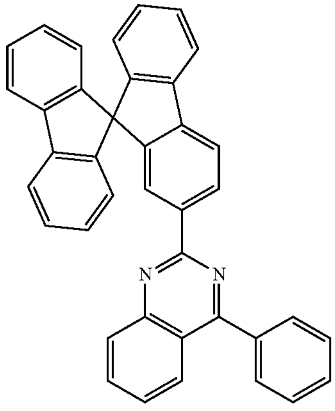
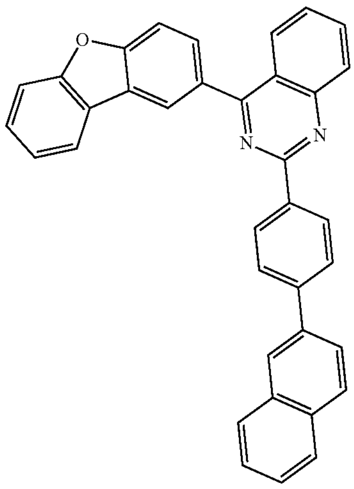
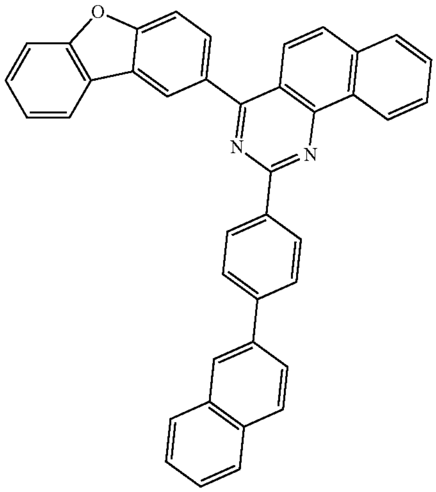

-continued
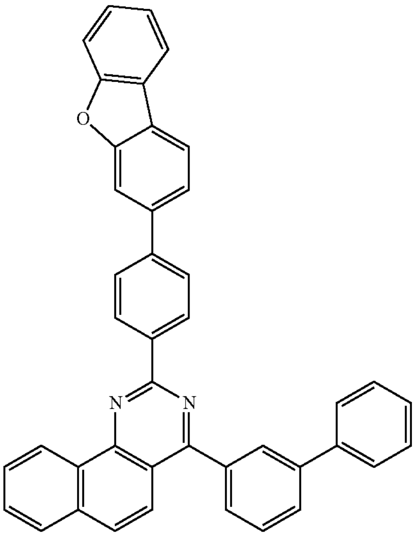
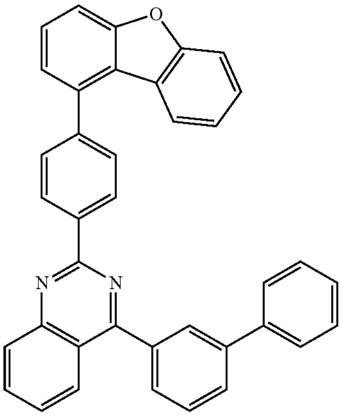
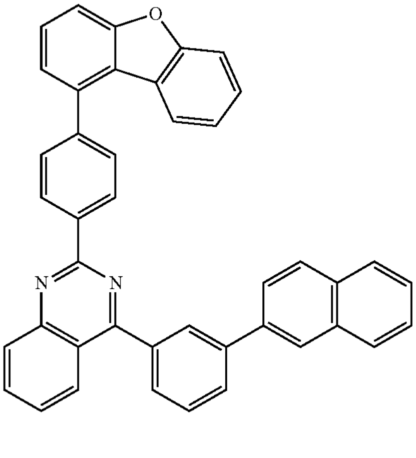
-continued
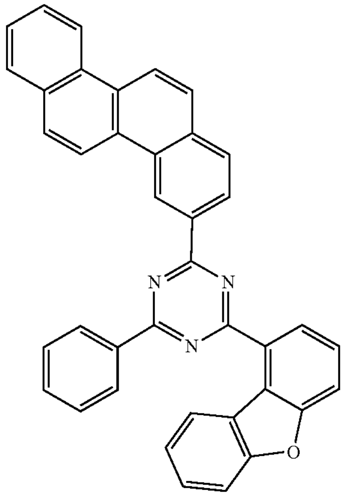
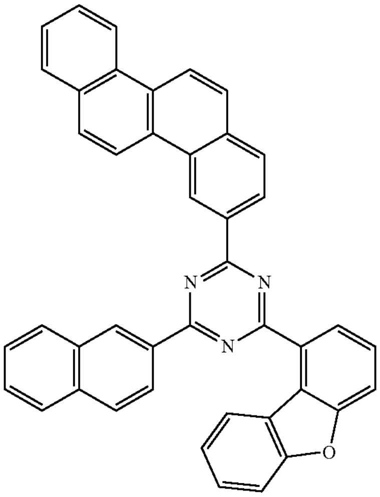
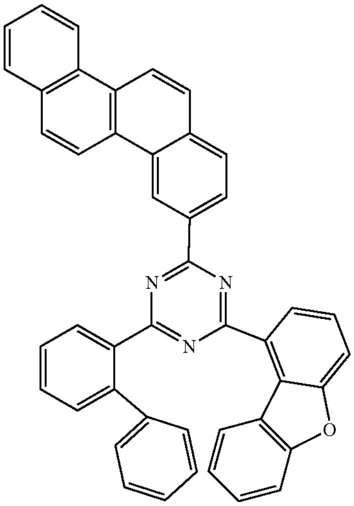

-continued
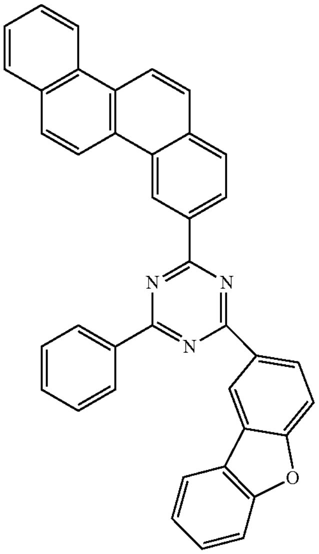
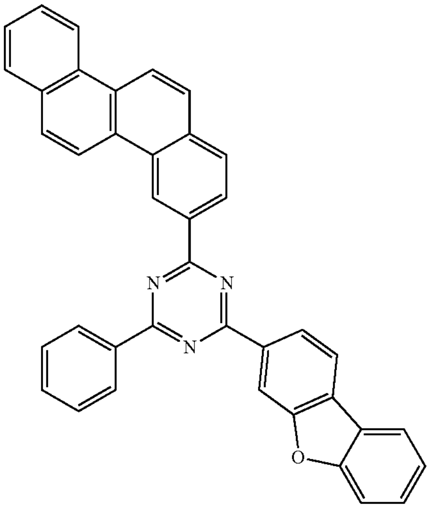
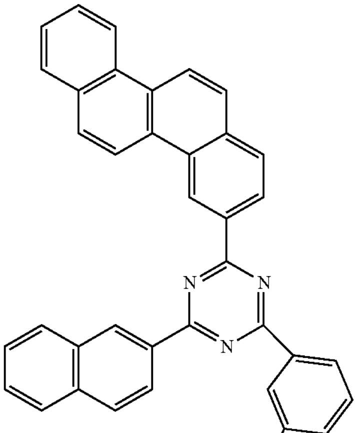
-continued
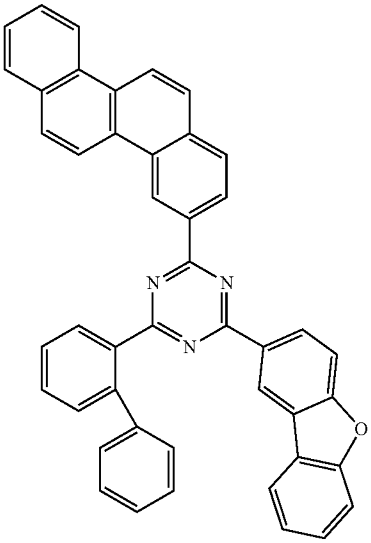
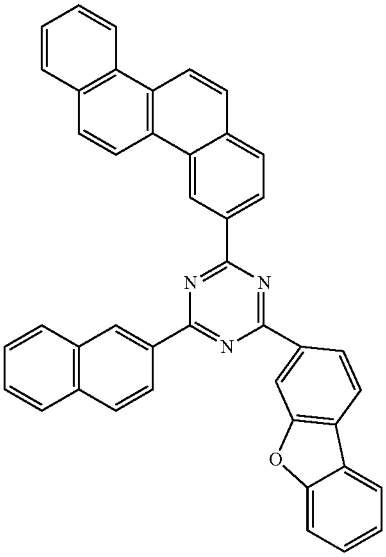
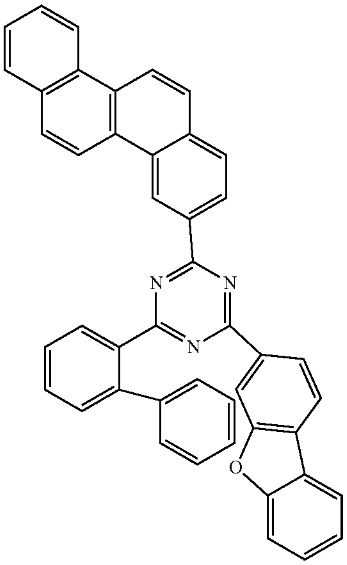

-continued
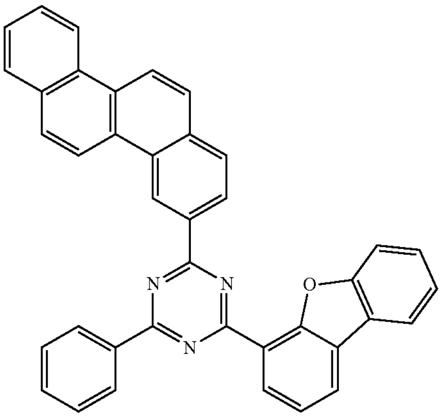
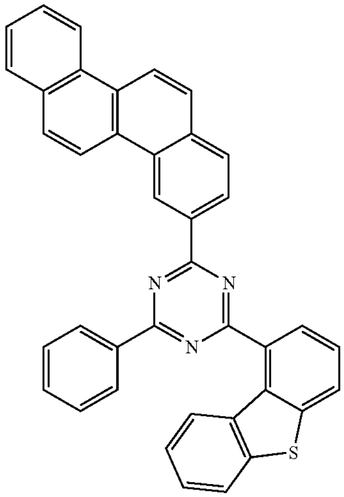
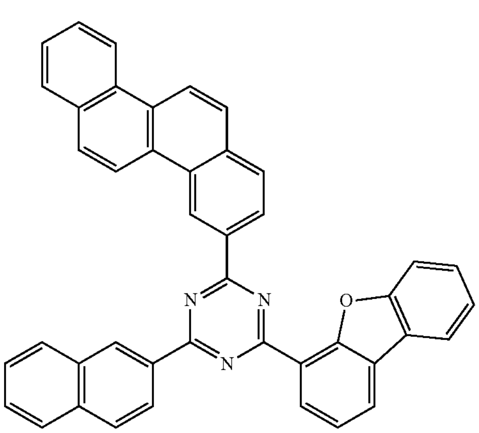
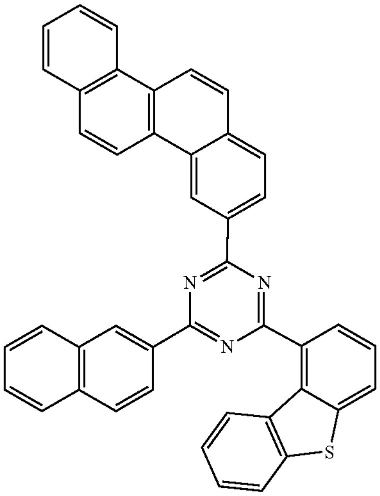
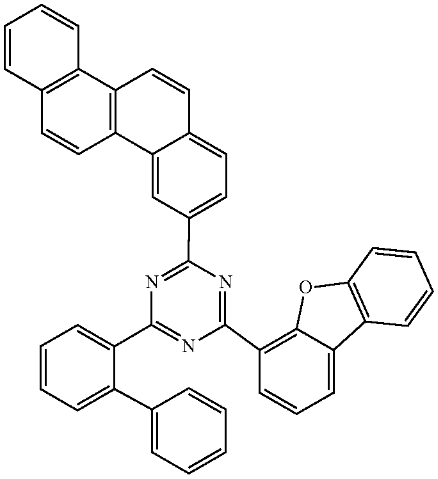
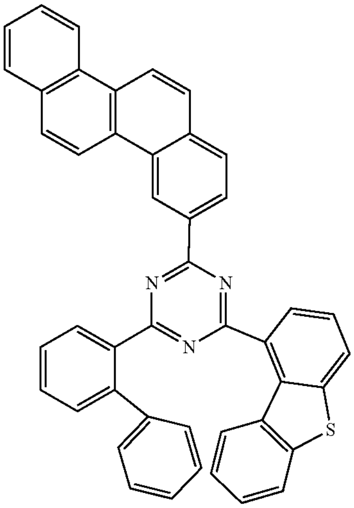
-continued -continued
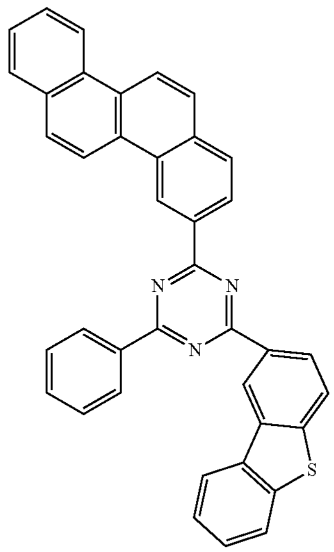
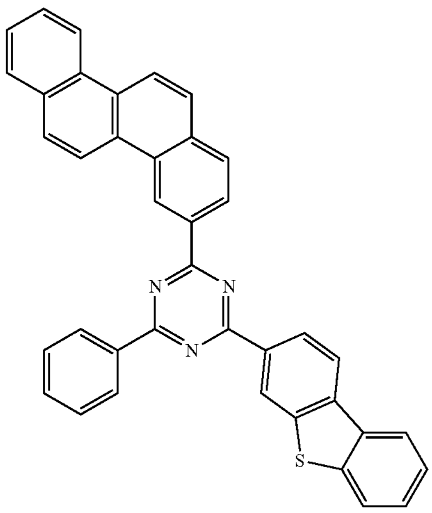
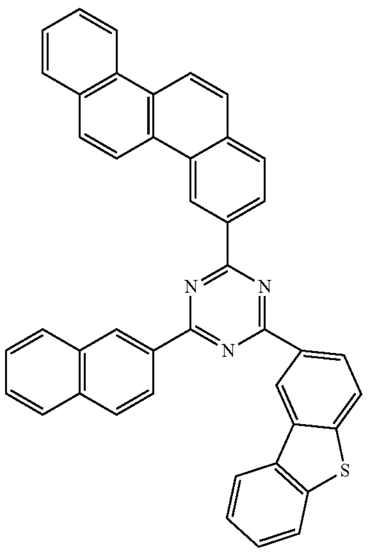
-continued
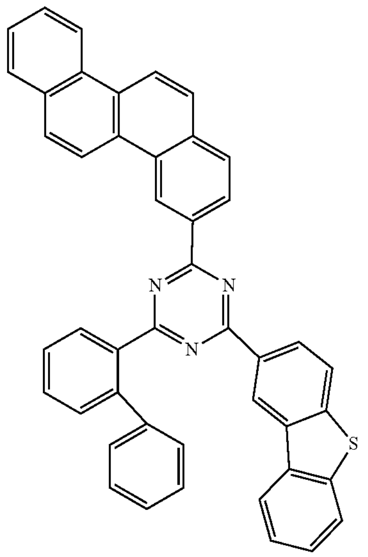
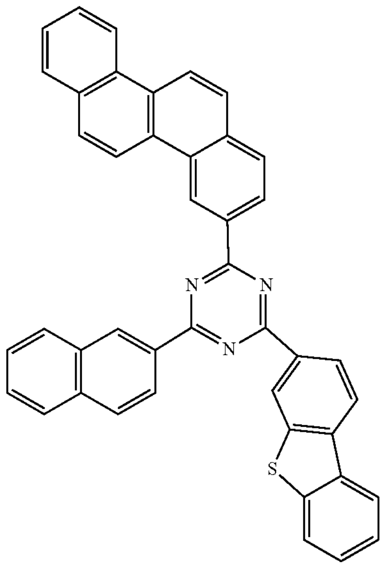
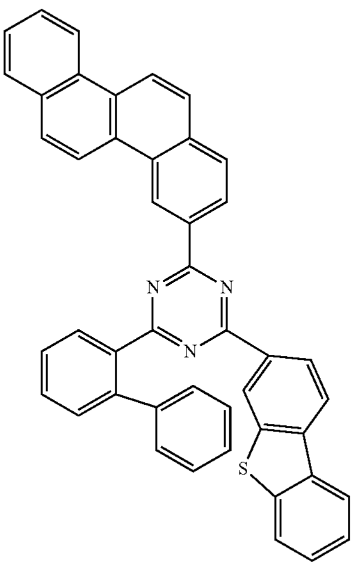

-continued
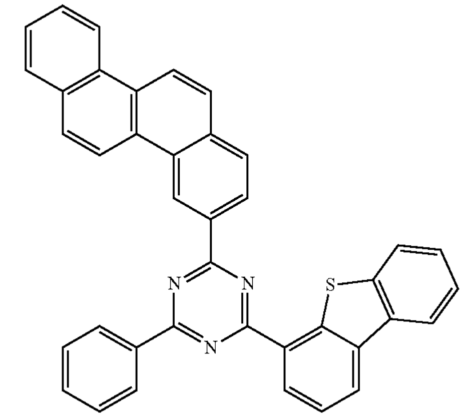
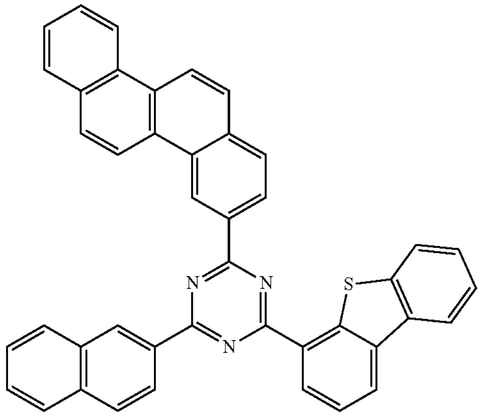
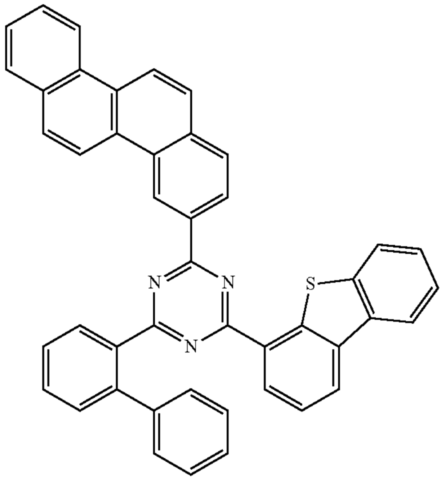
-continued
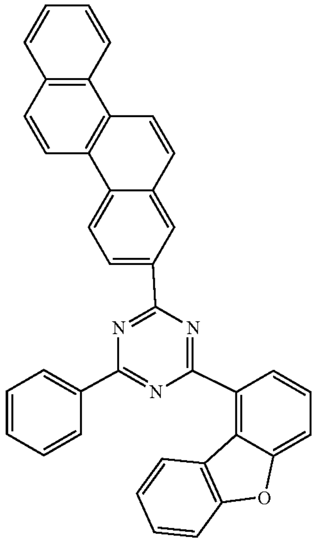
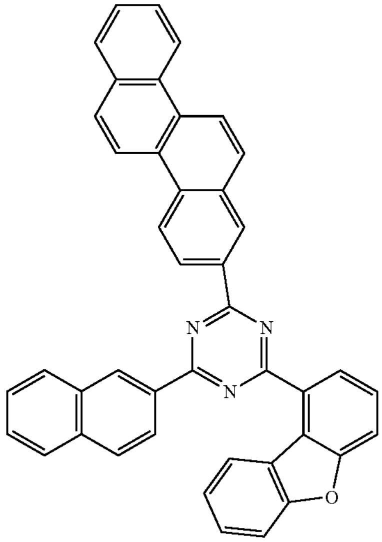
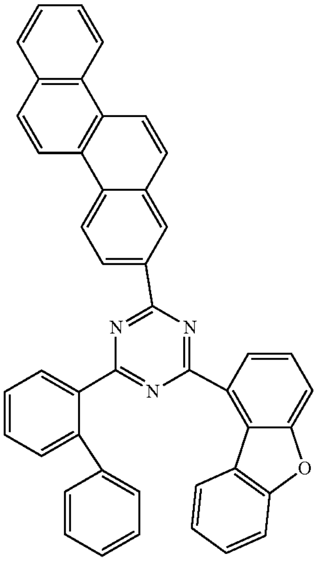

-continued
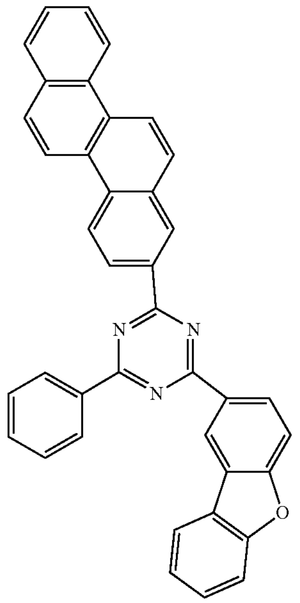
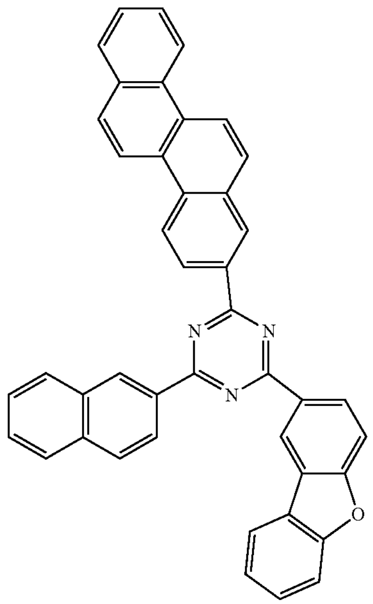
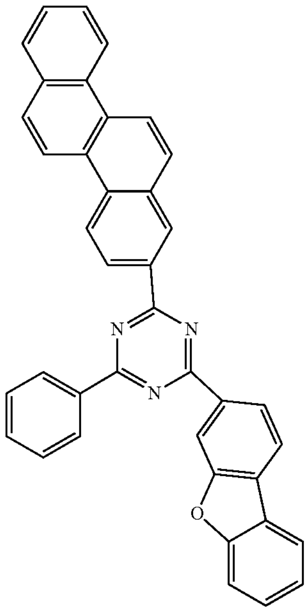
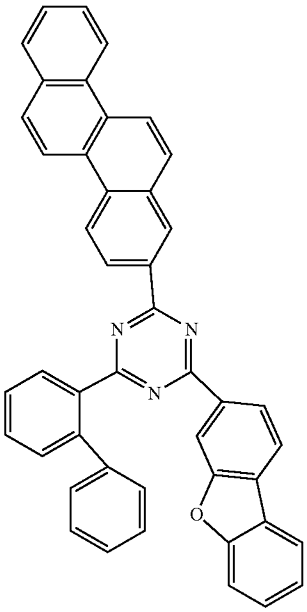

-continued
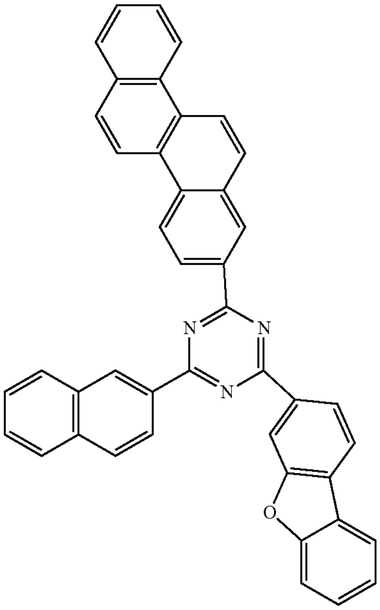
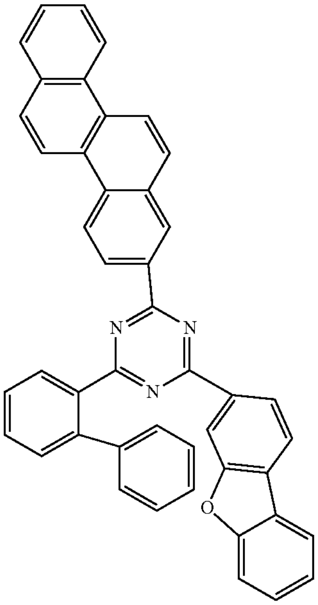
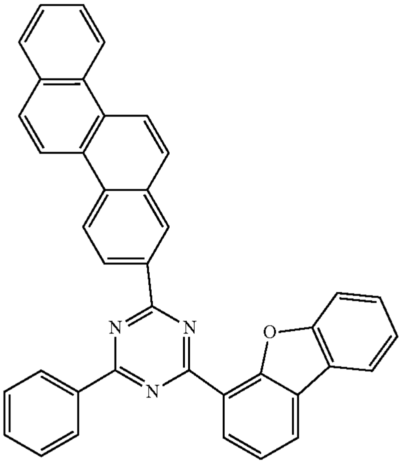
-continued
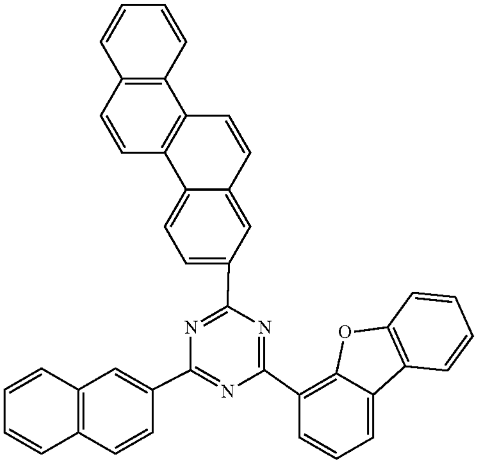
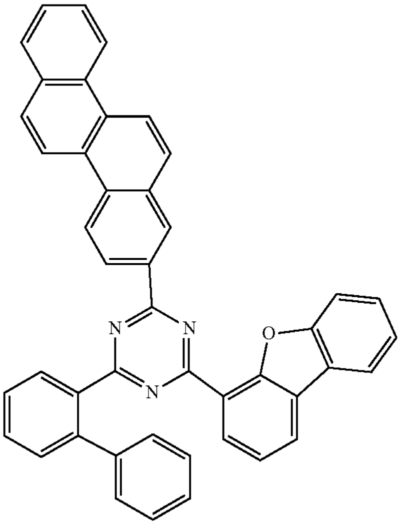
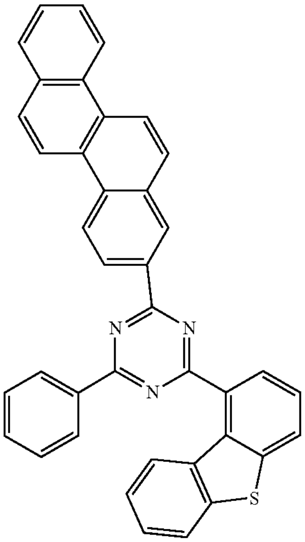

-continued
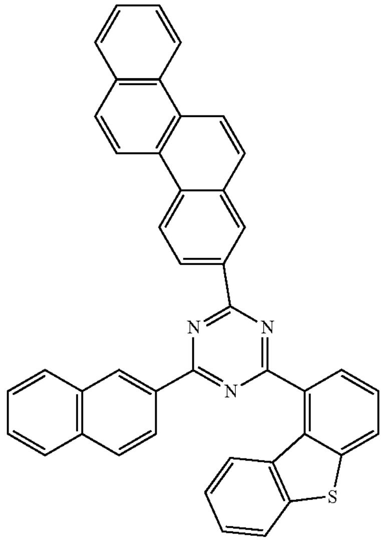
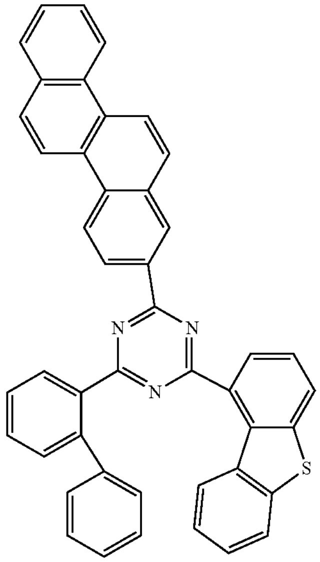
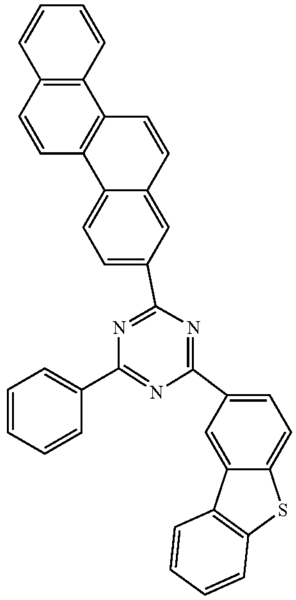
-continued
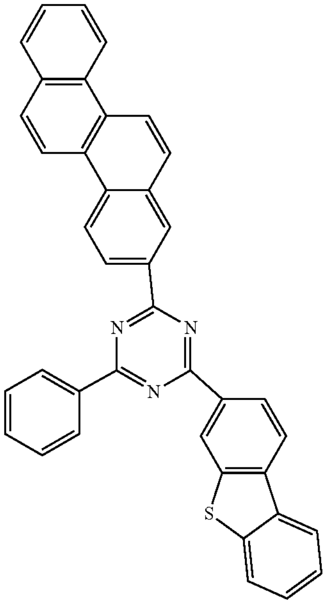
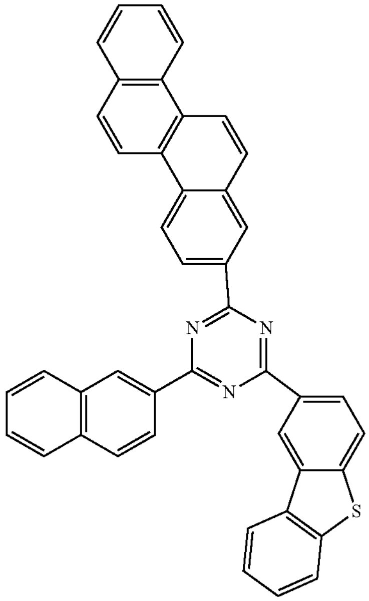

-continued
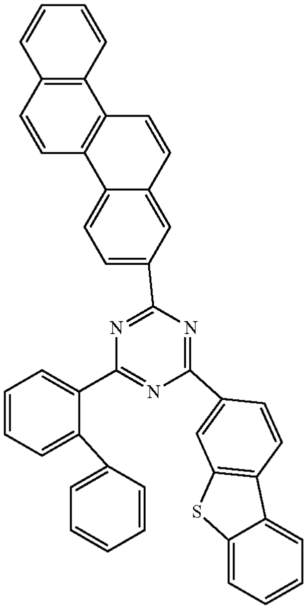
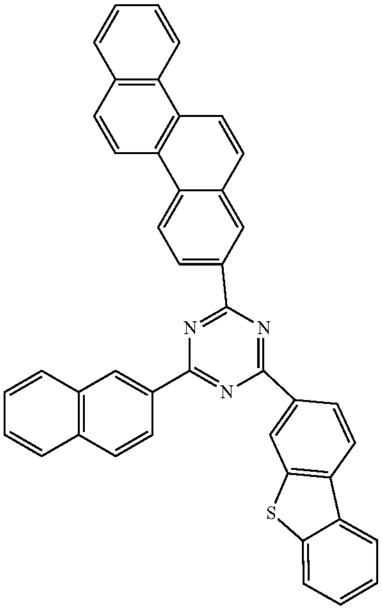
-continued
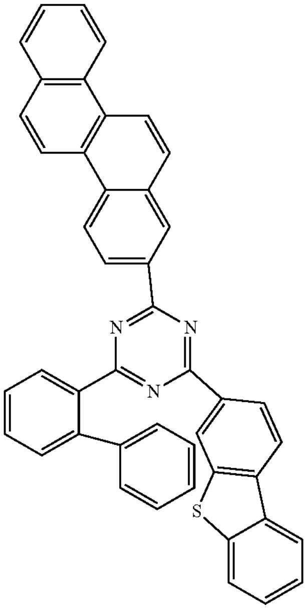
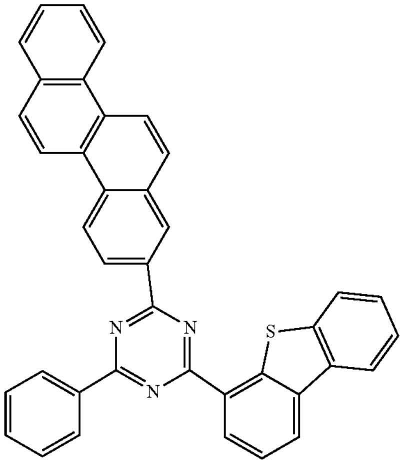
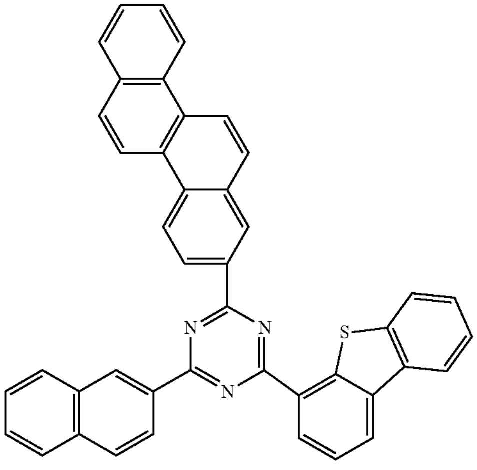

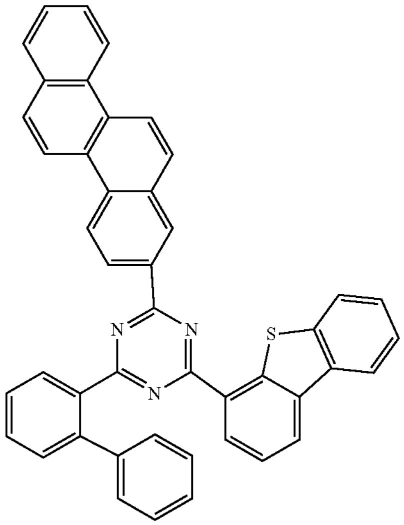
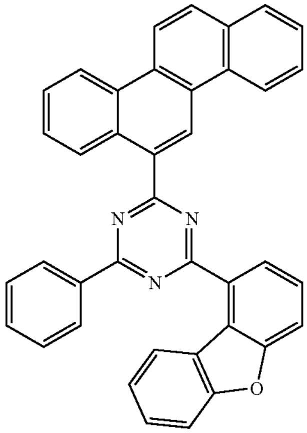
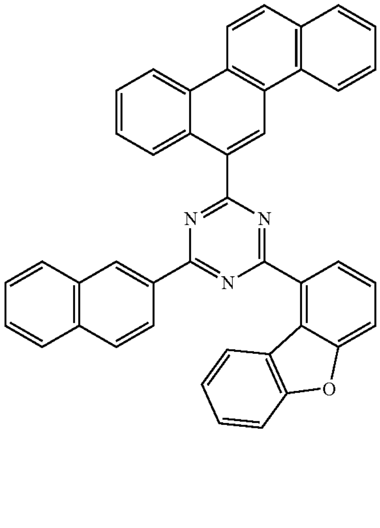
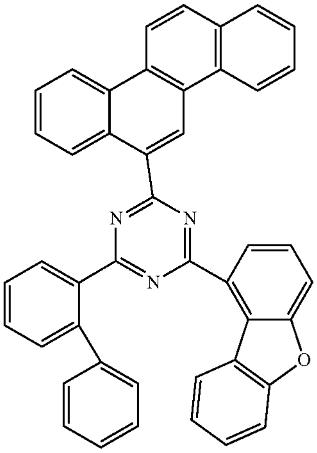
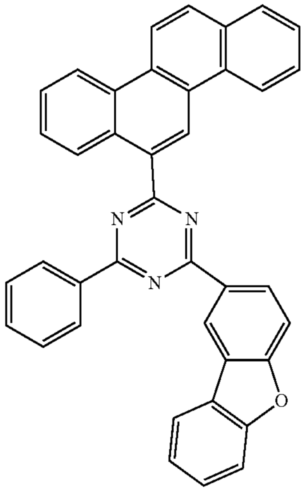
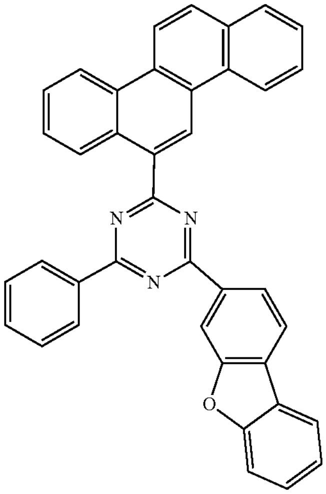

-continued
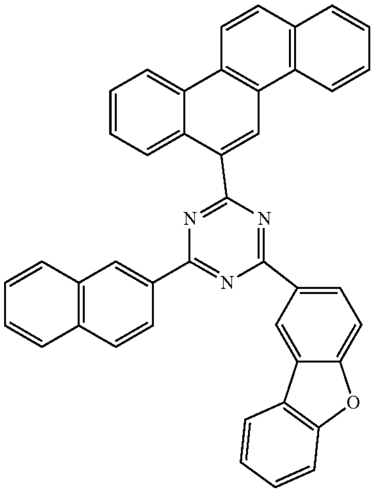
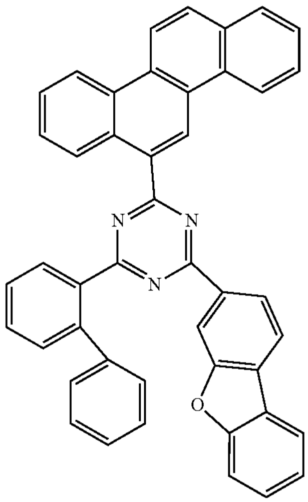
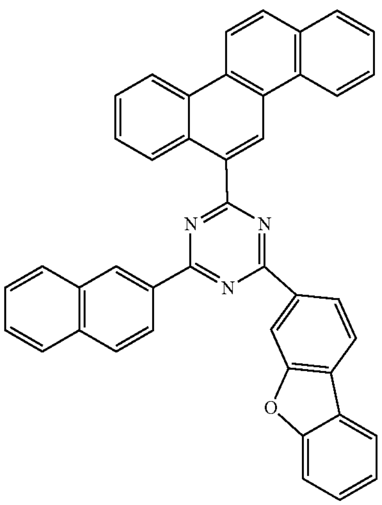
-continued
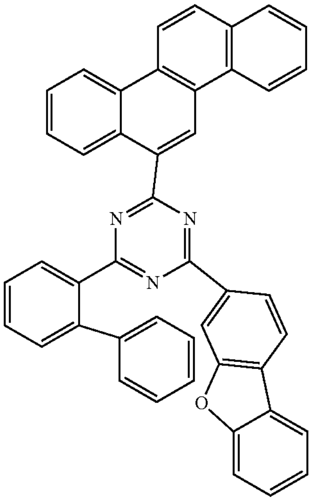
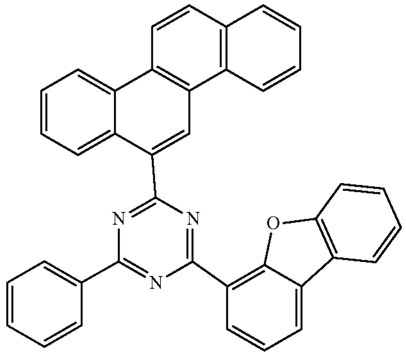
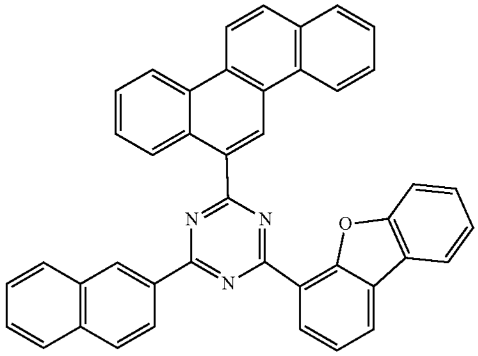
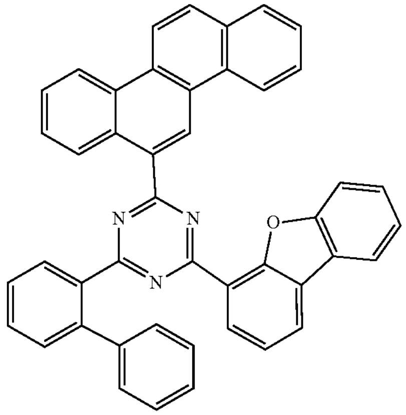

-continued
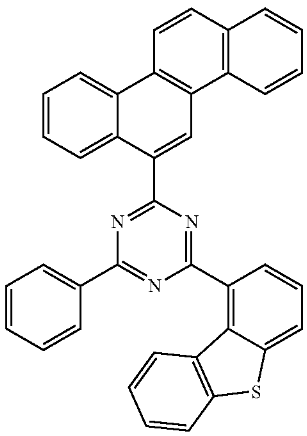
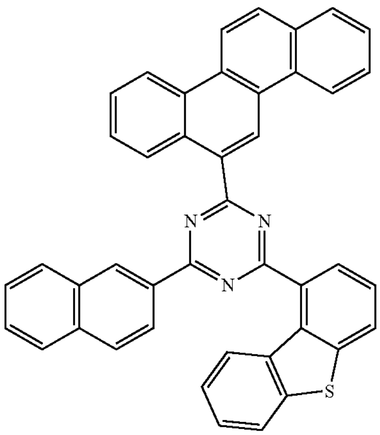
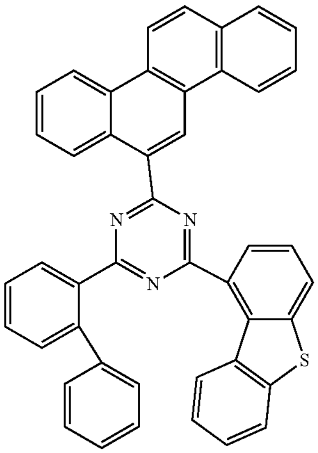
-continued
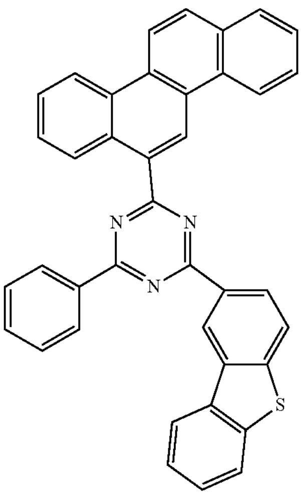
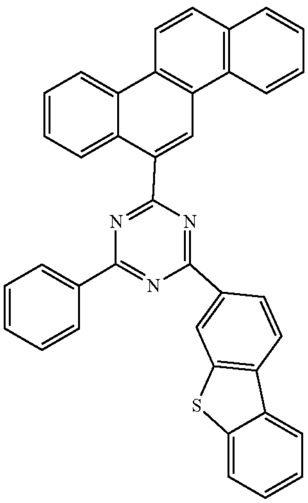
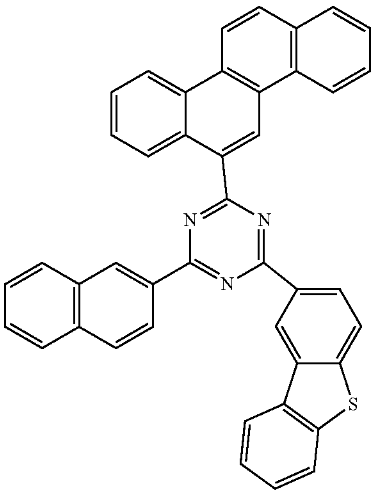

-continued
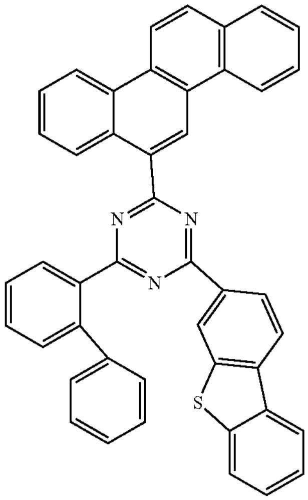
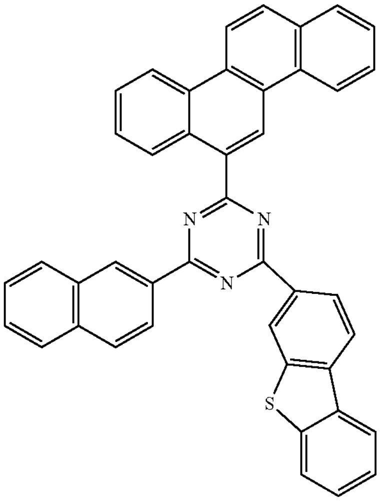
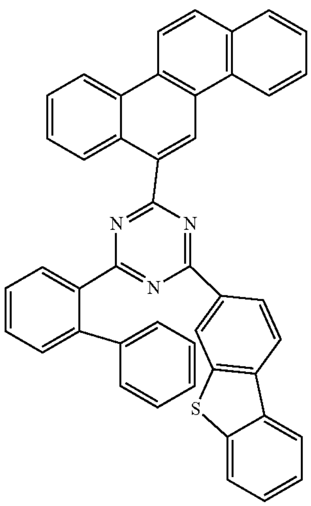
-continued
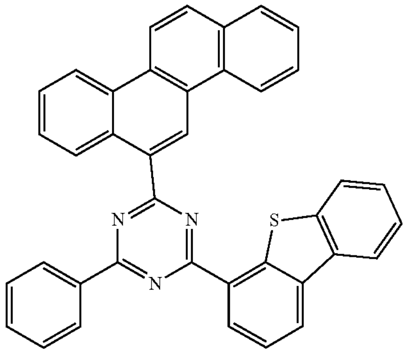
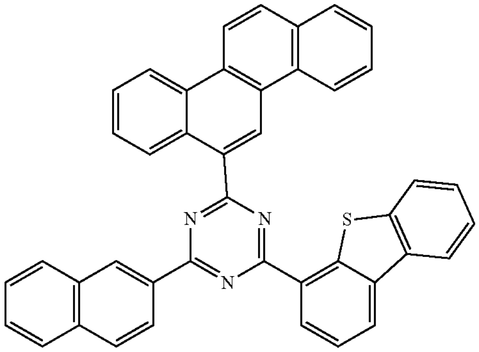
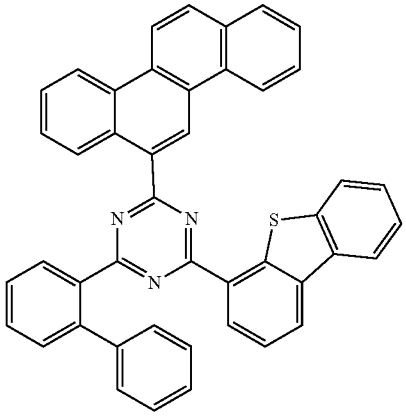
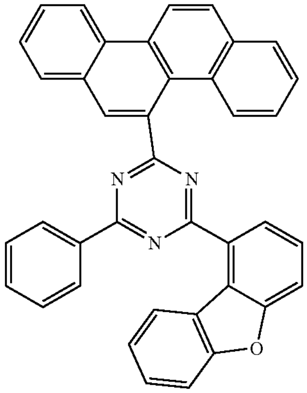

-continued
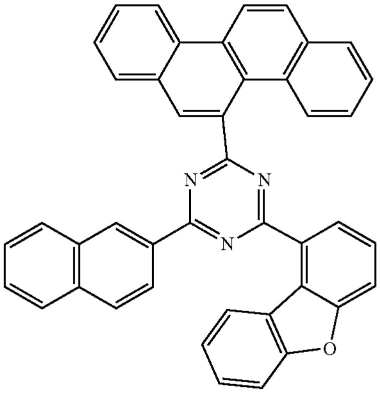
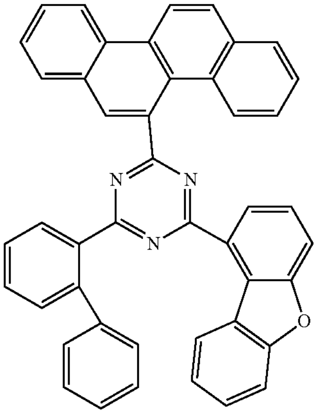
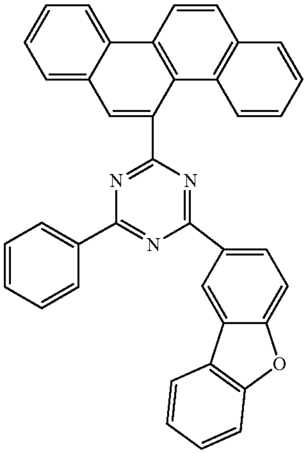
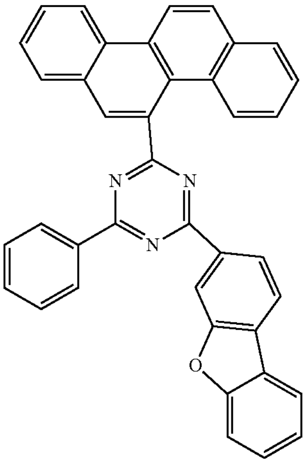
-continued
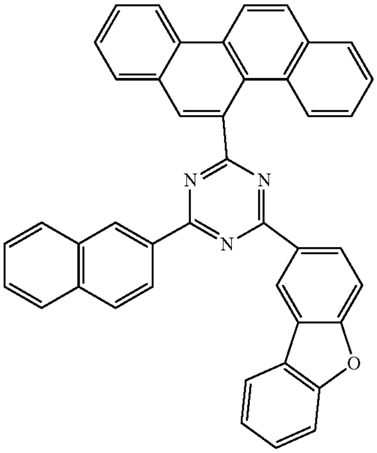
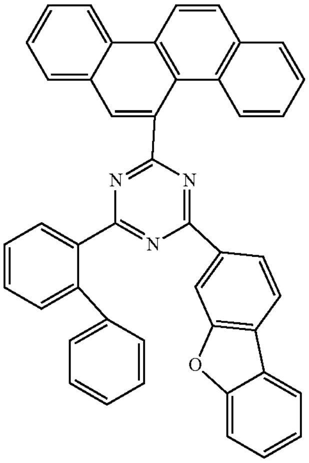
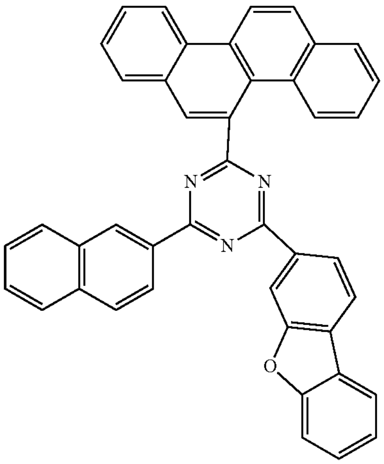

-continued
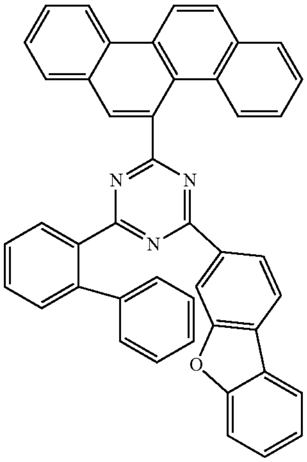
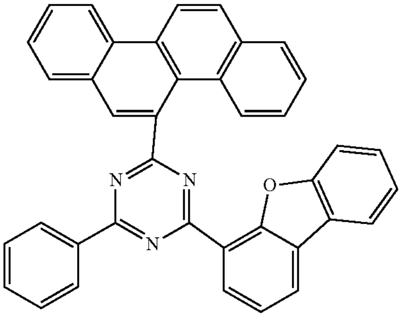
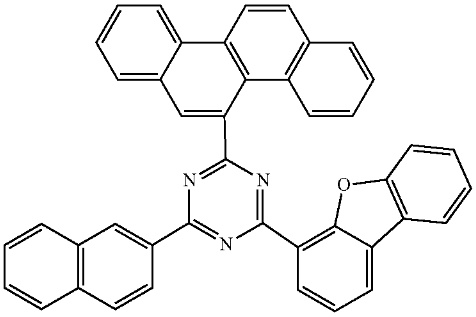
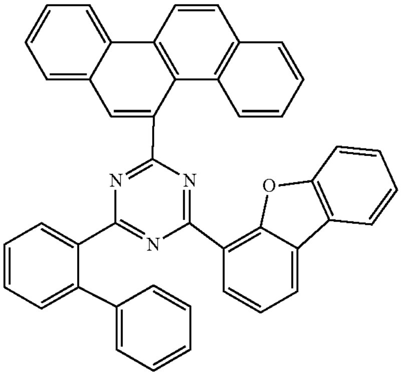
-continued
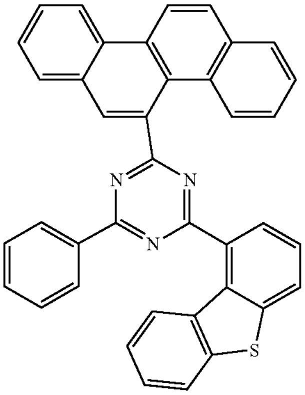
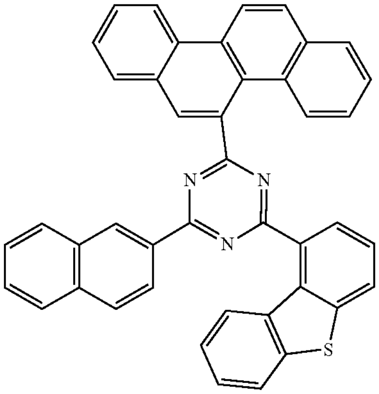
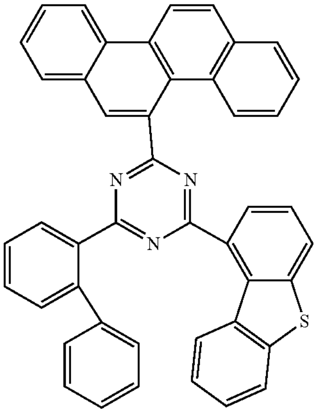
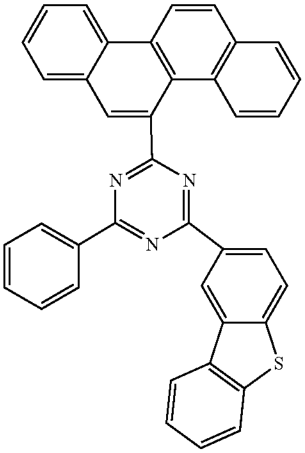

-continued
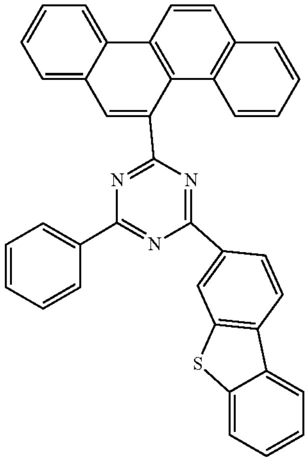
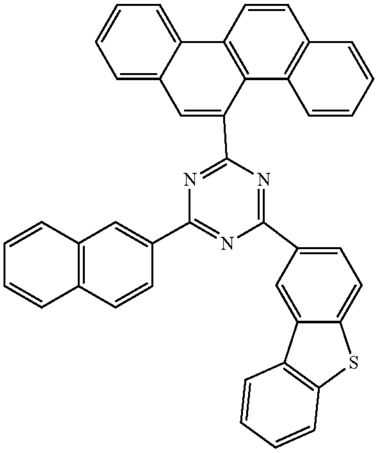
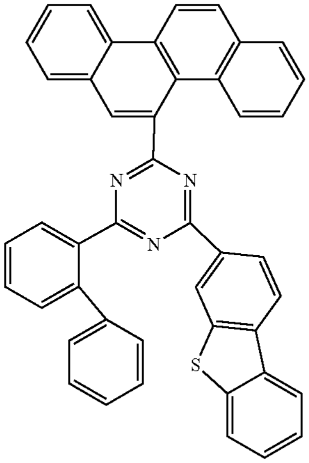
-continued
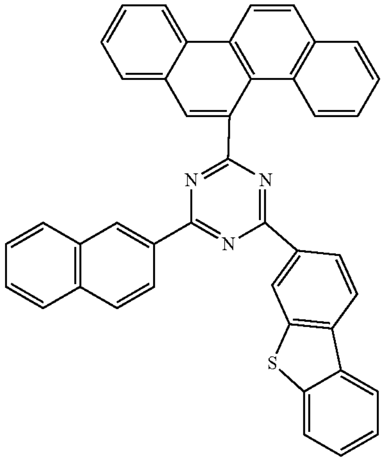
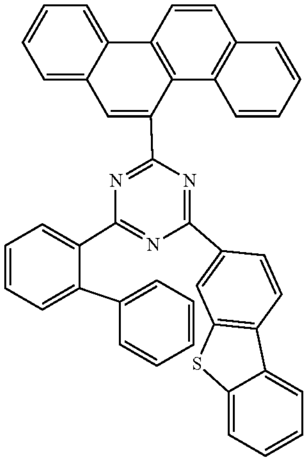
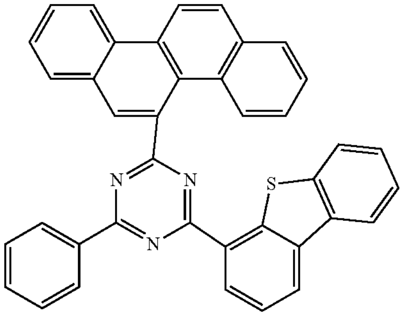
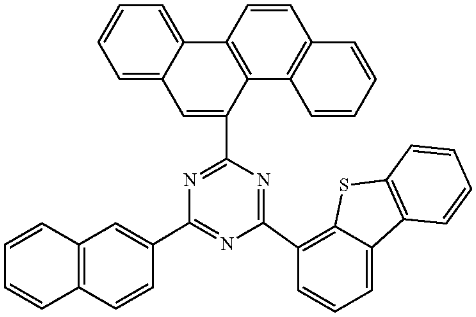

-continued

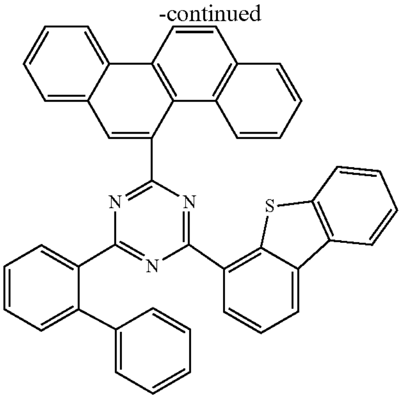

;

and the compound having a structure represented by Formula 1 and the compound having a structure represented by Formula 2-1 have a weight ratio of 1:9 to 9:1.

8. The organic material composition according to claim 7, wherein the compound having a structure represented by Formula 1 and the compound having a structure represented by Formula 2-1 have a weight ratio of 4:6 to 6:4.

9. An organic electroluminescence material, wherein the organic electroluminescence material comprises the organic material composition according to claim 1.

10. A method for preparing an optical element comprising an emitting layer, the method comprising: co-depositing a light-emitting host material and a guest material to form the emitting layer; wherein the light-emitting host material comprises the organic material composition according to claim 1, and the guest material comprises a phosphorescence dopant.

11. An organic electroluminescence element, wherein the organic electroluminescence element comprises an anode, a cathode and an organic layer disposed between the anode and the cathode; and the organic layer comprises the organic material composition according to claim 1.

12. An electronic device, wherein the electronic device comprises the organic electroluminescence element according to claim 11.

* * * * *